US010493136B2

(12) United States Patent
Ishibashi et al.

(10) Patent No.: US 10,493,136 B2
(45) Date of Patent: Dec. 3, 2019

(54) IMMUNE RESPONSE INDUCER

(71) Applicant: TORAY INDUSTRIES, INC., Tokyo (JP)

(72) Inventors: Masaki Ishibashi, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 168 days.

(21) Appl. No.: 15/299,137

(22) Filed: Oct. 20, 2016

(65) Prior Publication Data

US 2017/0035865 A1 Feb. 9, 2017

Related U.S. Application Data

(62) Division of application No. 12/739,723, filed as application No. PCT/JP2008/069267 on Oct. 23, 2008, now Pat. No. 9,504,737.

(30) Foreign Application Priority Data

Oct. 25, 2007 (JP) ................................ 2007-277240
Oct. 25, 2007 (JP) ................................ 2007-277578
Oct. 25, 2007 (JP) ................................ 2007-277611
Oct. 26, 2007 (JP) ................................ 2007-279113

(51) Int. Cl.
*A61K 39/395* (2006.01)
*A61K 39/00* (2006.01)
*A61K 38/20* (2006.01)
*A61K 38/21* (2006.01)

(52) U.S. Cl.
CPC ........ *A61K 39/0011* (2013.01); *A61K 38/208* (2013.01); *A61K 38/212* (2013.01); *A61K 38/215* (2013.01); *A61K 2039/53* (2013.01)

(58) Field of Classification Search
None
See application file for complete search history.

(56) References Cited

U.S. PATENT DOCUMENTS 5,698,396 A 12/1997 Pfreundschuh
7,241,738 B2 * 7/2007 Averback ........... C07K 14/4711 424/134.1
7,745,391 B2 6/2010 Mintz et al.
2002/0197679 A1 * 12/2002 Tang ...................... C07K 14/47 435/69.1

FOREIGN PATENT DOCUMENTS

WO WO 02/083876 A2 10/2002
WO WO 03/009814 A2 2/2003
WO WO 2004/024887 A2 3/2004
WO WO 2004/080148 A2 9/2004
WO WO 2005/040414 A1 5/2005

OTHER PUBLICATIONS

Domingues et al., ImmunoTargets and Therapy, 2018, vol. 7, pp. 35-49.*

Akiyoshi, "Cancer Vaccine Therapy Using Peptide Derived from Tumor-Rejection Antigens", Jpn. J. Cancer and Chemotherapy., vol. 24, No. 5, pp. 511-519, Mar. 1997.

Brass et al., "Translation initiation factor eIF-4gamma is encoded by an amplified gene and induces an immune response in squamous cell lung carcinoma", Human Molecular Genetics, vol. 6, No. 1, pp. 33-39, 1997.

Extended European Search Report issued in European Application No. 08840900.8 dated Dec. 13, 2010.

Gromley et al., "A novel human protein of the maternal centriole is required for the final stages of cytokinesis and entry into S phase", The Journal of Cell Biology, vol. 161, No. 3, pp. 535-545, May 12, 2003.

Guasch et al., "FGFR1 is fused to the centrosome-associated protein CEP110 in the 8p12 stem cell myeloproliferative disorder with t(8;9)(p12;q33)", Blood, vol. 95, No. 5, pp. 1788-1796, Mar. 1, 2000.

Gure et al., "Human Lung Cancer Antigens Recognized by Autologous Antibodies: Definition of a Novel cDNA Derived from the Tumor Suppressor Gene Locus on Chromosome 3p21.3", Cancer Research, vol. 58, pp. 1034-1041, Mar. 1, 1998.

Gure et al., "SSX: A Multigene Family with Several Members Transcribed in Normal Testis and Human Cancer", International Journal of Cancer, vol. 72, pp. 965-971, May 1, 1997.

Infante et al., "GMAP-210, A Cis-Golgi Network-associated Protein, Is a Minus End Microtubule-binding Protein", The Journal of Cell Biology, vol. 145, No. 1, pp. 83-98, Apr. 5, 1999.

Inoue et al., "How far was fertilization elucidated?", Protein, Nucleic Acid and Enzyme, Institute for Microbial Disease, vol. 50, No. 11, pp. 1405-1412, 2005 (Abstract only provided).

International Search Report dated Jan. 6, 2009 for International Application No. PCT/JP2008/069267.

Itoh et al., "Autoantigen frequently eliciting humoral immune response in patients with adult T cell leukemia", Int. J. Oncol., vol. 14, No. 4, pp. 703-708, Apr. 1999 (Abstract only provided).

Lee et al., "Two classes of proteins dependent on either the presence or absence of thyroid hormone for interaction with the thyroid hormone receptor", Mol Endocrinol, vol. 9, No. 2, pp. 243-254, Feb. 9, 1995 (Abstract only provided).

(Continued)

*Primary Examiner* — Yunsoo Kim
(74) *Attorney, Agent, or Firm* — Birch, Stewart, Kolasch & Birch, LLP

(57) ABSTRACT

An immunity-inducing agent comprising as an effective ingredient a specific polypeptide is disclosed. These polypeptides were isolated, by the SEREX method using a cDNA library derived from canine testis and serum from a cancer-bearing dog, as a polypeptide which binds to an antibody existing specifically in serum derived from a cancer-bearing living body. The polypeptides can induce immunity in a living body and cause regression of a tumor in a cancer-bearing living body. Therefore, these polypeptides are especially effective as a therapeutic and/or prophylactic agent for a cancer(s).

16 Claims, 5 Drawing Sheets

Specification includes a Sequence Listing.

(56) References Cited

OTHER PUBLICATIONS

Ou et al., "CEP110 and ninein are located in a specific domain of the centrosome associated with centrosome maturation", Journal of Cell Science, vol. 115, pp. 1825-1835, Feb. 16, 2002.
Scanlan et al., "Characterization of Human Colon Cancer Antigens Recognized by Autologous Antibodies", International Journal of Cancer, vol. 76, pp. 652-658, Jan. 5, 1998.
Tanaka et al., "Cloning and Characterization of the human Calmegin gene encoding putative testis-specific chaperone", Gene, vol. 204, pp. 159-163, 1997.
Tureci et al., "The SSX-2 Gene, Which is Involved in the t(X;18) Translocation of Synovial Sarcomas, Codes for the Human Tumor Antigen HOM-MEL-40", Cancer Research, vol. 56, pp. 4766-4772, Oct. 15, 1996.
U.S. Notice of Allowance for U.S. Appl. No. 12/739,723, dated Jul. 21, 2016.
U.S. Office Action for U.S. Appl. No. 12/739,723, dated Apr. 27, 2012.
U.S. Office Action for U.S. Appl. No. 12/739,723, dated Jan. 23, 2015.
U.S. Office Action for U.S. Appl. No. 12/739,723, dated Jan. 24, 2013.
U.S. Office Action for U.S. Appl. No. 12/739,723, dated Jul. 19, 2012.
U.S. Office Action for U.S. Appl. No. 12/739,723, dated May 27, 2015.
U.S. Office Action for U.S. Appl. No. 12/739,723, dated May 7, 2013.
U.S. Office Action for U.S. Appl. No. 12/739,723, dated May 8, 2014.
U.S. Office Action for U.S. Appl. No. 12/739,723, dated Nov. 13, 2015.
U.S. Office Action for U.S. Appl. No. 12/739,723, dated Sep. 18, 2014.

* cited by examiner

IMMUNE RESPONSE INDUCER

CROSS REFERENCE TO RELATED APPLICATIONS

This application is a Divisional of U.S. patent application Ser. No. 12/739,723 filed on Apr. 23, 2010, which is the National Stage of PCT International Application No. PCT/JP2008/069267, filed on Oct. 23, 2008, which claims priority to Patent Application Nos. 2007-277578, 2007-277611, 2007-277240 and 2007-279113, filed in Japan on Oct. 25, 2007, Oct. 25, 2007, Oct. 25, 2007 and Oct. 26, 2007, all of which are hereby expressly incorporated by reference into the present application.

TECHNICAL FIELD

The present invention relates to a novel immunity-inducing agent useful as a therapeutic and/or prophylactic agent for a cancer(s).

BACKGROUND ART

Cancers are the commonest cause for death among all of the causes for death, and the therapies therefor are mainly surgical treatment in combination with radiotherapy and chemotherapy. In spite of the developments of new surgical methods and discovery of new anti-cancer agents in recent years, treatment results of cancers are not improved very much at present except for some cancers. In recent years, by virtue of the development in molecular biology and cancer immunology, cancer antigens recognized by cytotoxic T cells reactive with cancers, as well as the genes encoding the cancer antigens, were identified, and expectations for antigen-specific immunotherapies have been raised (see Non-patent Literature 1). In immunotherapy, to reduce side effects, it is necessary that the peptide or protein recognized as the antigen exist hardly in normal cells and exist specifically in cancer cells. In 1991, Boon et al. of Ludwig Institute in Belgium isolated human melanoma antigen MAGE 1 recognized by CD8-positive T cells by a cDNA-expression cloning method using an autologous cancer cell line and cancer-reactive T cells (see Non-patent Literature 2). Thereafter, the SEREX (serological identifications of antigens by recombinant expression cloning) method, wherein tumor antigens recognized by antibodies produced in the living body of a cancer patient in response to the cancer of the patient himself are identified by application of a gene expression cloning method, was reported (Non-patent Literature 3; Patent Literature 1), and various cancer antigens have been isolated (see Non-patent Literatures 4 to 9). Using a part thereof as targets, clinical tests for cancer immunotherapy have started.

On the other hand, as in human, a number of tumors such as mammary gland tumor and squamous cell carcinoma are known in dogs and cats, and they rank high also in the statistics of diseases in dogs and cats. However, at present, no therapeutic, prophylactic or diagnostic agents exist which are effective for cancers in dogs and cats. Most of tumors in dogs and cats are realized by owners only after they advance to grow bigger, and in many cases, it is already too late to visit a hospital to receive surgical excision of the tumor or administration of a human drug (an anticancer preparation or the like), so that those dogs and cats die shortly after the treatment. Under such circumstances, if therapeutic agents, prophylactic agents and diagnostic agents for cancers effective for dogs and cats become available, their uses for canine cancers are expected to be developed.

Patent Literature 1: U.S. Pat. No. 5,698,396 B

Non-patent Literature 1: Tsuyoshi Akiyoshi, Cancer and Chemotherapy, 24, 551-519 (1997)

Non-patent Literature 2: Bruggen P. et al., Science, 254: 1643-1647 (1991)

Non-patent Literature 3: Proc. Natl. Acad. Sci. USA, 92:11810-11813 (1995)

Non-patent Literature 4: Int. J. Cancer, 72:965-971 (1997)

Non-patent Literature 5: Cancer Res., 58:1034-1041 (1998)

Non-patent Literature 6: Int. J. Cancer, 29:652-658 (1998)

Non-patent Literature 7: Int. J. Oncol., 14:703-708 (1999)

Non-patent Literature 8: Cancer Res., 56:4766-4772 (1996)

Non-patent Literature 9: Hum. Mol. Genet 6:33-39, 1997

Non-patent Literature 10: Naokazu Inoue, Ryo Yamaguchi and Masahito Ikawa, Protein, Nucleic Acid and Enzyme, Vol. 50, No. 11, 1405-1412

Non-patent Literature 11: J Cell Sci. 115:1825-35

Non-patent Literature 12: Blood. 95:1788-96

Non-patent Literature 13: Mol Endocrinol. 9:243-54 (1995)

Non-patent Literature 14: J Cell Biol. 145: 83-98 (1999)

DISCLOSURE OF THE INVENTION

Problems to be Solved by the Invention

An object of the present invention is to provide a novel immunity-inducing agent which is useful as a therapeutic and/or prophylactic agent for a cancer(s)

Means for Solving the Problems

The present inventors intensively studied to obtain a cDNA encoding a protein which binds to an antibody existing in serum derived from a cancer-bearing living body by the SEREX method using a cDNA library derived from canine testis and serum of a cancer-bearing dog, which cDNA was used to prepare a polypeptide having the amino acid sequence shown in SEQ ID NO:2, a canine calmegin protein having the amino acid sequence shown in SEQ ID NO:16, a canine centrosomal protein (which may be hereinafter abbreviated as CEP) having the amino acid sequence shown in SEQ ID NO:26, and the canine thyroid hormone receptor interactor 11 (which may be hereinafter described as "TRIP11") having the amino acid sequence shown in SEQ ID NO:39. Further, based on a registered canine gene having a high homology to the canine CEP of the above-described SEQ ID NO:26, a canine CEP having the amino acid sequence shown in SEQ ID NO:28 was prepared. Further, based on a human gene homologous to the obtained gene, a polypeptide having the amino acid sequence shown in SEQ ID NO:4, a human calmegin protein having the amino acid sequence shown in SEQ ID NO:18, a human CEP having the amino acid sequence shown in SEQ ID NO:30, and a human TRIP11 having the amino acid sequence shown in SEQ ID NO:41 were prepared. The inventors then discovered that these polypeptides can induce immunocytes in a living body and cause regression of an already occurred tumor when administered to the living body, thereby completing the present invention.

That is, the present invention provides an immunity-inducing agent comprising as an effective ingredient any one of the polypeptides (a) to (c) below, the polypeptide having an immunity-inducing activity, or as an effective ingredient a recombinant vector which comprises a polynucleotide encoding the polypeptide and is capable of expressing the polypeptide in vivo: (a) a polypeptide consisting of not less than 7 consecutive amino acids of the amino acid sequence shown in SEQ ID NO:2, 4, 16, 18, 26, 28, 30, 39 or 41 in SEQUENCE LISTING; (b) a polypeptide having a homology of not less than 80% to the polypeptide (a) and consisting of not less than 7 amino acids; and (c) a polypeptide comprising the polypeptide (a) or (b) as a partial sequence thereof. The present invention also provides a method for inducing immunity, the method comprising administering to an individual an effective amount of any one of the above-described polypeptides (a) to (c), the polypeptide having an immunity-inducing activity, or an effective amount of a recombinant vector which comprises a polynucleotide encoding the polypeptide and is capable of expressing the polypeptide in vivo. The present invention further provides a method for treating antigen-presenting cells, the method comprising bringing any one of the above-described polypeptides (a) to (c), the polypeptide having an immunity-inducing activity, into contact with antigen-presenting cells. The present invention further provides use of any one of the above-described polypeptides (a) to (c), the polypeptide having an immunity-inducing activity, or a recombinant vector which comprises a polynucleotide encoding the polypeptide and is capable of expressing the polypeptide in vivo, for production of an immunity-inducing agent.

Effect of the Invention

By the present invention, a novel immunity-inducing agent useful as a therapeutic and/or prophylactic agent for a cancer(s) was provided. As indicated in the Examples below, the polypeptide used in the present invention can induce immunocytes in a cancer-bearing dog and also can cause reduction or regression of an already occurred tumor when administered to a cancer-bearing dog. Therefore, the polypeptide is useful for therapy and prophylaxis of a cancer(s).

BEST MODE FOR CARRYING OUT THE INVENTION

Figure 1:
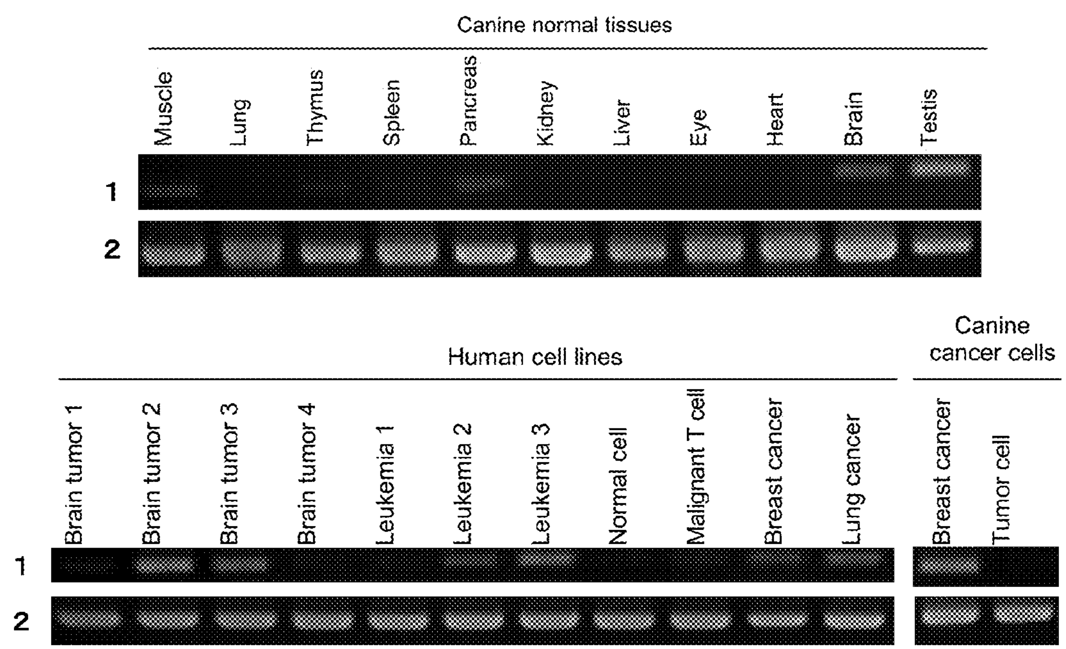
FIG. 1 shows the expression pattern of the gene identified in Example A-1 in normal tissues and tumor cell lines. Reference numeral 1: the expression pattern of the identified gene; Reference numeral 2: the expression pattern of the GAPDH gene.

The polypeptides contained in the immunity-inducing agents of the present invention as effective ingredients are as follows. It should be noted that the term “polypeptide” in the present invention means a molecule formed by peptide bonding of a plurality of amino acids, and includes not only polypeptide molecules having large numbers of amino acids constituting them, but also low molecular weight molecules having small numbers of amino acids (oligopeptides) and full-length proteins. Thus, in the present invention, proteins consisting of the full length of SEQ ID NO:2, 4, 16, 18, 26, 28, 30, 39 or 41 are also included in “polypeptide”.

(a) A polypeptide which consists of not less than 7 consecutive amino acids of a polypeptide having the amino acid sequence shown in SEQ ID NO:2, 4, 16, 18, 26, 28, 30, 39 or 41 in SEQUENCE LISTING and has an immunity-inducing activity.

(b) A polypeptide which has a homology of not less than 80% to the polypeptide (a), consists of not less than 7 amino acids, and has an immunity-inducing activity.

(c) A polypeptide which comprises the polypeptide (a) or (b) as a partial sequence thereof and has an immunity-inducing activity.

It should be noted that the term “having the amino acid sequence” in the present invention means that amino acid residues are aligned in that order. Accordingly, for example, “a polypeptide having the amino acid sequence shown in SEQ ID NO:2” means a polypeptide having a size of 306 amino acid residues, whose amino acid sequence is Met Ala Ala Leu . . . (snip) . . . Ile Thr Ser Pro as shown in SEQ ID NO:2. Further, “a polypeptide having the amino acid sequence shown in SEQ ID NO:2” may be abbreviated as “a polypeptide of SEQ ID NO:2”. This also applies to the term “having the base sequence”.

As used herein, the term “immunity-inducing activity” means an ability to induce immunocytes which secrete cytokines such as interferon in a living body. Whether or not a polypeptide has an immunity-inducing activity can be confirmed using, for example, the known ELISPOT assay. More particularly, for example, as described in the Examples below, cells such as peripheral blood mononuclear cells are obtained from a living body to which a polypeptide whose immunity-inducing activity is to be evaluated was administered, which cells are then cocultivated with the polypeptide, followed by measuring the amount of a cytokine produced by the cells using a specific antibody, thereby measuring the number of immunocytes in the cells, which enables evaluation of the immunity-inducing activity. Further, as described in the Examples below, a recombinant polypeptide prepared based on the amino acid sequence of SEQ ID NO:2, 4, 16, 18, 26, 28, 30, 39 or 41 can cause regression of a tumor by its immunity-inducing activity when administered to a cancer-bearing living body. Therefore, the above-described immunity-inducing activity can be evaluated also as the ability to inhibit the growth of cancer cells expressing the polypeptide of SEQ ID NO:2, 4, 16, 18, 26, 28, 30, 39 or 41 or to cause reduction or disappearance of a cancer tissue (tumor) (hereinafter referred to as "anti-tumor activity"). The anti-tumor activity of a polypeptide can be confirmed by, for example, observation of whether or not the tumor is reduced when the polypeptide was administered to a cancer-bearing living body, as more particularly described in the Examples below. Further, the anti-tumor activity of a polypeptide can be evaluated also by observation of whether or not T cells stimulated with the polypeptide (that is, T cells brought into contact with antigen-presenting cells which present the polypeptide) show a cytotoxic activity against tumor cells in vitro. The contact between T cells and antigen-presenting cells can be carried out by cocultivation of the both in a liquid medium, as mentioned below. Measurement of the cytotoxic activity can be carried out by, for example, a known method called 51Cr release assay described in Int. J. Cancer, 58:p 317, 1994. In cases where a polypeptide is used for therapy and/or prophylaxis of a cancer(s), the evaluation of the immunity-inducing activity is preferably carried out using the anti-tumor activity as an index, although the index is not restricted.

The amino acid sequence shown in SEQ ID NO:2 in SEQUENCE LISTING is the amino acid sequence of the polypeptide with unknown function isolated as a polypeptide which binds to an antibody existing specifically in serum derived from a cancer-bearing dog, which isolation was carried out by the SEREX method using a canine testis-derived cDNA library and serum of a cancer-bearing dog (see Example A-1). It is registered in the NCBI database under Accession No. XP_535343 (protein) and Accession No. XM_535343 (coding gene), but its function has not been reported. Further, the amino acid sequence shown in SEQ ID NO:4 is an amino acid sequence of a human homologous factor of the polypeptide of SEQ ID NO:2 isolated as described above. This human homologous factor is also a protein whose function is unknown, which is registered in the NCBI database under Accession No. NP_689873 (protein) and Accession No. NM_152660 (coding gene). The homology between them is 93% in terms of base sequence and 99% in terms of amino acid sequence.

The respective amino acid sequences shown in SEQ ID NOs:16 and 18 are those of the calmegin protein isolated as a polypeptide and a human homologous factor thereof, which polypeptide binds to an antibody existing specifically in serum derived from a cancer-bearing dog, which isolation was carried out by the SEREX method using a canine testis-derived cDNA library and serum of a cancer-bearing dog (see Example B-1). Calmegin was identified as a protein which is expressed specifically at the time of differentiation of a spermatid, and it has a chaperone activity in vitro. Since it is expressed only in testis and disappears in a mature sperm, calmegin is considered to have a function to fold proteins involved in differentiation of spermatid (Non-patent Literature 10, Naokazu Inoue, Ryo Yamaguchi and Masahito Ikawa, Protein, Nucleic Acid and Enzyme, Vol. 50, No. 11, 1405-1412). However, there has been no report showing that the protein is expressed in a cancer and useful for therapy or prophylaxis thereof. The homology between the canine calmegin gene and the human calmegin gene is 90% in terms of base sequence and 89% in terms of amino acid sequence.

The respective amino acid sequences shown in SEQ ID NOs:26, 28 and 30 are those of the CEP isolated as a polypeptide, a canine factor having a high homology to the polypeptide and a human homologous factor of the polypeptide, which polypeptide binds to an antibody existing specifically in serum derived from a cancer-bearing dog, which isolation was carried out by the SEREX method using a canine testis-derived cDNA library and serum of a cancer-bearing dog (see Example C-1). CEP is a protein which is required by the centrosome to control microtubules and also involved in maturation of the centrosome. It is known that chromosomal translocation frequently occurs in some of myeloproliferative disorders, and since the CEP gene exists at the point where the translocation occurs, CEP is considered to have a certain relationship with the disorders. However, there has been no report showing that the protein is expressed in a cancer and useful for therapy or prophylaxis thereof (Non-patent Literature 11: J Cell Sci. 115:1825-35; Non-patent Literature 12: Blood. 95:1788-96). The homology between the canine CEP gene encoding the CEP of SEQ ID NO:26 and the human CEP gene is 87% in terms of base sequence and 84% in terms of amino acid sequence.

The respective amino acid sequences shown in SEQ ID NOs:39 and 41 are those of the TRIP11 protein isolated as a polypeptide and a human homologous factor thereof, which polypeptide binds to an antibody existing specifically in serum derived from a cancer-bearing dog, which isolation was carried out by the SEREX method using a canine testis-derived cDNA library and serum of a cancer-bearing dog (see Example D-1). TRIP11 (thyroid hormone receptor interactor 11) was first identified as a factor which interacts with the thyroid hormone receptor β, and its binding to Golgi bodies and microtubules also became evident, so that TRIP11 is considered to play a role in maintaining the shapes of these organelles. However, there has been no report showing that the protein is expressed in a cancer and useful for therapy or prophylaxis thereof (Non-patent Literature 13, Mol Endocrinol. 9:243-54 (1995); Non-patent Literature 14, J Cell Biol. 145: 83-98 (1999)). The homology between the canine TRIP11 gene and the human TRIP11 gene is 88% in terms of base sequence and 86% in terms of amino acid sequence.

The polypeptide (a) consists of not less than 7 consecutive, preferably not less than 9 consecutive amino acids of a polypeptide having the amino acid sequence shown in SEQ ID NO:2, 4, 16, 18, 26, 28, 30, 39 or 41, and has an immunity-inducing activity. The polypeptide especially preferably has the amino acid sequence shown in SEQ ID NO:2, 4, 16, 18, 26, 28, 30, 39 or 41. As known in the art, a polypeptide consists of not less than about 7 amino acid residues can exert its antigenicity. Thus, a polypeptide consists of not less than 7 consecutive amino acid residues of the amino acid sequence shown in SEQ ID NO:2, 4, 16, 18, 26, 28, 30, 39 or 41 can have an immunity-inducing activity, so that it can be used for preparation of the immunity-inducing agent of the present invention. However, in view of the fact that antibodies produced against antigenic substances in a living body are polyclonal antibodies, it is thought that an antigenic substance composed of larger number of amino acid residues can induce more types of antibodies which can recognize various sites on the antigenic substance, thereby attaining higher immunity-inducing activity. Therefore, in order to increase the immunity-inducing activity, in the case of SEQ ID NO:2 or 4, the number of the amino acid residues may be preferably not less than 30, more preferably not less than 100, still more preferably not less than 200, still more preferably not less than 250. In the case of SEQ ID NO:16 or 18, the number of the amino acid residues may be preferably not less than 30, more preferably not less than 100, still more preferably not less than 200, still more preferably not less than 400, still more preferably not less than 550. In the case of SEQ ID NO:26, 28 or 30, the number of the amino acid residues may be preferably not less than 30, more preferably not less than 100, still more preferably not less than 300, still more preferably not less than 600, still more preferably not less than 1000, still more preferably not less than 1500, still more preferably not less than 2000. In the case of SEQ ID NO:39 or 41, the number of the amino acid residues may be preferably not less than 30, more preferably not less than 100, still more preferably not less than 300, still more preferably not less than 600, still more preferably not less than 1000, still more preferably not less than 1500.

As a principle of immune induction by administration of a cancer antigenic polypeptide, the following process is known: the polypeptide is incorporated into an antigen-presenting cell and then degraded into smaller fragments by peptidases in the cell, followed by presentation of the fragments on the surface of the cell. The fragments are then recognized by a cytotoxic T cell or the like, which selectively kills cells presenting the antigen.

The size of the polypeptide presented on the surface of the antigen-presenting cell is relatively small and about 7 to 30 amino acids. Therefore, from the view point of presenting thereof on the surface of the antigen-presenting cell, a polypeptide consisting of about 7 to 30, preferably about 9 to 30 consecutive amino acids of the amino acid sequence shown in SEQ ID NO:2, 4, 16, 18, 26, 28, 30, 39 or 41 is sufficient as the above-described polypeptide (a). In some cases, these relatively small polypeptides are presented directly on the surface of the antigen-presenting cells without incorporation thereof into the antigen-presenting cells.

However, as described above, since a polypeptide incorporated into an antigen-presenting cell is cleaved at random sites by peptidases in the cell to yield various polypeptide fragments, which are then presented on the surface of the antigen-presenting cell, administration of a large polypeptide such as the entire region of SEQ ID NO:2, 4, 16, 18, 26, 28, 30, 39 or 41 inevitably causes production of polypeptide fragments by degradation thereof in the antigen-presenting cell, which fragments are effective for immune induction via the antigen-presenting cell. Therefore, for immune induction via antigen-presenting cells, a large polypeptide can also be preferably used. In the case of SEQ ID NO:2 or 4, the number of the amino acids may be preferably not less than 30, more preferably not less than 100, still more preferably not less than 200, still more preferably not less than 250. In the case of SEQ ID NO:16 or 18, the number of the amino acids may be preferably not less than 30, more preferably not less than 100, still more preferably not less than 200, still more preferably not less than 400, still more preferably not less than 550. In the case of SEQ ID NO:26, 28 or 30, the number of the amino acids may be preferably not less than 30, more preferably not less than 100, still more preferably not less than 300, still more preferably not less than 600, still more preferably not less than 1000, still more preferably not less than 1500, still more preferably not less than 2000. In the case of SEQ ID NO:39 or 41, the number of the amino acids may be preferably not less than 30, more preferably not less than 100, still more preferably not less than 300, still more preferably not less than 600, still more preferably not less than 1000, still more preferably not less than 1500.

The above-described polypeptide (b) is the same polypeptide as the above-described polypeptide (a) except that a small number of amino acid residues are substituted, deleted and/or inserted, which has a homology of not less than 80%, preferably not less than 90%, more preferably not less than 95%, still more preferably not less than 98% to the original sequence, and has an immunity-inducing activity. It is well known in the art that, in general, there are cases where a protein antigen retains substantially the same antigenicity as the original even if the amino acid sequence of the protein is modified such that a small number of amino acids are substituted, deleted and/or inserted. Therefore, since the above-described polypeptide (b) may also exert an immunity-inducing activity, it can be used for preparation of the immunity-inducing agent of the present invention. Further, the above-described polypeptide (b) is also preferably the same polypeptide as one having the amino acid sequence shown in SEQ ID NO:2, 4, 16, 18, 26, 28, 30, 39 or 41 except that one or several amino acid residues are substituted, deleted and/or inserted.

As used herein, the term "homology" of amino acid sequences means a value expressed in percentage which is calculated by aligning two amino acid sequences to be compared such that the number of matched amino acid residues is the maximum, and dividing the number of the matched amino acid residues by the number of the total amino acid residues. When the above-described alignment is carried out, a gap(s) is/are inserted into one or both of the two sequences to be compared as required. Such alignment of sequences can be carried out using a well-known program such as BLAST, FASTA or CLUSTAL W. When a gap(s) is/are inserted, the above-described number of the total amino acid residues is calculated by counting one gap as one amino acid residue. When the thus counted numbers of the total amino acid residues are different between the two sequences to be compared, the homology (%) is calculated by dividing the number of matched amino acid residues by the number of the total amino acid residues in the longer sequence.

The 20 types of amino acids constituting the naturally occurring proteins may be classified into groups each of which has similar properties, for example, into neutral amino acids with side chains having low polarity (Gly, Ile, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His) and aromatic amino acids (Phe, Tyr, Trp). It is known that, in most cases, substitutions of amino acids within the same group do not change the properties of the polypeptide. Therefore, in cases where amino acid residue(s) in the above described polypeptide (a) in the present invention is/are substituted, the probability that the immunity-inducing activity can be maintained may be made high by conducting the substitution(s) within the same group.

The above-described polypeptide (c) comprises the above-described polypeptide (a) or (b) as a partial sequence and has an immunity-inducing activity. That is, the polypeptide (c) has another/other amino acid(s) or polypeptide(s) added at one or both ends of the polypeptide (a) or (b), and has an immunity-inducing activity. Such a polypeptide can also be used for preparation of the immunity-inducing agent of the present invention.

For example, the above-described polypeptides can be synthesized by a chemical synthesis method such as the Fmoc method (fluorenylmethylcarbonyl method) or the tBoc method (t-butyloxycarbonyl method). Further, they can be synthesized by conventional methods using various commercially available peptide synthesizers. Further, the polypeptide of interest can be obtained by a known genetic engineering method wherein a polynucleotide encoding the above-described polypeptide is prepared and incorporated into an expression vector, which is then introduced into a host cell, in which the polypeptide is produced.

The polynucleotide encoding the above-described polypeptide can be easily prepared by a known genetic engineering method or a conventional method using a commercially available nucleic acid synthesizer. For example, DNA having the base sequence of SEQ ID NO:1, 15, 25, 27 or 38 can be prepared by carrying out PCR using the chromosomal DNA or a cDNA library of a dog as a template and using a pair of primers designed such that the primers can amplify the base sequence described in SEQ ID NO:1, 15, 25, 27 or 38, respectively. DNA having the base sequence of SEQ ID NO:3, 17, 29 or 40 can be prepared similarly by using as the above-described template the human chromosomal DNA or a cDNA library. Conditions for the PCR reaction can be selected as appropriate, and examples of the conditions include, but are not limited to, those wherein a cycle comprising the reaction steps of 94° C. for 30 seconds (denaturing), 55° C. for 30 seconds to 1 minute (annealing), and 72° C. for 2 minutes (extension) is repeated, for example, 30 times, followed by allowing the reaction to proceed at 72° C. for 7 minutes. Further, a desired DNA can be isolated by preparing an appropriate probe or primer based on the information of the base sequence and the amino acid sequence shown in SEQ ID NOs:1 to 4, 15 to 18, 25 to 30, 38 to 41 in SEQUENCE LISTING of the present specification and then using the probe or primer for screening of a cDNA library from a dog or a human. The cDNA library is preferably prepared from cells, an organ or a tissue expressing the protein of SEQ ID NO:2, 4, 16, 18, 26, 28, 30, 39 or 41. Operations such as the above-described preparation of a probe or a primer, construction of a cDNA library, screening of a cDNA library and cloning of a gene of interest are known to those skilled in the art, and can be carried out according to, for example, Molecular Cloning, 2nd Ed. or Current Protocols in Molecular Biology. From the thus obtained DNA, DNA encoding the above-described polypeptide (a) can be obtained. Further, since codons encoding each amino acid are known, the base sequence of a polynucleotide encoding a specific amino acid sequence can be easily specified. Therefore, the base sequences of polynucleotides encoding the above-described polypeptide (b) and polypeptide (c) can also be easily specified, so that such polynucleotides can also be easily synthesized using a commercially available nucleic acid synthesizer according to a conventional method.

The above-described host cells are not restricted as long as they can express the above-described polypeptide, and examples thereof include, but are not limited to, prokaryotic cells such as *E. coli*; and eukaryotic cells such as mammalian cultured cells including monkey kidney cells COS 1 and Chinese hamster ovary cells CHO, budding yeast, fission yeast, silkworm cells, and *Xenopus laevis* egg cells.

In cases where prokaryotic cells are used as the host cells, an expression vector having the origin that enables its replication in a prokaryotic cell, a promoter, a ribosome binding site, a DNA cloning site, a terminator and the like is used as the expression vector. Examples of the expression vector for *E. coli* include the pUC system, pBluescript II, pET expression system and pGEX expression system. By incorporating DNA encoding the above-described polypeptide into such an expression vector and transforming prokaryotic host cells with the vector, followed by culturing the obtained transformant, the polypeptide encoded by the above-described DNA can be expressed in the prokaryotic host cells. In this case, the polypeptide can also be expressed as a fusion protein with another protein.

In cases where eukaryotic cells are used as the host cells, an expression vector for eukaryotic cells having a promoter, splicing site, poly(A) addition site and the like is used as the expression vector. Examples of such an expression vector include pKA1, pCDM8, pSVK3, pMSG, pSVL, pBK-CMV, pBK-RSV, the EBV vector, pRS, pcDNA3, pMSG and pYES2. In the same manner as described above, by incorporating DNA encoding the above-described polypeptide into such an expression vector and transforming eukaryotic host cells with the vector, followed by culturing the obtained transformant, the polypeptide encoded by the above-described DNA can be expressed in the eukaryotic host cells. In cases where pIND/V5-His, pFLAG-CMV-2, pEGFP-N1 or pEGFP-C1 was used as the expression vector, the above-described polypeptide can be expressed as a fusion protein having various added tags such as His tag, FLAG tag, myc tag, HA tag or GFP.

Introduction of the expression vector to the host cells can be carried out using a well-known method such as electroporation, the calcium phosphate method, the liposome method or the DEAE dextran method.

Isolation and purification of a polypeptide of interest from the host cells can be carried out by a combination of known separation operations. Examples of the operations include, but are not limited to, treatment by a denaturant such as urea or by a surfactant; ultrasonication treatment; enzyme digestion; salting-out and solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method include, as mentioned above, those in the form of a fusion protein with another arbitrary protein. Examples thereof include fusion proteins with glutathion S-transferase (GST) and with a His tag. Such a polypeptide in the form of a fusion protein is also included within the scope of the present invention as the above-described polypeptide (c). Further, in some cases, a polypeptide expressed in a transformed cell is modified in various ways in the cell after translation thereof. Such a polypeptide having a post-translational modification is also included within the scope of the present invention as long as it has an immunity-inducing activity. Examples of such a post-translational modification include elimination of N-terminus methionine, N-terminus acetylation, glycosylation, limited degradation by an intracellular protease, myristoylation, isoprenylation and phosphorylation.

As described concretely in the following Examples, the above-described polypeptide having an immunity-inducing activity can cause regression of an already occurred tumor when administered to a cancer-bearing living body. Therefore, the immunity-inducing agent of the present invention can be used as a therapeutic and/or prophylactic agent for a cancer(s). In this case, cancers to be treated are those expressing the gene encoding the polypeptide of SEQ ID NO:2 or 4, and examples thereof include, but are not limited to, brain tumor; squamous cell carcinomas of head, neck, lung, uterus and esophagus; melanoma; adenocarcinomas of lung, breast and uterus; renal cancer; malignant mixed tumor; hepatocellular carcinoma; basal cell carcinoma; acanthomatous epulis; intraoral tumor; perianal adenocarcinoma; anal sac tumor; anal sac apocrine carcinoma; Sertoli cell tumor; vulva cancer; sebaceous adenocarcinoma; sebaceous epithelioma; sebaceous adenoma; sweat gland carcinoma; intranasal adenocarcinoma; nasal adenocarcinoma; thyroid cancer; colon cancer; bronchial adenocarcinoma; adenocarcinoma; ductal carcinoma; mammary adenocarcinoma; combined mammary adenocarcinoma; mammary gland malignant mixed tumor; intraductal papillary adenocarcinoma; fibrosarcoma; hemangiopericytoma; osteosarcoma; chondrosarcoma; soft tissue sarcoma; histiocytic sarcoma; myxosarcoma; undifferentiated sarcoma; lung cancer; mastocytoma; cutaneous leiomyoma; intra-abdominal leiomyoma; leiomyoma; chronic lymphocytic leukemia; lymphoma; gastrointestinal lymphoma; digestive organ lymphoma; small cell or medium cell lymphoma; adrenomedullary tumor; granulosa cell tumor; pheochromocytoma; bladder cancer (transitional cell carcinoma); suppurative inflammation; intra-abdominal liver tumor; liver cancer; plasmacytoma; malignant hemangiopericytoma; angiosarcoma; anal sac adenocarcinoma; oral cancer; metastatic malignant melanoma; amelanotic malignant melanoma; cutaneous malignant melanoma; malignant myoepithelioma; malignant seminoma; seminoma; adenocarcinoma of the large intestine; gastric adenocarcinoma; low-grade sebaceous carcinoma; ceruminous adenocarcinoma; apocrine carcinoma; poorly differentiated apocrine sweat gland carcinoma; malignant fibrous histiocytoma; multiple myeloma; mesenchymal malignant tumor; liposarcoma; osteosarcoma; sarcoma of unknown origin; soft part sarcoma (spindle cell tumor); poorly differentiated sarcoma; synovial sarcoma; angiosarcoma; metastatic malignant epithelioma; tubular mammary adenocarcinoma; mammary ductal carcinoma; inflammatory breast cancer; germinoma; leukemia; invasive trichoepithelioma; medium cell lymphoma; multicentric lymphoma; osteosarcoma (mammary gland); mastocytoma (Patnaik II type); mastocytoma (Grade II); and leiomyosarcoma. The animals to be treated are mammals, especially preferably humans, dogs and cats.

The administration route of the immunity-inducing agent of the present invention to a living body may be either oral administration or parenteral administration, and is preferably parenteral administration such as intramuscular administration, subcutaneous administration, intravenous administration or intraarterial administration. In cases where the immunity-inducing agent is used for therapy of a cancer, it may be administered to a regional lymph node in the vicinity of the tumor to be treated, as described in the Examples below, in order to enhance its anticancer activity. The dose may be any dose as long as the dose is effective for immune induction, and in cases where the agent is used for therapy and/or prophylaxis of a cancer, the dose may be one effective for therapy and/or prophylaxis of the cancer. The dose effective for therapy and/or prophylaxis of a cancer is appropriately selected depending on the size of the tumor, the symptom and the like, and usually, 0.0001 μg to 1000 μg, preferably 0.001 μg to 1000 μg of the agent in terms of the effective ingredient may be administered once or in several times per day per animal to be treated. The agent is preferably administered in several times, every several days to several months. As concretely shown in the Examples below, the immunity-inducing agent of the present invention can cause regression of an already occurred tumor. Therefore, since the agent can exert its anticancer activity also against a small number of cancer cells in the early stage, development or recurrence of the cancer can be prevented by using the agent before development of a cancer or after therapy for a cancer. That is, the immunity-inducing agent of the present invention is effective for both therapy and prophylaxis of a cancer.

The immunity-inducing agent of the present invention may contain only a polypeptide or may be formulated by mixing as appropriate with an additive such as a pharmaceutically acceptable carrier, diluent or vehicle suitable for each administration mode. Formulation methods and additives which may be used are well-known in the field of formulation of pharmaceuticals, and any of the methods and additives may be used. Specific examples of the additive include, but are not limited to, diluents such as physiological buffer solutions; vehicles such as sucrose, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the formulation include oral preparations such as tablets, capsules, granules, powders and syrups; and parenteral preparations such as inhalants, injection solutions, suppositories and solutions. These formulations may be prepared by commonly known production methods.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Examples of the above-described immunoenhancer include adjuvants. Adjuvants can enhance the immune response by providing a reservoir of antigen (extracellularly or within macrophages), activating macrophages and stimulating specific sets of lymphocytes, thereby enhancing the anticancer activity. Therefore, especially in cases where the immunity-inducing agent of the present invention is used for therapy and/or prophylaxis of a cancer, the immunity-inducing agent preferably comprises an adjuvant, in addition to the above-described polypeptide as an effective ingredient. Many types of adjuvants are well-known in the art, and any of these adjuvants may be used. Specific examples of the adjuvants include MPL (SmithKline Beecham) and homologues of *Salmonella minnesota* Re 595 lipopolysaccharide obtained after purification and acid hydrolysis of the lipopolysaccharide; QS21 (SmithKline Beecham), pure QA-21 saponin purified from extract of *Quillja saponaria*; DQS21 described in WO96/33739 (SmithKline Beecham); QS-7, QS-17, QS-18 and QS-L1 (So and 10 others, "Molecules and cells", 1997, Vol. 7, p. 178-186); Freund's incomplete adjuvant; Freund's complete adjuvant; vitamin E; Montanide; alum; CpG oligonucleotides (see, for example, Kreig and 7 others, "Nature", Vol. 374, p. 546-549); poly-I:C and derivatives thereof (e.g., poly ICLC); and various water in oil emulsions prepared from biodegradable oils such as squalene and/or tocopherol. Among these, Freund's incomplete adjuvant; Montanide; poly-I:C and derivatives thereof, and CpG oligonucleotides are preferred. The mixing ratio between the above-described adjuvant and polypeptide is typically about 1:10 to 10:1, preferably about 1:5 to 5:1, more preferably about 1:1. However, the adjuvant is not limited to the above-described examples, and adjuvants known in the art other than the above-described ones (for example, see Goding, "Monoclonal Antibodies: Principles and Practice", 2nd edition, 1986) may be used when the immunity-inducing agent of the present invention is administered. Preparation methods for mixtures or emulsions of a polypeptide and an adjuvant are well-known to those skilled in the art of vaccination.

Further, in addition to the above-described adjuvants, factors that stimulate the immune response of the subject may be used as the above-described immunoenhancer. For example, various cytokines having a property to stimulate lymphocytes and/or antigen-presenting cells may be used as the immunoenhancer in combination with the immunity-inducing agent of the present invention. A number of such cytokines capable of enhancing the immune response are known to those skilled in the art, and examples thereof include, but are not limited to, interleukin-12 (IL-12), GM-CSF, IL-18, interferon-α, interferon-β, interferon-w, interferon-γ, and Flt3 ligand, which have been shown to promote the prophylactic action of vaccines. Such factors may also be used as the above-described immunoenhancer, and can be contained in the immunity-inducing agent of the present invention, or can be prepared as a separate composition to be administered to a patient in combination with the immunity-inducing agent of the present invention.

Further, by bringing the above-described polypeptide into contact with antigen-presenting cells in vitro, the antigen-presenting cells can be made to present the polypeptide. That is, the above-described polypeptides (a) to (c) can be used as agents for treating antigen-presenting cells. As the antigen-presenting cells, dendritic cells or B cells, which have MHC class I molecules, may preferably be employed. Various MHC class I molecules have been identified and well-known. MHC molecules in human are called HLA. Examples of HLA class I molecules include HLA-A, HLA-B and HLA-C, more specifically, HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602.

The dendritic cells or B cells having MHC class I molecules can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system. By administering an effective amount of such dendritic cells, a response desired for therapy of a cancer can be induced. As the cells to be used, bone marrow or umbilical cord blood donated by a healthy individual, or bone marrow, peripheral blood or the like from the patient himself may be used. When autologous cells of the patient are used, high safety can be attained and serious side effects are expected to be avoided. The peripheral blood or bone marrow may be a fresh sample, cold-stored sample or frozen sample. As for the peripheral blood, whole blood may be cultured or the leukocyte components alone may be separated and cultured, and the latter is efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are originated, and also CD4-positive cells and the like. As for the cytokine to be used, the production method thereof is not restricted and naturally-occurring or recombinant cytokine or the like may be employed as long as its safety and physiological activity have been confirmed. Preferably, a preparation with assured quality for medical use is used in a minimum necessary amount. The concentration of the cytokine(s) to be added is not restricted as long as the dendritic cells are induced, and usually, the total concentration of the cytokine(s) is preferably about 10 to 1000 ng/mL, more preferably about 20 to 500 ng/mL. The culture may be carried out using a well-known medium usually used for the culture of leukocytes. The culturing temperature is not restricted as long as the proliferation of the leukocytes is attained, and about 37° C. which is the body temperature of human is most preferred. The atmospheric environment during the culturing is not restricted as long as the proliferation of the leukocytes is attained, and to flow 5% $CO_2$ is preferred. The culturing period is not restricted as long as the necessary number of the cells is induced, and is usually 3 days to 2 weeks. As for the apparatuses used for separation and culturing of the cells, appropriate apparatuses, preferably those whose safety when applied to medical uses have been confirmed, and whose operations are stable and simple, may be employed. Particularly, as for the cell-culturing apparatus, not only the general vessels such as a Petri dish, flask and bottle, but also a layer type vessel, multistage vessel, roller bottle, spinner type bottle, bag type culturing vessel, hollow fiber column and the like may be used.

Bringing the above-described peptide of the present invention into contact with the antigen presenting cells in vitro may be carried out by a well-known method. For example, it may be carried out by culturing the antigen-presenting cells in a culture medium containing the above-described polypeptide. The concentration of the peptide in the medium is not restricted, and usually about 1 μg/ml to 100 μg/ml, preferably about 5 μg/ml to 20 μg/ml. The cell density during the culturing is not restricted and is usually about $10^3$ cells/ml to $10^7$ cells/ml, preferably about $5\times10^4$ cells/ml to $5\times10^6$ cells/ml. The culturing may be carried out according to a conventional method, and is preferably carried out at 37° C. under atmosphere of 5% $CO_2$. The maximum length of the peptide which can be presented on the surface of the antigen-presenting cells is usually about 30 amino acid residues. Therefore, in cases where the antigen-presenting cells are brought into contact with the polypeptide in vitro, the polypeptide may be prepared such that its length is not more than about 30 amino acid residues.

By culturing the antigen-presenting cells in the coexistence of the above-described polypeptide, the polypeptide is incorporated into MHC molecules of the antigen-presenting cells and presented on the surface of the antigen-presenting cells. Therefore, using the above-described polypeptide, isolated antigen-presenting cells containing the complex between the polypeptide and the MHC molecule can be prepared. Such antigen-presenting cells can present the polypeptide against T cells in vivo or in vitro, and induce, and allow proliferation of, cytotoxic T cells specific to the polypeptide.

By bringing the antigen-presenting cells prepared as described above having the complex between the above-described polypeptide and the MHC molecule into contact with T cells in vitro, cytotoxic T cells specific to the polypeptide can be induced and allowed to proliferate. This may be carried out by cocultivating the above-described antigen-presenting cells and T cells in a liquid medium. For example, it may be attained by suspending the antigen-presenting cells in a liquid medium, placing the suspension in vessels such as wells of a microplate, adding thereto T cells and then culturing the cells. The mixing ratio of the antigen-presenting cells to the T cells in the cocultivation is not restricted, and is usually about 1:1 to 1:100, preferably about 1:5 to 1:20 in terms of the number of cells. The density of the antigen-presenting cells suspended in the liquid medium is not restricted, and is usually about 100 to 10,000,000 cells/ml, preferably about 10,000 to 1,000,000 cells/ml. The cocultivation is preferably carried out at 37° C. under atmosphere of 5% $CO_2$ in accordance with a conventional method. The culturing time is not restricted, and is usually 2 days to 3 weeks, preferably about 4 days to 2 weeks. The cocultivation is preferably carried out in the presence of one or more interleukins such as IL-2, IL-6, IL-7 and IL-12. In this case, the concentration of IL-2 and IL-7 is usually about 5 U/ml to 20 U/ml, the concentration of IL-6 is usually about 500 U/ml to 2000 U/ml, and the concentration of IL-12 is usually about 5 ng/ml to 20 ng/ml, but the concentrations of the interleukins are not restricted thereto. The above-described cocultivation may be repeated once to several times adding fresh antigen-presenting cells. For example, the operation of discarding the culture supernatant after the cocultivation and adding a fresh suspension of antigen-presenting cells to further conduct the cocultivation may be repeated once to several times. The conditions of the each cocultivation may be the same as described above.

By the above-described cocultivation, cytotoxic T cells specific to the polypeptide are induced and allowed to proliferate. Thus, using the above-described polypeptide, isolated T cells can be prepared which selectively bind the complex between the polypeptide and the MHC molecule.

As described in the Examples below, the genes encoding the polypeptides of SEQ ID NOs:2, 16, 26, 28 and 39 and SEQ ID NOs:4, 18, 30 and 41 are expressed specifically in cancer cells and testis of dogs and humans, respectively. Thus, in cancer cells, significantly higher numbers of the polypeptides of SEQ ID NOs:2, 16, 26, 28 and 39 or SEQ ID NOs:4, 18, 30 and 41 exist than in normal cells. When cytotoxic T cells prepared as described above are administered to a living body while a part of the polypeptides existing in cancer cells are presented by MHC molecules on the surfaces of the cancer cells, the cytotoxic T cells can damage the cancer cells using the presented polypeptides as markers. Since antigen-presenting cells presenting the above-described polypeptides can induce, and allow proliferation of, cytotoxic T cells specific to the polypeptides also in vivo, cancer cells can be damaged also by administering the antigen-presenting cells to a living body. That is, the above-described cytotoxic T cells and the above-described antigen-presenting cells prepared using the above-described polypeptide are also effective as therapeutic and/or prophylactic agents for a cancer(s).

In cases where the above-described isolated antigen-presenting cells or isolated T cells are administered to a living body, these are preferably prepared by treating antigen presenting cells or T cells collected from the patient to be treated with the polypeptide (a) to (c) as described above in order to avoid the immune response in the living body that attacks these cells as foreign bodies.

The therapeutic and/or prophylactic agent for a cancer(s) comprising as an effective ingredient the antigen-presenting cells or T cells is preferably administered via a parenteral administration route such as intravenous or intraarterial administration. The dose is appropriately selected depending on the symptom, the purpose of administration and the like, and is usually 1 cell to 10,000,000,000,000 cells, preferably 1,000,000 cells to 1,000,000,000 cells, which dose is preferably administered once per several days to once per several months. The formulation may be, for example, the cells suspended in physiological buffered saline, and the formulation may be used in combination with another/other anticancer preparation(s) and/or cytokine(s). Further, one or more additives well-known in the field of formulation of pharmaceuticals may also be added.

Also by expression of the polynucleotide encoding the above-described polypeptide (a) to (c) in the body of the animal to be treated, antibody production and cytotoxic T cells can be induced in the living body, and an effect comparable to the administration of a polypeptide can be obtained. That is, the immunity-inducing agent of the present invention may be one comprising as an effective ingredient a recombinant vector having a polynucleotide encoding the above-described polynucleotide (a) to (c), which recombinant vector is capable of expressing the polypeptide in a living body. Such a recombinant vector capable of expressing an antigenic polypeptide is also called gene vaccine. The vector used for production of a gene vaccine is not restricted as long as it is a vector capable of expressing a polypeptide in cells of the animal to be treated (preferably in a mammalian cell), and may be either a plasmid vector or a virus vector, and any known vector in the field of gene vaccines may be used. The polynucleotide such as DNA or RNA encoding the above-described polypeptide can be easily prepared, as mentioned above, by a conventional method. Incorporation of the polynucleotide into a vector can be carried out using a method well-known to those skilled in the art.

The administration route of the gene vaccine is preferably a parenteral route such as intramuscular, subcutaneous, intravenous or intraarterial administration, and the dose may be appropriately selected depending on the type of the antigen and the like, and usually about 0.1 μg to 100 mg, preferably about 1 μg to 10 mg in terms of the weight of the gene vaccine per 1 kg of body weight.

Methods using a virus vector include those wherein a polynucleotide encoding the above-described polypeptide is incorporated into an RNA virus or DNA virus such as retrovirus, adenovirus, adeno-associated virus, herpes virus, vaccinia virus, pox virus, poliovirus or Sindbis virus, and then the animal to be treated is infected by the resulting virus. Among these methods, those using retrovirus, adenovirus, adeno-associated virus, vaccinia virus or the like are especially preferred.

Other methods include a method wherein an expression plasmid is directly intramuscularly administered (DNA vaccine method), the liposome method, lipofectin method, microinjection method, calcium phosphate method, electroporation method and the like, and the DNA vaccine method and liposome method are especially preferred.

Methods for actually making the gene encoding the above-described polypeptide of the present invention act as a pharmaceutical include the in vivo method wherein the gene is directly introduced into the body, and the ex vivo method wherein a kind of cells are collected from the animal to be treated, the gene is introduced into the cells ex vivo, and then the cells are returned to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these papers and the like). The in vivo method is more preferred.

In cases where the gene is administered by the in vivo method, the gene may be administered through an appropriate administration route depending on the disease to be treated, symptom and so on. It may be administered, for example, by intravenous, intraarterial, subcutaneous, intramuscular administration or the like. In cases where the gene is administered by the in vivo method, the gene may be formulated into a preparation such as a solution, and in general, it is formulated into an injection solution or the like containing the DNA encoding the above-described peptide of the present invention as an effective ingredient. A commonly used carrier(s) may be added as required. In the case of a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence shown in SEQ ID NO:1" includes not only the base sequence expressly written in SEQ ID NO:1, but also the sequence complementary thereto. Thus, "a polynucleotide having the base sequence shown in SEQ ID NO:1" includes a single-stranded polynucleotide having the base sequence expressly written in SEQ ID NO:1, a single-stranded polynucleotide having the base sequence complementary thereto, and a double-stranded polynucleotide composed of these single strand polynucleotides. When the polynucleotide encoding the polypeptide used in the present invention is prepared, any one of these base sequences should be appropriately selected, and those skilled in the art can easily carry out the selection.

EXAMPLES

The present invention will now be described more concretely by way of Examples.

Example A-1: Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3\times10^6$ pfu/ml.

(2) Screening of cDNA Library with Serum

Using the dog testis-derived cDNA phage library prepared as described above, immunoscreening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking it at 4° C. overnight to suppress non-specific reactions. This filter was allowed to react with 500-fold diluted canine patient serum at room temperature for 2 to 3 hours.

As the above-described canine patient serum, serum collected from canine patients suffering from squamous cell carcinoma was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M $NaHCO_3$, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+I HRP conjugated: manufactured by BETHYL Laboratories) 5000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM $MgClSO_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host *E. coli* (XL1-Blue MRF') such that the absorbance $OD_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 μl of a solution prepared to contain a phagemid host *E. coli* (SOLR) such that the absorbance $OD_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:1 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the gene (Accession No. XM_535343) encoding a protein (Accession No. XP_535343) whose function is unknown. The human homologous factor of this gene was the gene (Accession No. NM_152660) encoding a protein (Accession No. NP_689873) whose function is also unknown (homology: base sequence, 93%; amino acid sequence, 99%). The base sequence of the human homologous factor is shown in SEQ ID NO:3, and the amino acid sequence thereof is shown in SEQ ID NO:4.

(4) Analysis of Expression in Each Tissue

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to $10\times10^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:7 and 8) specific to the obtained canine gene and its human homologous gene. That is, respective reagents and the attached buffer were mixed such that the mixture should contain 0.25 μl of the sample prepared by the reverse transcription reaction, 2 μM each of the above primers, 0.2 mM each of dNTP and 0.65 U of ExTaq polymerase (manufactured by Takara Shuzo Co., Ltd.) in a total volume of 25 μl, and the reaction was carried out with 30 cycles of 94° C. for 30 seconds, 55° C. for 30 seconds and 72° C. for 1 minute using Thermal Cycler (manufactured by BIO RAD). The gene-specific primers having the base sequences shown in the above-described SEQ ID NOs:7 and 8 were those which amplify the regions of the 87th to 606th bases of the base sequence of SEQ ID NO:1 and the 173rd to 695th bases of the base sequence of SEQ ID NO:3, and can be used for investigation of the expression of both the canine gene and its human homologous gene. As a control for comparison, primers (described in SEQ ID NOs:9 and 10) specific to GAPDH were used simultaneously. As a result, as shown in FIG. 1, strong expression of the obtained canine gene was observed in testis among the normal dog tissues, and on the other hand, strong expression was observed in the canine breast cancer cell line. Expression of the human homologous gene was confirmed, as is the case with the canine gene, only in testis among the human normal tissues, but the expression was detected in brain tumor, leukemia, breast cancer and lung cancer cells among human cancer cell lines. Thus, the human homologous gene was also confirmed to be specifically expressed in testis and cancer cells.

In FIG. 1, reference numeral 1 in the ordinate indicates the expression pattern of the above identified gene, and reference numeral 2 indicates the expression pattern of the GAPDH gene as a control for comparison.

Example A-2: Preparation of Novel Cancer Antigen Proteins (1) Preparation of Recombinant Protein Based on the gene of SEQ ID NO:1 obtained in Example A-1, a recombinant protein was prepared by the following method. Respective reagents and the attached buffer were mixed such that the mixture should contain 1 μl of the vector which was prepared from the phagemid solution obtained in Example A-1 and was subjected to the sequence analysis, 0.4 μM each of two kinds of primers having NdeI and XhoI restriction sites (described in SEQ ID NOs:11 and 12), 0.2 mM dNTP and 1.25 U of PrimeSTAR HS polymerase (manufactured by Takara Shuzo Co., Ltd.) in a total volume of 50 μl, and PCR was carried out with 30 cycles of 98° C. for 10 seconds, 55° C. for 15 seconds and 72° C. for 1 minute using Thermal Cycler (manufactured by BIO RAD). The above-described two kinds of primers were those which amplify the region encoding the entire amino acid sequence of SEQ ID NO:2. After the PCR, the amplified DNA was subjected to electrophoresis using 1% agarose gel, and a DNA fragment of about 930 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes NdeI and XhoI and purified using QIAquick Gel Extraction Kit, followed by inserting the gene sequence of interest into an expression vector for *E. coli*, pET16b (manufactured by Novagen) that had been treated with NdeI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

On the other hand, based on the gene of SEQ ID NO: 3, a recombinant protein of the human homologous gene was prepared by the following method. Respective reagents and the attached buffer were mixed such that the mixture should contain 1 μl of the cDNA prepared in Example A-1 whose expression could be confirmed by the RT-PCR method in various tissues/cells, 0.4 μM each of two kinds of primers having EcoRV and EcoRI restriction sites (described in SEQ ID NOs:13 and 14), 0.2 mM dNTP and 1.25 U of PrimeSTAR HS polymerase (manufactured by Takara Shuzo Co., Ltd.) in a total volume of 50 μl, and PCR was carried out with 30 cycles of 98° C. for 10 seconds, 55° C. for 15 seconds and 72° C. for 1 minute using Thermal Cycler (manufactured by BIO RAD). The above-described two kinds of primers were those which amplify the region encoding the entire amino acid sequence of SEQ ID NO:4. After the PCR, the amplified DNA was subjected to electrophoresis using 1% agarose gel, and a DNA fragment of about 930 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes EcoRV and EcoRI and purified using QIAquick Gel Extraction Kit, followed by inserting the gene sequence of interest into an expression vector for *E. coli*, pET30a (manufactured by Novagen) that had been treated with EcoRV and EcoRI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:1 and SEQ ID NO:3, respectively, were cultured in 100 μg/ml ampicillin-containing LB medium at 37° C. until the absorbance at 600 nm reached about 0.7, and then isopropyl-3-D-1-thiogalactopyranoside was added thereto such that its final concentration should be 1 mM, followed by culturing them at 37° C. for 4 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in 50 mM Tris-HCl buffer (pH 8.0) and subjected to sonication on ice. The sonicated solution of *E. coli* was centrifuged at 6,000 rpm for 20 minutes to obtain the supernatant as the soluble fraction and the precipitate as the insoluble fraction.

The insoluble fraction was suspended in 50 mM Tris-HCl buffer (pH 8.0) and centrifuged at 6,000 rpm for 15 minutes. This operation was repeated twice and an operation of removal of proteases was carried out.

The residue was suspended in 6M guanidine hydrochloride, 0.15 M sodium chloride-containing 50 mM Tris-HCl buffer (pH 8.0), and the resulting suspension was left to stand at 4° C. for 20 hours to denature proteins. Thereafter, the suspension was centrifuged at 6,000 rpm for 30 minutes, and the obtained soluble fraction was placed in a nickel chelate column prepared by a conventional method (carrier: Chelating Sepharose (trademark) Fast Flow (GE Health Care); column volume: 5 mL; equilibration buffer: 6M guanidine hydrochloride, 0.15 M sodium chloride-containing 50 mM Tris-HCl buffer (pH 8.0)), followed by leaving it to stand at 4° C. overnight to allow adsorption to the nickel-chelated carrier. The supernatant was recovered by centrifugation of this column carrier at 1,500 rpm for 5 minutes, and the column carrier was suspended in phosphate-buffered saline, followed by refilling the column with the resulting suspension.

Figure 2:
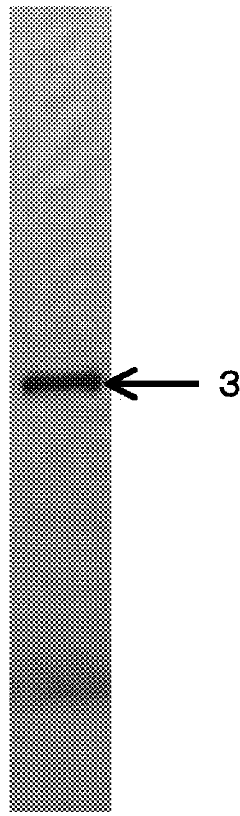
FIG. 2 shows the detection by Coomassie staining of the canine-derived protein produced in *E. coli* and purified in Example A, which protein was identified in the present invention. Reference numeral 3: the band for the canine-derived protein of the present invention.

The fraction that was not adsorbed to the column was washed away with 10 column volumes of 0.5 M sodium chloride-containing 0.1 M acetate buffer (pH 4.0), and elution was immediately carried out with 0.5 M sodium chloride-containing 0.1 M acetate buffer (pH 3.0) to obtain a purified fraction, which was used as the material for administration tests thereafter. The proteins of interest in respective eluted fractions were confirmed by Coomassie staining carried out according to a conventional method. Among these, the canine protein of interest is shown in FIG. 2.

The buffer contained in the purified preparation obtained by the above-described method was replaced with a reaction buffer (50 mM Tris-HCl, 100 mM NaCl, 5 mM $CaCl_2$; pH8.0), and cleavage of His tag by Factor Xa protease and purification of the protein of interest were carried out, using FactorXa Cleavage Capture Kit (manufactured by Novagen), in accordance with the protocols attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 μm (manufactured by PALL) and used in the following experiments.

Example A-3: Test of Administration of Recombinant Protein to Cancer-Bearing Dogs (1) Antitumor Assay The anti-tumor effect of the two kinds of recombinant proteins which were purified as described above was assessed in two individuals of cancer-bearing dogs having epidermal tumor (2 individuals having mammary gland tumor).

An equal amount of Freund's incomplete adjuvant (manufactured by Wako Pure Chemicals) was mixed with 100 μg (0.5 ml) of the recombinant polypeptides (derived from dog and human), respectively, to prepare two kinds of therapeutic agents for a cancer(s). Each of these agents was administered to a regional lymph node in the vicinity of the tumor a total of 3 times, by carrying out the subsequent administrations 3 days and 7 days after the first administration. As a result, the tumors with a size of about 25 $mm^3$ and 50 $mm^3$ at the time of administration of the therapeutic agents for a cancer(s) (derived from dog and human), respectively, were reduced in size to 20 $mm^3$ and 42 $mm^3$, respectively, 10 days after the first administration; 13 $mm^3$ and 26 $mm^3$, respectively, 20 days after the first administration; and to 5 $mm^3$ and 10 $mm^3$, respectively, 30 days after the first administration.

Further, to a canine patient suffering from malignant melanoma, a mixture of 100 μg (0.5 ml) of the above-described polypeptide derived from dog and 0.5 ml of Freund's incomplete adjuvant was administered intracutaneously at the periphery of the tumor a total of 3 times at the same intervals as described above. Further, concurrently with the respective administrations, 10 MU of "Intercat" which is a recombinant feline interferon was administered subcutaneously. As a result, the tumor with a size of about 142 $mm^3$ at the time of administration of the therapeutic agent for a cancer(s) completely regressed 29 days after the first administration.

Further, to a canine patient suffering from nasal adenocarcinoma, a mixture of 100 μg (0.5 ml) of the above-described polypeptide derived from dog and 0.5 ml of Freund's incomplete adjuvant was administered in the same manner as described above a total of 3 times. Further, concurrently with the respective administrations, 100 μg of canine interleukin 12 was administered subcutaneously. As a result, the tumor with a size of about 57 $mm^3$ at the time of administration of the therapeutic agent for a cancer(s) completely regressed 14 days after the first administration.

(2) Immune Inducibility Assay

Blood from the canine patient in which the anti-tumor effect was obtained in the administration test in the above-described (1) was collected before administration of the therapeutic agent for a cancer(s), and 10 days and 30 days after the first administration. Peripheral blood mononuclear cells were isolated according to a conventional method, and by the ELISPOT assay for IFNγ using it, the immune inducibility of each administered recombinant protein was assayed.

In a 96-well plate manufactured by Millipore (MultiScreen-IP, MAIPS 4510), 100 μL/well of 70% ethanol was placed and the plate was left to stand for 5 minutes, followed by removal of the ethanol by aspiration. The plate was washed with sterile water and 300 μl/well of 200 mM Sodium Bicarbonate (pH8.2) was placed therein. After leaving it to stand for 5 minutes, Sodium Bicarbonate was removed by aspiration, and then the plate was washed. Subsequently, 0.5 μl/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 μL/well of a blocking solution (1% BSA-5% sucrose-200 mM Sodium Bicarbonate (pH8.2)) was added to the wells, and the plate was incubated at 4° C. overnight to block the plate. After removal of the blocking solution by aspiration, 300 μL/well of 10% fetal calf serum-containing RPMI medium (manufactured by Invitrogen) was placed in the wells, and the plate was left to stand for 5 minutes, followed by removal of the medium by aspiration. Subsequently, $5\times10^5$ cells/well of the canine peripheral blood mononuclear cells suspended in 10% fetal calf serum-containing RPMI medium were placed in the plate, and 10 μL/well of the canine-derived polypeptide or human-derived polypeptide used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 μL of rabbit anti-dog polyclonal antibody 1000-fold diluted with the above-described blocking solution was placed, and the plate was incubated at 4° C. overnight. After washing the wells 3 times with the above-described washing solution, 100 μL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and the number of the appeared spots was counted using KS ELISPOT (manufactured by Carl Zeiss, Inc.).

As a result, in either canine patient to which the canine polypeptide or the human polypeptide was administered, peripheral blood mononuclear cells sampled before the administration of the polypeptide showed no spots. On the other hand, in the canine patient to which the canine polypeptide was administered, peripheral blood mononuclear cells sampled 10 days and 30 days after the administration showed 20 and 36 spots, respectively. In the canine patient to which the human polypeptide was administered, peripheral blood mononuclear cells sampled 10 days and 30 days after the administration showed 24 and 36 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in (1) was exerted by immunoreactions in which these immunocytes are mainly involved.

Example B-1: Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3\times10^6$ pfu/ml.

(2) Screening of cDNA Library with Serum

Using the dog testis-derived cDNA phage library prepared as described above, immunoscreening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking at 4° C. overnight to suppress non-specific reactions. This filter was allowed to react with 500-fold diluted canine patient serum at room temperature for 2 to 3 hours.

As the above-described canine patient serum, serum collected from canine patients suffering from tumor proximal to the anus was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M $NaHCO_3$, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+I HRP conjugated: manufactured by BETHYL Laboratories) 5000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM $MgClSO_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host *E. coli* (XL1-Blue MRF') such that the absorbance $OD_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 μl of a solution prepared to contain a phagemid host *E. coli* (SOLR) such that the absorbance $OD_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:15 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the calmegin gene. The human homologous factor of the canine calmegin gene was human calmegin (homology: base sequence, 90%; amino acid sequence, 89%). The base sequence of human calmegin is shown in SEQ ID NO:17, and the amino acid sequence thereof is shown in SEQ ID NO:18.

(4) Analysis of Expression in Each Tissue

Figure 3:
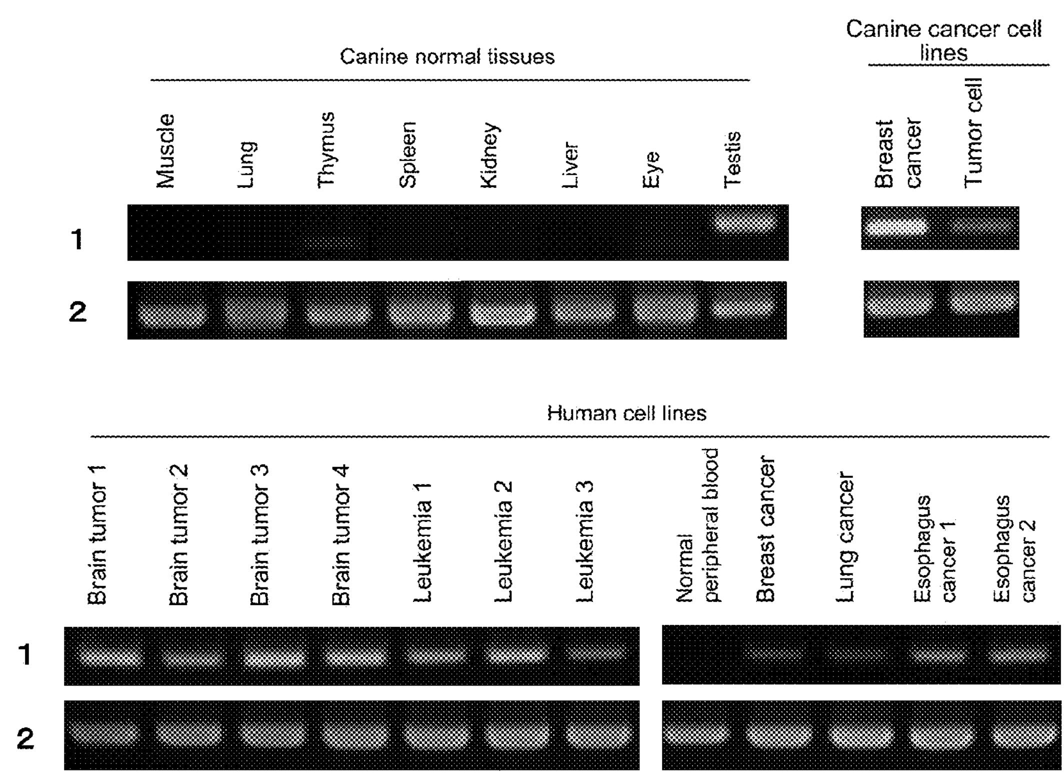
FIG. 3 shows the expression pattern of the calmegin gene identified in the present invention in normal tissues and tumor cell lines. Reference numeral 1: the expression pattern of the calmegin gene; Reference numeral 2: the expression pattern of the GAPDH gene.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to $10\times10^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:19 and 20) specific to the obtained gene. That is, respective reagents and the attached buffer were mixed such that the mixture should contain 0.25 μl of the sample prepared by the reverse transcription reaction, 2 μM each of the above primers, 0.2 mM each of dNTP and 0.65 U of ExTaq polymerase (manufactured by Takara Shuzo Co., Ltd.) in a total volume of 25 and the reaction was carried out with 30 cycles of 94° C. for 30 seconds, 55° C. for 30 seconds and 72° C. for 1 minute using Thermal Cycler (manufactured by BIO RAD). The above-described gene-specific primers were those which amplify the regions of the 755th to 1318th bases of the base sequence of SEQ ID NO:15 (canine calmegin gene) and the 795th to 1358th bases of the base sequence of SEQ ID NO:17 (human calmegin gene), and can be used for investigation of the expression of both the canine calmegin gene and the human calmegin gene. As a control for comparison, primers (described in SEQ ID NOs:9 and 10) specific to GAPDH were used simultaneously. As a result, as shown in FIG. 3, strong expression of the canine calmegin gene was observed in testis among the normal dog tissues, and on the other hand, strong expression was observed in canine tumor cell lines. Expression of the human calmegin gene was confirmed, as is the case with the canine calmegin gene, only in testis among the human normal tissues, but the expression was detected in brain tumor, leukemia and esophagus cancer cells among human cancer cell lines. Thus, the human calmegin gene was also confirmed to be specifically expressed in testis and cancer cells.

In FIG. 3, reference numeral 1 in the ordinate indicates the expression pattern of the calmegin gene, and reference numeral 2 indicates the expression pattern of the GAPDH gene as a control for comparison.

Example B-2: Preparation of Canine and Human Calmegin Proteins (1) Preparation of Recombinant Protein Based on the gene of SEQ ID NO:15 obtained in Example B-1, a recombinant protein was prepared by the following method. Respective reagents and the attached buffer were mixed such that the mixture should contain 1 μl of the vector that was prepared from the phagemid solution obtained in Example B-1 and was subjected to the sequence analysis, 0.4 μM each of two kinds of primers having BamHI and EcoRI restriction sites (described in SEQ ID NOs:21 and 22), 0.2 mM dNTP and 1.25 U of PrimeSTAR HS polymerase (manufactured by Takara Shuzo Co., Ltd.) in a total volume of 50 μl, and PCR was carried out with 30 cycles of 98° C. for 10 seconds, 55° C. for 15 seconds and 72° C. for 2 minutes using Thermal Cycler (manufactured by BIO RAD). The above-described two kinds of primers were those which amplify the region encoding the entire amino acid sequence of SEQ ID NO:16. After the PCR, the amplified DNA was subjected to electrophoresis using 1% agarose gel, and a DNA fragment of about 1.9 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and EcoRI and purified using QIAquick Gel Extraction Kit, followed by inserting the gene sequence of interest into an expression vector for *E. coli*, pET30a (manufactured by Novagen) that had been treated with BamHI and EcoRI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

On the other hand, based on the gene of SEQ ID NO:17, a recombinant protein of the human homologous gene was prepared by the following method. Respective reagents and the attached buffer were mixed such that the mixture should contain 1 μl of the cDNA prepared in Example B-1 whose expression could be confirmed by the RT-PCR method in various tissues/cells, 0.4 μM each of two kinds of primers having EcoRI and XhoI restriction sites (described in SEQ ID NOs:23 and 24), 0.2 mM dNTP and 1.25 U of PrimeSTAR HS polymerase (manufactured by Takara Shuzo Co., Ltd.) in a total volume of 50 μl, and PCR was carried out with 30 cycles of 98° C. for 10 seconds, 55° C. for 15 seconds and 72° C. for 2 minutes using Thermal Cycler (manufactured by BIO RAD). The above-described two kinds of primers were those which amplify the region encoding the entire amino acid sequence of SEQ ID NO:18. After the PCR, the amplified DNA was subjected to electrophoresis using 1% agarose gel, and a DNA fragment of about 1.9 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes EcoRI and XhoI and purified using QIAquick Gel Extraction Kit, followed by inserting the gene sequence of interest into an expression vector for *E. coli*, pET30a (manufactured by Novagen) that had been treated with EcoRI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:15 and SEQ ID NO:17, respectively, were cultured in 30 μg/ml kanamycin-containing LB medium at 37° C. until the absorbance at 600 nm reached about 0.7, and then isopropyl-β-D-1-thiogalactopyranoside was added thereto such that its final concentration should be 1 mM, followed by culturing them at 37° C. for 4 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The obtained pellet of *E. coli* cells was suspended in 20 mM phosphate buffer (pH 7.0) and subjected to sonication on ice. The sonicated solution of *E. coli* was centrifuged at 6,000 rpm for 20 minutes to obtain the supernatant as the soluble fraction and the precipitate as the insoluble fraction.

The soluble fraction was placed in an ion-exchange column (carrier: SP Sepharose (trademark) Fast Flow (GE Health Care); column volume: 5 mL; equilibration buffer: 20 mM phosphate buffer (pH 7.0)). The column was washed with 10 column volumes of 20 mM phosphate buffer (pH 7.0), and elution was carried out with density gradient of salt by 0.3 M-1.0 M sodium chloride-containing 20 mM phosphate buffer (pH 7.0). Six column volumes of the eluted fraction was collected in each elution step.

Among these eluted fractions, the 1st to 6th fractions eluted with 0.3 M sodium chloride-containing 20 mM phosphate buffer (pH 7.0) and the 1st fraction eluted with 1.0 M sodium chloride-containing 20 mM phosphate buffer (pH 7.0) were combined, and the resulting solution was subjected to additional purification by a secondary column.

Figure 4:
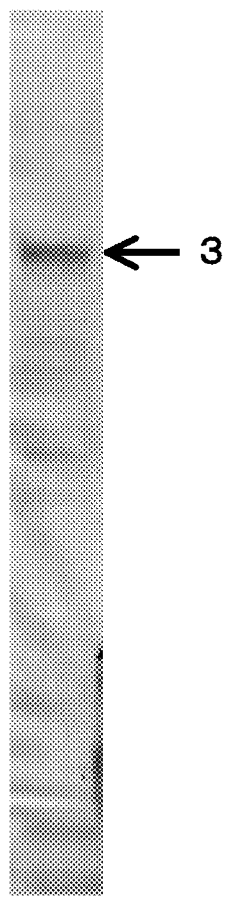
FIG. 4 shows the detection by Coomassie staining of the canine calmegin protein, which is an example of the polypeptide used in the present invention, produced in *E. coli* and purified in Example B. Reference numeral 3: the band for the canine calmegin protein.

For the secondary column, a column carrier Bio gel HT Type II (BioRad) was used. The column volume was 5 mL. The column was equilibrated with 10 column volumes of 0.3 M sodium chloride-containing 20 mM phosphate buffer (pH 7.0), and the above-described eluted fractions were placed in the column. The fractions that were not adsorbed to the column was washed away with 10 column volumes of 0.3 M sodium chloride-containing 20 mM phosphate buffer (pH 7.0) and 0.1 M phosphate buffer (pH 7.0), and elution was carried out with 0.2 M phosphate buffer (pH 7.0) to obtain a purified fraction, which was used as the material for administration tests thereafter. The proteins of interest in the eluted fractions were confirmed by Coomassie staining carried out according to a conventional method. Among these, the canine calmegin protein is shown in FIG. 4.

To 1 ml of a reaction buffer (20 mM Tris-HCl, 50 mM NaCl, 2 mM $CaCl_2$; pH 7.4), 200 μl of the purified preparation obtained by the above-described method was aliquoted, and 2 μl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 μm (manufactured by PALL) and used in the following experiments.

Example B-3: Test of Administration of Recombinant Protein to Cancer-Bearing Dogs (1) Antitumor Assay The anti-tumor effect of the two kinds of recombinant proteins which were purified as described above was assessed in two individuals of cancer-bearing dogs having epidermal tumor (2 individuals having mammary gland tumor).

An equal amount of Freund's incomplete adjuvant (manufactured by Wako Pure Chemicals) was mixed with 100 μg (0.5 ml) of the recombinant canine calmegin and human calmegin proteins, respectively, to prepare therapeutic agents for a cancer(s). Each of these agents was administered to a regional lymph node in the vicinity of the tumor a total of 3 times, by carrying out the subsequent administrations 3 days and 7 days after the first administration. As a result, the tumors with a size of about 45 $mm^3$ and 78 $mm^3$, respectively, at the time of administration of the therapeutic agents were reduced to 27 $mm^3$ and 46 $mm^3$, respectively, 10 days after the first administration; 15 $mm^3$ and 26 $mm^3$, respectively, 20 days after the first administration; and to 7 $mm^3$ and 15 $mm^3$, respectively, 30 days after the first administration.

Further, to a canine patient suffering from malignant melanoma, a mixture of 100 μg (0.5 ml) of the above-described canine calmegin protein and 0.5 ml of Freund's incomplete adjuvant was administered a total of 3 times in the same manner as described above. Further, concurrently with the respective administrations, 100 μg of canine interleukin 12 was administered subcutaneously. As a result, the tumor with a size of about 38 $mm^3$ at the time of administration of the therapeutic agent completely regressed 21 days after the first administration of the therapeutic agent.

(2) Immune Inducibility Assay

Blood from the canine patient in which the anti-tumor effect was obtained in the administration test in the above-described (1) was collected before administration of the therapeutic agent for a cancer(s) and 10 days and 30 days after the first administration. Peripheral blood mononuclear cells were isolated according to a conventional method, and by the ELISPOT assay for IFNγ using it, the immune inducibility of each administered recombinant protein was assayed.

In a 96-well plate manufactured by Millipore (MultiScreen-IP, MAIPS 4510), 100 μL/well of 70% ethanol was placed and the plate was left to stand for 5 minutes, followed by removal of the ethanol by aspiration. The plate was washed with sterile water and 300 μl/well of 200 mM Sodium Bicarbonate (pH8.2) was placed therein. After leaving it to stand for 5 minutes, Sodium Bicarbonate was removed by aspiration, and then the plate was washed. Subsequently, 0.5 μg/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 μL/well of a blocking solution (1% BSA-5% sucrose-200 mM Sodium Bicarbonate (pH8.2)) was added to the wells, and the plate was incubated at 4° C. overnight to block the plate. After removal of the blocking solution by aspiration, 300 μL/well of 10% fetal calf serum-containing RPMI medium (manufactured by Invitrogen) was placed in the wells, and the plate was left to stand for 5 minutes, followed by removal of the medium by aspiration. Subsequently, $5\times10^5$ cells/well of the canine peripheral blood mononuclear cells suspended in 10% fetal calf serum-containing RPMI medium were placed in the plate, and 10 μL/well of the canine calmegin or human calmegin protein used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 μL of rabbit anti-dog polyclonal antibody 1000-fold diluted with the above-described blocking solution was placed, and the resulting mixture was incubated at 4° C. overnight. After washing the wells 3 times with the above-described washing solution, 100 μL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and image processing of the wells was carried out, followed by counting the number of spot-forming cells (SFC) using KS ELISPOT compact system (Carl Zeiss, Inc., Germany).

As a result, in either canine patient to which canine calmegin or human calmegin was administered, peripheral blood mononuclear cells sampled before the administration showed no spots. On the other hand, in the canine patient to which canine calmegin was administered, peripheral blood mononuclear cells sampled 10 days and 30 days after the administration showed 15 and 45 spots, respectively. In the canine patient to which human calmegin was administered, peripheral blood mononuclear cells sampled 10 days and 30 days after the administration showed 12 and 39 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in (1) was exerted by immunoreactions in which these immunocytes are mainly involved.

Example C-1: Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3\times10^6$ pfu/ml.

(2) Screening of cDNA Library with Serum

Using the dog testis-derived cDNA phage library prepared as described above, immunoscreening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking it at 4° C. overnight to suppress non-specific reactions. This filter was allowed to react with 500-fold diluted canine patient serum at room temperature for 2 to 3 hours.

As the above-described canine patient serum, serum collected from canine patients suffering from breast cancer was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M $NaHCO_3$, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+I HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM $MgClSO_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host *E. coli* (XL1-Blue MRF') such that the absorbance $OD_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 μl of a solution prepared to contain a phagemid host *E. coli* (SOLR) such that the absorbance $OD_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:25 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene has 99% homology (which was calculated only in the overlapping region) to the CEP gene described in SEQ ID NO:27 in terms of base sequence and amino acid sequence, so that the gene was judged as the CEP gene. The human homologous factor of the canine CEP was human CEP (homology to the CEP gene described in SEQ ID NO:25: base sequence, 87%; amino acid sequence, 84%). The base sequence of human CEP is shown in SEQ ID NO:29, and the amino acid sequence thereof is shown in SEQ ID NO:30.

(4) Analysis of Expression in Each Tissue

Figure 5:
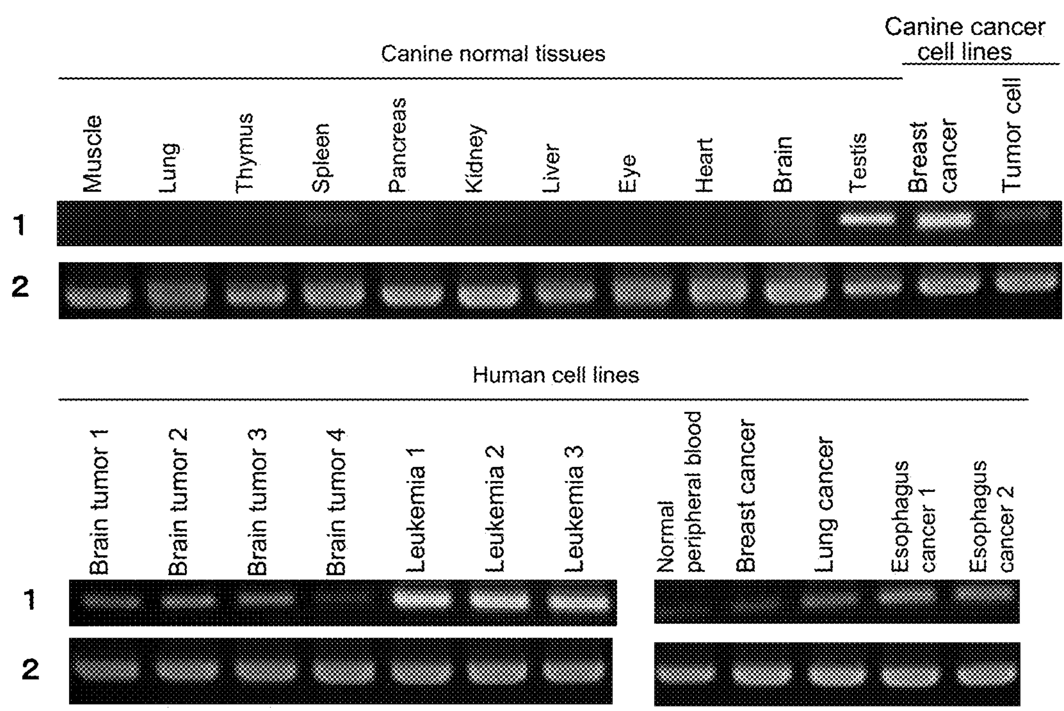
FIG. 5 shows the expression pattern of the gene encoding the CEP protein in normal tissues and tumor cell lines. Reference numeral 1: the expression pattern of the gene encoding the CEP protein; Reference numeral 2: the expression pattern of the GAPDH gene.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to $10\times10^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:31 and 32) specific to the obtained gene. That is, respective reagents and the attached buffer were mixed such that the mixture should contain 0.25 μl of the sample prepared by the reverse transcription reaction, 2 μM each of the above primers, 0.2 mM each of dNTP and 0.65 U of ExTaq polymerase (manufactured by Takara Shuzo Co., Ltd.) in a total volume of 25 μl, and the reaction was carried out with 30 cycles of 94° C. for 30 seconds, 55° C. for 30 seconds and 72° C. for 30 seconds using Thermal Cycler (manufactured by BIO RAD). The above-described gene-specific primers were those which amplify the regions of the 4582nd to 5124th bases of the base sequences of SEQ ID NOs:25 and 27 (canine CEP gene) and the 4610th to 5152nd bases of the base sequence of SEQ ID NO:29 (human CEP gene), and can be used for investigation of the expression of both the canine CEP gene and the human CEP gene. As a control for comparison, primers (described in SEQ ID NOs:9 and 10) specific to GAPDH were used simultaneously. As a result, as shown in FIG. 5, strong expression of the canine CEP gene was observed in testis among the normal dog tissues, and on the other hand, strong expression was observed in the canine breast cancer cell line. Expression of the human CEP gene was confirmed, as is the case with the canine CEP gene, only in testis among the human normal tissues, but the expression was detected in brain tumor, leukemia and esophagus cancer cells among human cancer cell lines, and especially, strong expression was observed in the leukemia cell line. Thus, the human CEP gene was also confirmed to be specifically expressed in testis and cancer cells.

In FIG. 5, reference numeral 1 in the ordinate indicates the expression pattern of the CEP gene, and reference numeral 2 indicates the expression pattern of the GAPDH gene as a control for comparison.

Example C-2: Preparation of Canine and Human CEPs (1) Preparation of Recombinant Protein Based on the gene of SEQ ID NO:25 obtained in Example C-1, a recombinant protein was prepared by the following method. Respective reagents and the attached buffer were mixed such that the mixture should contain 1 μl of the vector that was prepared from the phagemid solution obtained in Example C-1 and was subjected to the sequence analysis, 0.4 μM each of two kinds of primers having BamHI and SalI restriction sites (described in SEQ ID NOs:33 and 34), 0.2 mM dNTP and 1.25 U of PrimeSTAR HS polymerase (manufactured by Takara Shuzo Co., Ltd.) in a total volume of 50 μl, and PCR was carried out with 30 cycles of 98° C. for 10 seconds, 55° C. for 5 seconds and 72° C. for 7 minutes using Thermal Cycler (manufactured by BIO RAD). The above-described two kinds of primers were those which amplify the region encoding the entire amino acid sequence of SEQ ID NO:26. After the PCR, the amplified DNA was subjected to electrophoresis using 1% agarose gel, and a DNA fragment of about 7.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and SalI and purified using QIAquick Gel Extraction Kit, followed by inserting the gene sequence of interest into an expression vector for *E. coli*, pET30a (manufactured by Novagen) that had been treated with BamHI and SalI. Usage of this vector enables production of a His-tag fusion recombinant protein. *E. coli* for expression, BL21 (DE3), was transformed with this plasmid, and expression of the protein of interest was induced in *E. coli* with 1 mM IPTG. In the same manner, based on the gene of SEQ ID NO:27, using the canine testis cDNA as a template and two kinds of primers having BamHI and SalI restriction sites (SEQ ID NOs:33 and 35), a recombinant protein of the registered canine CEP gene was prepared. The above-described two kinds of primers were those which amplify the region of about 7.8 kbp encoding the entire amino acid sequence of SEQ ID NO:28.

Further, based on the gene of SEQ ID NO:29, a recombinant protein of the human homologous gene was prepared by the following method. Respective reagents and the attached buffer were mixed such that the mixture should contain 1 μl of the cDNA prepared in Example C-1 whose expression could be confirmed by the RT-PCR method in various tissues/cells, 0.4 μM each of two kinds of primers having BamHI and SalI restriction sites (described in SEQ ID NOs:36 and 37), 0.2 mM dNTP and 1.25 U of PrimeSTAR HS polymerase (manufactured by Takara Shuzo Co., Ltd.) in a total volume of 50 μl, and PCR was carried out with 30 cycles of 98° C. for 10 seconds, 55° C. for 5 seconds and 72° C. for 7 minutes using Thermal Cycler (manufactured by BIO RAD). The above-described two kinds of primers were those which amplify the region encoding the entire amino acid sequence of SEQ ID NO:30. After the PCR, the amplified DNA was subjected to electrophoresis using 1% agarose gel, and a DNA fragment of about 7.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and SalI and purified using QIAquick Gel Extraction Kit, followed by inserting the gene sequence of interest into an expression vector for *E. coli*, pET30a (manufactured by Novagen) that had been treated with BamHI and SalI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:25, SEQ ID NO:27, and SEQ ID NO:29, respectively, were cultured in 30 μg/ml kanamycin-containing LB medium at 37° C. until the absorbance at 600 nm reached about 0.7, and then isopropyl-β-D-1-thiogalactopyranoside was added thereto such that its final concentration should be 1 mM, followed by culturing them at 30° C. for 20 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in phosphate-buffered saline and subjected to sonication on ice. The sonicated solution of *E. coli* was centrifuged at 7000 rpm for 20 minutes to obtain the supernatant as the soluble fraction and the precipitate as the insoluble fraction. The insoluble fraction was suspended in 4% Triton X-100 solution and the resulting suspension was centrifuged at 7000 rpm for 20 minutes. This operation was repeated twice and an operation of removal of proteases was carried out. The residue was suspended in 8 M urea-containing 10 mM Tris-HCl, 100 mM phosphate buffer (hereinafter referred to as 8 M urea solution) and a protease inhibitor cocktail solution, and the resulting suspension was left to stand at 4° C. for 20 hours to denature proteins.

Figure 6:
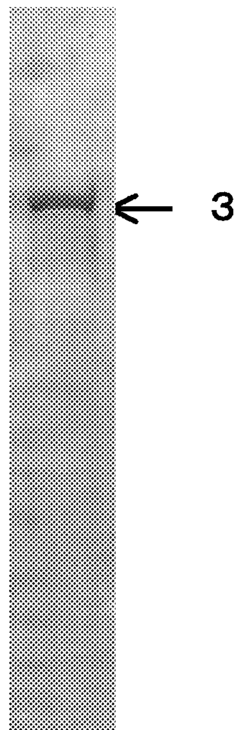
FIG. 6 shows the detection by Coomassie staining of the canine CEP of SEQ ID NO:26, which is an example of the polypeptide used in the present invention, produced in *E. coli* and purified in Example C. Reference numeral 3: the band for the canine CEP protein.

Thereafter, the suspension was centrifuged at 7,000 rpm for 20 minutes, and the obtained soluble fraction was placed in a nickel chelate column prepared by a conventional method (carrier: Chelating Sepharose (trademark) Fast Flow (GE Health Care); column volume: 5 mL; equilibration buffer: 8M urea solution), followed by leaving it to stand at 4° C. overnight. The supernatant was recovered by centrifugation of this column carrier at 1,500 rpm for 5 minutes, and the column carrier was suspended in phosphate-buffered saline, followed by refilling the column with the resulting suspension. The fraction that was not adsorbed to the column was washed away with 5 column volumes of 8 M urea solution, 10 column volumes of 0.5 M sodium chloride-containing 0.1 M acetate buffer (pH 5.0) and 10 mM imidazole-containing 20 mM phosphate buffer (pH 8.0), and elution was immediately carried out with a five-step density gradient of 100 mM-500 mM imidazole to obtain a purified fraction, which was used as the material for administration tests thereafter. The proteins of interest in respective eluted fractions were confirmed by Coomassie staining carried out according to a conventional method. Among these, the recombinant canine CEP described in SEQ ID NO:26 is shown in FIG. 6.

To 1 ml of a reaction buffer (20 mM Tris-HCl, 50 mM NaCl, 2 mM $CaCl_2$; pH 7.4), 200 μl of the purified preparation obtained by the above-described method was aliquoted, and 2 μl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 μm (manufactured by PALL) and used in the following experiments.

Example C-3: Test of Administration of Recombinant Protein to Cancer-Bearing Dogs (1) Antitumor Assay The anti-tumor effect of the two kinds of recombinant proteins which were purified as described above was assessed in two individuals of cancer-bearing dogs having epidermal tumor (2 individuals having perianal adenoma).

An equal amount of Freund's incomplete adjuvant (manufactured by Wako Pure Chemicals) was mixed with 100 μg (0.5 ml) each of the recombinant canine CEP described in SEQ ID NO:26 and human CEP purified as described above to prepare therapeutic agents for a cancer(s). Each of these agents was administered to a regional lymph node in the vicinity of the tumor a total of 3 times, by carrying out the subsequent administrations 3 days and 7 days after the first administration. As a result, the tumors with a size of about 87 $mm^3$ and 69 $mm^3$ at the time of administration of the therapeutic agents, respectively, were reduced to 69 $mm^3$ and 56 $mm^3$, respectively, 10 days after the first administration; 24 $mm^3$ and 31 $mm^3$, respectively, 20 days after the first administration; and to 10 $mm^3$ and 8 $mm^3$, respectively, 30 days after the first administration of the therapeutic agent.

Further, to a canine patient suffering from mammary adenocarcinoma, a mixture of 100 μg (0.5 ml) of the canine CEP protein described in SEQ ID NO:26 with 0.5 ml of Freund's incomplete adjuvant was administered a total of 3 times in the same manner as described above. Further, concurrently with the respective administrations, 10 MU of "Intercat" which is a recombinant feline interferon was administered subcutaneously. As a result, the tumor with a size of about 126 $mm^3$ at the time of administration of the therapeutic agent completely regressed 26 days after the first administration of the therapeutic agent. Similarly, in the case where the canine CEP described in SEQ ID NO:28 was used, an anti-tumor effect was also observed in a cancer-bearing dog.

Further, to a canine patient of mastocytoma, a mixture of 100 μg (0.5 ml) of the canine CEP protein described in SEQ ID NO:26 with 0.5 ml of Freund's incomplete adjuvant was administered a total of 3 times in the same manner as described above. Further, concurrently with the respective administrations, 100 μg of canine interleukin-12 was subcutaneously administered. As a result, the tumor with a size of about 83 $mm^3$ at the time of administration of the therapeutic agent completely regressed 18 days after the first administration of the therapeutic agent.

(2) Immune Inducibility Assay

Blood from the canine patient suffering from perianal adenoma in which the anti-tumor effect was obtained in the administration test in the above-described (1) was collected before administration of the therapeutic agent for a cancer(s) and 10 days and 30 days after the first administration. Peripheral blood mononuclear cells were isolated according to a conventional method, and by the ELISPOT assay for IFNγ using it, the immune inducibility of each administered protein was assayed.

In a 96-well plate manufactured by Millipore (MultiScreen-IP, MAIPS 4510), 100 μL/well of 70% ethanol was placed and the plate was left to stand for 5 minutes, followed by removal of the ethanol by aspiration. The plate was washed with sterile water and 300 μl/well of 200 mM Sodium Bicarbonate (pH8.2) was placed therein. After leaving it to stand for 5 minutes, Sodium Bicarbonate was removed by aspiration, and then the plate was washed. Subsequently, 0.5 μl/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 μL/well of a blocking solution (1% BSA-5% sucrose-200 mM Sodium Bicarbonate (pH8.2)) was added to the wells, and the plate was incubated at 4° C. overnight to block the plate. After removal of the blocking solution by aspiration, 300 μL/well of 10% fetal calf serum-containing RPMI medium (manufactured by Invitrogen) was placed in the wells, and the plate was left to stand for 5 minutes, followed by removal of the medium by aspiration. Subsequently, $5\times10^5$ cells/well of the canine peripheral blood mononuclear cells suspended in 10% fetal calf serum-containing RPMI medium were placed in the plate, and 10 μL/well of the canine CEP described in SEQ ID NO:26 or the human CEP used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 μL of rabbit anti-canine polyclonal antibody 1000-fold diluted with the above-described blocking solution was placed, and the plate was incubated at 4° C. overnight. After washing the wells 3 times with the above-described washing solution, 100 μL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and image processing of the wells was carried out, followed by counting the number of spot-forming cells (SFC) using KS ELISPOT compact system (Carl Zeiss, Inc., Germany).

As a result, in either canine patient to which the canine CEP described in SEQ ID NO: 26 or the human CEP was administered, peripheral blood mononuclear cells sampled before the administration showed no spots. On the other hand, in the canine patient to which the canine CEP was administered, peripheral blood mononuclear cells sampled 10 days and 30 days after the administration showed 23 and 52 spots, respectively. In the canine patient to which the human CEP was administered, peripheral blood mononuclear cells sampled 10 days and 30 days after the administration showed 19 and 49 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in (1) was exerted by immunoreactions in which these immunocytes are mainly involved.

Example D-1: Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3\times10^6$ pfu/ml.

(2) Screening of cDNA Library with Serum

Using the dog testis-derived cDNA phage library prepared as described above, immunoscreening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking at 4° C. overnight to suppress non-specific reactions. This filter was allowed to react with 500-fold diluted canine patient serum at room temperature for 2 to 3 hours.

As the above-described canine patient serum, serum collected from canine patients suffering from breast cancer was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M $NaHCO_3$, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+I HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM $MgClSO_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host *E. coli* (XL1-Blue MRF') such that the absorbance $OD_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 μl of a solution prepared to contain a phagemid host *E. coli* (SOLR) such that the absorbance $OD_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:38 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the TRIP11 gene. The human homologous factor of canine TRIP11 was human TRIP11 (homology: base sequence, 88%; amino acid sequence, 86%). The base sequence of human TRIP11 is shown in SEQ ID NO:40, and the amino acid sequence thereof is shown in SEQ ID NO:41.

(4) Analysis of Expression in Each Tissue

Figure 7:
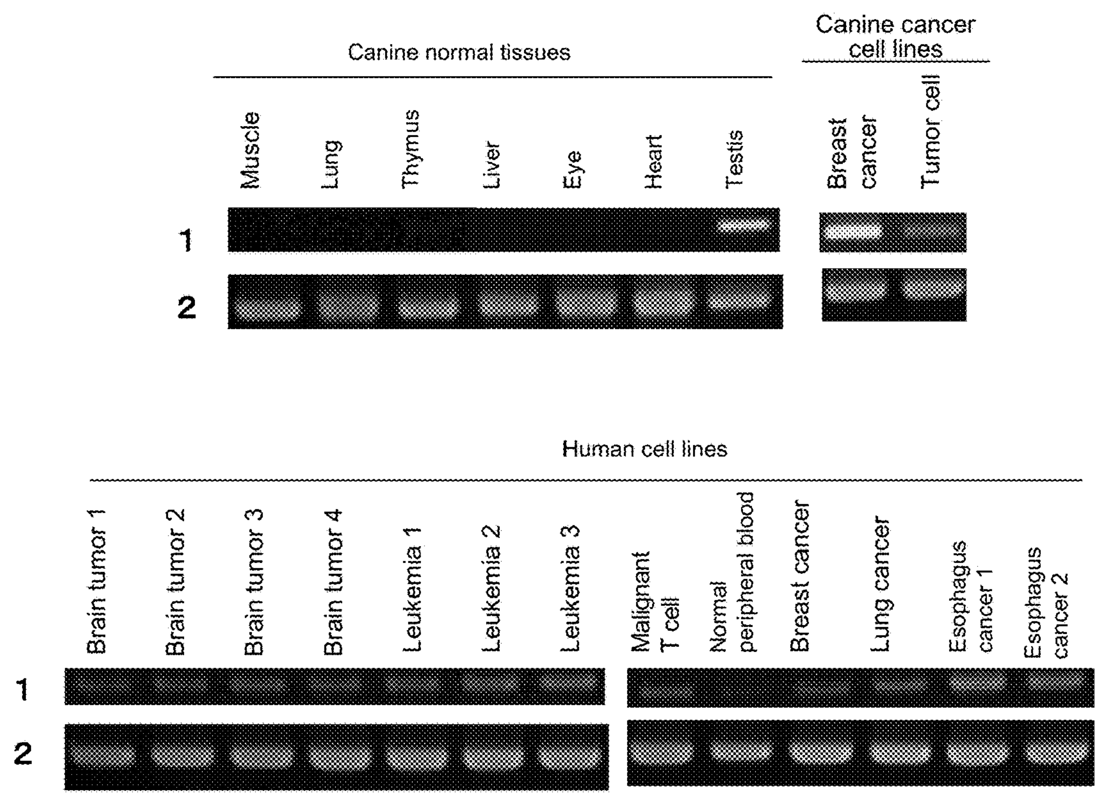
FIG. 7 shows the expression pattern of the gene encoding the TRIP11 protein in normal tissues and tumor cell lines. Reference numeral 1: the expression pattern of the gene encoding the TRIP11 protein; Reference numeral 2: the expression pattern of the GAPDH gene.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to $10\times10^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:42 and 43) specific to the obtained gene. That is, respective reagents and the attached buffer were mixed such that the mixture should contain 0.25 μl of the sample prepared by the reverse transcription reaction, 2 μM each of the above primers, 0.2 mM each of dNTP and 0.65 U of ExTaq polymerase (manufactured by Takara Shuzo Co., Ltd.) in a total volume of 25 μl, and the reaction was carried out with 30 cycles of 94° C. for 30 seconds, 55° C. for 30 seconds and 72° C. for 1.5 minutes using Thermal Cycler (manufactured by BIO RAD). The above-described gene-specific primers were those which amplify the regions of the 1519th to 2957th bases of the base sequence of SEQ ID NO:38 (canine TRIP11 gene) and the 1872nd to 3310th bases of the base sequence of SEQ ID NO:40 (human TRIP11 gene), and can be used for investigation of the expression of both the canine TRIP11 gene and the human TRIP11 gene. As a control for comparison, primers (described in SEQ ID NOs:9 and 10) specific to GAPDH were used simultaneously. As a result, as shown in FIG. 7, strong expression of the canine TRIP11 gene was observed in testis among the normal dog tissues, and on the other hand, strong expression was observed in the canine breast cancer cell line. Expression of the human gene was confirmed, as is the case with the canine TRIP11 gene, only in testis among the human normal tissues, but the expression was detected in many types of cancer cell lines such as brain tumor, leukemia, breast cancer, lung cancer and esophagus cancer cell lines among human cancer cell lines. Thus, the human TRIP11 gene was also confirmed to be specifically expressed in testis and cancer cells.

In FIG. 7, reference numeral 1 in the ordinate indicates the expression pattern of the TRIP11 gene, and reference numeral 2 indicates the expression pattern of the GAPDH gene as a control for comparison.

Example D-2: Preparation of Canine and Human TRIP11 Proteins (1) Preparation of Recombinant Protein Based on the gene of SEQ ID NO:38 obtained in Example D-1, a recombinant protein was prepared by the following method. NO:Respective reagents and the attached buffer were mixed such that the mixture should contain 1 μl of the vector which was prepared from the phagemid solution obtained in Example D-1 and was subjected to the sequence analysis, 0.4 μM each of two kinds of primers having SalI and XhoI restriction sites (described in SEQ ID NOs:44 and 45), 0.2 mM dNTP and 1.25 U of PrimeSTAR HS polymerase (manufactured by Takara Shuzo Co., Ltd.) in a total volume of 50 μl, and PCR was carried out with 30 cycles of 98° C. for 10 seconds, 55° C. for 5 seconds and 72° C. for 6 minutes using Thermal Cycler (manufactured by BIO RAD). The above-described two kinds of primers were those which amplify the region encoding the entire amino acid sequence of SEQ ID NO:39. After the PCR, the amplified DNA was subjected to electrophoresis using 1% agarose gel, and a DNA fragment of about 6.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes SalI and XhoI and purified using QIAquick Gel Extraction Kit, followed by inserting the gene sequence of interest into an expression vector for *E. coli*, pET30b (manufactured by Novagen) that had been treated with SalI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

Further, based on the gene of SEQ ID NO:40, a recombinant protein of the human homologous gene was prepared by the following method. Respective reagents and the attached buffer were mixed such that the mixture should contain 1 μl of the cDNA prepared in Example D-1 whose expression could be confirmed by the RT-PCR method in various tissues/cells, 0.4 μM each of two kinds of primers having NdeI and KpnI restriction sites (described in SEQ ID NOs:46 and 47), 0.2 mM dNTP and 1.25 U of PrimeSTAR HS polymerase (manufactured by Takara Shuzo Co., Ltd.) in a total volume of 50 μl, and PCR was carried out with 30 cycles of 98° C. for 10 seconds, 55° C. for 5 seconds and 72° C. for 6 minutes using Thermal Cycler (manufactured by BIO RAD). The above-described two kinds of primers were those which amplify the region encoding the entire amino acid sequence of SEQ ID NO:41. After the PCR, the amplified DNA was subjected to electrophoresis using 1% agarose gel, and a DNA fragment of about 6.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes NdeI and KpnI and purified using QIAquick Gel Extraction Kit, followed by inserting the gene sequence of interest into an expression vector for *E. coli*, pET30b (manufactured by Novagen) that had been treated with NdeI and KpnI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Proteins

The above-obtained recombinant *E. coli* cells that expressed SEQ ID NO:38 and SEQ ID NO:40, respectively, were cultured in 30 μg/ml kanamycin-containing LB medium at 37° C. until the absorbance at 600 nm reached about 0.7, and then isopropyl-3-D-1-thiogalactopyranoside was added thereto such that its final concentration should be 1 mM, followed by culturing them at 30° C. for 20 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The obtained pellet of *E. coli* cells was suspended in phosphate-buffered saline and subjected to sonication on ice. The sonicated solution of *E. coli* was centrifuged at 7,000 rpm for 15 minutes to obtain the supernatant as the soluble fraction and the precipitate as the insoluble fraction.

The insoluble fraction was suspended in 4% Triton X-100 solution and the resulting suspension was centrifuged at 7,000 rpm for 10 minutes. This operation was repeated twice and an operation of removal of proteases was carried out. Thereafter, the residue was suspended in phosphate-buffered saline and an operation of removal of the surfactant was carried out.

Figure 8:
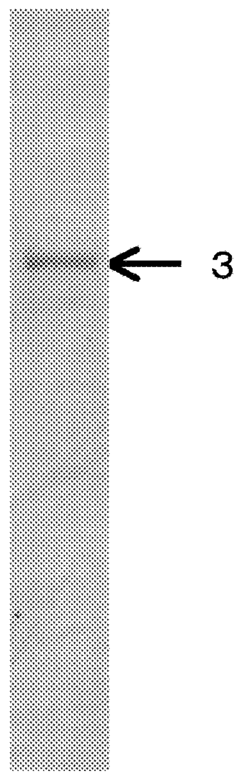
FIG. 8 shows the detection by Coomassie staining of the canine TRIP11 protein, which is one of the polypeptides used in the present invention, produced in *E. coli* and purified in Example D. Reference numeral 3: the band for the canine TRIP11 protein.

The residue was suspended in 6M guanidine hydrochloride-containing 20 mM phosphate buffer (pH 8.0), and the resulting suspension was left to stand at 4° C. for 20 hours to denature proteins. Thereafter, the suspension was centrifuged at 7,000 rpm for 20 minutes, and the obtained soluble fraction was placed in a nickel chelate column prepared by a conventional method (carrier: Chelating Sepharose (trademark) Fast Flow (GE Health Care); column volume: 5 mL; equilibration buffer: 6M guanidine hydrochloride-containing 20 mM phosphate buffer (pH 8.0)). The fraction that was not adsorbed to the column was washed away with 10 column volumes of 6 M sodium chloride-containing 20 mM phosphate buffer (pH 8.0) and 10 mM imidazole-containing 20 mM phosphate buffer (pH 8.0), and elution was immediately carried out with a four-step density gradient of 50 mM-500 mM imidazole to obtain a purified fraction, which was used as the material for administration tests thereafter. The proteins of interest in the eluted fractions were confirmed by Coomassie staining carried out according to a conventional method. Among these, the canine TRIP11 protein is shown in FIG. 8.

To 1 ml of a reaction buffer (20 mM Tris-HCl, 50 mM NaCl, 2 mM $CaCl_2$; pH 7.4), 200 μl of the purified preparation obtained by the above-described method was aliquoted, and 2 μl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 μm (manufactured by PALL) and used in the following experiments.

Example D-3: Test of Administration of Recombinant Protein to Cancer-Bearing Dogs (1) Antitumor Assay The anti-tumor effect of the two kinds of recombinant proteins which were purified as described above was assessed in two individuals of cancer-bearing dogs having epidermal tumor (2 individuals having mammary gland tumor).

Therapeutic agents for a cancer(s) were prepared by mixing 0.5 ml of Freund's incomplete adjuvant (manufactured by Wako Pure Chemicals) with 100 μg (0.5 ml) of the recombinant canine TRIP11 and human TRIP11 proteins, respectively, purified as described above. Each of these agents was administered to a regional lymph node in the vicinity of the tumor a total of 3 times, by carrying out the subsequent administrations 3 days and 7 days after the first administration. As a result, the tumors with a size of about 75 $mm^3$ and 102 $mm^3$, respectively, at the time of administration of the therapeutic agents were reduced to 63 $mm^3$ and 85 $mm^3$, respectively, 10 days after the first administration; 35 $mm^3$ and 42 $mm^3$, respectively, 20 days after the first administration; and to 15 $mm^3$ and 19 $mm^3$, respectively, 30 days after the first administration of the therapeutic agent for a cancer(s).

Further, to a canine patient suffering from mastocytoma, a mixture of 100 μg (0.5 ml) of the canine TRP11 protein with 0.5 ml of Freund's incomplete adjuvant was administered a total of 3 times in the same manner as described above. Concurrently with the respective administrations, 100 μg of canine interleukin-12 was subcutaneously administered. As a result, the tumor with a size of about 165 $mm^3$ at the time of administration of the therapeutic agent completely regressed 23 days after the first administration of the therapeutic agent.

(2) Immune Inducibility Assay

Blood from the canine patient suffering from mammary gland tumor in which the anti-tumor effect was obtained in the administration test in the above-described (1) was collected. Peripheral blood mononuclear cells were isolated according to a conventional method, and by the ELISPOT assay for IFNγ using it, the immune inducibility of each administered protein was assayed.

In a 96-well plate manufactured by Millipore (MultiScreen-IP, MAIPS 4510), 100 μL/well of 70% ethanol was placed and the plate was left to stand for 5 minutes, followed by removal of the ethanol by aspiration. The plate was washed with sterile water and 300 μl/well of 200 mM Sodium Bicarbonate (pH8.2) was placed therein. After leaving it to stand for 5 minutes, Sodium Bicarbonate was removed by aspiration, and then the plate was washed. Subsequently, 0.5 μg/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 μL/well of a blocking solution (1% BSA-5% sucrose-200 mM Sodium Bicarbonate (pH8.2)) was added to the wells, and the plate was incubated at 4° C. overnight to block the plate. After removal of the blocking solution by aspiration, 300 μL/well of 10% fetal calf serum-containing RPMI medium (manufactured by Invitrogen) was placed in the wells and the plate was left to stand for 5 minutes, followed by removal of the medium by aspiration. Subsequently, $5\times10^5$ cells/well of the canine peripheral blood mononuclear cells suspended in 10% fetal calf serum-containing RPMI medium were placed in the plate, and 10 μL/well of the canine TRIP11 or the human TRIP11 protein used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 μL of rabbit anti-dog polyclonal antibody 1000-fold diluted with the above-described blocking solution was placed, and the plate was incubated at 4° C. overnight. After washing the wells 3 times with the above-described washing solution, 100 μL of HRP-labeled anti-rabbit antibody 1,000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and image processing of the wells was carried out, followed by counting the number of spot-forming cells (SFC) using KS ELISPOT compact system (Carl Zeiss, Inc., Germany).

As a result, in either canine patient to which the canine TRIP11 protein or the human TRIP11 protein was administered, peripheral blood mononuclear cells sampled before the administration showed no spots. On the other hand, in the canine patient to which the canine TRIP11 was administered, peripheral blood mononuclear cells sampled 10 days and 30 days after the administration showed 26 and 65 spots, respectively. In the canine patient to which the human TRIP11 was administered, peripheral blood mononuclear cells sampled 10 days and 30 days after the administration showed 31 and 72 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in the above-described (1) was exerted by immunoreactions in which these immunocytes are mainly involved.

The invention claimed is:

1. A method for exerting an anti-tumor effect, said method comprising administering an effective amount of any one of the polypeptides (a) to (b) below to an individual having a cancer, said polypeptide having an immunity-inducing activity:

(a) a polypeptide comprising the amino acid sequence shown in SEQ ID NO: 2 or 4; and (b) a polypeptide having a homology of not less than 95% to the polypeptide (a), wherein said cancer is cancer that expresses a cancer antigen protein comprising the amino acid sequence shown in SEQ ID NO:2 or 4 or an amino acid sequence having a homology of not less than 95% to SEQ ID NO:2 or 4.

2. A method for exerting an anti-tumor effect, said method comprising administering an effective amount of a recombinant vector which comprises a polynucleotide encoding an immunity-inducing polypeptide selected from any one of the polypeptides (a) to (b) below to an individual having a cancer, said recombinant vector being capable of expressing said polypeptide in vivo:

(a) a polypeptide comprising the amino acid sequence shown in SEQ ID NO:2 or 4 in; and (b) a polypeptide having a homology of not less than 95% to the polypeptide (a), wherein said cancer is cancer that expresses a cancer antigen protein comprising the amino acid sequence shown in SEQ ID NO:2 or 4 or an amino acid sequence having a homology of not less than 95% to SEQ ID NO:2 or 4.

3. The method according to claim 1, wherein said polypeptide (b) has a homology of not less than 98% to said polypeptide (a).

4. The method according to claim 1, wherein said polypeptide having an immunity-inducing activity has the amino acid sequence shown in SEQ ID NO:2 or 4.

5. The method according to claim 1, which is a method of therapy for the cancer.

6. The method according to claim 5, wherein said individual is a human, a dog or a cat.

7. The method according to claim 5, further comprising administering an immunoenhancer.

8. The method according to claim 7, wherein said immunoenhancer is at least one selected from the group consisting of Freund's incomplete adjuvant; Montanide; poly I:C and derivatives thereof; CpG oligonucleotides; interleukin-12; interleukin-18; interferon-α; interferon-β; interferon-ω; interferon-γ; and Flt3 ligand.

9. The method according to claim 2, wherein said polypeptide (b) has a homology of not less than 98% to said polypeptide (a).

10. The method according to claim 2, wherein said polypeptide having an immunity-inducing activity has the amino acid sequence shown in SEQ ID NO:2 or 4.

11. The method according to claim 2, which is a method of therapy for the cancer.

12. The method according to claim 11, wherein said individual is a human, a dog or a cat.

13. The method according to claim 11, further comprising administering an immunoenhancer.

14. The method according to claim 13, wherein said immunoenhancer is at least one selected from the group consisting of Freund's incomplete adjuvant; Montanide; poly I:C and derivatives thereof; CpG oligonucleotides; interleukin-12; interleukin-18; interferon-α; interferon-β; interferon-ω; interferon-γ; and Flt3 ligand.

15. The method according to claim 1, wherein immunocytes that exert an antitumor effect are induced in said individual.

16. The method according to claim 2, wherein immunocytes that exert an antitumor effect are induced in said individual.

* * * * *

```
                              SEQUENCE LISTING


<160> NUMBER OF SEQ ID NOS: 47

<210> SEQ ID NO 1
<211> LENGTH: 1508
<212> TYPE: DNA
<213> ORGANISM: Canis familiaris
<220> FEATURE:
<221> NAME/KEY: CDS
<222> LOCATION: (17)..(937)

<400> SEQUENCE: 1

gcggcccggg cgggac atg gcg gcg ctc tac gcc tgc acc aag tgc cac cag   52
                  Met Ala Ala Leu Tyr Ala Cys Thr Lys Cys His Gln
                  1               5                   10

cgc ttc ccc ttc gag gcg ctg tct cag ggg cag cag ctg tgc aag gaa     100
Arg Phe Pro Phe Glu Ala Leu Ser Gln Gly Gln Gln Leu Cys Lys Glu
        15                  20                  25

tgt cgg att gca cac cct gtt gtg aag tgc acc tac tgt aga act gag     148
Cys Arg Ile Ala His Pro Val Val Lys Cys Thr Tyr Cys Arg Thr Glu
    30                  35                  40

tac cag caa gag agt aaa acc aat aca ata tgc aaa aaa tgt gct cag     196
Tyr Gln Gln Glu Ser Lys Thr Asn Thr Ile Cys Lys Lys Cys Ala Gln
45                  50                  55                  60

aat gtg cag tta tat gga acg ccc aaa cct tgt cag tac tgc aac ata     244
Asn Val Gln Leu Tyr Gly Thr Pro Lys Pro Cys Gln Tyr Cys Asn Ile
                65                  70                  75

att gca gca ttt att ggc aac aaa tgc cag cga tgc acg aat tca gag     292
Ile Ala Ala Phe Ile Gly Asn Lys Cys Gln Arg Cys Thr Asn Ser Glu
            80                  85                  90

aag aag tat gga cca cca tat tca tgt gaa cag tgt aaa caa cag tgt     340
Lys Lys Tyr Gly Pro Pro Tyr Ser Cys Glu Gln Cys Lys Gln Gln Cys
        95                  100                 105

gca ttt gac agg aaa gat gat aga aag aag gta gat ggg aaa ttg ctg     388
Ala Phe Asp Arg Lys Asp Asp Arg Lys Lys Val Asp Gly Lys Leu Leu
    110                 115                 120

tgt tgg ctg tgc aca ctt tca tac aaa cgg gtc ctt caa aag acc aaa     436
Cys Trp Leu Cys Thr Leu Ser Tyr Lys Arg Val Leu Gln Lys Thr Lys
125                 130                 135                 140

gag cag agg aaa cat ctg agc agc tct tcc cgt gcc agc cac cag gag     484
Glu Gln Arg Lys His Leu Ser Ser Ser Ser Arg Ala Ser His Gln Glu
                145                 150                 155

aag gaa cag tat cga ctg agt ggt ggc agc cat tat aac agc cag aaa     532
Lys Glu Gln Tyr Arg Leu Ser Gly Gly Ser His Tyr Asn Ser Gln Lys
            160                 165                 170

aca ctt tct acg tct tca att caa aat gaa atc cca aag aaa aaa tcc     580
Thr Leu Ser Thr Ser Ser Ile Gln Asn Glu Ile Pro Lys Lys Lys Ser
        175                 180                 185

aag ttt gag tca atc aca act aat gga gac agc ttt tcc cca gac ctg     628
Lys Phe Glu Ser Ile Thr Thr Asn Gly Asp Ser Phe Ser Pro Asp Leu
    190                 195                 200

gct ctg gac tca cca ggc act gac cac ttt gtc atc att gcc cag ctg     676
Ala Leu Asp Ser Pro Gly Thr Asp His Phe Val Ile Ile Ala Gln Leu
205                 210                 215                 220

aag gaa gaa gtg gcc act ttg aag aag atg ctg cat caa aag gat caa     724
Lys Glu Glu Val Ala Thr Leu Lys Lys Met Leu His Gln Lys Asp Gln
                225                 230                 235

atg att tta gag aaa gag aag aag atc aca gag ttg aag gct gat ttt     772
Met Ile Leu Glu Lys Glu Lys Lys Ile Thr Glu Leu Lys Ala Asp Phe
            240                 245                 250
```

```
caa tac caa gaa tct cag atg aga gcc aaa atg aac cag atg gag aaa      820
Gln Tyr Gln Glu Ser Gln Met Arg Ala Lys Met Asn Gln Met Glu Lys
        255                 260                 265

act cac aaa gaa gtc aca gag caa ttg cag gcc aaa aac cga gaa ctc      868
Thr His Lys Glu Val Thr Glu Gln Leu Gln Ala Lys Asn Arg Glu Leu
    270                 275                 280

ctg aag cag gca gct gcc ttg tcc aag agc aag aag tca gag aag tca      916
Leu Lys Gln Ala Ala Ala Leu Ser Lys Ser Lys Lys Ser Glu Lys Ser
285                 290                 295                 300

gga gct ata act tct cca tga gagaccataa ggaggcttcc agccacagca         967
Gly Ala Ile Thr Ser Pro
                305

aaggggtttc ctgggttagg gttggtggcc tggctgttat ctgggaattg cccacgctcc   1027

cgggaagggc ctgtcccagt cggctctgcc ctaccgccgc agcgtcccca cctggctgaa   1087

gctgacgtcc gacgacgtga aggagcagat ctacaaactg gccaagaagg gtctgactcc   1147

ctcgcagatc ggtgtgatcc tgagagactc ccatggtgtt gcacaagtac gttttgtgac   1207

aggcaataaa atcttgagaa ttcttaagtc caagggactt gcacctgatc tccctgagga   1267

tctgtaccat ttgattaaga aagctgttgc tgttcgaaag catcttgaga ggaacagaaa   1327

ggataaggat gccaaattcc gactgattct gattgagagc cgtattcacc gattggctcg   1387

atattataag accaaaagag ttctccctcc caattggaaa tacgagtcat ccacagcctc   1447

tgccctggtc gcataaattt ggctatgtac tcaagcaata aaatcattgt ctactagaaa   1507

a                                                                   1508


<210> SEQ ID NO 2
<211> LENGTH: 306
<212> TYPE: PRT
<213> ORGANISM: Canis familiaris

<400> SEQUENCE: 2

Met Ala Ala Leu Tyr Ala Cys Thr Lys Cys His Gln Arg Phe Pro Phe
1               5                   10                  15

Glu Ala Leu Ser Gln Gly Gln Gln Leu Cys Lys Glu Cys Arg Ile Ala
            20                  25                  30

His Pro Val Val Lys Cys Thr Tyr Cys Arg Thr Glu Tyr Gln Gln Glu
        35                  40                  45

Ser Lys Thr Asn Thr Ile Cys Lys Lys Cys Ala Gln Asn Val Gln Leu
    50                  55                  60

Tyr Gly Thr Pro Lys Pro Cys Gln Tyr Cys Asn Ile Ile Ala Ala Phe
65                  70                  75                  80

Ile Gly Asn Lys Cys Gln Arg Cys Thr Asn Ser Glu Lys Lys Tyr Gly
                85                  90                  95

Pro Pro Tyr Ser Cys Glu Gln Cys Lys Gln Gln Cys Ala Phe Asp Arg
            100                 105                 110

Lys Asp Asp Arg Lys Lys Val Asp Gly Lys Leu Leu Cys Trp Leu Cys
        115                 120                 125

Thr Leu Ser Tyr Lys Arg Val Leu Gln Lys Thr Lys Glu Gln Arg Lys
    130                 135                 140

His Leu Ser Ser Ser Ser Arg Ala Ser His Gln Glu Lys Glu Gln Tyr
145                 150                 155                 160

Arg Leu Ser Gly Gly Ser His Tyr Asn Ser Gln Lys Thr Leu Ser Thr
                165                 170                 175

Ser Ser Ile Gln Asn Glu Ile Pro Lys Lys Lys Ser Lys Phe Glu Ser
```

```
            180                 185                 190

Ile Thr Thr Asn Gly Asp Ser Phe Ser Pro Asp Leu Ala Leu Asp Ser
        195                 200                 205

Pro Gly Thr Asp His Phe Val Ile Ile Ala Gln Leu Lys Glu Glu Val
    210                 215                 220

Ala Thr Leu Lys Lys Met Leu His Gln Lys Asp Gln Met Ile Leu Glu
225                 230                 235                 240

Lys Glu Lys Lys Ile Thr Glu Leu Lys Ala Asp Phe Gln Tyr Gln Glu
                245                 250                 255

Ser Gln Met Arg Ala Lys Met Asn Gln Met Glu Lys Thr His Lys Glu
            260                 265                 270

Val Thr Glu Gln Leu Gln Ala Lys Asn Arg Glu Leu Leu Lys Gln Ala
        275                 280                 285

Ala Ala Leu Ser Lys Ser Lys Lys Ser Glu Lys Ser Gly Ala Ile Thr
    290                 295                 300

Ser Pro
305


<210> SEQ ID NO 3
<211> LENGTH: 2161
<212> TYPE: DNA
<213> ORGANISM: Homo sapiens
<220> FEATURE:
<221> NAME/KEY: CDS
<222> LOCATION: (103)..(1026)

<400> SEQUENCE: 3

gccgcagcca gcagcctgca gccgccgccg ggttgtgcct cagactgtca gataaatcgg      60

cgggccgggc cggcgggtcg gtgagcgcgg cccgggccgg ac atg gcg gcg ctc       114
                                               Met Ala Ala Leu
                                               1

tac gcc tgc acc aag tgc cac cag cgc ttc ccc ttc gag gcg ctg tct      162
Tyr Ala Cys Thr Lys Cys His Gln Arg Phe Pro Phe Glu Ala Leu Ser
5                   10                  15                  20

cag ggg cag cag ctg tgc aag gaa tgt cgg att gca cac cct gtt gtg      210
Gln Gly Gln Gln Leu Cys Lys Glu Cys Arg Ile Ala His Pro Val Val
                25                  30                  35

aag tgc acc tac tgc agg act gag tac cag cag gag agt aaa acc aat      258
Lys Cys Thr Tyr Cys Arg Thr Glu Tyr Gln Gln Glu Ser Lys Thr Asn
            40                  45                  50

aca ata tgc aag aaa tgt gct cag aac gtg cag ttg tat gga acg ccc      306
Thr Ile Cys Lys Lys Cys Ala Gln Asn Val Gln Leu Tyr Gly Thr Pro
        55                  60                  65

aaa cct tgt cag tat tgc aac ata att gca gca ttt att ggg aat aaa      354
Lys Pro Cys Gln Tyr Cys Asn Ile Ile Ala Ala Phe Ile Gly Asn Lys
    70                  75                  80

tgc cag cgc tgc aca aat tca gaa aag aag tat gga cca ccc tat tct      402
Cys Gln Arg Cys Thr Asn Ser Glu Lys Lys Tyr Gly Pro Pro Tyr Ser
85                  90                  95                  100

tgt gaa cag tgc aag cag cag tgt gca ttt gac agg aaa gat gat aga      450
Cys Glu Gln Cys Lys Gln Gln Cys Ala Phe Asp Arg Lys Asp Asp Arg
                105                 110                 115

aag aag gta gat ggg aaa ttg ctg tgc tgg ctg tgc aca ctt tca tac      498
Lys Lys Val Asp Gly Lys Leu Leu Cys Trp Leu Cys Thr Leu Ser Tyr
            120                 125                 130

aaa cgg gtc ctt cag aag acc aaa gag cag agg aaa cac ctg agt agc      546
Lys Arg Val Leu Gln Lys Thr Lys Glu Gln Arg Lys His Leu Ser Ser
        135                 140                 145
```

-continued

```
tct tct cgt gct ggc cac cag gag aag gag cag tat agt cgc ctg agt      594
Ser Ser Arg Ala Gly His Gln Glu Lys Glu Gln Tyr Ser Arg Leu Ser
    150                 155                 160

ggt ggt ggc cat tat aac agc cag aaa aca ctt tct aca tct tca att      642
Gly Gly Gly His Tyr Asn Ser Gln Lys Thr Leu Ser Thr Ser Ser Ile
165                 170                 175                 180

caa aat gaa atc cca aag aaa aag tcc aag ttt gag tca atc aca act      690
Gln Asn Glu Ile Pro Lys Lys Lys Ser Lys Phe Glu Ser Ile Thr Thr
                185                 190                 195

aat gga gac agc ttc tcc cca gac ctg gct ctg gac tca cca ggc act      738
Asn Gly Asp Ser Phe Ser Pro Asp Leu Ala Leu Asp Ser Pro Gly Thr
            200                 205                 210

gac cac ttt gtc atc att gcc caa ctg aag gaa gaa gtg gct acc ctg      786
Asp His Phe Val Ile Ile Ala Gln Leu Lys Glu Glu Val Ala Thr Leu
        215                 220                 225

aag aag atg ttg cat caa aag gat caa atg att tta gag aaa gag aag      834
Lys Lys Met Leu His Gln Lys Asp Gln Met Ile Leu Glu Lys Glu Lys
    230                 235                 240

aag att aca gag ttg aag gct gat ttt cag tac cag gaa tcg cag atg      882
Lys Ile Thr Glu Leu Lys Ala Asp Phe Gln Tyr Gln Glu Ser Gln Met
245                 250                 255                 260

aga gcc aaa atg aac cag atg gag aaa acc cac aaa gaa gtc aca gaa      930
Arg Ala Lys Met Asn Gln Met Glu Lys Thr His Lys Glu Val Thr Glu
                265                 270                 275

caa ctg cag gcc aaa aac cga gag ctc ctg aag cag gca gct gct ttg      978
Gln Leu Gln Ala Lys Asn Arg Glu Leu Leu Lys Gln Ala Ala Ala Leu
            280                 285                 290

tcc aag agc aag aag tca gag aag tca gga gct ata acc tct cca tga     1026
Ser Lys Ser Lys Lys Ser Glu Lys Ser Gly Ala Ile Thr Ser Pro
        295                 300                 305

cagacctcaa ggaggctccc tagcaacagc aaatggagtt gtccagggtt agggttggag   1086

acctggctgt tctgtgggaa ttgcaagctt tcttaagaaa tctctatttt attacagtta   1146

tccttctttg tgcgattgca gtgggctgaa tggaaacacc tggtttgtgc tgtgttagac   1206

tgcatgcttg agtgtttggg atttcaagct cgctctcttt ctctcactat taggactttt   1266

ctttttcttc ttcctcttct ctctattttg gttctattct tttttttct tttttctttt    1326

ttttttttt ttttttttg tggtggtcac tgctcagtgt aatgtgcaga atgatttgtt     1386

ttttgttttt ttttttttt tttggtcctt cattgcatcc tgccataccc atgagcaaac    1446

agtttggcat taattatata tcactgccac cctctgaact ttgaaaactg ccatcttcag   1506

acttggtata atggaagagg ctttctctct ccaataaacc ttttgcttca gggtatactc   1566

ttcggttttt ttccagatgt attatgtatg aactttgtac tatgtatagc cagagtttta   1626

tttatttttt aaaaaagaaa ctttttcttg ataaaggaat aatggtggtc tagctagttc   1686

ttgtaaaagt gatgcctctt gaaaaaaaac agtcctattc actagctttt agtaaaagaa   1746

tcagatcttt tctttcttgt taccttggag tcttaaaaac tgattgctaa ggtgaaacaa   1806

ttcaatgcat aagtatggag ctaagtgcct tttggaggat ttcttggaag agcatttatg   1866

gagatactta agggaggtag caaagatttg aaccgtctgt ctttttaagt aagggcagaa   1926

agcaaggttg tccaggttgt actggacact tctctcccca cccctttcct gattgtttta   1986

tgtgattgat tttaaattct cacactgcca cttctttaaa aaataaaatc ctttatttgc   2046

ttaaaaaaaa aaaaaaaaaa aaaaaaaaaa aaaaaaaaaa aaaaaaaaaa aaaaaaaaaa   2106

aaaaaaaaaa aaaaaaaaaa aaaaaaaaaa aaaaaaaaaa aaaaaaaaaa aaaaa        2161
```

```
<210> SEQ ID NO 4
<211> LENGTH: 307
<212> TYPE: PRT
<213> ORGANISM: Homo sapiens

<400> SEQUENCE: 4

Met Ala Ala Leu Tyr Ala Cys Thr Lys Cys His Gln Arg Phe Pro Phe
1               5                   10                  15

Glu Ala Leu Ser Gln Gly Gln Gln Leu Cys Lys Glu Cys Arg Ile Ala
            20                  25                  30

His Pro Val Val Lys Cys Thr Tyr Cys Arg Thr Glu Tyr Gln Gln Glu
        35                  40                  45

Ser Lys Thr Asn Thr Ile Cys Lys Lys Cys Ala Gln Asn Val Gln Leu
    50                  55                  60

Tyr Gly Thr Pro Lys Pro Cys Gln Tyr Cys Asn Ile Ile Ala Ala Phe
65                  70                  75                  80

Ile Gly Asn Lys Cys Gln Arg Cys Thr Asn Ser Glu Lys Lys Tyr Gly
                85                  90                  95

Pro Pro Tyr Ser Cys Glu Gln Cys Lys Gln Gln Cys Ala Phe Asp Arg
            100                 105                 110

Lys Asp Asp Arg Lys Lys Val Asp Gly Lys Leu Leu Cys Trp Leu Cys
        115                 120                 125

Thr Leu Ser Tyr Lys Arg Val Leu Gln Lys Thr Lys Glu Gln Arg Lys
    130                 135                 140

His Leu Ser Ser Ser Ser Arg Ala Gly His Gln Glu Lys Glu Gln Tyr
145                 150                 155                 160

Ser Arg Leu Ser Gly Gly Gly His Tyr Asn Ser Gln Lys Thr Leu Ser
                165                 170                 175

Thr Ser Ser Ile Gln Asn Glu Ile Pro Lys Lys Lys Ser Lys Phe Glu
            180                 185                 190

Ser Ile Thr Thr Asn Gly Asp Ser Phe Ser Pro Asp Leu Ala Leu Asp
        195                 200                 205

Ser Pro Gly Thr Asp His Phe Val Ile Ile Ala Gln Leu Lys Glu Glu
    210                 215                 220

Val Ala Thr Leu Lys Lys Met Leu His Gln Lys Asp Gln Met Ile Leu
225                 230                 235                 240

Glu Lys Glu Lys Lys Ile Thr Glu Leu Lys Ala Asp Phe Gln Tyr Gln
                245                 250                 255

Glu Ser Gln Met Arg Ala Lys Met Asn Gln Met Glu Lys Thr His Lys
            260                 265                 270

Glu Val Thr Glu Gln Leu Gln Ala Lys Asn Arg Glu Leu Leu Lys Gln
        275                 280                 285

Ala Ala Ala Leu Ser Lys Ser Lys Lys Ser Glu Lys Ser Gly Ala Ile
    290                 295                 300

Thr Ser Pro
305


<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5

aattaaccct cactaaaggg                                                20
```

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
taatacgact cactatagg 19

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
agctgtgcaa ggaatgtc 18

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
ccattagttg tgattgac 18

<210> SEQ ID NO 9
<211> LENGTH: 18
<212> TYPE: DNA
<213> ORGANISM: Artificial Sequence
<220> FEATURE:
<223> OTHER INFORMATION: Synthetic GAPDH primer

<400> SEQUENCE: 9
gggctgcttt taactctg 18

<210> SEQ ID NO 10
<211> LENGTH: 18
<212> TYPE: DNA
<213> ORGANISM: Artificial Sequence
<220> FEATURE:
<223> OTHER INFORMATION: Synthetic GAPDH primer

<400> SEQUENCE: 10
ccaggaaatg agcttgac 18

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
atcatatggc ggcgctctac gc 22

<210> SEQ ID NO 12
<211> LENGTH: 25
<212> TYPE: DNA
<213> ORGANISM: Artificial Sequence
<220> FEATURE:
<223> OTHER INFORMATION: Synthetic primer

```
<400> SEQUENCE: 12

cgctcgagtg gagaagttat agctc                                          25


<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13

gatatcatgg cggcgctcta cgc                                            23


<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14

gaattctcat ggagaggtta tagc                                           24


<210> SEQ ID NO 15
<211> LENGTH: 2326
<212> TYPE: DNA
<213> ORGANISM: Canis familiaris
<220> FEATURE:
<221> NAME/KEY: CDS
<222> LOCATION: (62)..(1894)

<400> SEQUENCE: 15

cagcgcctcg gacatcggag ctgccgctgc cgaacacggg cccgcaacac aggtaatcag      60

t atg cat ttc caa agc ttt tgg cta tgt ctg gga ctt ctg ttc atc tca     109
  Met His Phe Gln Ser Phe Trp Leu Cys Leu Gly Leu Leu Phe Ile Ser
  1               5                   10                  15

gtt aat gca gaa ttt atg gat gat gat gtt gag atg gaa gat ttt gat      157
Val Asn Ala Glu Phe Met Asp Asp Asp Val Glu Met Glu Asp Phe Asp
            20                  25                  30

gaa aat tca gaa gag att gat gtt aat gaa ggt gaa ctc ccc tca gag      205
Glu Asn Ser Glu Glu Ile Asp Val Asn Glu Gly Glu Leu Pro Ser Glu
        35                  40                  45

att aat tat aag aca cct cag cct atg gga gaa gta tat ttt aca gaa      253
Ile Asn Tyr Lys Thr Pro Gln Pro Met Gly Glu Val Tyr Phe Thr Glu
    50                  55                  60

act ttt gat agt gga agg ttg gct ggg tgg gtc tta tca aaa gca aag      301
Thr Phe Asp Ser Gly Arg Leu Ala Gly Trp Val Leu Ser Lys Ala Lys
65                  70                  75                  80

aaa gat gat aca gat gca gag att tcc ata tat gat gga aga tgg gaa      349
Lys Asp Asp Thr Asp Ala Glu Ile Ser Ile Tyr Asp Gly Arg Trp Glu
                85                  90                  95

ata gaa gaa ttg aaa gaa aac cga gtg cct ggt gac aga ggg ctg gta      397
Ile Glu Glu Leu Lys Glu Asn Arg Val Pro Gly Asp Arg Gly Leu Val
            100                 105                 110

ctg aaa tct aga gca aag cat cat gca ata gct gct gta tta gca aaa      445
Leu Lys Ser Arg Ala Lys His His Ala Ile Ala Ala Val Leu Ala Lys
        115                 120                 125

ccc ttc att ttt gct gac aaa ccc ttg atc gtt caa tat gaa gta aat      493
Pro Phe Ile Phe Ala Asp Lys Pro Leu Ile Val Gln Tyr Glu Val Asn
    130                 135                 140

ttt caa gat ggt att gat tgt gga ggt gca tac att aaa ctc cta gca      541
```

```
Phe Gln Asp Gly Ile Asp Cys Gly Gly Ala Tyr Ile Lys Leu Leu Ala
145                 150                 155                 160

gac act gat ggt ttg aat ctg gaa aac ttt tat gat aaa aca tcc tat      589
Asp Thr Asp Gly Leu Asn Leu Glu Asn Phe Tyr Asp Lys Thr Ser Tyr
                165                 170                 175

acc att atg ttt gga cca gat aaa tgt gga gaa gat tat aaa ctt cat      637
Thr Ile Met Phe Gly Pro Asp Lys Cys Gly Glu Asp Tyr Lys Leu His
            180                 185                 190

ttc atc ttc aga cac aaa cat cct aaa act gga gtt ttt gaa gag aaa      685
Phe Ile Phe Arg His Lys His Pro Lys Thr Gly Val Phe Glu Glu Lys
        195                 200                 205

cat gcc aaa cct cca gat gta gac ctt aaa aag ttc ttt aca gac agg      733
His Ala Lys Pro Pro Asp Val Asp Leu Lys Lys Phe Phe Thr Asp Arg
    210                 215                 220

aag act cat ctt tat acc ctt gtg atg aat cca gat gac aca ttt gaa      781
Lys Thr His Leu Tyr Thr Leu Val Met Asn Pro Asp Asp Thr Phe Glu
225                 230                 235                 240

gta cta att gat caa gta gtt gta aac caa gga agc ctc cta gaa gat      829
Val Leu Ile Asp Gln Val Val Val Asn Gln Gly Ser Leu Leu Glu Asp
                245                 250                 255

gtg gtt cct cct atc aat cct ccc aaa gaa att gaa gac ccc agt gat      877
Val Val Pro Pro Ile Asn Pro Pro Lys Glu Ile Glu Asp Pro Ser Asp
            260                 265                 270

aaa aag cct gat gaa tgg gat gaa aga gca aaa atc cct gat cct tct      925
Lys Lys Pro Asp Glu Trp Asp Glu Arg Ala Lys Ile Pro Asp Pro Ser
        275                 280                 285

gct gtc aaa cca gaa gac tgg gat gaa agt gaa cct gcc caa ata gaa      973
Ala Val Lys Pro Glu Asp Trp Asp Glu Ser Glu Pro Ala Gln Ile Glu
    290                 295                 300

gat tta agt gtt gtt aaa cct gat ggc tgg ctt gat gat gaa cca aaa     1021
Asp Leu Ser Val Val Lys Pro Asp Gly Trp Leu Asp Asp Glu Pro Lys
305                 310                 315                 320

ttt att cca gat cca aat gct gaa aaa cct gat gac tgg aat gaa gac     1069
Phe Ile Pro Asp Pro Asn Ala Glu Lys Pro Asp Asp Trp Asn Glu Asp
                325                 330                 335

atg gat gga gaa tgg gag gca cct cgt att tct aat cca gca tgt cga     1117
Met Asp Gly Glu Trp Glu Ala Pro Arg Ile Ser Asn Pro Ala Cys Arg
            340                 345                 350

att ggg tgt ggt gag tgg tca cct ccc atg ata gat aat ccc aaa tac     1165
Ile Gly Cys Gly Glu Trp Ser Pro Pro Met Ile Asp Asn Pro Lys Tyr
        355                 360                 365

aaa gga gta tgg aga cct cca atg ata gat aat cct aac tac cag gga     1213
Lys Gly Val Trp Arg Pro Pro Met Ile Asp Asn Pro Asn Tyr Gln Gly
    370                 375                 380

atc tgg agt cct cga aaa atc ccg aat cca gat tat ttt gaa gat gat     1261
Ile Trp Ser Pro Arg Lys Ile Pro Asn Pro Asp Tyr Phe Glu Asp Asp
385                 390                 395                 400

cat cca ttt ctt ctg act tct ttc cgt gct ctt ggt tta gag ctt tgg     1309
His Pro Phe Leu Leu Thr Ser Phe Arg Ala Leu Gly Leu Glu Leu Trp
                405                 410                 415

tct atg acc tct aat att tac ttt gat aat ttt att atc tgc tcg gaa     1357
Ser Met Thr Ser Asn Ile Tyr Phe Asp Asn Phe Ile Ile Cys Ser Glu
            420                 425                 430

aag gaa aca gca gat cgc tgg gct gca gat ggg tgg gga gtg aag ata     1405
Lys Glu Thr Ala Asp Arg Trp Ala Ala Asp Gly Trp Gly Val Lys Ile
        435                 440                 445

ctg gta gca aat gct aac gag cct ggt ata ttt aaa cag tta atg gca     1453
Leu Val Ala Asn Ala Asn Glu Pro Gly Ile Phe Lys Gln Leu Met Ala
    450                 455                 460
```

```
gct gct gaa gag cgc cca tgg ctt tgg ctc att tat ttt gtg aca gca      1501
Ala Ala Glu Glu Arg Pro Trp Leu Trp Leu Ile Tyr Phe Val Thr Ala
465                 470                 475                 480

ggg ctt cca ata gca tta att gct tca ttt tgt tgg cca aga aaa gtc      1549
Gly Leu Pro Ile Ala Leu Ile Ala Ser Phe Cys Trp Pro Arg Lys Val
                485                 490                 495

aag aaa aaa tat gaa gat tca gag tat aaa aag act gac ata tgc aag      1597
Lys Lys Lys Tyr Glu Asp Ser Glu Tyr Lys Lys Thr Asp Ile Cys Lys
            500                 505                 510

cca caa aca aag gga gca cta gag caa gaa gtg aag gaa aag aaa gct      1645
Pro Gln Thr Lys Gly Ala Leu Glu Gln Glu Val Lys Glu Lys Lys Ala
        515                 520                 525

gcc ctg gag aaa cca gta gac ttg gaa gaa gaa aaa aag caa agt gat      1693
Ala Leu Glu Lys Pro Val Asp Leu Glu Glu Glu Lys Lys Gln Ser Asp
    530                 535                 540

ggt gaa act gtt gaa aaa gaa gag gaa gct gaa cct gag gaa aag agt      1741
Gly Glu Thr Val Glu Lys Glu Glu Glu Ala Glu Pro Glu Glu Lys Ser
545                 550                 555                 560

gaa gaa gaa att gaa atc ata gaa gga caa gaa gaa ggt aat aaa tca      1789
Glu Glu Glu Ile Glu Ile Ile Glu Gly Gln Glu Glu Gly Asn Lys Ser
                565                 570                 575

aat aag tct gga tca gag gat gag atg aag gaa gcg gat gag agc aca      1837
Asn Lys Ser Gly Ser Glu Asp Glu Met Lys Glu Ala Asp Glu Ser Thr
            580                 585                 590

gga tct gga gat ggg cca gtg aag tca gtg cgc aaa aga aga gta cga      1885
Gly Ser Gly Asp Gly Pro Val Lys Ser Val Arg Lys Arg Arg Val Arg
        595                 600                 605

aag gaa taa actatattca agtattttta attcctgagc gagatatttg              1934
Lys Glu
    610

gcattctaaa atcagtgtgc cagagctgaa cttgagtcag tctgcacatg tttctaatat    1994

ctagcaatgt tattctttca gacacttatt ttagtctttc ttttcaggaa aaaaaaaact    2054

ttcaagttac ctggtctttg gatttagagt aaaaaagagg ggcatgttac gtatcagatt    2114

taagagacta ataccattag aagttaccaa gttttaatag ttggagaaag ttttggtttg    2174

tacagagaaa aataatatgc agcagctttg ctgctgttgg aaaatcagtt attggaattt    2234

ccccttaaac agctatacaa caatattact ggtagttcta taataaaaat gagagtgtgt    2294

tctgttgtac agagctaact gcaaaaaaaa aa                                  2326


<210> SEQ ID NO 16
<211> LENGTH: 610
<212> TYPE: PRT
<213> ORGANISM: Canis familiaris

<400> SEQUENCE: 16

Met His Phe Gln Ser Phe Trp Leu Cys Leu Gly Leu Leu Phe Ile Ser
1               5                   10                  15

Val Asn Ala Glu Phe Met Asp Asp Asp Val Glu Met Glu Asp Phe Asp
            20                  25                  30

Glu Asn Ser Glu Glu Ile Asp Val Asn Glu Gly Glu Leu Pro Ser Glu
        35                  40                  45

Ile Asn Tyr Lys Thr Pro Gln Pro Met Gly Glu Val Tyr Phe Thr Glu
    50                  55                  60

Thr Phe Asp Ser Gly Arg Leu Ala Gly Trp Val Leu Ser Lys Ala Lys
65                  70                  75                  80

Lys Asp Asp Thr Asp Ala Glu Ile Ser Ile Tyr Asp Gly Arg Trp Glu
                85                  90                  95
```

```
Ile Glu Glu Leu Lys Glu Asn Arg Val Pro Gly Asp Arg Gly Leu Val
            100                 105                 110

Leu Lys Ser Arg Ala Lys His His Ala Ile Ala Ala Val Leu Ala Lys
        115                 120                 125

Pro Phe Ile Phe Ala Asp Lys Pro Leu Ile Val Gln Tyr Glu Val Asn
    130                 135                 140

Phe Gln Asp Gly Ile Asp Cys Gly Gly Ala Tyr Ile Lys Leu Leu Ala
145                 150                 155                 160

Asp Thr Asp Gly Leu Asn Leu Glu Asn Phe Tyr Asp Lys Thr Ser Tyr
                165                 170                 175

Thr Ile Met Phe Gly Pro Asp Lys Cys Gly Glu Asp Tyr Lys Leu His
            180                 185                 190

Phe Ile Phe Arg His Lys His Pro Lys Thr Gly Val Phe Glu Glu Lys
        195                 200                 205

His Ala Lys Pro Pro Asp Val Asp Leu Lys Lys Phe Phe Thr Asp Arg
    210                 215                 220

Lys Thr His Leu Tyr Thr Leu Val Met Asn Pro Asp Asp Thr Phe Glu
225                 230                 235                 240

Val Leu Ile Asp Gln Val Val Val Asn Gln Gly Ser Leu Leu Glu Asp
                245                 250                 255

Val Val Pro Pro Ile Asn Pro Pro Lys Glu Ile Glu Asp Pro Ser Asp
            260                 265                 270

Lys Lys Pro Asp Glu Trp Asp Glu Arg Ala Lys Ile Pro Asp Pro Ser
        275                 280                 285

Ala Val Lys Pro Glu Asp Trp Asp Glu Ser Glu Pro Ala Gln Ile Glu
    290                 295                 300

Asp Leu Ser Val Val Lys Pro Asp Gly Trp Leu Asp Asp Glu Pro Lys
305                 310                 315                 320

Phe Ile Pro Asp Pro Asn Ala Glu Lys Pro Asp Asp Trp Asn Glu Asp
                325                 330                 335

Met Asp Gly Glu Trp Glu Ala Pro Arg Ile Ser Asn Pro Ala Cys Arg
            340                 345                 350

Ile Gly Cys Gly Glu Trp Ser Pro Pro Met Ile Asp Asn Pro Lys Tyr
        355                 360                 365

Lys Gly Val Trp Arg Pro Pro Met Ile Asp Asn Pro Asn Tyr Gln Gly
    370                 375                 380

Ile Trp Ser Pro Arg Lys Ile Pro Asn Pro Asp Tyr Phe Glu Asp Asp
385                 390                 395                 400

His Pro Phe Leu Leu Thr Ser Phe Arg Ala Leu Gly Leu Glu Leu Trp
                405                 410                 415

Ser Met Thr Ser Asn Ile Tyr Phe Asp Asn Phe Ile Ile Cys Ser Glu
            420                 425                 430

Lys Glu Thr Ala Asp Arg Trp Ala Ala Asp Gly Trp Gly Val Lys Ile
        435                 440                 445

Leu Val Ala Asn Ala Asn Glu Pro Gly Ile Phe Lys Gln Leu Met Ala
    450                 455                 460

Ala Ala Glu Glu Arg Pro Trp Leu Trp Leu Ile Tyr Phe Val Thr Ala
465                 470                 475                 480

Gly Leu Pro Ile Ala Leu Ile Ala Ser Phe Cys Trp Pro Arg Lys Val
                485                 490                 495

Lys Lys Lys Tyr Glu Asp Ser Glu Tyr Lys Lys Thr Asp Ile Cys Lys
            500                 505                 510
```

```
Pro Gln Thr Lys Gly Ala Leu Glu Gln Glu Val Lys Glu Lys Lys Ala
        515                 520                 525

Ala Leu Glu Lys Pro Val Asp Leu Glu Glu Glu Lys Lys Gln Ser Asp
    530                 535                 540

Gly Glu Thr Val Glu Lys Glu Glu Glu Ala Glu Pro Glu Glu Lys Ser
545                 550                 555                 560

Glu Glu Glu Ile Glu Ile Ile Glu Gly Gln Glu Glu Gly Asn Lys Ser
                565                 570                 575

Asn Lys Ser Gly Ser Glu Asp Glu Met Lys Glu Ala Asp Glu Ser Thr
            580                 585                 590

Gly Ser Gly Asp Gly Pro Val Lys Ser Val Arg Lys Arg Arg Val Arg
        595                 600                 605

Lys Glu
    610


<210> SEQ ID NO 17
<211> LENGTH: 2710
<212> TYPE: DNA
<213> ORGANISM: Homo sapiens
<220> FEATURE:
<221> NAME/KEY: CDS
<222> LOCATION: (102)..(1934)

<400> SEQUENCE: 17

cgccggcggg actggtctga agagacgcgg ggacaaagtg gcaacgactt ggacatctga      60

gctgtcactg ccgaaaacag gccgcaagag agataatcaa t atg cat ttc caa gcc    116
                                              Met His Phe Gln Ala
                                              1               5

ttt tgg cta tgt ttg ggt ctt ctg ttc atc tca att aat gca gaa ttt      164
Phe Trp Leu Cys Leu Gly Leu Leu Phe Ile Ser Ile Asn Ala Glu Phe
                10                  15                  20

atg gat gat gat gtt gag acg gaa gac ttt gaa gaa aat tca gaa gaa      212
Met Asp Asp Asp Val Glu Thr Glu Asp Phe Glu Glu Asn Ser Glu Glu
            25                  30                  35

att gat gtt aat gaa agt gaa ctt tcc tca gag att aaa tat aag aca      260
Ile Asp Val Asn Glu Ser Glu Leu Ser Ser Glu Ile Lys Tyr Lys Thr
        40                  45                  50

cct caa cct ata gga gaa gta tat ttt gca gaa act ttt gat agt gga      308
Pro Gln Pro Ile Gly Glu Val Tyr Phe Ala Glu Thr Phe Asp Ser Gly
    55                  60                  65

agg ttg gct gga tgg gtc tta tca aaa gca aag aaa gat gac atg gat      356
Arg Leu Ala Gly Trp Val Leu Ser Lys Ala Lys Lys Asp Asp Met Asp
70                  75                  80                  85

gag gaa att tca ata tac gat gga aga tgg gaa att gaa gag ttg aaa      404
Glu Glu Ile Ser Ile Tyr Asp Gly Arg Trp Glu Ile Glu Glu Leu Lys
                90                  95                  100

gaa aac cag gta cct ggt gac aga gga ctg gta tta aaa tct aga gca      452
Glu Asn Gln Val Pro Gly Asp Arg Gly Leu Val Leu Lys Ser Arg Ala
            105                 110                 115

aag cat cat gca ata tct gct gta tta gca aaa cca ttc att ttt gct      500
Lys His His Ala Ile Ser Ala Val Leu Ala Lys Pro Phe Ile Phe Ala
        120                 125                 130

gat aaa ccc ttg ata gtt caa tat gaa gta aat ttt caa gat ggt att      548
Asp Lys Pro Leu Ile Val Gln Tyr Glu Val Asn Phe Gln Asp Gly Ile
    135                 140                 145

gat tgt gga ggt gca tac att aaa ctc cta gca gac act gat gat ttg      596
Asp Cys Gly Gly Ala Tyr Ile Lys Leu Leu Ala Asp Thr Asp Asp Leu
150                 155                 160                 165

att ctg gaa aac ttt tat gat aaa aca tcc tat atc att atg ttt gga      644
```

```
Ile Leu Glu Asn Phe Tyr Asp Lys Thr Ser Tyr Ile Ile Met Phe Gly
                170                 175                 180

cca gat aaa tgt gga gaa gat tat aaa ctt cat ttt atc ttc aga cat      692
Pro Asp Lys Cys Gly Glu Asp Tyr Lys Leu His Phe Ile Phe Arg His
            185                 190                 195

aaa cat ccc aaa act gga gtt ttc gaa gag aaa cat gcc aaa cct cca      740
Lys His Pro Lys Thr Gly Val Phe Glu Glu Lys His Ala Lys Pro Pro
        200                 205                 210

gat gta gac ctt aaa aag ttc ttt aca gac agg aag act cat ctt tat      788
Asp Val Asp Leu Lys Lys Phe Phe Thr Asp Arg Lys Thr His Leu Tyr
    215                 220                 225

acc ctt gtg atg aat cca gat gac aca ttt gag gtg tta gtt gat caa      836
Thr Leu Val Met Asn Pro Asp Asp Thr Phe Glu Val Leu Val Asp Gln
230                 235                 240                 245

aca gtt gta aac aaa gga agc ctc cta gag gat gtg gtt cct cct atc      884
Thr Val Val Asn Lys Gly Ser Leu Leu Glu Asp Val Val Pro Pro Ile
                250                 255                 260

aaa cct ccc aaa gaa att gaa gat ccc aat gat aaa aaa cct gag gaa      932
Lys Pro Pro Lys Glu Ile Glu Asp Pro Asn Asp Lys Lys Pro Glu Glu
            265                 270                 275

tgg gat gaa aga gca aaa att cct gat cct tct gcc gtc aaa cca gaa      980
Trp Asp Glu Arg Ala Lys Ile Pro Asp Pro Ser Ala Val Lys Pro Glu
        280                 285                 290

gac tgg gat gaa agt gaa cct gcc caa ata gaa gat tca agt gtt gtt     1028
Asp Trp Asp Glu Ser Glu Pro Ala Gln Ile Glu Asp Ser Ser Val Val
    295                 300                 305

aaa cct gct ggc tgg ctt gat gat gaa cca aaa ttt atc cct gat cct     1076
Lys Pro Ala Gly Trp Leu Asp Asp Glu Pro Lys Phe Ile Pro Asp Pro
310                 315                 320                 325

aat gct gaa aaa cct gat gac tgg aat gaa gac acg gat gga gaa tgg     1124
Asn Ala Glu Lys Pro Asp Asp Trp Asn Glu Asp Thr Asp Gly Glu Trp
                330                 335                 340

gag gca cct cag att ctt aat cca gca tgt cgg att ggg tgt ggt gag     1172
Glu Ala Pro Gln Ile Leu Asn Pro Ala Cys Arg Ile Gly Cys Gly Glu
            345                 350                 355

tgg aaa cct ccc atg ata gat aac cca aaa tac aaa gga gta tgg aga     1220
Trp Lys Pro Pro Met Ile Asp Asn Pro Lys Tyr Lys Gly Val Trp Arg
        360                 365                 370

cct cca ctg gtc gat aat cct aac tat cag gga atc tgg agt cct cga     1268
Pro Pro Leu Val Asp Asn Pro Asn Tyr Gln Gly Ile Trp Ser Pro Arg
    375                 380                 385

aaa att cct aat cca gat tat ttc gaa gat gat cat cca ttt ctt ctg     1316
Lys Ile Pro Asn Pro Asp Tyr Phe Glu Asp Asp His Pro Phe Leu Leu
390                 395                 400                 405

act tct ttc agt gct ctt ggt tta gag ctt tgg tct atg acc tct gat     1364
Thr Ser Phe Ser Ala Leu Gly Leu Glu Leu Trp Ser Met Thr Ser Asp
                410                 415                 420

atc tac ttt gat aat ttt att atc tgt tcg gaa aag gaa gta gca gat     1412
Ile Tyr Phe Asp Asn Phe Ile Ile Cys Ser Glu Lys Glu Val Ala Asp
            425                 430                 435

cac tgg gct gca gat ggt tgg aga tgg aaa ata atg ata gca aat gct     1460
His Trp Ala Ala Asp Gly Trp Arg Trp Lys Ile Met Ile Ala Asn Ala
        440                 445                 450

aat aag cct ggt gta tta aaa cag tta atg gca gct gct gaa ggg cac     1508
Asn Lys Pro Gly Val Leu Lys Gln Leu Met Ala Ala Ala Glu Gly His
    455                 460                 465

cca tgg ctt tgg ttg att tat ctt gtg aca gca gga gtg cca ata gca     1556
Pro Trp Leu Trp Leu Ile Tyr Leu Val Thr Ala Gly Val Pro Ile Ala
470                 475                 480                 485
```

```
tta att act tca ttt tgt tgg cca aga aaa gta aag aaa aaa cat aaa     1604
Leu Ile Thr Ser Phe Cys Trp Pro Arg Lys Val Lys Lys Lys His Lys
                490                 495                 500

gat aca gag tat aaa aaa acc gac ata tgt ata cca caa aca aaa gga     1652
Asp Thr Glu Tyr Lys Lys Thr Asp Ile Cys Ile Pro Gln Thr Lys Gly
            505                 510                 515

gta cta gag caa gaa gaa aag gaa gag aaa gca gcc ctg gaa aaa cca     1700
Val Leu Glu Gln Glu Glu Lys Glu Glu Lys Ala Ala Leu Glu Lys Pro
        520                 525                 530

atg gac ctg gaa gag gaa aaa aag caa aat gat ggt gaa atg ctt gaa     1748
Met Asp Leu Glu Glu Glu Lys Lys Gln Asn Asp Gly Glu Met Leu Glu
    535                 540                 545

aaa gaa gag gaa agt gaa cct gag gaa aag agt gaa gaa gaa att gaa     1796
Lys Glu Glu Glu Ser Glu Pro Glu Glu Lys Ser Glu Glu Glu Ile Glu
550                 555                 560                 565

atc ata gaa ggg caa gaa gaa agt aat caa tca aat aag tct ggg tca     1844
Ile Ile Glu Gly Gln Glu Glu Ser Asn Gln Ser Asn Lys Ser Gly Ser
                570                 575                 580

gag gat gag atg aaa gaa gca gat gag agc aca gga tct gga gat ggg     1892
Glu Asp Glu Met Lys Glu Ala Asp Glu Ser Thr Gly Ser Gly Asp Gly
            585                 590                 595

ccg ata aag tca gta cgc aaa aga aga gta cga aag gac taa             1934
Pro Ile Lys Ser Val Arg Lys Arg Arg Val Arg Lys Asp
        600                 605                 610

actagattga aatattttta attcccgaga ggatgtttgg cattgtaaaa atcagcatgc   1994

cagacctgaa ctttaatcag tctgcacatc ctgtttctaa tatctagcaa cattatattc   2054

tttcagacat ttattttagt ccttcatttc cgaggaaaaa gaagcaactt tgaagttacc   2114

tcatctttga atttagaata aaagtggcac attacatatc ggatctaaga gattaatacc   2174

attagaagtt acacagtttt agttgtttgg agatagtttt ggtttgtaca gaacaaaata   2234

atatgtagca gcttcattgc tattggaaaa atcagttatt ggaatttcca cttaaatggc   2294

tatacaacaa tataactggt agttctataa taaaaatgag catatgttct gttgtgaaga   2354

gctaaatgca ataaagtttc tgtatggttg tttgattcta tcaacaattg aaagtgttgt   2414

atatgaccca catttaccta gtttgtgtca aattatagtt acagtgagtt gtttgcttaa   2474

attatagatt cctttaagga catgccttgt tcataaaatc actggattat attgcagcat   2534

attttacatt tgaatacaag gataatgggt tttatcaaaa caaaatgatg tacagatttt   2594

ttttcaagtt tttatagttg ctttatgcca gagtggttta ccccattcac aaaatttctt   2654

atgcatacat tgctattgaa aataaaattt aaatattttt tcatcctgaa aaaaaa       2710


<210> SEQ ID NO 18
<211> LENGTH: 610
<212> TYPE: PRT
<213> ORGANISM: Homo sapiens

<400> SEQUENCE: 18

Met His Phe Gln Ala Phe Trp Leu Cys Leu Gly Leu Leu Phe Ile Ser
1               5                   10                  15

Ile Asn Ala Glu Phe Met Asp Asp Asp Val Glu Thr Glu Asp Phe Glu
            20                  25                  30

Glu Asn Ser Glu Glu Ile Asp Val Asn Glu Ser Glu Leu Ser Ser Glu
        35                  40                  45

Ile Lys Tyr Lys Thr Pro Gln Pro Ile Gly Glu Val Tyr Phe Ala Glu
    50                  55                  60

Thr Phe Asp Ser Gly Arg Leu Ala Gly Trp Val Leu Ser Lys Ala Lys
```

```
65                  70                  75                  80

Lys Asp Asp Met Asp Glu Glu Ile Ser Ile Tyr Asp Gly Arg Trp Glu
                85                  90                  95

Ile Glu Glu Leu Lys Glu Asn Gln Val Pro Gly Asp Arg Gly Leu Val
            100                 105                 110

Leu Lys Ser Arg Ala Lys His His Ala Ile Ser Ala Val Leu Ala Lys
        115                 120                 125

Pro Phe Ile Phe Ala Asp Lys Pro Leu Ile Val Gln Tyr Glu Val Asn
    130                 135                 140

Phe Gln Asp Gly Ile Asp Cys Gly Gly Ala Tyr Ile Lys Leu Leu Ala
145                 150                 155                 160

Asp Thr Asp Asp Leu Ile Leu Glu Asn Phe Tyr Asp Lys Thr Ser Tyr
                165                 170                 175

Ile Ile Met Phe Gly Pro Asp Lys Cys Gly Glu Asp Tyr Lys Leu His
            180                 185                 190

Phe Ile Phe Arg His Lys His Pro Lys Thr Gly Val Phe Glu Glu Lys
        195                 200                 205

His Ala Lys Pro Pro Asp Val Asp Leu Lys Lys Phe Phe Thr Asp Arg
    210                 215                 220

Lys Thr His Leu Tyr Thr Leu Val Met Asn Pro Asp Asp Thr Phe Glu
225                 230                 235                 240

Val Leu Val Asp Gln Thr Val Val Asn Lys Gly Ser Leu Leu Glu Asp
                245                 250                 255

Val Val Pro Pro Ile Lys Pro Pro Lys Glu Ile Glu Asp Pro Asn Asp
            260                 265                 270

Lys Lys Pro Glu Glu Trp Asp Glu Arg Ala Lys Ile Pro Asp Pro Ser
        275                 280                 285

Ala Val Lys Pro Glu Asp Trp Asp Glu Ser Glu Pro Ala Gln Ile Glu
    290                 295                 300

Asp Ser Ser Val Val Lys Pro Ala Gly Trp Leu Asp Asp Glu Pro Lys
305                 310                 315                 320

Phe Ile Pro Asp Pro Asn Ala Glu Lys Pro Asp Asp Trp Asn Glu Asp
                325                 330                 335

Thr Asp Gly Glu Trp Glu Ala Pro Gln Ile Leu Asn Pro Ala Cys Arg
            340                 345                 350

Ile Gly Cys Gly Glu Trp Lys Pro Pro Met Ile Asp Asn Pro Lys Tyr
        355                 360                 365

Lys Gly Val Trp Arg Pro Pro Leu Val Asp Asn Pro Asn Tyr Gln Gly
    370                 375                 380

Ile Trp Ser Pro Arg Lys Ile Pro Asn Pro Asp Tyr Phe Glu Asp Asp
385                 390                 395                 400

His Pro Phe Leu Leu Thr Ser Phe Ser Ala Leu Gly Leu Glu Leu Trp
                405                 410                 415

Ser Met Thr Ser Asp Ile Tyr Phe Asp Asn Phe Ile Ile Cys Ser Glu
            420                 425                 430

Lys Glu Val Ala Asp His Trp Ala Ala Asp Gly Trp Arg Trp Lys Ile
        435                 440                 445

Met Ile Ala Asn Ala Asn Lys Pro Gly Val Leu Lys Gln Leu Met Ala
    450                 455                 460

Ala Ala Glu Gly His Pro Trp Leu Trp Leu Ile Tyr Leu Val Thr Ala
465                 470                 475                 480

Gly Val Pro Ile Ala Leu Ile Thr Ser Phe Cys Trp Pro Arg Lys Val
                485                 490                 495
```

```
Lys Lys Lys His Lys Asp Thr Glu Tyr Lys Lys Thr Asp Ile Cys Ile
            500                 505                 510

Pro Gln Thr Lys Gly Val Leu Glu Gln Glu Glu Lys Glu Glu Lys Ala
        515                 520                 525

Ala Leu Glu Lys Pro Met Asp Leu Glu Glu Glu Lys Lys Gln Asn Asp
    530                 535                 540

Gly Glu Met Leu Glu Lys Glu Glu Glu Ser Glu Pro Glu Glu Lys Ser
545                 550                 555                 560

Glu Glu Glu Ile Glu Ile Ile Glu Gly Gln Glu Glu Ser Asn Gln Ser
                565                 570                 575

Asn Lys Ser Gly Ser Glu Asp Glu Met Lys Glu Ala Asp Glu Ser Thr
            580                 585                 590

Gly Ser Gly Asp Gly Pro Ile Lys Ser Val Arg Lys Arg Arg Val Arg
        595                 600                 605

Lys Asp
    610


<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19

gtgatgaatc cagatgac                                                     18


<210> SEQ ID NO 20
<211> LENGTH: 18
<212> TYPE: DNA
<213> ORGANISM: Artificial Sequence
<220> FEATURE:
<223> OTHER INFORMATION: Synthetic primer

<400> SEQUENCE: 20

ggtcatagac caaagctc                                                     18


<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21

aaggatccat gcatttccaa agc                                               23


<210> SEQ ID NO 22
<211> LENGTH: 25
<212> TYPE: DNA
<213> ORGANISM: Artificial Sequence
<220> FEATURE:
<223> OTHER INFORMATION: Synthetic primer

<400> SEQUENCE: 22

ccgaattctt attcctttcg tactc                                             25


<210> SEQ ID NO 23
<211> LENGTH: 26
<212> TYPE: DNA
<213> ORGANISM: Artificial Sequence
<220> FEATURE:
```

<223> OTHER INFORMATION: Synthetic primer

<400> SEQUENCE: 23

```
gaattcatgc atttccaagc cttttg                                    26
```

<210> SEQ ID NO 24
<211> LENGTH: 23
<212> TYPE: DNA
<213> ORGANISM: Artificial Sequence
<220> FEATURE:
<223> OTHER INFORMATION: Synthetic primer

<400> SEQUENCE: 24

```
ctcgagttag tcctttcgta ctc                                       23
```

<210> SEQ ID NO 25
<211> LENGTH: 7353
<212> TYPE: DNA
<213> ORGANISM: Canis familiaris
<220> FEATURE:
<221> NAME/KEY: CDS
<222> LOCATION: (1)..(7020)

<400> SEQUENCE: 25

```
atg aag aaa ggt tct cag caa aag ttt ttg aaa gca aag atg cca cca       48
Met Lys Lys Gly Ser Gln Gln Lys Phe Leu Lys Ala Lys Met Pro Pro
1               5                   10                  15

tca tct cac tct cct agt cca cca tcc ctt acg tcc aat atg aga tct       96
Ser Ser His Ser Pro Ser Pro Pro Ser Leu Thr Ser Asn Met Arg Ser
            20                  25                  30

agg tca ctt tcg cct cta agt gga tct gag act ctg cct ttt cat ttt      144
Arg Ser Leu Ser Pro Leu Ser Gly Ser Glu Thr Leu Pro Phe His Phe
        35                  40                  45

gga gga ccg tgg cat gag caa gtt gag att aca gat gaa agc aca gtg      192
Gly Gly Pro Trp His Glu Gln Val Glu Ile Thr Asp Glu Ser Thr Val
    50                  55                  60

gtt tta gac tac caa gac cat aaa gaa gct gat tca cat gca gga gtc      240
Val Leu Asp Tyr Gln Asp His Lys Glu Ala Asp Ser His Ala Gly Val
65                  70                  75                  80

cga tat att aca gag gcc ctt gtt aga aaa ctt act aaa cag gac aat      288
Arg Tyr Ile Thr Glu Ala Leu Val Arg Lys Leu Thr Lys Gln Asp Asn
                85                  90                  95

ttg gcc ttg gta aaa tct ctg aac ctt tca ctt gct aaa ggt ggt ggc      336
Leu Ala Leu Val Lys Ser Leu Asn Leu Ser Leu Ala Lys Gly Gly Gly
            100                 105                 110

aag aaa ttc agg tgt atc gaa aat ttg gaa aaa tgt gtt aaa ctt gaa      384
Lys Lys Phe Arg Cys Ile Glu Asn Leu Glu Lys Cys Val Lys Leu Glu
        115                 120                 125

gta ctg aat ctc agc tat aat cta ata gga aag att gag aaa gtg gac      432
Val Leu Asn Leu Ser Tyr Asn Leu Ile Gly Lys Ile Glu Lys Val Asp
    130                 135                 140

aaa ctg tta aaa tta cgt gaa ctc aac tta tcg tat aac aaa atc cgc      480
Lys Leu Leu Lys Leu Arg Glu Leu Asn Leu Ser Tyr Asn Lys Ile Arg
145                 150                 155                 160

aaa att gaa ggc ata gaa aat tta tat aat ctg caa aag ctg aac ctt      528
Lys Ile Glu Gly Ile Glu Asn Leu Tyr Asn Leu Gln Lys Leu Asn Leu
                165                 170                 175

gca gga aat gaa atc gaa cat atc cca gta tgg tta ggg aag aag tta      576
Ala Gly Asn Glu Ile Glu His Ile Pro Val Trp Leu Gly Lys Lys Leu
            180                 185                 190

aaa tct ttg cga atc ctg aat ctg aaa ggc aac aag ata tca tcg ctc      624
Lys Ser Leu Arg Ile Leu Asn Leu Lys Gly Asn Lys Ile Ser Ser Leu
```

```
        195                 200                 205

caa gat gta agc aag ttg aaa cca ctt caa gat ttg act tct ctg atc      672
Gln Asp Val Ser Lys Leu Lys Pro Leu Gln Asp Leu Thr Ser Leu Ile
    210                 215                 220

cta ctt gaa aat cca gtt gcg acc ctt cct cat tat atc cag ttt acc      720
Leu Leu Glu Asn Pro Val Ala Thr Leu Pro His Tyr Ile Gln Phe Thr
225                 230                 235                 240

att ttt cac ctt cgc tca ttg gaa agt ttg gaa ggt cag cca gta act      768
Ile Phe His Leu Arg Ser Leu Glu Ser Leu Glu Gly Gln Pro Val Thr
                245                 250                 255

agt cag gac aga caa gaa gct ttt gcg aga ttc agt tta gat gag gta      816
Ser Gln Asp Arg Gln Glu Ala Phe Ala Arg Phe Ser Leu Asp Glu Val
            260                 265                 270

gaa aga ctg gaa aga gac ctg gag aag aag aca atg gaa act gaa gag      864
Glu Arg Leu Glu Arg Asp Leu Glu Lys Lys Thr Met Glu Thr Glu Glu
        275                 280                 285

ctt agg agt gag cag aca agg ttc ctt gag gaa att aaa agt cag gat      912
Leu Arg Ser Glu Gln Thr Arg Phe Leu Glu Glu Ile Lys Ser Gln Asp
    290                 295                 300

aaa ttg aac aaa tca ctg aaa gag gag gcc aga cta caa aaa cag agc      960
Lys Leu Asn Lys Ser Leu Lys Glu Glu Ala Arg Leu Gln Lys Gln Ser
305                 310                 315                 320

tat gag gag ctg gag agt aac cta aac acc aaa aat gaa ttg cta aaa     1008
Tyr Glu Glu Leu Glu Ser Asn Leu Asn Thr Lys Asn Glu Leu Leu Lys
                325                 330                 335

cag aag acc atg gaa cta atg cga gca tgt cag aaa cag tat gag atg     1056
Gln Lys Thr Met Glu Leu Met Arg Ala Cys Gln Lys Gln Tyr Glu Met
            340                 345                 350

gaa cag gag ttg gcc ttt tat aaa att gat gcc aaa ttt gaa cca cta     1104
Glu Gln Glu Leu Ala Phe Tyr Lys Ile Asp Ala Lys Phe Glu Pro Leu
        355                 360                 365

aat tat tac cca tca gag tat gtc gaa att gat aaa acc cca gat gaa     1152
Asn Tyr Tyr Pro Ser Glu Tyr Val Glu Ile Asp Lys Thr Pro Asp Glu
    370                 375                 380

agc cct tac att ggc aaa tcc aga tac aag aga aat atg ttc act aca     1200
Ser Pro Tyr Ile Gly Lys Ser Arg Tyr Lys Arg Asn Met Phe Thr Thr
385                 390                 395                 400

gag agt tat att att gca aat gcc cag aca gta aag atc aag aag atg     1248
Glu Ser Tyr Ile Ile Ala Asn Ala Gln Thr Val Lys Ile Lys Lys Met
                405                 410                 415

gag cta gat gaa ggg gaa caa ctc aga aat gag cac gtg aac ttg gga     1296
Glu Leu Asp Glu Gly Glu Gln Leu Arg Asn Glu His Val Asn Leu Gly
            420                 425                 430

gca tcg cca aca gac ata caa ctg gaa gac aaa gaa aaa aaa ata agt     1344
Ala Ser Pro Thr Asp Ile Gln Leu Glu Asp Lys Glu Lys Lys Ile Ser
        435                 440                 445

gca gca caa act cga cta tca gaa cta cat gat gaa ata gaa aag gca     1392
Ala Ala Gln Thr Arg Leu Ser Glu Leu His Asp Glu Ile Glu Lys Ala
    450                 455                 460

gaa caa caa att tta aga gcc act gaa gaa ttt aaa caa ctg gaa gaa     1440
Glu Gln Gln Ile Leu Arg Ala Thr Glu Glu Phe Lys Gln Leu Glu Glu
465                 470                 475                 480

gct ata caa ctt aaa aaa att tca gaa gcg gag aaa gac ctt ctt ttc     1488
Ala Ile Gln Leu Lys Lys Ile Ser Glu Ala Glu Lys Asp Leu Leu Phe
                485                 490                 495

aag cag ttg agt ggt agg ata cag ctt ctc aat aaa tta cgc caa gaa     1536
Lys Gln Leu Ser Gly Arg Ile Gln Leu Leu Asn Lys Leu Arg Gln Glu
            500                 505                 510

gct gtg gat cta gaa aca cag atg gaa aag caa agg caa gaa att ggt     1584
```

```
Ala Val Asp Leu Glu Thr Gln Met Glu Lys Gln Arg Gln Glu Ile Gly
        515                 520                 525

gaa aag cag aat gag atc aag gac ctg gaa ata gtc aca gat agc ctg      1632
Glu Lys Gln Asn Glu Ile Lys Asp Leu Glu Ile Val Thr Asp Ser Leu
    530                 535                 540

gat tcc aga gac cca aaa cat tgc cat atg aag gct cag aaa aga ggt      1680
Asp Ser Arg Asp Pro Lys His Cys His Met Lys Ala Gln Lys Arg Gly
545                 550                 555                 560

aaa gaa caa caa ctt gac att atg aac aag cag tac aaa cag ctt gaa      1728
Lys Glu Gln Gln Leu Asp Ile Met Asn Lys Gln Tyr Lys Gln Leu Glu
                565                 570                 575

agc cgt ttg gat gag ata ctt tct aga att gcc aaa gaa act gaa gag      1776
Ser Arg Leu Asp Glu Ile Leu Ser Arg Ile Ala Lys Glu Thr Glu Glu
            580                 585                 590

att aag gac ctt gaa gaa cag ctt act gaa gga caa ata gcc gca aac      1824
Ile Lys Asp Leu Glu Glu Gln Leu Thr Glu Gly Gln Ile Ala Ala Asn
        595                 600                 605

gaa gcc ctg aag aag gac tta gaa agt gtc atc agt ggg ttg caa gaa      1872
Glu Ala Leu Lys Lys Asp Leu Glu Ser Val Ile Ser Gly Leu Gln Glu
    610                 615                 620

tac ctg gag act gtc aaa ggt cag gcc cgt cag gcc cag aat gag tgc      1920
Tyr Leu Glu Thr Val Lys Gly Gln Ala Arg Gln Ala Gln Asn Glu Cys
625                 630                 635                 640

aga aag cta cag gat gag aag gag aca ttg ctg cag aga ttg agt gag      1968
Arg Lys Leu Gln Asp Glu Lys Glu Thr Leu Leu Gln Arg Leu Ser Glu
                645                 650                 655

gtc gag cag gag agg gac caa ctg gaa ata gtg gcc ata gat gca gaa      2016
Val Glu Gln Glu Arg Asp Gln Leu Glu Ile Val Ala Ile Asp Ala Glu
            660                 665                 670

aat atg agg aag gag ctc gca gaa ctg gag aat gcc ctc cag gag cag      2064
Asn Met Arg Lys Glu Leu Ala Glu Leu Glu Asn Ala Leu Gln Glu Gln
        675                 680                 685

cat gag gtg aat ata tct ctg cag cag acc cag gga gat ctc agt gcc      2112
His Glu Val Asn Ile Ser Leu Gln Gln Thr Gln Gly Asp Leu Ser Ala
    690                 695                 700

tat gag gct gag cta gag gct cag ctg aaa ata cgg gat gct gaa gcc      2160
Tyr Glu Ala Glu Leu Glu Ala Gln Leu Lys Ile Arg Asp Ala Glu Ala
705                 710                 715                 720

aac cag ctc aag gag gag ttg gaa aaa ctt aga agg ttg agc cag tta      2208
Asn Gln Leu Lys Glu Glu Leu Glu Lys Leu Arg Arg Leu Ser Gln Leu
                725                 730                 735

gaa caa tcg gcc ctt caa gca gag ctt gag aag gaa aag caa gcc ttc      2256
Glu Gln Ser Ala Leu Gln Ala Glu Leu Glu Lys Glu Lys Gln Ala Phe
            740                 745                 750

aag act gct gtc aaa aaa gcc cag ctc tca gaa gga aag gac caa gaa      2304
Lys Thr Ala Val Lys Lys Ala Gln Leu Ser Glu Gly Lys Asp Gln Glu
        755                 760                 765

aat agt gag ctc cgc aca caa ctc caa cag ctg cag gat gac aat gac      2352
Asn Ser Glu Leu Arg Thr Gln Leu Gln Gln Leu Gln Asp Asp Asn Asp
    770                 775                 780

cta ttg aaa cag caa ctt aaa gat ttc cag agt cac ctt aac cat gtg      2400
Leu Leu Lys Gln Gln Leu Lys Asp Phe Gln Ser His Leu Asn His Val
785                 790                 795                 800

gtt gat ggt ttg att cgt cca gaa gaa gtg gca gct tgt gtg gat gag      2448
Val Asp Gly Leu Ile Arg Pro Glu Glu Val Ala Ala Cys Val Asp Glu
                805                 810                 815

cta agg aaa aaa ctg aag tca gga gct ggg gaa atg aga atc cat act      2496
Leu Arg Lys Lys Leu Lys Ser Gly Ala Gly Glu Met Arg Ile His Thr
            820                 825                 830
```

```
cct tca gat gtc tta ggg aaa agt ctt gct gac ttg cag aag caa ttc     2544
Pro Ser Asp Val Leu Gly Lys Ser Leu Ala Asp Leu Gln Lys Gln Phe
        835                 840                 845

agt gag atc ctg gca cgc tcc cag tgg gaa aga cag gaa gca caa gtg     2592
Ser Glu Ile Leu Ala Arg Ser Gln Trp Glu Arg Gln Glu Ala Gln Val
    850                 855                 860

aga gag aga aaa ctc cag gag gaa atg gct ctg caa caa gag aaa ctg     2640
Arg Glu Arg Lys Leu Gln Glu Glu Met Ala Leu Gln Gln Glu Lys Leu
865                 870                 875                 880

gcg agc gga caa gag gag ttc agg cac gcc tgc gag agg gcc ctg gaa     2688
Ala Ser Gly Gln Glu Glu Phe Arg His Ala Cys Glu Arg Ala Leu Glu
                885                 890                 895

gcc cga att agt ttt gat aag agg cag cac gaa gca aga atc cag cag     2736
Ala Arg Ile Ser Phe Asp Lys Arg Gln His Glu Ala Arg Ile Gln Gln
            900                 905                 910

ttg gag aat gaa att cac tat ttg caa gaa aat cta aaa agt atg gag     2784
Leu Glu Asn Glu Ile His Tyr Leu Gln Glu Asn Leu Lys Ser Met Glu
        915                 920                 925

gaa atc caa ggt ctc aca gac ctc caa ctt cag gaa gct gat gaa gag     2832
Glu Ile Gln Gly Leu Thr Asp Leu Gln Leu Gln Glu Ala Asp Glu Glu
    930                 935                 940

aag gag aga att ctg gcc caa ctc cgg gag tta gag aaa aag aag aaa     2880
Lys Glu Arg Ile Leu Ala Gln Leu Arg Glu Leu Glu Lys Lys Lys Lys
945                 950                 955                 960

ctt gag gat gcc aag tct cag gag cag ttt ctt gga tta gat aga gaa     2928
Leu Glu Asp Ala Lys Ser Gln Glu Gln Phe Leu Gly Leu Asp Arg Glu
                965                 970                 975

ttg aag aag cta aag aaa gct gtg gct gcc tct gat aag ctg gcc aca     2976
Leu Lys Lys Leu Lys Lys Ala Val Ala Ala Ser Asp Lys Leu Ala Thr
            980                 985                 990

gct gag ctc acc att gcc aaa gac  cag ctc aag tcc ctt  cat gga act   3024
Ala Glu Leu Thr Ile Ala Lys Asp  Gln Leu Lys Ser Leu  His Gly Thr
        995                 1000                1005

gtg atg  aaa att aac cag gag  cga gca gag gag ctg  cag gag acg     3069
Val Met  Lys Ile Asn Gln Glu  Arg Ala Glu Glu Leu  Gln Glu Thr
    1010                 1015                 1020

gag agg  ttc agc aga aag gca  gca caa gca gct agg  gat ctg atc     3114
Glu Arg  Phe Ser Arg Lys Ala  Ala Gln Ala Ala Arg  Asp Leu Ile
    1025                 1030                 1035

cga gca  gaa gcg gag att gaa  ctc ctg cag aag ctt  ctc aga gat     3159
Arg Ala  Glu Ala Glu Ile Glu  Leu Leu Gln Lys Leu  Leu Arg Asp
    1040                 1045                 1050

aaa gag  gag cag ttt cga aat  gag att gag aaa gta  gat gtc ggc     3204
Lys Glu  Glu Gln Phe Arg Asn  Glu Ile Glu Lys Val  Asp Val Gly
    1055                 1060                 1065

tct gga  gga gca aag tca cag  atg ctg gag atg gag  aaa cta aat     3249
Ser Gly  Gly Ala Lys Ser Gln  Met Leu Glu Met Glu  Lys Leu Asn
    1070                 1075                 1080

gag aca  atg gag agg caa aga  aca gag att gct agg  ctg agg aat     3294
Glu Thr  Met Glu Arg Gln Arg  Thr Glu Ile Ala Arg  Leu Arg Asn
    1085                 1090                 1095

tta cta  gac ctc acc ggg gct  gat aac aaa gga aac  ttt gaa aat     3339
Leu Leu  Asp Leu Thr Gly Ala  Asp Asn Lys Gly Asn  Phe Glu Asn
    1100                 1105                 1110

gtt ttg  gaa gaa att gct gaa  ctt cga cgt gaa gtt  tct cat cag     3384
Val Leu  Glu Glu Ile Ala Glu  Leu Arg Arg Glu Val  Ser His Gln
    1115                 1120                 1125

aat gat  tac atc agc agc atg  aca gat cct ttc aaa  aga cga ggc     3429
Asn Asp  Tyr Ile Ser Ser Met  Thr Asp Pro Phe Lys  Arg Arg Gly
    1130                 1135                 1140
```

-continued

```
tat tgg  tac ttt atg cca cca  cca tca tca tca aaa  gtt tcc agc      3474
Tyr Trp  Tyr Phe Met Pro Pro  Pro Ser Ser Ser Lys  Val Ser Ser
    1145                 1150                 1155

cac agt  tcc cag gcc acc aag  gac tct ggt gtt ggc  cta aag tac      3519
His Ser  Ser Gln Ala Thr Lys  Asp Ser Gly Val Gly  Leu Lys Tyr
    1160                 1165                 1170

aca gcc  tcc act ccg gtt aga  aaa cca cat cgt gga  cgg cag gat      3564
Thr Ala  Ser Thr Pro Val Arg  Lys Pro His Arg Gly  Arg Gln Asp
    1175                 1180                 1185

gga aag  gag aac agt ggg cct  cca cct gcc tca gga  tac tgg gtg      3609
Gly Lys  Glu Asn Ser Gly Pro  Pro Pro Ala Ser Gly  Tyr Trp Val
    1190                 1195                 1200

tat tct  cct atc agg agt ggg  tta cat aaa tcg ttc  tca aat aga      3654
Tyr Ser  Pro Ile Arg Ser Gly  Leu His Lys Ser Phe  Ser Asn Arg
    1205                 1210                 1215

gac gca  gac agt gga gga gat  agc cag gaa gag agc  gag cta gat      3699
Asp Ala  Asp Ser Gly Gly Asp  Ser Gln Glu Glu Ser  Glu Leu Asp
    1220                 1225                 1230

gac caa  gaa gac cac cca ttt  gta cct cct cct gga  tac atg atg      3744
Asp Gln  Glu Asp His Pro Phe  Val Pro Pro Pro Gly  Tyr Met Met
    1235                 1240                 1245

tac act  gtg ttt cct gat ggt  tct cct gta ccc cag  ggc atg gcc      3789
Tyr Thr  Val Phe Pro Asp Gly  Ser Pro Val Pro Gln  Gly Met Ala
    1250                 1255                 1260

ctg tat  gca ccc cct cct ccc  ttg ccc aac aat agc  cag cct ctt      3834
Leu Tyr  Ala Pro Pro Pro Pro  Leu Pro Asn Asn Ser  Gln Pro Leu
    1265                 1270                 1275

gac ctt  ggc act gtt gtt tat  ggc cca cct cct gtt  ggg gct ccc      3879
Asp Leu  Gly Thr Val Val Tyr  Gly Pro Pro Pro Val  Gly Ala Pro
    1280                 1285                 1290

atc gtg  tat ggg cct cca cct  ccc aac ttc tcc gta  ccc ctc atc      3924
Ile Val  Tyr Gly Pro Pro Pro  Pro Asn Phe Ser Val  Pro Leu Ile
    1295                 1300                 1305

ccc gtg  ggt gtg ctg cac tgc  aat gtc cca gaa cac  cat aac ttg      3969
Pro Val  Gly Val Leu His Cys  Asn Val Pro Glu His  His Asn Leu
    1310                 1315                 1320

gag aat  gaa gtt tct aga tta  gaa gac ata atg cag  cat tta aaa      4014
Glu Asn  Glu Val Ser Arg Leu  Glu Asp Ile Met Gln  His Leu Lys
    1325                 1330                 1335

tct ggg  aaa cgg gaa cag tgc  atg aaa aca ccc aag  ctg cag tcg      4059
Ser Gly  Lys Arg Glu Gln Cys  Met Lys Thr Pro Lys  Leu Gln Ser
    1340                 1345                 1350

gag aaa  gaa ctc gca gag ctg  cag cat aac att gat  ggt ctt ttg      4104
Glu Lys  Glu Leu Ala Glu Leu  Gln His Asn Ile Asp  Gly Leu Leu
    1355                 1360                 1365

caa gag  aag aaa gac tta gag  cat gaa gta gaa gaa  tta cat aga      4149
Gln Glu  Lys Lys Asp Leu Glu  His Glu Val Glu Glu  Leu His Arg
    1370                 1375                 1380

acc atc  caa aaa cat caa cag  cga aaa gat ttc att  gat gga aac      4194
Thr Ile  Gln Lys His Gln Gln  Arg Lys Asp Phe Ile  Asp Gly Asn
    1385                 1390                 1395

gtt gag  agt ctt gtg aat gat  cta gaa ata gag aag  tca ctc aaa      4239
Val Glu  Ser Leu Val Asn Asp  Leu Glu Ile Glu Lys  Ser Leu Lys
    1400                 1405                 1410

cac cat  gaa gat att gtt gat  gaa att gaa tgt att  gag agg acc      4284
His His  Glu Asp Ile Val Asp  Glu Ile Glu Cys Ile  Glu Arg Thr
    1415                 1420                 1425

ctt ctg  aag cgc cgt gca gag  ctc agg gaa gcc gac  cgg ctg ctg      4329
Leu Leu  Lys Arg Arg Ala Glu  Leu Arg Glu Ala Asp  Arg Leu Leu
```

```
    1430                1435                1440

acg gag  gct gaa agt gaa ctt  tca tgc acg aaa gag  aaa aca aaa      4374
Thr Glu  Ala Glu Ser Glu Leu  Ser Cys Thr Lys Glu  Lys Thr Lys
    1445                1450                1455

cat gct  gtt gag aag ttc act  gat gcc aag aga aat  tta ttg caa      4419
His Ala  Val Glu Lys Phe Thr  Asp Ala Lys Arg Asn  Leu Leu Gln
    1460                1465                1470

act gag  aaa gat gct gag gag  tta gaa agg aga gcc  cag gaa act      4464
Thr Glu  Lys Asp Ala Glu Glu  Leu Glu Arg Arg Ala  Gln Glu Thr
    1475                1480                1485

gcc att  aac ctc gtc aaa gcc  gac cag cag ctg aga  ttg ctc cag      4509
Ala Ile  Asn Leu Val Lys Ala  Asp Gln Gln Leu Arg  Leu Leu Gln
    1490                1495                1500

gct gac  acg aag gat ttg gag  cag cac aaa atg gag  caa gag gaa      4554
Ala Asp  Thr Lys Asp Leu Glu  Gln His Lys Met Glu  Gln Glu Glu
    1505                1510                1515

atc ttg  aaa gaa ata aac aaa  gtt gtt gca gca aaa  gac tca gac      4599
Ile Leu  Lys Glu Ile Asn Lys  Val Val Ala Ala Lys  Asp Ser Asp
    1520                1525                1530

ttc cag  agc cta aac aag aag  aag gaa gta ctg aca  gga gag ctg      4644
Phe Gln  Ser Leu Asn Lys Lys  Lys Glu Val Leu Thr  Gly Glu Leu
    1535                1540                1545

cag aaa  ctc cag aag gac att  gag act gca cgg cac  aat gag gat      4689
Gln Lys  Leu Gln Lys Asp Ile  Glu Thr Ala Arg His  Asn Glu Asp
    1550                1555                1560

cag cac  ctg cag gtc ctt aaa  gag tcg gag acc ctc  ctg cag gcc      4734
Gln His  Leu Gln Val Leu Lys  Glu Ser Glu Thr Leu  Leu Gln Ala
    1565                1570                1575

aag aaa  gct gag ctg gaa aat  ctg aaa agc cag gtg  tca gga cag      4779
Lys Lys  Ala Glu Leu Glu Asn  Leu Lys Ser Gln Val  Ser Gly Gln
    1580                1585                1590

cag cag  gag atg gcc gtc ttg  gac agg gag tta gga  cac aag aag      4824
Gln Gln  Glu Met Ala Val Leu  Asp Arg Glu Leu Gly  His Lys Lys
    1595                1600                1605

gaa gag  ctg cat ctc ctc cag  gaa agc atg gtc cag  gcc aaa gct      4869
Glu Glu  Leu His Leu Leu Gln  Glu Ser Met Val Gln  Ala Lys Ala
    1610                1615                1620

gac ctc  cag gaa gca ctg aga  cta gga gaa agc gaa  gta act gag      4914
Asp Leu  Gln Glu Ala Leu Arg  Leu Gly Glu Ser Glu  Val Thr Glu
    1625                1630                1635

aag tgc  aat cac att agg gaa  gta aaa tct ctt ctg  gaa gaa ctc      4959
Lys Cys  Asn His Ile Arg Glu  Val Lys Ser Leu Leu  Glu Glu Leu
    1640                1645                1650

agt ttt  cag aaa gga gaa ctg  aat gtc cag atc agt  gaa aaa aaa      5004
Ser Phe  Gln Lys Gly Glu Leu  Asn Val Gln Ile Ser  Glu Lys Lys
    1655                1660                1665

act caa  ctt gca ctc ata aag  cag gaa att gaa aaa  gag gaa gac      5049
Thr Gln  Leu Ala Leu Ile Lys  Gln Glu Ile Glu Lys  Glu Glu Asp
    1670                1675                1680

aat ctt  cag gta gtt tta ggg  caa atg tct aaa cat  aaa act gaa      5094
Asn Leu  Gln Val Val Leu Gly  Gln Met Ser Lys His  Lys Thr Glu
    1685                1690                1695

cta aag  aat att ctg gac atg  ttg caa ctt gaa aat  aat gag ctg      5139
Leu Lys  Asn Ile Leu Asp Met  Leu Gln Leu Glu Asn  Asn Glu Leu
    1700                1705                1710

caa ggt  ttg aag ctc caa cat  gac caa aag atg tct  gaa tta gag      5184
Gln Gly  Leu Lys Leu Gln His  Asp Gln Lys Met Ser  Glu Leu Glu
    1715                1720                1725

aag act  cgg gtt gaa gtg ctg  gag gag aaa ctg gag  tta gag agt      5229
```

-continued

```
Lys Thr  Arg Val Glu Val Leu  Glu Glu Lys Leu Glu  Leu Glu Ser
    1730                 1735                 1740

ctg cag  cag gca gcc ctg cga  cag aga ggg gag ata  gag tgg cag      5274
Leu Gln  Gln Ala Ala Leu Arg  Gln Arg Gly Glu Ile  Glu Trp Gln
    1745                 1750                 1755

aag cag  ctc ctc cag agg aac  aca cag gaa gta gag  cgg atg act      5319
Lys Gln  Leu Leu Gln Arg Asn  Thr Gln Glu Val Glu  Arg Met Thr
    1760                 1765                 1770

gct gag  acc cga gca tta cag  tcg tgt gtt gag tct  ttg tgc aaa      5364
Ala Glu  Thr Arg Ala Leu Gln  Ser Cys Val Glu Ser  Leu Cys Lys
    1775                 1780                 1785

gaa aag  caa gat ctc gaa gaa  aaa cag gac agc tgg  gaa aag aag      5409
Glu Lys  Gln Asp Leu Glu Glu  Lys Gln Asp Ser Trp  Glu Lys Lys
    1790                 1795                 1800

ttg gca  cag acc aaa cgg gtt  cta gca gct gca gaa  gag gac agc      5454
Leu Ala  Gln Thr Lys Arg Val  Leu Ala Ala Ala Glu  Glu Asp Ser
    1805                 1810                 1815

gag atg  gag cgg gca cgc tta  gaa aag ttg gaa ctg  gac gcc agg      5499
Glu Met  Glu Arg Ala Arg Leu  Glu Lys Leu Glu Leu  Asp Ala Arg
    1820                 1825                 1830

aag ctg  cag cag gag ttg gac  caa cga aac agg gag  aag ctc tcc      5544
Lys Leu  Gln Gln Glu Leu Asp  Gln Arg Asn Arg Glu  Lys Leu Ser
    1835                 1840                 1845

ctg cat  caa gac ctg gca gtg  gtg cag cag cag cta  caa gaa aaa      5589
Leu His  Gln Asp Leu Ala Val  Val Gln Gln Gln Leu  Gln Glu Lys
    1850                 1855                 1860

cag gaa  gca gta aac tca tta  cag aag gaa cta act  gat gtc cag      5634
Gln Glu  Ala Val Asn Ser Leu  Gln Lys Glu Leu Thr  Asp Val Gln
    1865                 1870                 1875

gag cat  ttg gac cta gca gaa  cag gag gtg ctc tgc  acc acc aag      5679
Glu His  Leu Asp Leu Ala Glu  Gln Glu Val Leu Cys  Thr Thr Lys
    1880                 1885                 1890

cgc aag  gac gca ctg ctc agc  gaa cag acc agg ctc  gag aag gac      5724
Arg Lys  Asp Ala Leu Leu Ser  Glu Gln Thr Arg Leu  Glu Lys Asp
    1895                 1900                 1905

gtg ggt  gaa tgg acg aag aag  ttt gaa gac tgc cag  aaa gaa ggg      5769
Val Gly  Glu Trp Thr Lys Lys  Phe Glu Asp Cys Gln  Lys Glu Gly
    1910                 1915                 1920

gag aca  aag cag caa cag ctt  caa ggg ctt cag aag  gag att gaa      5814
Glu Thr  Lys Gln Gln Gln Leu  Gln Gly Leu Gln Lys  Glu Ile Glu
    1925                 1930                 1935

gga aac  gag gcg aag cta gcc  caa caa gaa atg atg  ttt cag aga      5859
Gly Asn  Glu Ala Lys Leu Ala  Gln Gln Glu Met Met  Phe Gln Arg
    1940                 1945                 1950

ctc cag  aaa gag cga gaa tgt  gaa gaa aaa aag tta  gaa gct agt      5904
Leu Gln  Lys Glu Arg Glu Cys  Glu Glu Lys Lys Leu  Glu Ala Ser
    1955                 1960                 1965

aaa gtg  act ctg aag gag cag  cag caa cag ctg gaa  aag gaa ttg      5949
Lys Val  Thr Leu Lys Glu Gln  Gln Gln Gln Leu Glu  Lys Glu Leu
    1970                 1975                 1980

atg gag  cag aaa ggc aag ctg  gac cag gtg ctc gct  aag ctc ttg      5994
Met Glu  Gln Lys Gly Lys Leu  Asp Gln Val Leu Ala  Lys Leu Leu
    1985                 1990                 1995

gtg gct  gag gag cgt gtc agg  acc ttg cag gag gag  gga agg tgg      6039
Val Ala  Glu Glu Arg Val Arg  Thr Leu Gln Glu Glu  Gly Arg Trp
    2000                 2005                 2010

agc gag  acc ctg gag aag acg  ctc tcc cag acc aag  cga cag ctt      6084
Ser Glu  Thr Leu Glu Lys Thr  Leu Ser Gln Thr Lys  Arg Gln Leu
    2015                 2020                 2025
```

```
tca gaa  cgg gag cag cag tta  ctg gcc aag tca gac  gag ctg ctg      6129
Ser Glu  Arg Glu Gln Gln Leu  Leu Ala Lys Ser Asp  Glu Leu Leu
    2030                 2035                 2040

gcc ctg  cag aag gag acg gac  tcc atg agg gcg gac  ttc agc ctc      6174
Ala Leu  Gln Lys Glu Thr Asp  Ser Met Arg Ala Asp  Phe Ser Leu
    2045                 2050                 2055

ttg cgc  aac cag ttc ctg aca  gaa aga aag aaa gcc  gag aag cag      6219
Leu Arg  Asn Gln Phe Leu Thr  Glu Arg Lys Lys Ala  Glu Lys Gln
    2060                 2065                 2070

gtg gcc  agc ctg aag gaa gcc  ctt aag atc cag cgg  agc caa ctg      6264
Val Ala  Ser Leu Lys Glu Ala  Leu Lys Ile Gln Arg  Ser Gln Leu
    2075                 2080                 2085

gag aag  aac ctt ctg gag caa  aag cag gag aac agc  tgc atg cag      6309
Glu Lys  Asn Leu Leu Glu Gln  Lys Gln Glu Asn Ser  Cys Met Gln
    2090                 2095                 2100

agg gag  atg gca acc atc gaa  cag gtg gcc cag gac  aac cac gag      6354
Arg Glu  Met Ala Thr Ile Glu  Gln Val Ala Gln Asp  Asn His Glu
    2105                 2110                 2115

cgg gcc  cgg cgc cta atg agg  gag ctc aac cag atg  cag cgc gag      6399
Arg Ala  Arg Arg Leu Met Arg  Glu Leu Asn Gln Met  Gln Arg Glu
    2120                 2125                 2130

tac gtg  gag ctc agg aaa cag  atg aca aac caa aag  gat ttg gaa      6444
Tyr Val  Glu Leu Arg Lys Gln  Met Thr Asn Gln Lys  Asp Leu Glu
    2135                 2140                 2145

aga aga  cag atg gaa atc agt  gat gcg atg caa gca  ctt aaa tgt      6489
Arg Arg  Gln Met Glu Ile Ser  Asp Ala Met Gln Ala  Leu Lys Cys
    2150                 2155                 2160

gag gtg  aaa gat gaa atc cga  acc agc ctg aag aat  ctc aac cag      6534
Glu Val  Lys Asp Glu Ile Arg  Thr Ser Leu Lys Asn  Leu Asn Gln
    2165                 2170                 2175

ttt ctt  cca gaa ctg cca gcg  gac ctg gag gcc ctt  ctg gaa agg      6579
Phe Leu  Pro Glu Leu Pro Ala  Asp Leu Glu Ala Leu  Leu Glu Arg
    2180                 2185                 2190

aat gag  aac ctt gga gga ggc  ttg gag agc ttg aaa  gag aat ttc      6624
Asn Glu  Asn Leu Gly Gly Gly  Leu Glu Ser Leu Lys  Glu Asn Phe
    2195                 2200                 2205

ccg ttt  acc gtg agc gac aga  cca tca tct tgc gaa  gag aaa ctg      6669
Pro Phe  Thr Val Ser Asp Arg  Pro Ser Ser Cys Glu  Glu Lys Leu
    2210                 2215                 2220

aat ttt  ggc cag gct cac gtg  gcg gat gaa cag tgg  cgg gga gag      6714
Asn Phe  Gly Gln Ala His Val  Ala Asp Glu Gln Trp  Arg Gly Glu
    2225                 2230                 2235

gca ctc  cgg gag aag ctg cgc  cac cgc gag gac cgg  ctc aag gcc      6759
Ala Leu  Arg Glu Lys Leu Arg  His Arg Glu Asp Arg  Leu Lys Ala
    2240                 2245                 2250

cag ctg  cgc cgc tgc atg tcc  aag cag gcc gag gtg  ctg agc gag      6804
Gln Leu  Arg Arg Cys Met Ser  Lys Gln Ala Glu Val  Leu Ser Glu
    2255                 2260                 2265

ggc cgg  cgg cgc acg gag ggg  acc ctg cac agc ctg  cgg cgg cag      6849
Gly Arg  Arg Arg Thr Glu Gly  Thr Leu His Ser Leu  Arg Arg Gln
    2270                 2275                 2280

gtg gac  gcc ctg ggc gag ctg  gtc acc agc act tcc  ggg gac tcc      6894
Val Asp  Ala Leu Gly Glu Leu  Val Thr Ser Thr Ser  Gly Asp Ser
    2285                 2290                 2295

gcg tcc  acc cgc agt ctg tcg  cgc acc gag ggc tcg  ctc gcc gag      6939
Ala Ser  Thr Arg Ser Leu Ser  Arg Thr Glu Gly Ser  Leu Ala Glu
    2300                 2305                 2310

gac gaa  ccg ccg ggg ccc agc  cag agc tcc cgg cgg  ctc ccc cga      6984
Asp Glu  Pro Pro Gly Pro Ser  Gln Ser Ser Arg Arg  Leu Pro Arg
    2315                 2320                 2325
```

```
ggc ccg  tcg ccg cgg ctg gac  gcg cac cga ccc tga ggacccggag        7030
Gly Pro  Ser Pro Arg Leu Asp  Ala His Arg Pro
    2330                 2335

gacccggagg cccggcgtcc cctcggaacg cttcctccgc gtccgcggac accaggctca   7090

cgggaaggcg cgtccatgcg ggaagagccg cgagcggaac ccggatgccc gggctggtct   7150

ctgggccttg gaaacgtgtt gccgtaaaag cagcgcccgc ggctgcggac ttgaagcccc   7210

gaactggtaa actcggcggc tgccgggcga actgtactca ggactttttt cacggacacc   7270

gtcagatttt atttttggaa atctattttc atatgaaaat aaaagataaa agcgcctgaa   7330

aaaaaaaaaa aaaaaaaact agt                                           7353
```

<210> SEQ ID NO 26
<211> LENGTH: 2339
<212> TYPE: PRT
<213> ORGANISM: Canis familiaris

<400> SEQUENCE: 26

```
Met Lys Lys Gly Ser Gln Gln Lys Phe Leu Lys Ala Lys Met Pro Pro
1               5                   10                  15

Ser Ser His Ser Pro Ser Pro Pro Ser Leu Thr Ser Asn Met Arg Ser
            20                  25                  30

Arg Ser Leu Ser Pro Leu Ser Gly Ser Glu Thr Leu Pro Phe His Phe
        35                  40                  45

Gly Gly Pro Trp His Glu Gln Val Glu Ile Thr Asp Glu Ser Thr Val
    50                  55                  60

Val Leu Asp Tyr Gln Asp His Lys Glu Ala Asp Ser His Ala Gly Val
65                  70                  75                  80

Arg Tyr Ile Thr Glu Ala Leu Val Arg Lys Leu Thr Lys Gln Asp Asn
                85                  90                  95

Leu Ala Leu Val Lys Ser Leu Asn Leu Ser Leu Ala Lys Gly Gly Gly
            100                 105                 110

Lys Lys Phe Arg Cys Ile Glu Asn Leu Glu Lys Cys Val Lys Leu Glu
        115                 120                 125

Val Leu Asn Leu Ser Tyr Asn Leu Ile Gly Lys Ile Glu Lys Val Asp
    130                 135                 140

Lys Leu Leu Lys Leu Arg Glu Leu Asn Leu Ser Tyr Asn Lys Ile Arg
145                 150                 155                 160

Lys Ile Glu Gly Ile Glu Asn Leu Tyr Asn Leu Gln Lys Leu Asn Leu
                165                 170                 175

Ala Gly Asn Glu Ile Glu His Ile Pro Val Trp Leu Gly Lys Lys Leu
            180                 185                 190

Lys Ser Leu Arg Ile Leu Asn Leu Lys Gly Asn Lys Ile Ser Ser Leu
        195                 200                 205

Gln Asp Val Ser Lys Leu Lys Pro Leu Gln Asp Leu Thr Ser Leu Ile
    210                 215                 220

Leu Leu Glu Asn Pro Val Ala Thr Leu Pro His Tyr Ile Gln Phe Thr
225                 230                 235                 240

Ile Phe His Leu Arg Ser Leu Glu Ser Leu Glu Gly Gln Pro Val Thr
                245                 250                 255

Ser Gln Asp Arg Gln Glu Ala Phe Ala Arg Phe Ser Leu Asp Glu Val
            260                 265                 270

Glu Arg Leu Glu Arg Asp Leu Glu Lys Lys Thr Met Glu Thr Glu Glu
        275                 280                 285
```

```
Leu Arg Ser Glu Gln Thr Arg Phe Leu Glu Glu Ile Lys Ser Gln Asp
    290                 295                 300

Lys Leu Asn Lys Ser Leu Lys Glu Glu Ala Arg Leu Gln Lys Gln Ser
305                 310                 315                 320

Tyr Glu Glu Leu Glu Ser Asn Leu Asn Thr Lys Asn Glu Leu Leu Lys
                325                 330                 335

Gln Lys Thr Met Glu Leu Met Arg Ala Cys Gln Lys Gln Tyr Glu Met
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Val Glu Ile Asp Lys Thr Pro Asp Glu
    370                 375                 380

Ser Pro Tyr Ile Gly Lys Ser Arg Tyr Lys Arg Asn Met Phe Thr Thr
385                 390                 395                 400

Glu Ser Tyr Ile Ile Ala Asn Ala Gln Thr Val Lys Ile Lys Lys Met
                405                 410                 415

Glu Leu Asp Glu Gly Glu Gln Leu Arg Asn Glu His Val Asn Leu Gly
            420                 425                 430

Ala Ser Pro Thr Asp Ile Gln Leu Glu Asp Lys Glu Lys Lys Ile Ser
        435                 440                 445

Ala Ala Gln Thr Arg Leu Ser Glu Leu His Asp Glu Ile Glu Lys Ala
    450                 455                 460

Glu Gln Gln Ile Leu Arg Ala Thr Glu Glu Phe Lys Gln Leu Glu Glu
465                 470                 475                 480

Ala Ile Gln Leu Lys Lys Ile Ser Glu Ala Glu Lys Asp Leu Leu Phe
                485                 490                 495

Lys Gln Leu Ser Gly Arg Ile Gln Leu Leu Asn Lys Leu Arg Gln Glu
            500                 505                 510

Ala Val Asp Leu Glu Thr Gln Met Glu Lys Gln Arg Gln Glu Ile Gly
        515                 520                 525

Glu Lys Gln Asn Glu Ile Lys Asp Leu Glu Ile Val Thr Asp Ser Leu
    530                 535                 540

Asp Ser Arg Asp Pro Lys His Cys His Met Lys Ala Gln Lys Arg Gly
545                 550                 555                 560

Lys Glu Gln Gln Leu Asp Ile Met Asn Lys Gln Tyr Lys Gln Leu Glu
                565                 570                 575

Ser Arg Leu Asp Glu Ile Leu Ser Arg Ile Ala Lys Glu Thr Glu Glu
            580                 585                 590

Ile Lys Asp Leu Glu Glu Gln Leu Thr Glu Gly Gln Ile Ala Ala Asn
        595                 600                 605

Glu Ala Leu Lys Lys Asp Leu Glu Ser Val Ile Ser Gly Leu Gln Glu
    610                 615                 620

Tyr Leu Glu Thr Val Lys Gly Gln Ala Arg Gln Ala Gln Asn Glu Cys
625                 630                 635                 640

Arg Lys Leu Gln Asp Glu Lys Glu Thr Leu Leu Gln Arg Leu Ser Glu
                645                 650                 655

Val Glu Gln Glu Arg Asp Gln Leu Glu Ile Val Ala Ile Asp Ala Glu
            660                 665                 670

Asn Met Arg Lys Glu Leu Ala Glu Leu Glu Asn Ala Leu Gln Glu Gln
        675                 680                 685

His Glu Val Asn Ile Ser Leu Gln Gln Thr Gln Gly Asp Leu Ser Ala
    690                 695                 700

Tyr Glu Ala Glu Leu Glu Ala Gln Leu Lys Ile Arg Asp Ala Glu Ala
```

```
705                 710                 715                 720

Asn Gln Leu Lys Glu Glu Leu Glu Lys Leu Arg Arg Leu Ser Gln Leu
                725                 730                 735

Glu Gln Ser Ala Leu Gln Ala Glu Leu Glu Lys Glu Lys Gln Ala Phe
            740                 745                 750

Lys Thr Ala Val Lys Lys Ala Gln Leu Ser Glu Gly Lys Asp Gln Glu
        755                 760                 765

Asn Ser Glu Leu Arg Thr Gln Leu Gln Gln Leu Gln Asp Asp Asn Asp
    770                 775                 780

Leu Leu Lys Gln Gln Leu Lys Asp Phe Gln Ser His Leu Asn His Val
785                 790                 795                 800

Val Asp Gly Leu Ile Arg Pro Glu Glu Val Ala Ala Cys Val Asp Glu
                805                 810                 815

Leu Arg Lys Lys Leu Lys Ser Gly Ala Gly Glu Met Arg Ile His Thr
            820                 825                 830

Pro Ser Asp Val Leu Gly Lys Ser Leu Ala Asp Leu Gln Lys Gln Phe
        835                 840                 845

Ser Glu Ile Leu Ala Arg Ser Gln Trp Glu Arg Gln Glu Ala Gln Val
    850                 855                 860

Arg Glu Arg Lys Leu Gln Glu Glu Met Ala Leu Gln Gln Glu Lys Leu
865                 870                 875                 880

Ala Ser Gly Gln Glu Glu Phe Arg His Ala Cys Glu Arg Ala Leu Glu
                885                 890                 895

Ala Arg Ile Ser Phe Asp Lys Arg Gln His Glu Ala Arg Ile Gln Gln
            900                 905                 910

Leu Glu Asn Glu Ile His Tyr Leu Gln Glu Asn Leu Lys Ser Met Glu
        915                 920                 925

Glu Ile Gln Gly Leu Thr Asp Leu Gln Leu Gln Glu Ala Asp Glu Glu
    930                 935                 940

Lys Glu Arg Ile Leu Ala Gln Leu Arg Glu Leu Glu Lys Lys Lys Lys
945                 950                 955                 960

Leu Glu Asp Ala Lys Ser Gln Glu Gln Phe Leu Gly Leu Asp Arg Glu
                965                 970                 975

Leu Lys Lys Leu Lys Lys Ala Val Ala Ala Ser Asp Lys Leu Ala Thr
            980                 985                 990

Ala Glu Leu Thr Ile Ala Lys Asp  Gln Leu Lys Ser Leu  His Gly Thr
        995                 1000                 1005

Val Met  Lys Ile Asn Gln Glu  Arg Ala Glu Glu Leu  Gln Glu Thr
    1010                 1015                 1020

Glu Arg  Phe Ser Arg Lys Ala  Ala Gln Ala Ala Arg  Asp Leu Ile
    1025                 1030                 1035

Arg Ala  Glu Ala Glu Ile Glu  Leu Leu Gln Lys Leu  Leu Arg Asp
    1040                 1045                 1050

Lys Glu  Glu Gln Phe Arg Asn  Glu Ile Glu Lys Val  Asp Val Gly
    1055                 1060                 1065

Ser Gly  Gly Ala Lys Ser Gln  Met Leu Glu Met Glu  Lys Leu Asn
    1070                 1075                 1080

Glu Thr  Met Glu Arg Gln Arg  Thr Glu Ile Ala Arg  Leu Arg Asn
    1085                 1090                 1095

Leu Leu  Asp Leu Thr Gly Ala  Asp Asn Lys Gly Asn  Phe Glu Asn
    1100                 1105                 1110

Val Leu  Glu Glu Ile Ala Glu  Leu Arg Arg Glu Val  Ser His Gln
    1115                 1120                 1125
```

```
Asn Asp  Tyr Ile Ser Ser Met  Thr Asp Pro Phe Lys  Arg Arg Gly
    1130                 1135                 1140

Tyr Trp  Tyr Phe Met Pro Pro  Pro Ser Ser Ser Lys  Val Ser Ser
    1145                 1150                 1155

His Ser  Ser Gln Ala Thr Lys  Asp Ser Gly Val Gly  Leu Lys Tyr
    1160                 1165                 1170

Thr Ala  Ser Thr Pro Val Arg  Lys Pro His Arg Gly  Arg Gln Asp
    1175                 1180                 1185

Gly Lys  Glu Asn Ser Gly Pro  Pro Pro Ala Ser Gly  Tyr Trp Val
    1190                 1195                 1200

Tyr Ser  Pro Ile Arg Ser Gly  Leu His Lys Ser Phe  Ser Asn Arg
    1205                 1210                 1215

Asp Ala  Asp Ser Gly Gly Asp  Ser Gln Glu Glu Ser  Glu Leu Asp
    1220                 1225                 1230

Asp Gln  Glu Asp His Pro Phe  Val Pro Pro Pro Gly  Tyr Met Met
    1235                 1240                 1245

Tyr Thr  Val Phe Pro Asp Gly  Ser Pro Val Pro Gln  Gly Met Ala
    1250                 1255                 1260

Leu Tyr  Ala Pro Pro Pro Pro  Leu Pro Asn Asn Ser  Gln Pro Leu
    1265                 1270                 1275

Asp Leu  Gly Thr Val Val Tyr  Gly Pro Pro Pro Val  Gly Ala Pro
    1280                 1285                 1290

Ile Val  Tyr Gly Pro Pro Pro  Pro Asn Phe Ser Val  Pro Leu Ile
    1295                 1300                 1305

Pro Val  Gly Val Leu His Cys  Asn Val Pro Glu His  His Asn Leu
    1310                 1315                 1320

Glu Asn  Glu Val Ser Arg Leu  Glu Asp Ile Met Gln  His Leu Lys
    1325                 1330                 1335

Ser Gly  Lys Arg Glu Gln Cys  Met Lys Thr Pro Lys  Leu Gln Ser
    1340                 1345                 1350

Glu Lys  Glu Leu Ala Glu Leu  Gln His Asn Ile Asp  Gly Leu Leu
    1355                 1360                 1365

Gln Glu  Lys Lys Asp Leu Glu  His Glu Val Glu Glu  Leu His Arg
    1370                 1375                 1380

Thr Ile  Gln Lys His Gln Gln  Arg Lys Asp Phe Ile  Asp Gly Asn
    1385                 1390                 1395

Val Glu  Ser Leu Val Asn Asp  Leu Glu Ile Glu Lys  Ser Leu Lys
    1400                 1405                 1410

His His  Glu Asp Ile Val Asp  Glu Ile Glu Cys Ile  Glu Arg Thr
    1415                 1420                 1425

Leu Leu  Lys Arg Arg Ala Glu  Leu Arg Glu Ala Asp  Arg Leu Leu
    1430                 1435                 1440

Thr Glu  Ala Glu Ser Glu Leu  Ser Cys Thr Lys Glu  Lys Thr Lys
    1445                 1450                 1455

His Ala  Val Glu Lys Phe Thr  Asp Ala Lys Arg Asn  Leu Leu Gln
    1460                 1465                 1470

Thr Glu  Lys Asp Ala Glu Glu  Leu Glu Arg Arg Ala  Gln Glu Thr
    1475                 1480                 1485

Ala Ile  Asn Leu Val Lys Ala  Asp Gln Gln Leu Arg  Leu Leu Gln
    1490                 1495                 1500

Ala Asp  Thr Lys Asp Leu Glu  Gln His Lys Met Glu  Gln Glu Glu
    1505                 1510                 1515
```

```
Ile Leu  Lys Glu Ile Asn Lys  Val Val Ala Ala Lys  Asp Ser Asp
    1520                 1525                 1530

Phe Gln  Ser Leu Asn Lys Lys  Lys Glu Val Leu Thr  Gly Glu Leu
    1535                 1540                 1545

Gln Lys  Leu Gln Lys Asp Ile  Glu Thr Ala Arg His  Asn Glu Asp
    1550                 1555                 1560

Gln His  Leu Gln Val Leu Lys  Glu Ser Glu Thr Leu  Leu Gln Ala
    1565                 1570                 1575

Lys Lys  Ala Glu Leu Glu Asn  Leu Lys Ser Gln Val  Ser Gly Gln
    1580                 1585                 1590

Gln Gln  Glu Met Ala Val Leu  Asp Arg Glu Leu Gly  His Lys Lys
    1595                 1600                 1605

Glu Glu  Leu His Leu Leu Gln  Glu Ser Met Val Gln  Ala Lys Ala
    1610                 1615                 1620

Asp Leu  Gln Glu Ala Leu Arg  Leu Gly Glu Ser Glu  Val Thr Glu
    1625                 1630                 1635

Lys Cys  Asn His Ile Arg Glu  Val Lys Ser Leu Leu  Glu Glu Leu
    1640                 1645                 1650

Ser Phe  Gln Lys Gly Glu Leu  Asn Val Gln Ile Ser  Glu Lys Lys
    1655                 1660                 1665

Thr Gln  Leu Ala Leu Ile Lys  Gln Glu Ile Glu Lys  Glu Glu Asp
    1670                 1675                 1680

Asn Leu  Gln Val Val Leu Gly  Gln Met Ser Lys His  Lys Thr Glu
    1685                 1690                 1695

Leu Lys  Asn Ile Leu Asp Met  Leu Gln Leu Glu Asn  Asn Glu Leu
    1700                 1705                 1710

Gln Gly  Leu Lys Leu Gln His  Asp Gln Lys Met Ser  Glu Leu Glu
    1715                 1720                 1725

Lys Thr  Arg Val Glu Val Leu  Glu Glu Lys Leu Glu  Leu Glu Ser
    1730                 1735                 1740

Leu Gln  Gln Ala Ala Leu Arg  Gln Arg Gly Glu Ile  Glu Trp Gln
    1745                 1750                 1755

Lys Gln  Leu Leu Gln Arg Asn  Thr Gln Glu Val Glu  Arg Met Thr
    1760                 1765                 1770

Ala Glu  Thr Arg Ala Leu Gln  Ser Cys Val Glu Ser  Leu Cys Lys
    1775                 1780                 1785

Glu Lys  Gln Asp Leu Glu Glu  Lys Gln Asp Ser Trp  Glu Lys Lys
    1790                 1795                 1800

Leu Ala  Gln Thr Lys Arg Val  Leu Ala Ala Ala Glu  Glu Asp Ser
    1805                 1810                 1815

Glu Met  Glu Arg Ala Arg Leu  Glu Lys Leu Glu Leu  Asp Ala Arg
    1820                 1825                 1830

Lys Leu  Gln Gln Glu Leu Asp  Gln Arg Asn Arg Glu  Lys Leu Ser
    1835                 1840                 1845

Leu His  Gln Asp Leu Ala Val  Val Gln Gln Gln Leu  Gln Glu Lys
    1850                 1855                 1860

Gln Glu  Ala Val Asn Ser Leu  Gln Lys Glu Leu Thr  Asp Val Gln
    1865                 1870                 1875

Glu His  Leu Asp Leu Ala Glu  Gln Glu Val Leu Cys  Thr Thr Lys
    1880                 1885                 1890

Arg Lys  Asp Ala Leu Leu Ser  Glu Gln Thr Arg Leu  Glu Lys Asp
    1895                 1900                 1905

Val Gly  Glu Trp Thr Lys Lys  Phe Glu Asp Cys Gln  Lys Glu Gly
```

```
    1910                1915                1920

Glu Thr  Lys Gln Gln Gln Leu  Gln Gly Leu Gln Lys  Glu Ile Glu
    1925                1930                1935

Gly Asn  Glu Ala Lys Leu Ala  Gln Gln Glu Met Met  Phe Gln Arg
    1940                1945                1950

Leu Gln  Lys Glu Arg Glu Cys  Glu Glu Lys Lys Leu  Glu Ala Ser
    1955                1960                1965

Lys Val  Thr Leu Lys Glu Gln  Gln Gln Gln Leu Glu  Lys Glu Leu
    1970                1975                1980

Met Glu  Gln Lys Gly Lys Leu  Asp Gln Val Leu Ala  Lys Leu Leu
    1985                1990                1995

Val Ala  Glu Glu Arg Val Arg  Thr Leu Gln Glu Glu  Gly Arg Trp
    2000                2005                2010

Ser Glu  Thr Leu Glu Lys Thr  Leu Ser Gln Thr Lys  Arg Gln Leu
    2015                2020                2025

Ser Glu  Arg Glu Gln Gln Leu  Leu Ala Lys Ser Asp  Glu Leu Leu
    2030                2035                2040

Ala Leu  Gln Lys Glu Thr Asp  Ser Met Arg Ala Asp  Phe Ser Leu
    2045                2050                2055

Leu Arg  Asn Gln Phe Leu Thr  Glu Arg Lys Lys Ala  Glu Lys Gln
    2060                2065                2070

Val Ala  Ser Leu Lys Glu Ala  Leu Lys Ile Gln Arg  Ser Gln Leu
    2075                2080                2085

Glu Lys  Asn Leu Leu Glu Gln  Lys Gln Glu Asn Ser  Cys Met Gln
    2090                2095                2100

Arg Glu  Met Ala Thr Ile Glu  Gln Val Ala Gln Asp  Asn His Glu
    2105                2110                2115

Arg Ala  Arg Arg Leu Met Arg  Glu Leu Asn Gln Met  Gln Arg Glu
    2120                2125                2130

Tyr Val  Glu Leu Arg Lys Gln  Met Thr Asn Gln Lys  Asp Leu Glu
    2135                2140                2145

Arg Arg  Gln Met Glu Ile Ser  Asp Ala Met Gln Ala  Leu Lys Cys
    2150                2155                2160

Glu Val  Lys Asp Glu Ile Arg  Thr Ser Leu Lys Asn  Leu Asn Gln
    2165                2170                2175

Phe Leu  Pro Glu Leu Pro Ala  Asp Leu Glu Ala Leu  Leu Glu Arg
    2180                2185                2190

Asn Glu  Asn Leu Gly Gly Gly  Leu Glu Ser Leu Lys  Glu Asn Phe
    2195                2200                2205

Pro Phe  Thr Val Ser Asp Arg  Pro Ser Ser Cys Glu  Glu Lys Leu
    2210                2215                2220

Asn Phe  Gly Gln Ala His Val  Ala Asp Glu Gln Trp  Arg Gly Glu
    2225                2230                2235

Ala Leu  Arg Glu Lys Leu Arg  His Arg Glu Asp Arg  Leu Lys Ala
    2240                2245                2250

Gln Leu  Arg Arg Cys Met Ser  Lys Gln Ala Glu Val  Leu Ser Glu
    2255                2260                2265

Gly Arg  Arg Arg Thr Glu Gly  Thr Leu His Ser Leu  Arg Arg Gln
    2270                2275                2280

Val Asp  Ala Leu Gly Glu Leu  Val Thr Ser Thr Ser  Gly Asp Ser
    2285                2290                2295

Ala Ser  Thr Arg Ser Leu Ser  Arg Thr Glu Gly Ser  Leu Ala Glu
    2300                2305                2310
```

```
Asp Glu  Pro Pro Gly Pro Ser  Gln Ser Ser Arg Arg  Leu Pro Arg
    2315                 2320                 2325

Gly Pro  Ser Pro Arg Leu Asp  Ala His Arg Pro
    2330                 2335


<210> SEQ ID NO 27
<211> LENGTH: 7770
<212> TYPE: DNA
<213> ORGANISM: Canis familiaris
<220> FEATURE:
<221> NAME/KEY: CDS
<222> LOCATION: (1)..(7770)

<400> SEQUENCE: 27

atg aag aaa ggt tct cag caa aag ttt ttg aaa gca aag atg cca cca       48
Met Lys Lys Gly Ser Gln Gln Lys Phe Leu Lys Ala Lys Met Pro Pro
1               5                   10                  15

tca tct cac tct cct agt cca cca tcc ctt acg tcc aat atg aga tct       96
Ser Ser His Ser Pro Ser Pro Pro Ser Leu Thr Ser Asn Met Arg Ser
            20                  25                  30

agg tca ctt tcg cct cta agt gga tct gag act ctg cct ttt cat ttt      144
Arg Ser Leu Ser Pro Leu Ser Gly Ser Glu Thr Leu Pro Phe His Phe
        35                  40                  45

gga gga ccg tgg cat gag caa gtt gag att aca gat gaa agc aca gtg      192
Gly Gly Pro Trp His Glu Gln Val Glu Ile Thr Asp Glu Ser Thr Val
    50                  55                  60

gtt tta gac tac caa gac cat aaa gaa gct gat tca cat gca gga gtc      240
Val Leu Asp Tyr Gln Asp His Lys Glu Ala Asp Ser His Ala Gly Val
65                  70                  75                  80

cga tat att aca gag gcc ctt gtt aga aaa ctt act aaa cag gac aat      288
Arg Tyr Ile Thr Glu Ala Leu Val Arg Lys Leu Thr Lys Gln Asp Asn
                85                  90                  95

ttg gcc ttg gta aaa tct ctg aac ctt tca ctt gct aaa ggt ggt ggc      336
Leu Ala Leu Val Lys Ser Leu Asn Leu Ser Leu Ala Lys Gly Gly Gly
            100                 105                 110

aag aaa ttc agg tgt atc gaa aat ttg gaa aaa tgt gtt aaa ctt gaa      384
Lys Lys Phe Arg Cys Ile Glu Asn Leu Glu Lys Cys Val Lys Leu Glu
        115                 120                 125

gta ctg aat ctc agc tat aat cta ata gga aag att gag aaa gtg gac      432
Val Leu Asn Leu Ser Tyr Asn Leu Ile Gly Lys Ile Glu Lys Val Asp
    130                 135                 140

aaa ctg tta aaa tta cgt gaa ctc aac tta tcg tat aac aaa atc cgc      480
Lys Leu Leu Lys Leu Arg Glu Leu Asn Leu Ser Tyr Asn Lys Ile Arg
145                 150                 155                 160

aaa att gaa ggc ata gaa aat tta tat aat ctg caa aag ctg aac ctt      528
Lys Ile Glu Gly Ile Glu Asn Leu Tyr Asn Leu Gln Lys Leu Asn Leu
                165                 170                 175

gca gga aat gaa atc gaa cat atc cca gta tgg tta ggg aag aag tta      576
Ala Gly Asn Glu Ile Glu His Ile Pro Val Trp Leu Gly Lys Lys Leu
            180                 185                 190

aaa tct ttg cga atc ctg aat ctg aaa ggc aac aag ata tca tcg ctc      624
Lys Ser Leu Arg Ile Leu Asn Leu Lys Gly Asn Lys Ile Ser Ser Leu
        195                 200                 205

caa gat gta agc aag ttg aaa cca ctt caa gat ttg act tct ctg atc      672
Gln Asp Val Ser Lys Leu Lys Pro Leu Gln Asp Leu Thr Ser Leu Ile
    210                 215                 220

cta ctt gaa aat cca gtt gcg acc ctt cct cat tat atc cag ttt acc      720
Leu Leu Glu Asn Pro Val Ala Thr Leu Pro His Tyr Ile Gln Phe Thr
225                 230                 235                 240

att ttt cac ctt cgc tca ttg gaa agt ttg gaa ggt cag cca gta act      768
```

```
Ile Phe His Leu Arg Ser Leu Glu Ser Leu Glu Gly Gln Pro Val Thr
                245                 250                 255

agt cag gac aga caa gaa gct ttt gcg aga ttc agt tta gat gag gta      816
Ser Gln Asp Arg Gln Glu Ala Phe Ala Arg Phe Ser Leu Asp Glu Val
            260                 265                 270

gaa aga ctg gaa aga gac ctg gag aag aag aca atg gaa act gaa gag      864
Glu Arg Leu Glu Arg Asp Leu Glu Lys Lys Thr Met Glu Thr Glu Glu
        275                 280                 285

ctt agg agt gag cag aca agg ttc ctt gag gaa att aaa agt cag gat      912
Leu Arg Ser Glu Gln Thr Arg Phe Leu Glu Glu Ile Lys Ser Gln Asp
    290                 295                 300

aaa ttg aac aaa tca ctg aaa gag gag gcc aga cta caa aaa cag agc      960
Lys Leu Asn Lys Ser Leu Lys Glu Glu Ala Arg Leu Gln Lys Gln Ser
305                 310                 315                 320

tat gag gag ctg gag agt aac cta aac acc aaa aat gaa ttg cta aaa     1008
Tyr Glu Glu Leu Glu Ser Asn Leu Asn Thr Lys Asn Glu Leu Leu Lys
                325                 330                 335

cag aag acc atg gaa cta atg cga gca tgt cag aaa cag tat gag atg     1056
Gln Lys Thr Met Glu Leu Met Arg Ala Cys Gln Lys Gln Tyr Glu Met
            340                 345                 350

gaa cag gag ttg gcc ttt tat aaa att gat gcc aaa ttt gaa cca cta     1104
Glu Gln Glu Leu Ala Phe Tyr Lys Ile Asp Ala Lys Phe Glu Pro Leu
        355                 360                 365

aat tat tac cca tca gag tat gtc gaa att gat aaa acc cca gat gaa     1152
Asn Tyr Tyr Pro Ser Glu Tyr Val Glu Ile Asp Lys Thr Pro Asp Glu
    370                 375                 380

agc cct tac att ggc aaa tcc aga tac aag aga aat atg ttc act aca     1200
Ser Pro Tyr Ile Gly Lys Ser Arg Tyr Lys Arg Asn Met Phe Thr Thr
385                 390                 395                 400

gag agt tat att att gca aat gcc cag aca gta aag atc aag aag atg     1248
Glu Ser Tyr Ile Ile Ala Asn Ala Gln Thr Val Lys Ile Lys Lys Met
                405                 410                 415

gag cta gat gaa ggg gaa caa ctc aga aat gag cac gtg aac ttg gga     1296
Glu Leu Asp Glu Gly Glu Gln Leu Arg Asn Glu His Val Asn Leu Gly
            420                 425                 430

gca tcg cca aca gac ata caa ctg gaa gac aaa gaa aaa aaa ata agt     1344
Ala Ser Pro Thr Asp Ile Gln Leu Glu Asp Lys Glu Lys Lys Ile Ser
        435                 440                 445

gca gca caa act cga cta tca gaa cta cat gat gaa ata gaa aag gca     1392
Ala Ala Gln Thr Arg Leu Ser Glu Leu His Asp Glu Ile Glu Lys Ala
    450                 455                 460

gaa caa caa att tta aga gcc act gaa gaa ttt aaa caa ctg gaa gaa     1440
Glu Gln Gln Ile Leu Arg Ala Thr Glu Glu Phe Lys Gln Leu Glu Glu
465                 470                 475                 480

gct ata caa ctt aaa aaa att tca gaa gcg gag aaa gac ctt ctt ttc     1488
Ala Ile Gln Leu Lys Lys Ile Ser Glu Ala Glu Lys Asp Leu Leu Phe
                485                 490                 495

aag cag ttg agt ggt agg ata cag ctt ctc aat aaa tta cgc caa gaa     1536
Lys Gln Leu Ser Gly Arg Ile Gln Leu Leu Asn Lys Leu Arg Gln Glu
            500                 505                 510

gct gtg gat cta gaa aca cag atg gaa aag caa agg caa gaa att ggt     1584
Ala Val Asp Leu Glu Thr Gln Met Glu Lys Gln Arg Gln Glu Ile Gly
        515                 520                 525

gaa aag cag aat gag atc aag gac ctg gaa ata gtc aca gat agc ctg     1632
Glu Lys Gln Asn Glu Ile Lys Asp Leu Glu Ile Val Thr Asp Ser Leu
    530                 535                 540

gat tcc aga gac cca aaa cat tgc cat atg aag gct cag aaa aga ggt     1680
Asp Ser Arg Asp Pro Lys His Cys His Met Lys Ala Gln Lys Arg Gly
545                 550                 555                 560
```

-continued

```
aaa gaa caa caa ctt gac att atg aac aag cag tac aaa cag ctt gaa      1728
Lys Glu Gln Gln Leu Asp Ile Met Asn Lys Gln Tyr Lys Gln Leu Glu
                565                 570                 575

agc cgt ttg gat gag ata ctt tct aga att gcc aaa gaa act gaa gag      1776
Ser Arg Leu Asp Glu Ile Leu Ser Arg Ile Ala Lys Glu Thr Glu Glu
            580                 585                 590

att aag gac ctt gaa gaa cag ctt act gaa gga caa ata gcc gca aac      1824
Ile Lys Asp Leu Glu Glu Gln Leu Thr Glu Gly Gln Ile Ala Ala Asn
        595                 600                 605

gaa gcc ctg aag aag gac tta gaa agt gtc atc agt ggg ttg caa gaa      1872
Glu Ala Leu Lys Lys Asp Leu Glu Ser Val Ile Ser Gly Leu Gln Glu
    610                 615                 620

tac ctg gag act gtc aaa ggt cag gcc cgt cag gcc cag aat gag tgc      1920
Tyr Leu Glu Thr Val Lys Gly Gln Ala Arg Gln Ala Gln Asn Glu Cys
625                 630                 635                 640

aga aag cta cag gat gag aag gag aca ttg ctg cag aga ttg agt gag      1968
Arg Lys Leu Gln Asp Glu Lys Glu Thr Leu Leu Gln Arg Leu Ser Glu
                645                 650                 655

gtc gag cag gag agg gac caa ctg gaa ata gtg gcc ata gat gca gaa      2016
Val Glu Gln Glu Arg Asp Gln Leu Glu Ile Val Ala Ile Asp Ala Glu
            660                 665                 670

aat atg agg aag gag ctc gca gaa ctg gag aat gcc ctc cag gag cag      2064
Asn Met Arg Lys Glu Leu Ala Glu Leu Glu Asn Ala Leu Gln Glu Gln
        675                 680                 685

cat gag gtg aat ata tct ctg cag cag acc cag gga gat ctc agt gcc      2112
His Glu Val Asn Ile Ser Leu Gln Gln Thr Gln Gly Asp Leu Ser Ala
    690                 695                 700

tat gag gct gag cta gag gct cag ctg aaa ata cgg gat gct gaa gcc      2160
Tyr Glu Ala Glu Leu Glu Ala Gln Leu Lys Ile Arg Asp Ala Glu Ala
705                 710                 715                 720

aac cag ctc aag gag gag ttg gaa aaa ctt aga agg ttg agc cag tta      2208
Asn Gln Leu Lys Glu Glu Leu Glu Lys Leu Arg Arg Leu Ser Gln Leu
                725                 730                 735

gaa caa tcg gcc ctt caa gca gag ctt gag aag gaa aag caa gcc ttc      2256
Glu Gln Ser Ala Leu Gln Ala Glu Leu Glu Lys Glu Lys Gln Ala Phe
            740                 745                 750

aag act gct gtc aaa aaa gcc cag ctc tca gaa gga aag gac caa gaa      2304
Lys Thr Ala Val Lys Lys Ala Gln Leu Ser Glu Gly Lys Asp Gln Glu
        755                 760                 765

aat agt gag ctc cgc aca caa ctc caa cag ctg cag gat gac aat gac      2352
Asn Ser Glu Leu Arg Thr Gln Leu Gln Gln Leu Gln Asp Asp Asn Asp
    770                 775                 780

cta ttg aaa cag caa ctt aaa gat ttc cag agt cac ctt aac cat gtg      2400
Leu Leu Lys Gln Gln Leu Lys Asp Phe Gln Ser His Leu Asn His Val
785                 790                 795                 800

gtt gat ggt ttg att cgt cca gaa gaa gtg gca gct tgt gtg gat gag      2448
Val Asp Gly Leu Ile Arg Pro Glu Glu Val Ala Ala Cys Val Asp Glu
                805                 810                 815

cta agg aaa aaa ctg aag tca gga gct ggg gaa atg aga atc cat act      2496
Leu Arg Lys Lys Leu Lys Ser Gly Ala Gly Glu Met Arg Ile His Thr
            820                 825                 830

cct tca gat gtc tta ggg aaa agt ctt gct gac ttg cag aag caa ttc      2544
Pro Ser Asp Val Leu Gly Lys Ser Leu Ala Asp Leu Gln Lys Gln Phe
        835                 840                 845

agt gag atc ctg gca cgc tcc cag tgg gaa aga cag gaa gca caa gtg      2592
Ser Glu Ile Leu Ala Arg Ser Gln Trp Glu Arg Gln Glu Ala Gln Val
    850                 855                 860

aga gag aga aaa ctc cag gag gaa atg gct ctg caa caa gag aaa ctg      2640
Arg Glu Arg Lys Leu Gln Glu Glu Met Ala Leu Gln Gln Glu Lys Leu
865                 870                 875                 880
```

```
gcg agc gga caa gag gag ttc agg cac gcc tgc gag agg gcc ctg gaa      2688
Ala Ser Gly Gln Glu Glu Phe Arg His Ala Cys Glu Arg Ala Leu Glu
                885                 890                 895

gcc cga att agt ttt gat aag agg cag cac gaa gca aga atc cag cag      2736
Ala Arg Ile Ser Phe Asp Lys Arg Gln His Glu Ala Arg Ile Gln Gln
            900                 905                 910

ttg gag aat gaa att cac tat ttg caa gaa aat cta aaa agt atg gag      2784
Leu Glu Asn Glu Ile His Tyr Leu Gln Glu Asn Leu Lys Ser Met Glu
        915                 920                 925

gaa atc caa ggt ctc aca gac ctc caa ctt cag gaa gct gat gaa gag      2832
Glu Ile Gln Gly Leu Thr Asp Leu Gln Leu Gln Glu Ala Asp Glu Glu
    930                 935                 940

aag gag aga att ctg gcc caa ctc cgg gag tta gag aaa aag aag aaa      2880
Lys Glu Arg Ile Leu Ala Gln Leu Arg Glu Leu Glu Lys Lys Lys Lys
945                 950                 955                 960

ctt gag gat gcc aag tct cag gag cag ttt ctt gga tta gat aga gaa      2928
Leu Glu Asp Ala Lys Ser Gln Glu Gln Phe Leu Gly Leu Asp Arg Glu
                965                 970                 975

ttg aag aag cta aag aaa gct gtg gct gcc tct gat aag ctg gcc aca      2976
Leu Lys Lys Leu Lys Lys Ala Val Ala Ala Ser Asp Lys Leu Ala Thr
            980                 985                 990

gct gag ctc acc att gcc aaa gac  cag ctc aag tcc ctt  cat gga act    3024
Ala Glu Leu Thr Ile Ala Lys Asp  Gln Leu Lys Ser Leu  His Gly Thr
        995                 1000                1005

gtg atg  aaa att aac cag gag  cga gca gag gag ctg  cag gag acg      3069
Val Met  Lys Ile Asn Gln Glu  Arg Ala Glu Glu Leu  Gln Glu Thr
    1010                 1015                 1020

gag agg  ttc agc aga aag gca  gca caa gca gct agg  gat ctg atc      3114
Glu Arg  Phe Ser Arg Lys Ala  Ala Gln Ala Ala Arg  Asp Leu Ile
    1025                 1030                 1035

cga gca  gaa gcg gag att gaa  ctc ctg cag aag ctt  ctc aga gat      3159
Arg Ala  Glu Ala Glu Ile Glu  Leu Leu Gln Lys Leu  Leu Arg Asp
    1040                 1045                 1050

aaa gag  gag cag ttt cga aat  gag att gag aaa gta  gat gtc ggc      3204
Lys Glu  Glu Gln Phe Arg Asn  Glu Ile Glu Lys Val  Asp Val Gly
    1055                 1060                 1065

tct gga  gga gca aag tca cag  atg ctg gag atg gag  aaa cta aat      3249
Ser Gly  Gly Ala Lys Ser Gln  Met Leu Glu Met Glu  Lys Leu Asn
    1070                 1075                 1080

gag aca  atg gag agg caa aga  aca gag att gct agg  ctg agg aat      3294
Glu Thr  Met Glu Arg Gln Arg  Thr Glu Ile Ala Arg  Leu Arg Asn
    1085                 1090                 1095

tta cta  gac ctc acc ggg gct  gat aac aaa gga aac  ttt gaa aat      3339
Leu Leu  Asp Leu Thr Gly Ala  Asp Asn Lys Gly Asn  Phe Glu Asn
    1100                 1105                 1110

gtt ttg  gaa gaa att gct gaa  ctt cga cgt gaa gtt  tct cat cag      3384
Val Leu  Glu Glu Ile Ala Glu  Leu Arg Arg Glu Val  Ser His Gln
    1115                 1120                 1125

aat gat  tac atc agc agc atg  aca gat cct ttc aaa  aga cga ggc      3429
Asn Asp  Tyr Ile Ser Ser Met  Thr Asp Pro Phe Lys  Arg Arg Gly
    1130                 1135                 1140

tat tgg  tac ttt atg cca cca  cca tca tca tca aaa  gtt tcc agc      3474
Tyr Trp  Tyr Phe Met Pro Pro  Pro Ser Ser Ser Lys  Val Ser Ser
    1145                 1150                 1155

cac agt  tcc cag gcc acc aag  gac tct ggt gtt ggc  cta aag tac      3519
His Ser  Ser Gln Ala Thr Lys  Asp Ser Gly Val Gly  Leu Lys Tyr
    1160                 1165                 1170

aca gcc  tcc act ccg gtt aga  aaa cca cat cgt gga  cgg cag gat      3564
Thr Ala  Ser Thr Pro Val Arg  Lys Pro His Arg Gly  Arg Gln Asp
```

```
    1175                1180                1185

gga aag  gag aac agt ggg cct  cca cct gcc tca gga  tac tgg gtg      3609
Gly Lys  Glu Asn Ser Gly Pro  Pro Pro Ala Ser Gly  Tyr Trp Val
    1190                1195                1200

tat tct  cct atc agg agt ggg  tta cat aaa tcg ttc  tca aat aga      3654
Tyr Ser  Pro Ile Arg Ser Gly  Leu His Lys Ser Phe  Ser Asn Arg
    1205                1210                1215

gac gca  gac agt gga gga gat  agc cag gaa gag agc  gag cta gat      3699
Asp Ala  Asp Ser Gly Gly Asp  Ser Gln Glu Glu Ser  Glu Leu Asp
    1220                1225                1230

gac caa  gaa gac cac cca ttt  gta cct cct cct gga  tac atg atg      3744
Asp Gln  Glu Asp His Pro Phe  Val Pro Pro Pro Gly  Tyr Met Met
    1235                1240                1245

tac act  gtg ttt cct gat ggt  tct cct gta ccc cag  ggc atg gcc      3789
Tyr Thr  Val Phe Pro Asp Gly  Ser Pro Val Pro Gln  Gly Met Ala
    1250                1255                1260

ctg tat  gca ccc cct cct ccc  ttg ccc aac aat agc  cag cct ctt      3834
Leu Tyr  Ala Pro Pro Pro Pro  Leu Pro Asn Asn Ser  Gln Pro Leu
    1265                1270                1275

gac ctt  ggc act gtt gtt tat  ggc cca cct cct gtt  ggg gct ccc      3879
Asp Leu  Gly Thr Val Val Tyr  Gly Pro Pro Pro Val  Gly Ala Pro
    1280                1285                1290

atc gtg  tat ggg cct cca cct  ccc aac ttc tcc gta  ccc ctc atc      3924
Ile Val  Tyr Gly Pro Pro Pro  Pro Asn Phe Ser Val  Pro Leu Ile
    1295                1300                1305

ccc gtg  ggt gtg ctg cac tgc  aat gtc cca gaa cac  cat aac ttg      3969
Pro Val  Gly Val Leu His Cys  Asn Val Pro Glu His  His Asn Leu
    1310                1315                1320

gag aat  gaa gtt tct aga tta  gaa gac ata atg cag  cat tta aaa      4014
Glu Asn  Glu Val Ser Arg Leu  Glu Asp Ile Met Gln  His Leu Lys
    1325                1330                1335

tct ggg  aaa cgg gaa cag tgc  atg aaa aca ccc aag  ctg cag tcg      4059
Ser Gly  Lys Arg Glu Gln Cys  Met Lys Thr Pro Lys  Leu Gln Ser
    1340                1345                1350

gag aaa  gaa ctc gca gag ctg  cag cat aac att gat  ggt ctt ttg      4104
Glu Lys  Glu Leu Ala Glu Leu  Gln His Asn Ile Asp  Gly Leu Leu
    1355                1360                1365

caa gag  aag aaa gac tta gag  cat gaa gta gaa gaa  tta cat aga      4149
Gln Glu  Lys Lys Asp Leu Glu  His Glu Val Glu Glu  Leu His Arg
    1370                1375                1380

acc atc  caa aaa cat caa cag  cga aaa gat ttc att  gat gga aac      4194
Thr Ile  Gln Lys His Gln Gln  Arg Lys Asp Phe Ile  Asp Gly Asn
    1385                1390                1395

gtt gag  agt ctt gtg aat gat  cta gaa ata gag aag  tca ctc aaa      4239
Val Glu  Ser Leu Val Asn Asp  Leu Glu Ile Glu Lys  Ser Leu Lys
    1400                1405                1410

cac cat  gaa gat att gtt gat  gaa att gaa tgt att  gag agg acc      4284
His His  Glu Asp Ile Val Asp  Glu Ile Glu Cys Ile  Glu Arg Thr
    1415                1420                1425

ctt ctg  aag cgc cgt gca gag  ctc agg gaa gcc gac  cgg ctg ctg      4329
Leu Leu  Lys Arg Arg Ala Glu  Leu Arg Glu Ala Asp  Arg Leu Leu
    1430                1435                1440

acg gag  gct gaa agt gaa ctt  tca tgc acg aaa gag  aaa aca aaa      4374
Thr Glu  Ala Glu Ser Glu Leu  Ser Cys Thr Lys Glu  Lys Thr Lys
    1445                1450                1455

cat gct  gtt gag aag ttc act  gat gcc aag aga aat  tta ttg caa      4419
His Ala  Val Glu Lys Phe Thr  Asp Ala Lys Arg Asn  Leu Leu Gln
    1460                1465                1470

act gag  aaa gat gct gag gag  tta gaa agg aga gcc  cag gaa act      4464
```

```
Thr Glu  Lys Asp Ala Glu Glu  Leu Glu Arg Arg Ala  Gln Glu Thr
    1475                 1480                 1485

gcc att  aac ctc gtc aaa gcc  gac cag cag ctg aga  ttg ctc cag      4509
Ala Ile  Asn Leu Val Lys Ala  Asp Gln Gln Leu Arg  Leu Leu Gln
    1490                 1495                 1500

gct gac  acg aag gat ttg gag  cag cac aaa atg gag  caa gag gaa      4554
Ala Asp  Thr Lys Asp Leu Glu  Gln His Lys Met Glu  Gln Glu Glu
    1505                 1510                 1515

atc ttg  aaa gaa ata aac aaa  gtt gtt gca gca aaa  gac tca gac      4599
Ile Leu  Lys Glu Ile Asn Lys  Val Val Ala Ala Lys  Asp Ser Asp
    1520                 1525                 1530

ttc cag  agc cta aac aag aag  aag gaa gta ctg aca  gga gag ctg      4644
Phe Gln  Ser Leu Asn Lys Lys  Lys Glu Val Leu Thr  Gly Glu Leu
    1535                 1540                 1545

cag aaa  ctc cag aag gac att  gag act gca cgg cac  aat gag gat      4689
Gln Lys  Leu Gln Lys Asp Ile  Glu Thr Ala Arg His  Asn Glu Asp
    1550                 1555                 1560

cag cac  ctg cag gtc ctt aaa  gag tcg gag acc ctc  ctg cag gcc      4734
Gln His  Leu Gln Val Leu Lys  Glu Ser Glu Thr Leu  Leu Gln Ala
    1565                 1570                 1575

aag aaa  gct gag ctg gaa aat  ctg aaa agc cag gtg  tca gga cag      4779
Lys Lys  Ala Glu Leu Glu Asn  Leu Lys Ser Gln Val  Ser Gly Gln
    1580                 1585                 1590

cag cag  gag atg gcc gtc ttg  gac agg gag tta gga  cac aag aag      4824
Gln Gln  Glu Met Ala Val Leu  Asp Arg Glu Leu Gly  His Lys Lys
    1595                 1600                 1605

gaa gag  ctg cat ctc ctc cag  gaa agc atg gtc cag  gcc aaa gct      4869
Glu Glu  Leu His Leu Leu Gln  Glu Ser Met Val Gln  Ala Lys Ala
    1610                 1615                 1620

gac ctc  cag gaa gca ctg aga  cta gga gaa agt gaa  gta act gag      4914
Asp Leu  Gln Glu Ala Leu Arg  Leu Gly Glu Ser Glu  Val Thr Glu
    1625                 1630                 1635

aag tgc  aat cac att agg gaa  gta aaa tct ctt ctg  gaa gaa ctc      4959
Lys Cys  Asn His Ile Arg Glu  Val Lys Ser Leu Leu  Glu Glu Leu
    1640                 1645                 1650

agt ttt  cag aaa gga gaa ctg  aat gtc cag atc agt  gaa aaa aaa      5004
Ser Phe  Gln Lys Gly Glu Leu  Asn Val Gln Ile Ser  Glu Lys Lys
    1655                 1660                 1665

act caa  ctt gca ctc ata aag  cag gaa att gaa aaa  gag gaa gac      5049
Thr Gln  Leu Ala Leu Ile Lys  Gln Glu Ile Glu Lys  Glu Glu Asp
    1670                 1675                 1680

aat ctt  cag gta gtt tta ggg  caa atg tct aaa cat  aaa act gaa      5094
Asn Leu  Gln Val Val Leu Gly  Gln Met Ser Lys His  Lys Thr Glu
    1685                 1690                 1695

cta aag  aat att ctg gac atg  ttg caa ctt gaa aat  aat gag ctg      5139
Leu Lys  Asn Ile Leu Asp Met  Leu Gln Leu Glu Asn  Asn Glu Leu
    1700                 1705                 1710

caa ggt  ttg aag ctc caa cat  gac caa aag atg tct  gaa tta gag      5184
Gln Gly  Leu Lys Leu Gln His  Asp Gln Lys Met Ser  Glu Leu Glu
    1715                 1720                 1725

aag act  cgg gtt gaa gtg ctg  gag gag aaa ctg gag  tta gag agt      5229
Lys Thr  Arg Val Glu Val Leu  Glu Glu Lys Leu Glu  Leu Glu Ser
    1730                 1735                 1740

ctg cag  cag gca gcc ctg cga  cag aga ggg gag ata  gag tgg cag      5274
Leu Gln  Gln Ala Ala Leu Arg  Gln Arg Gly Glu Ile  Glu Trp Gln
    1745                 1750                 1755

aag cag  ctc ctc cag agg aac  aca cag gaa gta gag  cgg atg act      5319
Lys Gln  Leu Leu Gln Arg Asn  Thr Gln Glu Val Glu  Arg Met Thr
    1760                 1765                 1770
```

```
gct gag  acc cga gca tta cag  tca tgt gtt gag tct  ttg tgc aaa      5364
Ala Glu  Thr Arg Ala Leu Gln  Ser Cys Val Glu Ser  Leu Cys Lys
    1775                1780                1785

gaa aag  caa gat ctc gaa gaa  aaa cag gac agc tgg  gaa aag aag      5409
Glu Lys  Gln Asp Leu Glu Glu  Lys Gln Asp Ser Trp  Glu Lys Lys
    1790                1795                1800

ttg gca  cag acc aaa cgg gtt  cta gca gct gca gaa  gag gac agc      5454
Leu Ala  Gln Thr Lys Arg Val  Leu Ala Ala Ala Glu  Glu Asp Ser
    1805                1810                1815

gag atg  gag cgg gca cgc tta  gaa aag ttg gaa ctg  gac gcc agg      5499
Glu Met  Glu Arg Ala Arg Leu  Glu Lys Leu Glu Leu  Asp Ala Arg
    1820                1825                1830

aag ctg  cag cag gag ttg gac  caa cga aac agg gag  aag ctc tcc      5544
Lys Leu  Gln Gln Glu Leu Asp  Gln Arg Asn Arg Glu  Lys Leu Ser
    1835                1840                1845

ctg cat  caa gac ctg gca gtg  gtg cag cag cag cta  caa gaa aaa      5589
Leu His  Gln Asp Leu Ala Val  Val Gln Gln Gln Leu  Gln Glu Lys
    1850                1855                1860

cag gaa  gca gta aac tca tta  cag aag gaa cta gct  gat gtc cag      5634
Gln Glu  Ala Val Asn Ser Leu  Gln Lys Glu Leu Ala  Asp Val Gln
    1865                1870                1875

gag cat  ttg gac cta gca gaa  cag gag gtg ctc tgc  acc acc aag      5679
Glu His  Leu Asp Leu Ala Glu  Gln Glu Val Leu Cys  Thr Thr Lys
    1880                1885                1890

cgc aag  gac gca ctg ctc agc  gaa cag acc agg ctc  gag aag gac      5724
Arg Lys  Asp Ala Leu Leu Ser  Glu Gln Thr Arg Leu  Glu Lys Asp
    1895                1900                1905

gtg ggt  gaa tgg acg aag aag  ttt gaa gac tgc cag  aaa gaa ggg      5769
Val Gly  Glu Trp Thr Lys Lys  Phe Glu Asp Cys Gln  Lys Glu Gly
    1910                1915                1920

gag aca  aag cag caa cag ctt  caa ggg ctt cag aag  gag att gaa      5814
Glu Thr  Lys Gln Gln Gln Leu  Gln Gly Leu Gln Lys  Glu Ile Glu
    1925                1930                1935

gga aac  gag gcg aag cta gcc  caa caa gaa atg atg  ttt cag aga      5859
Gly Asn  Glu Ala Lys Leu Ala  Gln Gln Glu Met Met  Phe Gln Arg
    1940                1945                1950

ctc cag  aaa gag cga gaa tgt  gaa gaa aaa aag tta  gaa gct agt      5904
Leu Gln  Lys Glu Arg Glu Cys  Glu Glu Lys Lys Leu  Glu Ala Ser
    1955                1960                1965

aaa gtg  act ctg aag gag cag  cag caa cag ctg gaa  aag gaa ttg      5949
Lys Val  Thr Leu Lys Glu Gln  Gln Gln Gln Leu Glu  Lys Glu Leu
    1970                1975                1980

atg gag  cag aaa ggc aag ctg  gac cag gtg ctc gct  aag ctc ttg      5994
Met Glu  Gln Lys Gly Lys Leu  Asp Gln Val Leu Ala  Lys Leu Leu
    1985                1990                1995

gtg gct  gag gag cgt gtc agg  acc ttg cag gag gag  gga agg tgg      6039
Val Ala  Glu Glu Arg Val Arg  Thr Leu Gln Glu Glu  Gly Arg Trp
    2000                2005                2010

agc gag  acc ctg gag aag acg  ctc tcc cag acc aag  cga cag ctt      6084
Ser Glu  Thr Leu Glu Lys Thr  Leu Ser Gln Thr Lys  Arg Gln Leu
    2015                2020                2025

tca gaa  cgg gag cag cag tta  ctg gcc aag tca gac  gag ctg ctg      6129
Ser Glu  Arg Glu Gln Gln Leu  Leu Ala Lys Ser Asp  Glu Leu Leu
    2030                2035                2040

gcc ctg  cag aag gag acg gac  tcc atg agg gcg gac  ttc agc ctc      6174
Ala Leu  Gln Lys Glu Thr Asp  Ser Met Arg Ala Asp  Phe Ser Leu
    2045                2050                2055

ttg cgc  aac cag ttc ctg aca  gaa aga aag aaa gcc  gag aag cag      6219
Leu Arg  Asn Gln Phe Leu Thr  Glu Arg Lys Lys Ala  Glu Lys Gln
    2060                2065                2070
```

```
gtg gcc  agc ctg aag gaa gcc  ctt aag atc cag cgg  agc caa ctg      6264
Val Ala  Ser Leu Lys Glu Ala  Leu Lys Ile Gln Arg  Ser Gln Leu
    2075                 2080                 2085

gag aag  aac ctt ctg gag caa  aag cag gag aac agc  tgc atg cag      6309
Glu Lys  Asn Leu Leu Glu Gln  Lys Gln Glu Asn Ser  Cys Met Gln
    2090                 2095                 2100

agg gag  atg gca acc atc gaa  cag gtg gcc cag gac  aac cac gag      6354
Arg Glu  Met Ala Thr Ile Glu  Gln Val Ala Gln Asp  Asn His Glu
    2105                 2110                 2115

cgg gcc  cgg cgc ctg atg agg  gag ctc aac cag atg  cag cgc gag      6399
Arg Ala  Arg Arg Leu Met Arg  Glu Leu Asn Gln Met  Gln Arg Glu
    2120                 2125                 2130

tac gtg  gag ctc agg aaa cag  atg aca aac caa aag  gat ttg gaa      6444
Tyr Val  Glu Leu Arg Lys Gln  Met Thr Asn Gln Lys  Asp Leu Glu
    2135                 2140                 2145

aga aga  cag atg gaa atc agt  gat gcg atg caa gca  ctt aaa tgt      6489
Arg Arg  Gln Met Glu Ile Ser  Asp Ala Met Gln Ala  Leu Lys Cys
    2150                 2155                 2160

gag gtg  aaa gat gaa atc cga  acc agc ctg aag aat  ctc aac cag      6534
Glu Val  Lys Asp Glu Ile Arg  Thr Ser Leu Lys Asn  Leu Asn Gln
    2165                 2170                 2175

ttt ctt  cca gag ctg cca gcg  gac ctg gag gcc ctt  ctg gaa agg      6579
Phe Leu  Pro Glu Leu Pro Ala  Asp Leu Glu Ala Leu  Leu Glu Arg
    2180                 2185                 2190

aat gag  aac ctt gga gga ggc  ttg gag agc ttg aaa  gag aat ttc      6624
Asn Glu  Asn Leu Gly Gly Gly  Leu Glu Ser Leu Lys  Glu Asn Phe
    2195                 2200                 2205

ccg ttt  acc gtg agc gac aga  cca tca tct tgc gaa  gag aaa ctg      6669
Pro Phe  Thr Val Ser Asp Arg  Pro Ser Ser Cys Glu  Glu Lys Leu
    2210                 2215                 2220

aat ttt  ggc cag gct cac gtg  gcg gat gaa cag tgg  cgg gga gag      6714
Asn Phe  Gly Gln Ala His Val  Ala Asp Glu Gln Trp  Arg Gly Glu
    2225                 2230                 2235

gca ctc  cgg gag aag ctg cgc  cac cgc gag gac cgg  ctc aag gcc      6759
Ala Leu  Arg Glu Lys Leu Arg  His Arg Glu Asp Arg  Leu Lys Ala
    2240                 2245                 2250

cag ctg  cgc cgc tgc atg tcc  aag cag gcc gag gtg  ctg agc gag      6804
Gln Leu  Arg Arg Cys Met Ser  Lys Gln Ala Glu Val  Leu Ser Glu
    2255                 2260                 2265

ggc cgg  cgg cgc acg gag ggg  acc ctg cac agc ctg  cgg cgg cag      6849
Gly Arg  Arg Arg Thr Glu Gly  Thr Leu His Ser Leu  Arg Arg Gln
    2270                 2275                 2280

gtg gac  gcc ctg ggc gag ctg  gtc acc agc act tcc  ggg gac tcc      6894
Val Asp  Ala Leu Gly Glu Leu  Val Thr Ser Thr Ser  Gly Asp Ser
    2285                 2290                 2295

gcg tcc  acc cgc agt ctg tcg  cgc acc gag ggc tcg  ctc gcc gag      6939
Ala Ser  Thr Arg Ser Leu Ser  Arg Thr Glu Gly Ser  Leu Ala Glu
    2300                 2305                 2310

gac gaa  ccg ccg ggg ccc agc  cag gag ctg cac gtg  ctg ggg tcg      6984
Asp Glu  Pro Pro Gly Pro Ser  Gln Glu Leu His Val  Leu Gly Ser
    2315                 2320                 2325

ggc ggc  agc gac cga ggt gga  gga cgg ggc ggg ggc  agg aag ggc      7029
Gly Gly  Ser Asp Arg Gly Gly  Gly Arg Gly Gly Gly  Arg Lys Gly
    2330                 2335                 2340

ctt tcc  cga cgc cgc cgc tgg  aac cac gga gaa gcg  cgc ctc ggc      7074
Leu Ser  Arg Arg Arg Arg Trp  Asn His Gly Glu Ala  Arg Leu Gly
    2345                 2350                 2355

ccg cgg  agg ccc cca cgg gag  ggg gca ggg cgg ggc  gcg gcc ttc      7119
Pro Arg  Arg Pro Pro Arg Glu  Gly Ala Gly Arg Gly  Ala Ala Phe
```

```
    2360                2365                2370

cga gcc  ttg gtc tcc tgc tcc  cgc cct gca gag ctc  ccg gcg gct      7164
Arg Ala  Leu Val Ser Cys Ser  Arg Pro Ala Glu Leu  Pro Ala Ala
    2375                2380                2385

ccc ccg  agg ccc gtc gcc gcg  gct gga cgc gca ccg  acc ctg agg      7209
Pro Pro  Arg Pro Val Ala Ala  Ala Gly Arg Ala Pro  Thr Leu Arg
    2390                2395                2400

acc cgg  agg acc cgg agg ccc  ggc gtc ccc tcg gaa  cgc ttc ctc      7254
Thr Arg  Arg Thr Arg Arg Pro  Gly Val Pro Ser Glu  Arg Phe Leu
    2405                2410                2415

cgc gtc  cgc gga cac cag gct  cac ggg aag gcg cgt  cca tgc ggg      7299
Arg Val  Arg Gly His Gln Ala  His Gly Lys Ala Arg  Pro Cys Gly
    2420                2425                2430

aag agc  cgc gag cgg aac ccg  gat gcc cgg gct ggt  ctc tgg gcc      7344
Lys Ser  Arg Glu Arg Asn Pro  Asp Ala Arg Ala Gly  Leu Trp Ala
    2435                2440                2445

ttg gaa  acg tgt tgc cgt aaa  agc agc gcc cgc ggc  tgc gga ctt      7389
Leu Glu  Thr Cys Cys Arg Lys  Ser Ser Ala Arg Gly  Cys Gly Leu
    2450                2455                2460

gaa gcc  ccg aac tgc cgc cgt  gcc cgg tgc gga gcg  agc gtg cgg      7434
Glu Ala  Pro Asn Cys Arg Arg  Ala Arg Cys Gly Ala  Ser Val Arg
    2465                2470                2475

tac cct  ctc gtg cct cgg ggc  cgg act gga cga ggg  gcc gtg acc      7479
Tyr Pro  Leu Val Pro Arg Gly  Arg Thr Gly Arg Gly  Ala Val Thr
    2480                2485                2490

ccg tgg  ggc cgc ctg cag tcc  cga ggg acg cgg acc  acc ccc cgg      7524
Pro Trp  Gly Arg Leu Gln Ser  Arg Gly Thr Arg Thr  Thr Pro Arg
    2495                2500                2505

ccg gtg  cga cgg gag cat ccc  cag cac cag gaa agg  ccc cca ggg      7569
Pro Val  Arg Arg Glu His Pro  Gln His Gln Glu Arg  Pro Pro Gly
    2510                2515                2520

cgc gtt  acc gcg gcc cac act  gag acc gcc cct ccc  cgc cgg gtg      7614
Arg Val  Thr Ala Ala His Thr  Glu Thr Ala Pro Pro  Arg Arg Val
    2525                2530                2535

ttc cac  gcg cga gta gca gtc  ggg gag gtc agc ctc  ggg ccc ggc      7659
Phe His  Ala Arg Val Ala Val  Gly Glu Val Ser Leu  Gly Pro Gly
    2540                2545                2550

cgc ggt  ctc gag cga aca cgg  ggc ggg ggc ggg ggg  gcg ggg gcg      7704
Arg Gly  Leu Glu Arg Thr Arg  Gly Gly Gly Gly Gly  Ala Gly Ala
    2555                2560                2565

gga ctc  ctc gca gag gcc gcg  gcc acg gcc cgg tgc  gca gac ccc      7749
Gly Leu  Leu Ala Glu Ala Ala  Ala Thr Ala Arg Cys  Ala Asp Pro
    2570                2575                2580

tcc aca  gac ccc tcc gca tag                                        7770
Ser Thr  Asp Pro Ser Ala
    2585


<210> SEQ ID NO 28
<211> LENGTH: 2589
<212> TYPE: PRT
<213> ORGANISM: Canis familiaris

<400> SEQUENCE: 28

Met Lys Lys Gly Ser Gln Gln Lys Phe Leu Lys Ala Lys Met Pro Pro
1               5                   10                  15

Ser Ser His Ser Pro Ser Pro Pro Ser Leu Thr Ser Asn Met Arg Ser
            20                  25                  30

Arg Ser Leu Ser Pro Leu Ser Gly Ser Glu Thr Leu Pro Phe His Phe
        35                  40                  45
```

```
Gly Gly Pro Trp His Glu Gln Val Glu Ile Thr Asp Glu Ser Thr Val
    50                  55                  60

Val Leu Asp Tyr Gln Asp His Lys Glu Ala Asp Ser His Ala Gly Val
65                  70                  75                  80

Arg Tyr Ile Thr Glu Ala Leu Val Arg Lys Leu Thr Lys Gln Asp Asn
                85                  90                  95

Leu Ala Leu Val Lys Ser Leu Asn Leu Ser Leu Ala Lys Gly Gly Gly
            100                 105                 110

Lys Lys Phe Arg Cys Ile Glu Asn Leu Glu Lys Cys Val Lys Leu Glu
        115                 120                 125

Val Leu Asn Leu Ser Tyr Asn Leu Ile Gly Lys Ile Glu Lys Val Asp
    130                 135                 140

Lys Leu Leu Lys Leu Arg Glu Leu Asn Leu Ser Tyr Asn Lys Ile Arg
145                 150                 155                 160

Lys Ile Glu Gly Ile Glu Asn Leu Tyr Asn Leu Gln Lys Leu Asn Leu
                165                 170                 175

Ala Gly Asn Glu Ile Glu His Ile Pro Val Trp Leu Gly Lys Lys Leu
            180                 185                 190

Lys Ser Leu Arg Ile Leu Asn Leu Lys Gly Asn Lys Ile Ser Ser Leu
        195                 200                 205

Gln Asp Val Ser Lys Leu Lys Pro Leu Gln Asp Leu Thr Ser Leu Ile
    210                 215                 220

Leu Leu Glu Asn Pro Val Ala Thr Leu Pro His Tyr Ile Gln Phe Thr
225                 230                 235                 240

Ile Phe His Leu Arg Ser Leu Glu Ser Leu Glu Gly Gln Pro Val Thr
                245                 250                 255

Ser Gln Asp Arg Gln Glu Ala Phe Ala Arg Phe Ser Leu Asp Glu Val
            260                 265                 270

Glu Arg Leu Glu Arg Asp Leu Glu Lys Lys Thr Met Glu Thr Glu Glu
        275                 280                 285

Leu Arg Ser Glu Gln Thr Arg Phe Leu Glu Glu Ile Lys Ser Gln Asp
    290                 295                 300

Lys Leu Asn Lys Ser Leu Lys Glu Glu Ala Arg Leu Gln Lys Gln Ser
305                 310                 315                 320

Tyr Glu Glu Leu Glu Ser Asn Leu Asn Thr Lys Asn Glu Leu Leu Lys
                325                 330                 335

Gln Lys Thr Met Glu Leu Met Arg Ala Cys Gln Lys Gln Tyr Glu Met
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Val Glu Ile Asp Lys Thr Pro Asp Glu
    370                 375                 380

Ser Pro Tyr Ile Gly Lys Ser Arg Tyr Lys Arg Asn Met Phe Thr Thr
385                 390                 395                 400

Glu Ser Tyr Ile Ile Ala Asn Ala Gln Thr Val Lys Ile Lys Lys Met
                405                 410                 415

Glu Leu Asp Glu Gly Glu Gln Leu Arg Asn Glu His Val Asn Leu Gly
            420                 425                 430

Ala Ser Pro Thr Asp Ile Gln Leu Glu Asp Lys Glu Lys Lys Ile Ser
        435                 440                 445

Ala Ala Gln Thr Arg Leu Ser Glu Leu His Asp Glu Ile Glu Lys Ala
    450                 455                 460

Glu Gln Gln Ile Leu Arg Ala Thr Glu Glu Phe Lys Gln Leu Glu Glu
```

```
465                 470                 475                 480

Ala Ile Gln Leu Lys Lys Ile Ser Glu Ala Glu Lys Asp Leu Leu Phe
                485                 490                 495

Lys Gln Leu Ser Gly Arg Ile Gln Leu Leu Asn Lys Leu Arg Gln Glu
            500                 505                 510

Ala Val Asp Leu Glu Thr Gln Met Glu Lys Gln Arg Gln Glu Ile Gly
        515                 520                 525

Glu Lys Gln Asn Glu Ile Lys Asp Leu Glu Ile Val Thr Asp Ser Leu
    530                 535                 540

Asp Ser Arg Asp Pro Lys His Cys His Met Lys Ala Gln Lys Arg Gly
545                 550                 555                 560

Lys Glu Gln Gln Leu Asp Ile Met Asn Lys Gln Tyr Lys Gln Leu Glu
                565                 570                 575

Ser Arg Leu Asp Glu Ile Leu Ser Arg Ile Ala Lys Glu Thr Glu Glu
            580                 585                 590

Ile Lys Asp Leu Glu Glu Gln Leu Thr Glu Gly Gln Ile Ala Ala Asn
        595                 600                 605

Glu Ala Leu Lys Lys Asp Leu Glu Ser Val Ile Ser Gly Leu Gln Glu
    610                 615                 620

Tyr Leu Glu Thr Val Lys Gly Gln Ala Arg Gln Ala Gln Asn Glu Cys
625                 630                 635                 640

Arg Lys Leu Gln Asp Glu Lys Glu Thr Leu Leu Gln Arg Leu Ser Glu
                645                 650                 655

Val Glu Gln Glu Arg Asp Gln Leu Glu Ile Val Ala Ile Asp Ala Glu
            660                 665                 670

Asn Met Arg Lys Glu Leu Ala Glu Leu Glu Asn Ala Leu Gln Glu Gln
        675                 680                 685

His Glu Val Asn Ile Ser Leu Gln Gln Thr Gln Gly Asp Leu Ser Ala
    690                 695                 700

Tyr Glu Ala Glu Leu Glu Ala Gln Leu Lys Ile Arg Asp Ala Glu Ala
705                 710                 715                 720

Asn Gln Leu Lys Glu Glu Leu Glu Lys Leu Arg Arg Leu Ser Gln Leu
                725                 730                 735

Glu Gln Ser Ala Leu Gln Ala Glu Leu Glu Lys Glu Lys Gln Ala Phe
            740                 745                 750

Lys Thr Ala Val Lys Lys Ala Gln Leu Ser Glu Gly Lys Asp Gln Glu
        755                 760                 765

Asn Ser Glu Leu Arg Thr Gln Leu Gln Gln Leu Gln Asp Asp Asn Asp
    770                 775                 780

Leu Leu Lys Gln Gln Leu Lys Asp Phe Gln Ser His Leu Asn His Val
785                 790                 795                 800

Val Asp Gly Leu Ile Arg Pro Glu Glu Val Ala Ala Cys Val Asp Glu
                805                 810                 815

Leu Arg Lys Lys Leu Lys Ser Gly Ala Gly Glu Met Arg Ile His Thr
            820                 825                 830

Pro Ser Asp Val Leu Gly Lys Ser Leu Ala Asp Leu Gln Lys Gln Phe
        835                 840                 845

Ser Glu Ile Leu Ala Arg Ser Gln Trp Glu Arg Gln Glu Ala Gln Val
    850                 855                 860

Arg Glu Arg Lys Leu Gln Glu Glu Met Ala Leu Gln Gln Glu Lys Leu
865                 870                 875                 880

Ala Ser Gly Gln Glu Glu Phe Arg His Ala Cys Glu Arg Ala Leu Glu
                885                 890                 895
```

```
Ala Arg Ile Ser Phe Asp Lys Arg Gln His Glu Ala Arg Ile Gln Gln
            900                 905                 910

Leu Glu Asn Glu Ile His Tyr Leu Gln Glu Asn Leu Lys Ser Met Glu
        915                 920                 925

Glu Ile Gln Gly Leu Thr Asp Leu Gln Leu Gln Glu Ala Asp Glu Glu
    930                 935                 940

Lys Glu Arg Ile Leu Ala Gln Leu Arg Glu Leu Glu Lys Lys Lys Lys
945                 950                 955                 960

Leu Glu Asp Ala Lys Ser Gln Glu Gln Phe Leu Gly Leu Asp Arg Glu
                965                 970                 975

Leu Lys Lys Leu Lys Lys Ala Val Ala Ala Ser Asp Lys Leu Ala Thr
            980                 985                 990

Ala Glu Leu Thr Ile Ala Lys Asp  Gln Leu Lys Ser Leu  His Gly Thr
        995                 1000                 1005

Val Met  Lys Ile Asn Gln Glu  Arg Ala Glu Glu Leu  Gln Glu Thr
    1010                 1015                 1020

Glu Arg  Phe Ser Arg Lys Ala  Ala Gln Ala Ala Arg  Asp Leu Ile
    1025                 1030                 1035

Arg Ala  Glu Ala Glu Ile Glu  Leu Leu Gln Lys Leu  Leu Arg Asp
    1040                 1045                 1050

Lys Glu  Glu Gln Phe Arg Asn  Glu Ile Glu Lys Val  Asp Val Gly
    1055                 1060                 1065

Ser Gly  Gly Ala Lys Ser Gln  Met Leu Glu Met Glu  Lys Leu Asn
    1070                 1075                 1080

Glu Thr  Met Glu Arg Gln Arg  Thr Glu Ile Ala Arg  Leu Arg Asn
    1085                 1090                 1095

Leu Leu  Asp Leu Thr Gly Ala  Asp Asn Lys Gly Asn  Phe Glu Asn
    1100                 1105                 1110

Val Leu  Glu Glu Ile Ala Glu  Leu Arg Arg Glu Val  Ser His Gln
    1115                 1120                 1125

Asn Asp  Tyr Ile Ser Ser Met  Thr Asp Pro Phe Lys  Arg Arg Gly
    1130                 1135                 1140

Tyr Trp  Tyr Phe Met Pro Pro  Pro Ser Ser Ser Lys  Val Ser Ser
    1145                 1150                 1155

His Ser  Ser Gln Ala Thr Lys  Asp Ser Gly Val Gly  Leu Lys Tyr
    1160                 1165                 1170

Thr Ala  Ser Thr Pro Val Arg  Lys Pro His Arg Gly  Arg Gln Asp
    1175                 1180                 1185

Gly Lys  Glu Asn Ser Gly Pro  Pro Pro Ala Ser Gly  Tyr Trp Val
    1190                 1195                 1200

Tyr Ser  Pro Ile Arg Ser Gly  Leu His Lys Ser Phe  Ser Asn Arg
    1205                 1210                 1215

Asp Ala  Asp Ser Gly Gly Asp  Ser Gln Glu Glu Ser  Glu Leu Asp
    1220                 1225                 1230

Asp Gln  Glu Asp His Pro Phe  Val Pro Pro Pro Gly  Tyr Met Met
    1235                 1240                 1245

Tyr Thr  Val Phe Pro Asp Gly  Ser Pro Val Pro Gln  Gly Met Ala
    1250                 1255                 1260

Leu Tyr  Ala Pro Pro Pro Pro  Leu Pro Asn Asn Ser  Gln Pro Leu
    1265                 1270                 1275

Asp Leu  Gly Thr Val Val Tyr  Gly Pro Pro Pro Val  Gly Ala Pro
    1280                 1285                 1290
```

```
Ile Val  Tyr Gly Pro Pro Pro  Pro Asn Phe Ser Val  Pro Leu Ile
    1295                 1300                 1305

Pro Val  Gly Val Leu His Cys  Asn Val Pro Glu His  His Asn Leu
    1310                 1315                 1320

Glu Asn  Glu Val Ser Arg Leu  Glu Asp Ile Met Gln  His Leu Lys
    1325                 1330                 1335

Ser Gly  Lys Arg Glu Gln Cys  Met Lys Thr Pro Lys  Leu Gln Ser
    1340                 1345                 1350

Glu Lys  Glu Leu Ala Glu Leu  Gln His Asn Ile Asp  Gly Leu Leu
    1355                 1360                 1365

Gln Glu  Lys Lys Asp Leu Glu  His Glu Val Glu Glu  Leu His Arg
    1370                 1375                 1380

Thr Ile  Gln Lys His Gln Gln  Arg Lys Asp Phe Ile  Asp Gly Asn
    1385                 1390                 1395

Val Glu  Ser Leu Val Asn Asp  Leu Glu Ile Glu Lys  Ser Leu Lys
    1400                 1405                 1410

His His  Glu Asp Ile Val Asp  Glu Ile Glu Cys Ile  Glu Arg Thr
    1415                 1420                 1425

Leu Leu  Lys Arg Arg Ala Glu  Leu Arg Glu Ala Asp  Arg Leu Leu
    1430                 1435                 1440

Thr Glu  Ala Glu Ser Glu Leu  Ser Cys Thr Lys Glu  Lys Thr Lys
    1445                 1450                 1455

His Ala  Val Glu Lys Phe Thr  Asp Ala Lys Arg Asn  Leu Leu Gln
    1460                 1465                 1470

Thr Glu  Lys Asp Ala Glu Glu  Leu Glu Arg Arg Ala  Gln Glu Thr
    1475                 1480                 1485

Ala Ile  Asn Leu Val Lys Ala  Asp Gln Gln Leu Arg  Leu Leu Gln
    1490                 1495                 1500

Ala Asp  Thr Lys Asp Leu Glu  Gln His Lys Met Glu  Gln Glu Glu
    1505                 1510                 1515

Ile Leu  Lys Glu Ile Asn Lys  Val Val Ala Ala Lys  Asp Ser Asp
    1520                 1525                 1530

Phe Gln  Ser Leu Asn Lys Lys  Lys Glu Val Leu Thr  Gly Glu Leu
    1535                 1540                 1545

Gln Lys  Leu Gln Lys Asp Ile  Glu Thr Ala Arg His  Asn Glu Asp
    1550                 1555                 1560

Gln His  Leu Gln Val Leu Lys  Glu Ser Glu Thr Leu  Leu Gln Ala
    1565                 1570                 1575

Lys Lys  Ala Glu Leu Glu Asn  Leu Lys Ser Gln Val  Ser Gly Gln
    1580                 1585                 1590

Gln Gln  Glu Met Ala Val Leu  Asp Arg Glu Leu Gly  His Lys Lys
    1595                 1600                 1605

Glu Glu  Leu His Leu Leu Gln  Glu Ser Met Val Gln  Ala Lys Ala
    1610                 1615                 1620

Asp Leu  Gln Glu Ala Leu Arg  Leu Gly Glu Ser Glu  Val Thr Glu
    1625                 1630                 1635

Lys Cys  Asn His Ile Arg Glu  Val Lys Ser Leu Leu  Glu Glu Leu
    1640                 1645                 1650

Ser Phe  Gln Lys Gly Glu Leu  Asn Val Gln Ile Ser  Glu Lys Lys
    1655                 1660                 1665

Thr Gln  Leu Ala Leu Ile Lys  Gln Glu Ile Glu Lys  Glu Glu Asp
    1670                 1675                 1680

Asn Leu  Gln Val Val Leu Gly  Gln Met Ser Lys His  Lys Thr Glu
```

```
    1685                1690                1695

Leu Lys  Asn Ile Leu Asp Met  Leu Gln Leu Glu Asn  Asn Glu Leu
    1700                1705                1710

Gln Gly  Leu Lys Leu Gln His  Asp Gln Lys Met Ser  Glu Leu Glu
    1715                1720                1725

Lys Thr  Arg Val Glu Val Leu  Glu Glu Lys Leu Glu  Leu Glu Ser
    1730                1735                1740

Leu Gln  Gln Ala Ala Leu Arg  Gln Arg Gly Glu Ile  Glu Trp Gln
    1745                1750                1755

Lys Gln  Leu Leu Gln Arg Asn  Thr Gln Glu Val Glu  Arg Met Thr
    1760                1765                1770

Ala Glu  Thr Arg Ala Leu Gln  Ser Cys Val Glu Ser  Leu Cys Lys
    1775                1780                1785

Glu Lys  Gln Asp Leu Glu Glu  Lys Gln Asp Ser Trp  Glu Lys Lys
    1790                1795                1800

Leu Ala  Gln Thr Lys Arg Val  Leu Ala Ala Ala Glu  Glu Asp Ser
    1805                1810                1815

Glu Met  Glu Arg Ala Arg Leu  Glu Lys Leu Glu Leu  Asp Ala Arg
    1820                1825                1830

Lys Leu  Gln Gln Glu Leu Asp  Gln Arg Asn Arg Glu  Lys Leu Ser
    1835                1840                1845

Leu His  Gln Asp Leu Ala Val  Val Gln Gln Gln Leu  Gln Glu Lys
    1850                1855                1860

Gln Glu  Ala Val Asn Ser Leu  Gln Lys Glu Leu Ala  Asp Val Gln
    1865                1870                1875

Glu His  Leu Asp Leu Ala Glu  Gln Glu Val Leu Cys  Thr Thr Lys
    1880                1885                1890

Arg Lys  Asp Ala Leu Leu Ser  Glu Gln Thr Arg Leu  Glu Lys Asp
    1895                1900                1905

Val Gly  Glu Trp Thr Lys Lys  Phe Glu Asp Cys Gln  Lys Glu Gly
    1910                1915                1920

Glu Thr  Lys Gln Gln Gln Leu  Gln Gly Leu Gln Lys  Glu Ile Glu
    1925                1930                1935

Gly Asn  Glu Ala Lys Leu Ala  Gln Gln Glu Met Met  Phe Gln Arg
    1940                1945                1950

Leu Gln  Lys Glu Arg Glu Cys  Glu Glu Lys Lys Leu  Glu Ala Ser
    1955                1960                1965

Lys Val  Thr Leu Lys Glu Gln  Gln Gln Gln Leu Glu  Lys Glu Leu
    1970                1975                1980

Met Glu  Gln Lys Gly Lys Leu  Asp Gln Val Leu Ala  Lys Leu Leu
    1985                1990                1995

Val Ala  Glu Glu Arg Val Arg  Thr Leu Gln Glu Glu  Gly Arg Trp
    2000                2005                2010

Ser Glu  Thr Leu Glu Lys Thr  Leu Ser Gln Thr Lys  Arg Gln Leu
    2015                2020                2025

Ser Glu  Arg Glu Gln Gln Leu  Leu Ala Lys Ser Asp  Glu Leu Leu
    2030                2035                2040

Ala Leu  Gln Lys Glu Thr Asp  Ser Met Arg Ala Asp  Phe Ser Leu
    2045                2050                2055

Leu Arg  Asn Gln Phe Leu Thr  Glu Arg Lys Lys Ala  Glu Lys Gln
    2060                2065                2070

Val Ala  Ser Leu Lys Glu Ala  Leu Lys Ile Gln Arg  Ser Gln Leu
    2075                2080                2085
```

```
Glu Lys  Asn Leu Leu Glu Gln  Lys Gln Glu Asn Ser  Cys Met Gln
    2090                 2095                 2100

Arg Glu  Met Ala Thr Ile Glu  Gln Val Ala Gln Asp  Asn His Glu
    2105                 2110                 2115

Arg Ala  Arg Arg Leu Met Arg  Glu Leu Asn Gln Met  Gln Arg Glu
    2120                 2125                 2130

Tyr Val  Glu Leu Arg Lys Gln  Met Thr Asn Gln Lys  Asp Leu Glu
    2135                 2140                 2145

Arg Arg  Gln Met Glu Ile Ser  Asp Ala Met Gln Ala  Leu Lys Cys
    2150                 2155                 2160

Glu Val  Lys Asp Glu Ile Arg  Thr Ser Leu Lys Asn  Leu Asn Gln
    2165                 2170                 2175

Phe Leu  Pro Glu Leu Pro Ala  Asp Leu Glu Ala Leu  Leu Glu Arg
    2180                 2185                 2190

Asn Glu  Asn Leu Gly Gly Gly  Leu Glu Ser Leu Lys  Glu Asn Phe
    2195                 2200                 2205

Pro Phe  Thr Val Ser Asp Arg  Pro Ser Ser Cys Glu  Glu Lys Leu
    2210                 2215                 2220

Asn Phe  Gly Gln Ala His Val  Ala Asp Glu Gln Trp  Arg Gly Glu
    2225                 2230                 2235

Ala Leu  Arg Glu Lys Leu Arg  His Arg Glu Asp Arg  Leu Lys Ala
    2240                 2245                 2250

Gln Leu  Arg Arg Cys Met Ser  Lys Gln Ala Glu Val  Leu Ser Glu
    2255                 2260                 2265

Gly Arg  Arg Arg Thr Glu Gly  Thr Leu His Ser Leu  Arg Arg Gln
    2270                 2275                 2280

Val Asp  Ala Leu Gly Glu Leu  Val Thr Ser Thr Ser  Gly Asp Ser
    2285                 2290                 2295

Ala Ser  Thr Arg Ser Leu Ser  Arg Thr Glu Gly Ser  Leu Ala Glu
    2300                 2305                 2310

Asp Glu  Pro Pro Gly Pro Ser  Gln Glu Leu His Val  Leu Gly Ser
    2315                 2320                 2325

Gly Gly  Ser Asp Arg Gly Gly  Gly Arg Gly Gly Gly  Arg Lys Gly
    2330                 2335                 2340

Leu Ser  Arg Arg Arg Arg Trp  Asn His Gly Glu Ala  Arg Leu Gly
    2345                 2350                 2355

Pro Arg  Arg Pro Pro Arg Glu  Gly Ala Gly Arg Gly  Ala Ala Phe
    2360                 2365                 2370

Arg Ala  Leu Val Ser Cys Ser  Arg Pro Ala Glu Leu  Pro Ala Ala
    2375                 2380                 2385

Pro Pro  Arg Pro Val Ala Ala  Ala Gly Arg Ala Pro  Thr Leu Arg
    2390                 2395                 2400

Thr Arg  Arg Thr Arg Arg Pro  Gly Val Pro Ser Glu  Arg Phe Leu
    2405                 2410                 2415

Arg Val  Arg Gly His Gln Ala  His Gly Lys Ala Arg  Pro Cys Gly
    2420                 2425                 2430

Lys Ser  Arg Glu Arg Asn Pro  Asp Ala Arg Ala Gly  Leu Trp Ala
    2435                 2440                 2445

Leu Glu  Thr Cys Cys Arg Lys  Ser Ser Ala Arg Gly  Cys Gly Leu
    2450                 2455                 2460

Glu Ala  Pro Asn Cys Arg Arg  Ala Arg Cys Gly Ala  Ser Val Arg
    2465                 2470                 2475
```

```
Tyr Pro  Leu Val Pro Arg Gly  Arg Thr Gly Arg Gly  Ala Val Thr
    2480                 2485                 2490

Pro Trp  Gly Arg Leu Gln Ser  Arg Gly Thr Arg Thr  Thr Pro Arg
    2495                 2500                 2505

Pro Val  Arg Arg Glu His Pro  Gln His Gln Glu Arg  Pro Pro Gly
    2510                 2515                 2520

Arg Val  Thr Ala Ala His Thr  Glu Thr Ala Pro Pro  Arg Arg Val
    2525                 2530                 2535

Phe His  Ala Arg Val Ala Val  Gly Glu Val Ser Leu  Gly Pro Gly
    2540                 2545                 2550

Arg Gly  Leu Glu Arg Thr Arg  Gly Gly Gly Gly Gly  Ala Gly Ala
    2555                 2560                 2565

Gly Leu  Leu Ala Glu Ala Ala  Ala Thr Ala Arg Cys  Ala Asp Pro
    2570                 2575                 2580

Ser Thr  Asp Pro Ser Ala
    2585


<210> SEQ ID NO 29
<211> LENGTH: 7431
<212> TYPE: DNA
<213> ORGANISM: Homo sapiens
<220> FEATURE:
<221> NAME/KEY: CDS
<222> LOCATION: (32)..(7009)

<400> SEQUENCE: 29

gttttgatga acacctggct ttattcttgc a atg aag aaa ggt tct caa caa        52
                                   Met Lys Lys Gly Ser Gln Gln
                                   1               5

aaa ata ttc tcc aaa gca aag ata cca tca tca tct cac tct cct atc      100
Lys Ile Phe Ser Lys Ala Lys Ile Pro Ser Ser Ser His Ser Pro Ile
        10                  15                  20

cca tca tct atg tcc aat atg aga tct agg tca ctt tca cct ttg att      148
Pro Ser Ser Met Ser Asn Met Arg Ser Arg Ser Leu Ser Pro Leu Ile
    25                  30                  35

gga tca gag act cta cct ttt cat tct gga gga cag tgg tgt gag caa      196
Gly Ser Glu Thr Leu Pro Phe His Ser Gly Gly Gln Trp Cys Glu Gln
40                  45                  50                  55

gtt gag att gca gat gaa aac aat atg ctt ttg gac tat caa gac cat      244
Val Glu Ile Ala Asp Glu Asn Asn Met Leu Leu Asp Tyr Gln Asp His
                60                  65                  70

aaa gga gct gat tca cat gca gga gtt aga tat att aca gag gcc ctc      292
Lys Gly Ala Asp Ser His Ala Gly Val Arg Tyr Ile Thr Glu Ala Leu
            75                  80                  85

att aaa aaa ctt act aaa cag gat aat ttg gct ttg ata aaa tct ctg      340
Ile Lys Lys Leu Thr Lys Gln Asp Asn Leu Ala Leu Ile Lys Ser Leu
        90                  95                  100

aac ctt tca ctt tct aaa gac ggt ggc aag aaa ttt aag tat att gag      388
Asn Leu Ser Leu Ser Lys Asp Gly Gly Lys Lys Phe Lys Tyr Ile Glu
    105                 110                 115

aat ttg gaa aaa tgt gtt aaa ctt gaa gta ctg aat ctc agc tat aat      436
Asn Leu Glu Lys Cys Val Lys Leu Glu Val Leu Asn Leu Ser Tyr Asn
120                 125                 130                 135

cta ata ggg aag att gaa aag ttg gac aag ctg tta aaa tta cgt gaa      484
Leu Ile Gly Lys Ile Glu Lys Leu Asp Lys Leu Leu Lys Leu Arg Glu
                140                 145                 150

ctc aac tta tca tat aac aaa atc agc aaa att gaa ggc ata gaa aat      532
Leu Asn Leu Ser Tyr Asn Lys Ile Ser Lys Ile Glu Gly Ile Glu Asn
            155                 160                 165
```

-continued

```
atg tgt aat ctg caa aag ctt aac ctt gca gga aat gaa att gag cat      580
Met Cys Asn Leu Gln Lys Leu Asn Leu Ala Gly Asn Glu Ile Glu His
        170                 175                 180

att cca gta tgg tta ggg aag aag tta aaa tct ttg cga gtc ctc aat      628
Ile Pro Val Trp Leu Gly Lys Lys Leu Lys Ser Leu Arg Val Leu Asn
    185                 190                 195

ttg aaa ggc aac aag ata tca tcg ctc caa gat ata agc aag ttg aaa      676
Leu Lys Gly Asn Lys Ile Ser Ser Leu Gln Asp Ile Ser Lys Leu Lys
200                 205                 210                 215

ccg ctt caa gat ttg att tct ctg atc cta gtt gaa aat cca gtt gtg      724
Pro Leu Gln Asp Leu Ile Ser Leu Ile Leu Val Glu Asn Pro Val Val
                220                 225                 230

acc ctt cct cat tac ctc cag ttt acc att ttc cac ctc cgt tca ttg      772
Thr Leu Pro His Tyr Leu Gln Phe Thr Ile Phe His Leu Arg Ser Leu
            235                 240                 245

gaa agt ttg gaa ggt cag cca gta acc act cag gat aga cag gag gct      820
Glu Ser Leu Glu Gly Gln Pro Val Thr Thr Gln Asp Arg Gln Glu Ala
        250                 255                 260

ttt gag aga ttc agt tta gaa gag gta gaa aga ctg gaa aga gac cta      868
Phe Glu Arg Phe Ser Leu Glu Glu Val Glu Arg Leu Glu Arg Asp Leu
    265                 270                 275

gaa aaa aag atg ata gaa act gaa gag ctt aag agc aaa caa aca agg      916
Glu Lys Lys Met Ile Glu Thr Glu Glu Leu Lys Ser Lys Gln Thr Arg
280                 285                 290                 295

ttc ctt gag gaa att aaa aat caa gat aaa ttg aat aaa tca tta aaa      964
Phe Leu Glu Glu Ile Lys Asn Gln Asp Lys Leu Asn Lys Ser Leu Lys
                300                 305                 310

gag gag gcc atg tta cag aaa cag agc tgt gag gaa ctc aag agt gac     1012
Glu Glu Ala Met Leu Gln Lys Gln Ser Cys Glu Glu Leu Lys Ser Asp
            315                 320                 325

tta aac aca aaa aat gaa ttg cta aaa cag aag acc ata gaa tta aca     1060
Leu Asn Thr Lys Asn Glu Leu Leu Lys Gln Lys Thr Ile Glu Leu Thr
        330                 335                 340

cga gca tgt cag aag caa tat gag ctg gaa cag gaa ttg gcc ttt tat     1108
Arg Ala Cys Gln Lys Gln Tyr Glu Leu Glu Gln Glu Leu Ala Phe Tyr
    345                 350                 355

aaa att gat gct aaa ttt gag cca cta aat tat tat cca tca gag tat     1156
Lys Ile Asp Ala Lys Phe Glu Pro Leu Asn Tyr Tyr Pro Ser Glu Tyr
360                 365                 370                 375

gct gaa att gat aaa gcc cca gat gaa agc cct tac att ggc aaa tcc     1204
Ala Glu Ile Asp Lys Ala Pro Asp Glu Ser Pro Tyr Ile Gly Lys Ser
                380                 385                 390

aga tac aag aga aat atg ttt gcc aca gag agt tat att att gac agt     1252
Arg Tyr Lys Arg Asn Met Phe Ala Thr Glu Ser Tyr Ile Ile Asp Ser
            395                 400                 405

gct cag gca gta cag atc aag aag atg gag cca gat gaa caa ctt aga     1300
Ala Gln Ala Val Gln Ile Lys Lys Met Glu Pro Asp Glu Gln Leu Arg
        410                 415                 420

aat gat cac atg aac ttg aga ggc cac aca cca ctg gac acg caa ctg     1348
Asn Asp His Met Asn Leu Arg Gly His Thr Pro Leu Asp Thr Gln Leu
    425                 430                 435

gaa gac aaa gaa aaa aaa ata agt gca gca caa act cga cta tca gaa     1396
Glu Asp Lys Glu Lys Lys Ile Ser Ala Ala Gln Thr Arg Leu Ser Glu
440                 445                 450                 455

ctg cat gat gaa ata gaa aag gca gaa caa caa att ttg aga gct act     1444
Leu His Asp Glu Ile Glu Lys Ala Glu Gln Gln Ile Leu Arg Ala Thr
                460                 465                 470

gaa gaa ttt aaa caa ctg gaa gaa gct ata caa cta aaa aag att tca     1492
Glu Glu Phe Lys Gln Leu Glu Glu Ala Ile Gln Leu Lys Lys Ile Ser
            475                 480                 485
```

```
gaa gca ggg aaa gac ctt ctt tac aag cag ttg agt ggt aga cta caa      1540
Glu Ala Gly Lys Asp Leu Leu Tyr Lys Gln Leu Ser Gly Arg Leu Gln
        490                 495                 500

ctt gta aat aaa tta cgc cag gaa gct ctg gat cta gaa ctg cag atg      1588
Leu Val Asn Lys Leu Arg Gln Glu Ala Leu Asp Leu Glu Leu Gln Met
    505                 510                 515

gaa aag caa aag cag gaa att gcc gga aag cag aag gag att aag gac      1636
Glu Lys Gln Lys Gln Glu Ile Ala Gly Lys Gln Lys Glu Ile Lys Asp
520                 525                 530                 535

ctg caa ata gcc ata gat agc ctg gat tcc aaa gac cca aaa cat tcc      1684
Leu Gln Ile Ala Ile Asp Ser Leu Asp Ser Lys Asp Pro Lys His Ser
                540                 545                 550

cat atg aag gct caa aag agc ggt aaa gaa caa cag ctt gac att atg      1732
His Met Lys Ala Gln Lys Ser Gly Lys Glu Gln Gln Leu Asp Ile Met
            555                 560                 565

aac aag cag tac caa caa ctt gaa agt cgt ttg gat gag ata ctt tct      1780
Asn Lys Gln Tyr Gln Gln Leu Glu Ser Arg Leu Asp Glu Ile Leu Ser
        570                 575                 580

aga att gct aag gaa acg gaa gag att aag gac ctt gaa gaa cag ctt      1828
Arg Ile Ala Lys Glu Thr Glu Glu Ile Lys Asp Leu Glu Glu Gln Leu
    585                 590                 595

act gaa ggc cag ata gca gca aat gaa gcc ctg aag aag gat tta gaa      1876
Thr Glu Gly Gln Ile Ala Ala Asn Glu Ala Leu Lys Lys Asp Leu Glu
600                 605                 610                 615

ggt gtt atc agt ggg ttg caa gaa tac ctg ggg acc att aaa ggc cag      1924
Gly Val Ile Ser Gly Leu Gln Glu Tyr Leu Gly Thr Ile Lys Gly Gln
                620                 625                 630

gca act cag gcc cag aat gag tgc agg aag ctg cgg gat gag aaa gag      1972
Ala Thr Gln Ala Gln Asn Glu Cys Arg Lys Leu Arg Asp Glu Lys Glu
            635                 640                 645

aca ttg ttg cag aga ttg aca gaa gtc gag cag gag aga gac cag ctg      2020
Thr Leu Leu Gln Arg Leu Thr Glu Val Glu Gln Glu Arg Asp Gln Leu
        650                 655                 660

gaa ata gtt gcc atg gat gca gaa aat atg agg aag gag ctt gca gag      2068
Glu Ile Val Ala Met Asp Ala Glu Asn Met Arg Lys Glu Leu Ala Glu
    665                 670                 675

cta gaa agt gcc ctc caa gag cag cat gag gtg aat gca tct ttg cag      2116
Leu Glu Ser Ala Leu Gln Glu Gln His Glu Val Asn Ala Ser Leu Gln
680                 685                 690                 695

cag acc cag gga gat ctc agt gcc tat gaa gct gag cta gag gct cgg      2164
Gln Thr Gln Gly Asp Leu Ser Ala Tyr Glu Ala Glu Leu Glu Ala Arg
                700                 705                 710

cta aac cta agg gat gct gaa gcc aac cag ctc aag gaa gag ttg gaa      2212
Leu Asn Leu Arg Asp Ala Glu Ala Asn Gln Leu Lys Glu Glu Leu Glu
            715                 720                 725

aaa gta aca aga ctt acc cag tta gaa caa tca gcc ctt caa gca gaa      2260
Lys Val Thr Arg Leu Thr Gln Leu Glu Gln Ser Ala Leu Gln Ala Glu
        730                 735                 740

ctt gag aag gaa agg caa gcc ctc aag aat gcc ctt gga aaa gcc cag      2308
Leu Glu Lys Glu Arg Gln Ala Leu Lys Asn Ala Leu Gly Lys Ala Gln
    745                 750                 755

ttc tca gaa gaa aag gag caa gag aac agt gag ctc cat gca aaa ctt      2356
Phe Ser Glu Glu Lys Glu Gln Glu Asn Ser Glu Leu His Ala Lys Leu
760                 765                 770                 775

aaa cac ttg cag gat gac aat aat ctg tta aaa cag caa ctt aaa gat      2404
Lys His Leu Gln Asp Asp Asn Asn Leu Leu Lys Gln Gln Leu Lys Asp
                780                 785                 790

ttc cag aat cac ctt aac cat gtg gtt gat ggt ttg gtt cgt cca gaa      2452
Phe Gln Asn His Leu Asn His Val Val Asp Gly Leu Val Arg Pro Glu
```

```
            795                 800                 805

gaa gtg gca gct cgt gtg gat gag cta aga aga aaa ctg aaa tta gga      2500
Glu Val Ala Ala Arg Val Asp Glu Leu Arg Arg Lys Leu Lys Leu Gly
        810                 815                 820

act ggg gaa atg aac atc cat agt cct tca gat gtc tta ggg aaa agt      2548
Thr Gly Glu Met Asn Ile His Ser Pro Ser Asp Val Leu Gly Lys Ser
    825                 830                 835

ctt gct gat tta cag aaa caa ttc agt gaa att ctt gca cgc tcc aag      2596
Leu Ala Asp Leu Gln Lys Gln Phe Ser Glu Ile Leu Ala Arg Ser Lys
840                 845                 850                 855

tgg gaa aga gat gaa gca caa gtt aga gag aga aaa ctc caa gaa gaa      2644
Trp Glu Arg Asp Glu Ala Gln Val Arg Glu Arg Lys Leu Gln Glu Glu
                860                 865                 870

atg gct ctg cag caa gag aaa ctg gca act gga caa gaa gag ttc agg      2692
Met Ala Leu Gln Gln Glu Lys Leu Ala Thr Gly Gln Glu Glu Phe Arg
            875                 880                 885

cag gcc tgt gag aga gcc ctg gaa gca aga atg aat ttt gat aag agg      2740
Gln Ala Cys Glu Arg Ala Leu Glu Ala Arg Met Asn Phe Asp Lys Arg
        890                 895                 900

caa cat gaa gca aga atc cag caa atg gag aat gaa att cac tat ttg      2788
Gln His Glu Ala Arg Ile Gln Gln Met Glu Asn Glu Ile His Tyr Leu
    905                 910                 915

caa gaa aat cta aaa agt atg gag gaa atc caa ggc ctt aca gat ctc      2836
Gln Glu Asn Leu Lys Ser Met Glu Glu Ile Gln Gly Leu Thr Asp Leu
920                 925                 930                 935

caa ctt cag gaa gct gat gaa gag aag gag aga att ctg gcc caa ctc      2884
Gln Leu Gln Glu Ala Asp Glu Glu Lys Glu Arg Ile Leu Ala Gln Leu
                940                 945                 950

cga gag tta gag aaa aag aag aaa ctt gaa gat gcc aaa tct cag gag      2932
Arg Glu Leu Glu Lys Lys Lys Lys Leu Glu Asp Ala Lys Ser Gln Glu
            955                 960                 965

caa gtt ttt ggt tta gat aaa gaa ctg aag aaa cta aag aaa gcc gtg      2980
Gln Val Phe Gly Leu Asp Lys Glu Leu Lys Lys Leu Lys Lys Ala Val
        970                 975                 980

gcc acc tct gat aag cta gcc aca gct gag ctc acc att gcc aaa gac      3028
Ala Thr Ser Asp Lys Leu Ala Thr Ala Glu Leu Thr Ile Ala Lys Asp
    985                 990                 995

cag  ctg aag tcc ctt cat  gga act gtt atg aaa  att aac cag gag      3073
Gln  Leu Lys Ser Leu His  Gly Thr Val Met Lys  Ile Asn Gln Glu
1000                 1005                 1010

cga  gca gag gag ttg cag  gaa gca gag agg ttc  agc aga aag gca      3118
Arg  Ala Glu Glu Leu Gln  Glu Ala Glu Arg Phe  Ser Arg Lys Ala
1015                 1020                 1025

gca  caa gca gcc aga gat  ctc acc cga gca gaa  gct gag atc gaa      3163
Ala  Gln Ala Ala Arg Asp  Leu Thr Arg Ala Glu  Ala Glu Ile Glu
1030                 1035                 1040

ctc  ctg cag aat ctc ctc  agg cag aag ggg gag  cag ttt cga ctt      3208
Leu  Leu Gln Asn Leu Leu  Arg Gln Lys Gly Glu  Gln Phe Arg Leu
1045                 1050                 1055

gag  atg gag aaa aca ggt  gta ggt act gga gca  aac tca cag gtc      3253
Glu  Met Glu Lys Thr Gly  Val Gly Thr Gly Ala  Asn Ser Gln Val
1060                 1065                 1070

cta  gaa att gag aaa ctg  aat gag aca atg gaa  cga caa agg aca      3298
Leu  Glu Ile Glu Lys Leu  Asn Glu Thr Met Glu  Arg Gln Arg Thr
1075                 1080                 1085

gag  att gca agg ctg cag  aat gta cta gac ctc  act gga agt gac      3343
Glu  Ile Ala Arg Leu Gln  Asn Val Leu Asp Leu  Thr Gly Ser Asp
1090                 1095                 1100

aac  aaa gga ggc ttt gaa  aat gtt tta gaa gaa  att gct gaa ctt      3388
```

```
Asn  Lys Gly Gly Phe Glu  Asn Val Leu Glu Glu  Ile Ala Glu Leu
1105                1110                1115

cga  cgt gaa gtt tct tat  cag aat gat tac ata  agc agc atg gca     3433
Arg  Arg Glu Val Ser Tyr  Gln Asn Asp Tyr Ile  Ser Ser Met Ala
1120                1125                1130

gat  cct ttc aaa aga cga  ggc tat tgg tac ttt  atg cca cca cca     3478
Asp  Pro Phe Lys Arg Arg  Gly Tyr Trp Tyr Phe  Met Pro Pro Pro
1135                1140                1145

cca  tca tca aaa gtt tcc  agc cat agt tcc cag  gcc acc aag gac     3523
Pro  Ser Ser Lys Val Ser  Ser His Ser Ser Gln  Ala Thr Lys Asp
1150                1155                1160

tct  ggt gtt ggc ctt aag  tac tca gcc tca act  cct gtt aga aaa     3568
Ser  Gly Val Gly Leu Lys  Tyr Ser Ala Ser Thr  Pro Val Arg Lys
1165                1170                1175

cca  cgc cct ggg cag cag  gat ggg aag gaa ggc  agt caa cct ccc     3613
Pro  Arg Pro Gly Gln Gln  Asp Gly Lys Glu Gly  Ser Gln Pro Pro
1180                1185                1190

cct  gcc tca gga tac tgg  gtt tat tct ccc atc  agg agt ggg tta     3658
Pro  Ala Ser Gly Tyr Trp  Val Tyr Ser Pro Ile  Arg Ser Gly Leu
1195                1200                1205

cat  aaa ctg ttt cca agt  aga gat gca gac agt  gga gga gat agt     3703
His  Lys Leu Phe Pro Ser  Arg Asp Ala Asp Ser  Gly Gly Asp Ser
1210                1215                1220

cag  gaa gag agt gag ctg  gat gac caa gaa gaa  ccc cca ttt gtg     3748
Gln  Glu Glu Ser Glu Leu  Asp Asp Gln Glu Glu  Pro Pro Phe Val
1225                1230                1235

cct  cct cct gga tac atg  atg tat act gtg ctt  cct gat ggt tct     3793
Pro  Pro Pro Gly Tyr Met  Met Tyr Thr Val Leu  Pro Asp Gly Ser
1240                1245                1250

cct  gta ccc cag ggc atg  gcc ctg tat gca cca  cct cct ccc ttg     3838
Pro  Val Pro Gln Gly Met  Ala Leu Tyr Ala Pro  Pro Pro Pro Leu
1255                1260                1265

cca  aac aat agc cga cct  ctc acc cct ggc act  gtt gtt tat ggc     3883
Pro  Asn Asn Ser Arg Pro  Leu Thr Pro Gly Thr  Val Val Tyr Gly
1270                1275                1280

cca  cct cct gct ggg gcc  ccc atg gtg tat ggg  cct cca ccc ccc     3928
Pro  Pro Pro Ala Gly Ala  Pro Met Val Tyr Gly  Pro Pro Pro Pro
1285                1290                1295

aac  ttc tcc atc ccc ttc  atc cct atg ggt gtg  ctg cat tgc aac     3973
Asn  Phe Ser Ile Pro Phe  Ile Pro Met Gly Val  Leu His Cys Asn
1300                1305                1310

gtc  cct gaa cac cat aac  tta gag aat gaa gtt  tct aga tta gaa     4018
Val  Pro Glu His His Asn  Leu Glu Asn Glu Val  Ser Arg Leu Glu
1315                1320                1325

gac  ata atg cag cat tta  aaa tca aag aag cgg  gaa gaa agg tgg     4063
Asp  Ile Met Gln His Leu  Lys Ser Lys Lys Arg  Glu Glu Arg Trp
1330                1335                1340

atg  aga gca tcc aag cgg  cag tcg gag aaa gaa  atg gaa gaa ctg     4108
Met  Arg Ala Ser Lys Arg  Gln Ser Glu Lys Glu  Met Glu Glu Leu
1345                1350                1355

cat  cat aat att gat gat  ctt ttg caa gag aag  aaa agc tta gag     4153
His  His Asn Ile Asp Asp  Leu Leu Gln Glu Lys  Lys Ser Leu Glu
1360                1365                1370

tgt  gaa gta gaa gaa tta  cat aga act gtc cag  aaa cgt caa cag     4198
Cys  Glu Val Glu Glu Leu  His Arg Thr Val Gln  Lys Arg Gln Gln
1375                1380                1385

caa  aag gac ttc att gat  gga aat gtt gag agt  ctt atg act gaa     4243
Gln  Lys Asp Phe Ile Asp  Gly Asn Val Glu Ser  Leu Met Thr Glu
1390                1395                1400
```

```
cta  gaa ata gaa aaa tca  ctc aaa cat cat gaa  gat att gta gat      4288
Leu  Glu Ile Glu Lys Ser  Leu Lys His His Glu  Asp Ile Val Asp
1405                 1410                 1415

gaa  att gag tgc att gag  aag act ctt ctg aaa  cgt cgc tca gag      4333
Glu  Ile Glu Cys Ile Glu  Lys Thr Leu Leu Lys  Arg Arg Ser Glu
1420                 1425                 1430

ctc  agg gaa gct gac cga  ctc ctg gca gag gct  gag agt gaa ctt      4378
Leu  Arg Glu Ala Asp Arg  Leu Leu Ala Glu Ala  Glu Ser Glu Leu
1435                 1440                 1445

tca  tgc act aaa gaa aag  aca aaa aat gct gtt  gaa aag ttc act      4423
Ser  Cys Thr Lys Glu Lys  Thr Lys Asn Ala Val  Glu Lys Phe Thr
1450                 1455                 1460

gat  gcc aag aga agt tta  ttg caa act gag tca  gat gct gag gaa      4468
Asp  Ala Lys Arg Ser Leu  Leu Gln Thr Glu Ser  Asp Ala Glu Glu
1465                 1470                 1475

tta  gaa agg aga gct cag  gaa act gct gtt aac  ctc gtc aaa gct      4513
Leu  Glu Arg Arg Ala Gln  Glu Thr Ala Val Asn  Leu Val Lys Ala
1480                 1485                 1490

gat  cag cag cta aga tcg  ctc cag gct gat gca  aag gat ttg gag      4558
Asp  Gln Gln Leu Arg Ser  Leu Gln Ala Asp Ala  Lys Asp Leu Glu
1495                 1500                 1505

cag  cac aaa atc aag caa  gaa gaa atc ttg aaa  gaa ata aac aaa      4603
Gln  His Lys Ile Lys Gln  Glu Glu Ile Leu Lys  Glu Ile Asn Lys
1510                 1515                 1520

att  gta gca gca aaa gac  tca gac ttc caa tgt  tta agc aag aag      4648
Ile  Val Ala Ala Lys Asp  Ser Asp Phe Gln Cys  Leu Ser Lys Lys
1525                 1530                 1535

aag  gaa aaa ctg aca gaa  gag ctt cag aaa cta  cag aaa gac ata      4693
Lys  Glu Lys Leu Thr Glu  Glu Leu Gln Lys Leu  Gln Lys Asp Ile
1540                 1545                 1550

gag  atg gca gaa cgc aat  gag gat cac cac ctg  cag gtc ctt aaa      4738
Glu  Met Ala Glu Arg Asn  Glu Asp His His Leu  Gln Val Leu Lys
1555                 1560                 1565

gaa  tct gag gtg ctt ctt  cag gcc aaa aga gcc  gag ctg gaa aag      4783
Glu  Ser Glu Val Leu Leu  Gln Ala Lys Arg Ala  Glu Leu Glu Lys
1570                 1575                 1580

ctg  aaa agc cag gtg aca  agt cag cag cag gag  atg gct gtc ttg      4828
Leu  Lys Ser Gln Val Thr  Ser Gln Gln Gln Glu  Met Ala Val Leu
1585                 1590                 1595

gac  agg cag tta ggg cat  aaa aag gag gag ctg  cat cta ctc caa      4873
Asp  Arg Gln Leu Gly His  Lys Lys Glu Glu Leu  His Leu Leu Gln
1600                 1605                 1610

gga  agc atg gtc cag gca  aaa gct gac ctc cag  gaa gct ctg aga      4918
Gly  Ser Met Val Gln Ala  Lys Ala Asp Leu Gln  Glu Ala Leu Arg
1615                 1620                 1625

ctg  gga gag act gaa gta  act gag aag tgc aat  cac att agg gaa      4963
Leu  Gly Glu Thr Glu Val  Thr Glu Lys Cys Asn  His Ile Arg Glu
1630                 1635                 1640

gta  aaa tct ctt ctg gaa  gaa ctg agt ttt cag  aaa gga gaa cta      5008
Val  Lys Ser Leu Leu Glu  Glu Leu Ser Phe Gln  Lys Gly Glu Leu
1645                 1650                 1655

aat  gtt cag att agt gaa  aga aaa act caa ctt  aca ctt ata aag      5053
Asn  Val Gln Ile Ser Glu  Arg Lys Thr Gln Leu  Thr Leu Ile Lys
1660                 1665                 1670

cag  gaa att gaa aaa gag  gaa gaa aat ctt cag  gtt gtt tta agg      5098
Gln  Glu Ile Glu Lys Glu  Glu Glu Asn Leu Gln  Val Val Leu Arg
1675                 1680                 1685

cag  atg tct aaa cat aaa  acc gaa cta aag aat  att ctg gac atg      5143
Gln  Met Ser Lys His Lys  Thr Glu Leu Lys Asn  Ile Leu Asp Met
1690                 1695                 1700
```

```
ttg  caa ctt gaa aac cat  gag cta caa ggt ttg  aag cta caa cat      5188
Leu  Gln Leu Glu Asn His  Glu Leu Gln Gly Leu  Lys Leu Gln His
1705                 1710                 1715

gac  caa agg gta tct gaa  tta gag aag act cag  gtg gca gtg cta      5233
Asp  Gln Arg Val Ser Glu  Leu Glu Lys Thr Gln  Val Ala Val Leu
1720                 1725                 1730

gag  gag aaa ctg gag tta  gag aat ttg cag cag  ata tcc cag cag      5278
Glu  Glu Lys Leu Glu Leu  Glu Asn Leu Gln Gln  Ile Ser Gln Gln
1735                 1740                 1745

cag  aaa ggg gaa ata gag  tgg cag aag cag ctc  ctt gag agg gat      5323
Gln  Lys Gly Glu Ile Glu  Trp Gln Lys Gln Leu  Leu Glu Arg Asp
1750                 1755                 1760

aaa  cga gaa ata gaa cga  atg act gct gag tcc  cga gct tta caa      5368
Lys  Arg Glu Ile Glu Arg  Met Thr Ala Glu Ser  Arg Ala Leu Gln
1765                 1770                 1775

tcg  tgt gtt gag tgt ttg  agc aaa gaa aag gaa  gat ctc caa gag      5413
Ser  Cys Val Glu Cys Leu  Ser Lys Glu Lys Glu  Asp Leu Gln Glu
1780                 1785                 1790

aaa  tgt gac att tgg gaa  aaa aag ttg gca caa  acc aaa agg gtt      5458
Lys  Cys Asp Ile Trp Glu  Lys Lys Leu Ala Gln  Thr Lys Arg Val
1795                 1800                 1805

tta  gca gca gca gaa gaa  aat agc aaa atg gag  caa tca aac tta      5503
Leu  Ala Ala Ala Glu Glu  Asn Ser Lys Met Glu  Gln Ser Asn Leu
1810                 1815                 1820

gaa  aag ttg gaa ttg aat  gtc aga aaa ctg cag  cag gaa cta gac      5548
Glu  Lys Leu Glu Leu Asn  Val Arg Lys Leu Gln  Gln Glu Leu Asp
1825                 1830                 1835

caa  cta aac aga gac aag  ttg tca ctg cat aac  gac att tca gca      5593
Gln  Leu Asn Arg Asp Lys  Leu Ser Leu His Asn  Asp Ile Ser Ala
1840                 1845                 1850

atg  caa cag cag ctc caa  gaa aaa cga gaa gca  gta aac tca ctg      5638
Met  Gln Gln Gln Leu Gln  Glu Lys Arg Glu Ala  Val Asn Ser Leu
1855                 1860                 1865

cag  gag gaa cta gct aat  gtc caa gac cat ttg  aac cta gca aaa      5683
Gln  Glu Glu Leu Ala Asn  Val Gln Asp His Leu  Asn Leu Ala Lys
1870                 1875                 1880

cag  gac ctg ctt cac acc  acc aag cat cag gat  gtg ttg ctc agt      5728
Gln  Asp Leu Leu His Thr  Thr Lys His Gln Asp  Val Leu Leu Ser
1885                 1890                 1895

gag  cag acc cga ctc cag  aag gac atc agt gaa  tgg gca aat agg      5773
Glu  Gln Thr Arg Leu Gln  Lys Asp Ile Ser Glu  Trp Ala Asn Arg
1900                 1905                 1910

ttt  gaa gac tgt cag aaa  gaa gag gag aca aaa  caa caa caa ctt      5818
Phe  Glu Asp Cys Gln Lys  Glu Glu Glu Thr Lys  Gln Gln Gln Leu
1915                 1920                 1925

caa  gtg ctt cag aat gag  att gaa gaa aac aag  ctc aaa cta gtc      5863
Gln  Val Leu Gln Asn Glu  Ile Glu Glu Asn Lys  Leu Lys Leu Val
1930                 1935                 1940

caa  caa gaa atg atg ttt  cag aga ctc cag aaa  gag aga gaa agt      5908
Gln  Gln Glu Met Met Phe  Gln Arg Leu Gln Lys  Glu Arg Glu Ser
1945                 1950                 1955

gaa  gaa agc aaa tta gaa  acc agt aaa gtg aca  ctg aag gag caa      5953
Glu  Glu Ser Lys Leu Glu  Thr Ser Lys Val Thr  Leu Lys Glu Gln
1960                 1965                 1970

cag  cac cag ctg gaa aag  gaa tta aca gac cag  aaa agc aaa ctg      5998
Gln  His Gln Leu Glu Lys  Glu Leu Thr Asp Gln  Lys Ser Lys Leu
1975                 1980                 1985

gac  caa gtg ctc tca aag  gtg ctg gca gct gaa  gag cgt gtt agg      6043
Asp  Gln Val Leu Ser Lys  Val Leu Ala Ala Glu  Glu Arg Val Arg
```

```
1990                1995                2000

act  ctg cag gaa gag gag  agg tgg tgt gag agc  ctg gag aag aca     6088
Thr  Leu Gln Glu Glu Glu  Arg Trp Cys Glu Ser  Leu Glu Lys Thr
2005                2010                2015

ctc  tcc caa act aaa cgg  cag ctt tca gaa agg  gag cag caa ttg     6133
Leu  Ser Gln Thr Lys Arg  Gln Leu Ser Glu Arg  Glu Gln Gln Leu
2020                2025                2030

gtg  gag aaa tca ggt gag  ctg ttg gcc ctc cag  aaa gag gca gat     6178
Val  Glu Lys Ser Gly Glu  Leu Leu Ala Leu Gln  Lys Glu Ala Asp
2035                2040                2045

tct  atg agg gca gac ttc  agc ctt ctg cgg aac  cag ttc ttg aca     6223
Ser  Met Arg Ala Asp Phe  Ser Leu Leu Arg Asn  Gln Phe Leu Thr
2050                2055                2060

gaa  aga aag aaa gct gag  aag cag gtg gcc agc  ctg aag gaa gca     6268
Glu  Arg Lys Lys Ala Glu  Lys Gln Val Ala Ser  Leu Lys Glu Ala
2065                2070                2075

ctt  aag atc cag cgg agc  cag ctg gag aaa aac  ctt ctt gag caa     6313
Leu  Lys Ile Gln Arg Ser  Gln Leu Glu Lys Asn  Leu Leu Glu Gln
2080                2085                2090

aaa  cag gag aac agc tgc  ata caa aag gaa atg  gca aca att gaa     6358
Lys  Gln Glu Asn Ser Cys  Ile Gln Lys Glu Met  Ala Thr Ile Glu
2095                2100                2105

ctg  gta gcc cag gac aac  cat gag cgg gcc agg  cgc ctg atg aag     6403
Leu  Val Ala Gln Asp Asn  His Glu Arg Ala Arg  Arg Leu Met Lys
2110                2115                2120

gag  ctc aac cag atg cag  tat gag tac acg gag  ctc aag aaa cag     6448
Glu  Leu Asn Gln Met Gln  Tyr Glu Tyr Thr Glu  Leu Lys Lys Gln
2125                2130                2135

atg  gca aac caa aaa gat  ttg gag aga aga caa  atg gaa atc agt     6493
Met  Ala Asn Gln Lys Asp  Leu Glu Arg Arg Gln  Met Glu Ile Ser
2140                2145                2150

gat  gca atg agg aca ctt  aaa tct gag gtg aag  gat gaa atc aga     6538
Asp  Ala Met Arg Thr Leu  Lys Ser Glu Val Lys  Asp Glu Ile Arg
2155                2160                2165

acc  agc ttg aag aat ctt  aat cag ttt ctt cca  gaa cta cca gca     6583
Thr  Ser Leu Lys Asn Leu  Asn Gln Phe Leu Pro  Glu Leu Pro Ala
2170                2175                2180

gat  cta gaa gct att ttg  gaa aga aac gaa aac  cta gaa gga gaa     6628
Asp  Leu Glu Ala Ile Leu  Glu Arg Asn Glu Asn  Leu Glu Gly Glu
2185                2190                2195

ttg  gaa agc ttg aaa gag  aac ctt cca ttt acc  atg aat gag gga     6673
Leu  Glu Ser Leu Lys Glu  Asn Leu Pro Phe Thr  Met Asn Glu Gly
2200                2205                2210

cct  ttt gaa gaa aaa ctg  aac ttt tcc caa gtt  cac ata atg gat     6718
Pro  Phe Glu Glu Lys Leu  Asn Phe Ser Gln Val  His Ile Met Asp
2215                2220                2225

gaa  cac tgg cgt gga gaa  gca ctc cgg gag aaa  ctg cgt cac cgg     6763
Glu  His Trp Arg Gly Glu  Ala Leu Arg Glu Lys  Leu Arg His Arg
2230                2235                2240

gaa  gac cga ctc aag gcc  caa ctc cga cac tgt  atg tcc aag caa     6808
Glu  Asp Arg Leu Lys Ala  Gln Leu Arg His Cys  Met Ser Lys Gln
2245                2250                2255

gca  gaa gta tta att aaa  gga aag cgg cag aca  gag ggc act tta     6853
Ala  Glu Val Leu Ile Lys  Gly Lys Arg Gln Thr  Glu Gly Thr Leu
2260                2265                2270

cac  agt ttg agg aga caa  gta gat gct tta ggg  gaa ttg gtc acc     6898
His  Ser Leu Arg Arg Gln  Val Asp Ala Leu Gly  Glu Leu Val Thr
2275                2280                2285

agc  acc tct gca gat tca  gcg tca tca ccc agt  ctg tct cag ctg     6943
```

```
Ser  Thr Ser Ala Asp Ser  Ala Ser Ser Pro Ser  Leu Ser Gln Leu
2290                2295                2300

gag  tct tcc ctc aca gag  gac tct caa ctt gga  caa aat cag gaa      6988
Glu  Ser Ser Leu Thr Glu  Asp Ser Gln Leu Gly  Gln Asn Gln Glu
2305                2310                2315

aag  aat gcc tca gcc aga  tga ggaatactgt cttgtgtaaa tatattcaag      7039
Lys  Asn Ala Ser Ala Arg
2320                2325

gaaaacacct ccactacctc actgacttca taattggaat gtcacatggt ttttttaatc   7099

aagatgcagt gaactgagat tctgaaactc cactgtagtt tactttgcct gtaccattaa   7159

tgccaatgtt tttataaatc acttgtacat agtacatatg ggaatagttg catatgggaa   7219

tttaaaccaa catgtggctg agcctttttt tttttaatct tcgtaacatg tttaaaaaaa   7279

aacagtgatt ttaactgcat atttgaacct acaaactggt aaatcttatt aacaaaaaga   7339

atgtacttaa ggccctcttt atttatagtg tcgagttatt tttgaatttt gcttaaaatc   7399

tatttttcat atgaaaataa aagataacaa tc                                 7431


<210> SEQ ID NO 30
<211> LENGTH: 2325
<212> TYPE: PRT
<213> ORGANISM: Homo sapiens

<400> SEQUENCE: 30

Met Lys Lys Gly Ser Gln Gln Lys Ile Phe Ser Lys Ala Lys Ile Pro
1               5                   10                  15

Ser Ser Ser His Ser Pro Ile Pro Ser Ser Met Ser Asn Met Arg Ser
            20                  25                  30

Arg Ser Leu Ser Pro Leu Ile Gly Ser Glu Thr Leu Pro Phe His Ser
        35                  40                  45

Gly Gly Gln Trp Cys Glu Gln Val Glu Ile Ala Asp Glu Asn Asn Met
    50                  55                  60

Leu Leu Asp Tyr Gln Asp His Lys Gly Ala Asp Ser His Ala Gly Val
65                  70                  75                  80

Arg Tyr Ile Thr Glu Ala Leu Ile Lys Lys Leu Thr Lys Gln Asp Asn
                85                  90                  95

Leu Ala Leu Ile Lys Ser Leu Asn Leu Ser Leu Ser Lys Asp Gly Gly
            100                 105                 110

Lys Lys Phe Lys Tyr Ile Glu Asn Leu Glu Lys Cys Val Lys Leu Glu
        115                 120                 125

Val Leu Asn Leu Ser Tyr Asn Leu Ile Gly Lys Ile Glu Lys Leu Asp
    130                 135                 140

Lys Leu Leu Lys Leu Arg Glu Leu Asn Leu Ser Tyr Asn Lys Ile Ser
145                 150                 155                 160

Lys Ile Glu Gly Ile Glu Asn Met Cys Asn Leu Gln Lys Leu Asn Leu
                165                 170                 175

Ala Gly Asn Glu Ile Glu His Ile Pro Val Trp Leu Gly Lys Lys Leu
            180                 185                 190

Lys Ser Leu Arg Val Leu Asn Leu Lys Gly Asn Lys Ile Ser Ser Leu
        195                 200                 205

Gln Asp Ile Ser Lys Leu Lys Pro Leu Gln Asp Leu Ile Ser Leu Ile
    210                 215                 220

Leu Val Glu Asn Pro Val Val Thr Leu Pro His Tyr Leu Gln Phe Thr
225                 230                 235                 240

Ile Phe His Leu Arg Ser Leu Glu Ser Leu Glu Gly Gln Pro Val Thr
```

```
                245                 250                 255

Thr Gln Asp Arg Gln Glu Ala Phe Glu Arg Phe Ser Leu Glu Glu Val
            260                 265                 270

Glu Arg Leu Glu Arg Asp Leu Glu Lys Lys Met Ile Glu Thr Glu Glu
        275                 280                 285

Leu Lys Ser Lys Gln Thr Arg Phe Leu Glu Glu Ile Lys Asn Gln Asp
    290                 295                 300

Lys Leu Asn Lys Ser Leu Lys Glu Glu Ala Met Leu Gln Lys Gln Ser
305                 310                 315                 320

Cys Glu Glu Leu Lys Ser Asp Leu Asn Thr Lys Asn Glu Leu Leu Lys
                325                 330                 335

Gln Lys Thr Ile Glu Leu Thr Arg Ala Cys Gln Lys Gln Tyr Glu Leu
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Ala Glu Ile Asp Lys Ala Pro Asp Glu
    370                 375                 380

Ser Pro Tyr Ile Gly Lys Ser Arg Tyr Lys Arg Asn Met Phe Ala Thr
385                 390                 395                 400

Glu Ser Tyr Ile Ile Asp Ser Ala Gln Ala Val Gln Ile Lys Lys Met
                405                 410                 415

Glu Pro Asp Glu Gln Leu Arg Asn Asp His Met Asn Leu Arg Gly His
            420                 425                 430

Thr Pro Leu Asp Thr Gln Leu Glu Asp Lys Glu Lys Lys Ile Ser Ala
        435                 440                 445

Ala Gln Thr Arg Leu Ser Glu Leu His Asp Glu Ile Glu Lys Ala Glu
    450                 455                 460

Gln Gln Ile Leu Arg Ala Thr Glu Glu Phe Lys Gln Leu Glu Glu Ala
465                 470                 475                 480

Ile Gln Leu Lys Lys Ile Ser Glu Ala Gly Lys Asp Leu Leu Tyr Lys
                485                 490                 495

Gln Leu Ser Gly Arg Leu Gln Leu Val Asn Lys Leu Arg Gln Glu Ala
            500                 505                 510

Leu Asp Leu Glu Leu Gln Met Glu Lys Gln Lys Gln Glu Ile Ala Gly
        515                 520                 525

Lys Gln Lys Glu Ile Lys Asp Leu Gln Ile Ala Ile Asp Ser Leu Asp
    530                 535                 540

Ser Lys Asp Pro Lys His Ser His Met Lys Ala Gln Lys Ser Gly Lys
545                 550                 555                 560

Glu Gln Gln Leu Asp Ile Met Asn Lys Gln Tyr Gln Gln Leu Glu Ser
                565                 570                 575

Arg Leu Asp Glu Ile Leu Ser Arg Ile Ala Lys Glu Thr Glu Glu Ile
            580                 585                 590

Lys Asp Leu Glu Glu Gln Leu Thr Glu Gly Gln Ile Ala Ala Asn Glu
        595                 600                 605

Ala Leu Lys Lys Asp Leu Glu Gly Val Ile Ser Gly Leu Gln Glu Tyr
    610                 615                 620

Leu Gly Thr Ile Lys Gly Gln Ala Thr Gln Ala Gln Asn Glu Cys Arg
625                 630                 635                 640

Lys Leu Arg Asp Glu Lys Glu Thr Leu Leu Gln Arg Leu Thr Glu Val
                645                 650                 655

Glu Gln Glu Arg Asp Gln Leu Glu Ile Val Ala Met Asp Ala Glu Asn
            660                 665                 670
```

```
Met Arg Lys Glu Leu Ala Glu Leu Glu Ser Ala Leu Gln Glu Gln His
        675                 680                 685

Glu Val Asn Ala Ser Leu Gln Gln Thr Gln Gly Asp Leu Ser Ala Tyr
    690                 695                 700

Glu Ala Glu Leu Glu Ala Arg Leu Asn Leu Arg Asp Ala Glu Ala Asn
705                 710                 715                 720

Gln Leu Lys Glu Glu Leu Glu Lys Val Thr Arg Leu Thr Gln Leu Glu
                725                 730                 735

Gln Ser Ala Leu Gln Ala Glu Leu Glu Lys Glu Arg Gln Ala Leu Lys
            740                 745                 750

Asn Ala Leu Gly Lys Ala Gln Phe Ser Glu Glu Lys Glu Gln Glu Asn
        755                 760                 765

Ser Glu Leu His Ala Lys Leu Lys His Leu Gln Asp Asp Asn Asn Leu
    770                 775                 780

Leu Lys Gln Gln Leu Lys Asp Phe Gln Asn His Leu Asn His Val Val
785                 790                 795                 800

Asp Gly Leu Val Arg Pro Glu Glu Val Ala Ala Arg Val Asp Glu Leu
                805                 810                 815

Arg Arg Lys Leu Lys Leu Gly Thr Gly Glu Met Asn Ile His Ser Pro
            820                 825                 830

Ser Asp Val Leu Gly Lys Ser Leu Ala Asp Leu Gln Lys Gln Phe Ser
        835                 840                 845

Glu Ile Leu Ala Arg Ser Lys Trp Glu Arg Asp Glu Ala Gln Val Arg
    850                 855                 860

Glu Arg Lys Leu Gln Glu Glu Met Ala Leu Gln Gln Glu Lys Leu Ala
865                 870                 875                 880

Thr Gly Gln Glu Glu Phe Arg Gln Ala Cys Glu Arg Ala Leu Glu Ala
                885                 890                 895

Arg Met Asn Phe Asp Lys Arg Gln His Glu Ala Arg Ile Gln Gln Met
            900                 905                 910

Glu Asn Glu Ile His Tyr Leu Gln Glu Asn Leu Lys Ser Met Glu Glu
        915                 920                 925

Ile Gln Gly Leu Thr Asp Leu Gln Leu Gln Glu Ala Asp Glu Glu Lys
    930                 935                 940

Glu Arg Ile Leu Ala Gln Leu Arg Glu Leu Glu Lys Lys Lys Lys Leu
945                 950                 955                 960

Glu Asp Ala Lys Ser Gln Glu Gln Val Phe Gly Leu Asp Lys Glu Leu
                965                 970                 975

Lys Lys Leu Lys Lys Ala Val Ala Thr Ser Asp Lys Leu Ala Thr Ala
            980                 985                 990

Glu Leu Thr Ile Ala Lys Asp Gln  Leu Lys Ser Leu His  Gly Thr Val
        995                 1000                 1005

Met Lys  Ile Asn Gln Glu Arg  Ala Glu Glu Leu Gln  Glu Ala Glu
    1010                 1015                 1020

Arg Phe  Ser Arg Lys Ala Ala  Gln Ala Ala Arg Asp  Leu Thr Arg
    1025                 1030                 1035

Ala Glu  Ala Glu Ile Glu Leu  Leu Gln Asn Leu Leu  Arg Gln Lys
    1040                 1045                 1050

Gly Glu  Gln Phe Arg Leu Glu  Met Glu Lys Thr Gly  Val Gly Thr
    1055                 1060                 1065

Gly Ala  Asn Ser Gln Val Leu  Glu Ile Glu Lys Leu  Asn Glu Thr
    1070                 1075                 1080
```

```
Met Glu  Arg Gln Arg Thr Glu  Ile Ala Arg Leu Gln  Asn Val Leu
    1085                 1090                 1095

Asp Leu  Thr Gly Ser Asp Asn  Lys Gly Gly Phe Glu  Asn Val Leu
    1100                 1105                 1110

Glu Glu  Ile Ala Glu Leu Arg  Arg Glu Val Ser Tyr  Gln Asn Asp
    1115                 1120                 1125

Tyr Ile  Ser Ser Met Ala Asp  Pro Phe Lys Arg Arg  Gly Tyr Trp
    1130                 1135                 1140

Tyr Phe  Met Pro Pro Pro Pro  Ser Ser Lys Val Ser  Ser His Ser
    1145                 1150                 1155

Ser Gln  Ala Thr Lys Asp Ser  Gly Val Gly Leu Lys  Tyr Ser Ala
    1160                 1165                 1170

Ser Thr  Pro Val Arg Lys Pro  Arg Pro Gly Gln Gln  Asp Gly Lys
    1175                 1180                 1185

Glu Gly  Ser Gln Pro Pro Pro  Ala Ser Gly Tyr Trp  Val Tyr Ser
    1190                 1195                 1200

Pro Ile  Arg Ser Gly Leu His  Lys Leu Phe Pro Ser  Arg Asp Ala
    1205                 1210                 1215

Asp Ser  Gly Gly Asp Ser Gln  Glu Glu Ser Glu Leu  Asp Asp Gln
    1220                 1225                 1230

Glu Glu  Pro Pro Phe Val Pro  Pro Pro Gly Tyr Met  Met Tyr Thr
    1235                 1240                 1245

Val Leu  Pro Asp Gly Ser Pro  Val Pro Gln Gly Met  Ala Leu Tyr
    1250                 1255                 1260

Ala Pro  Pro Pro Pro Leu Pro  Asn Asn Ser Arg Pro  Leu Thr Pro
    1265                 1270                 1275

Gly Thr  Val Val Tyr Gly Pro  Pro Pro Ala Gly Ala  Pro Met Val
    1280                 1285                 1290

Tyr Gly  Pro Pro Pro Pro Asn  Phe Ser Ile Pro Phe  Ile Pro Met
    1295                 1300                 1305

Gly Val  Leu His Cys Asn Val  Pro Glu His His Asn  Leu Glu Asn
    1310                 1315                 1320

Glu Val  Ser Arg Leu Glu Asp  Ile Met Gln His Leu  Lys Ser Lys
    1325                 1330                 1335

Lys Arg  Glu Glu Arg Trp Met  Arg Ala Ser Lys Arg  Gln Ser Glu
    1340                 1345                 1350

Lys Glu  Met Glu Glu Leu His  His Asn Ile Asp Asp  Leu Leu Gln
    1355                 1360                 1365

Glu Lys  Lys Ser Leu Glu Cys  Glu Val Glu Glu Leu  His Arg Thr
    1370                 1375                 1380

Val Gln  Lys Arg Gln Gln Gln  Lys Asp Phe Ile Asp  Gly Asn Val
    1385                 1390                 1395

Glu Ser  Leu Met Thr Glu Leu  Glu Ile Glu Lys Ser  Leu Lys His
    1400                 1405                 1410

His Glu  Asp Ile Val Asp Glu  Ile Glu Cys Ile Glu  Lys Thr Leu
    1415                 1420                 1425

Leu Lys  Arg Arg Ser Glu Leu  Arg Glu Ala Asp Arg  Leu Leu Ala
    1430                 1435                 1440

Glu Ala  Glu Ser Glu Leu Ser  Cys Thr Lys Glu Lys  Thr Lys Asn
    1445                 1450                 1455

Ala Val  Glu Lys Phe Thr Asp  Ala Lys Arg Ser Leu  Leu Gln Thr
    1460                 1465                 1470

Glu Ser  Asp Ala Glu Glu Leu  Glu Arg Arg Ala Gln  Glu Thr Ala
```

```
    1475                1480                1485

Val Asn  Leu Val Lys Ala Asp  Gln Gln Leu Arg Ser  Leu Gln Ala
    1490                1495                1500

Asp Ala  Lys Asp Leu Glu Gln  His Lys Ile Lys Gln  Glu Glu Ile
    1505                1510                1515

Leu Lys  Glu Ile Asn Lys Ile  Val Ala Ala Lys Asp  Ser Asp Phe
    1520                1525                1530

Gln Cys  Leu Ser Lys Lys Lys  Glu Lys Leu Thr Glu  Glu Leu Gln
    1535                1540                1545

Lys Leu  Gln Lys Asp Ile Glu  Met Ala Glu Arg Asn  Glu Asp His
    1550                1555                1560

His Leu  Gln Val Leu Lys Glu  Ser Glu Val Leu Leu  Gln Ala Lys
    1565                1570                1575

Arg Ala  Glu Leu Glu Lys Leu  Lys Ser Gln Val Thr  Ser Gln Gln
    1580                1585                1590

Gln Glu  Met Ala Val Leu Asp  Arg Gln Leu Gly His  Lys Lys Glu
    1595                1600                1605

Glu Leu  His Leu Leu Gln Gly  Ser Met Val Gln Ala  Lys Ala Asp
    1610                1615                1620

Leu Gln  Glu Ala Leu Arg Leu  Gly Glu Thr Glu Val  Thr Glu Lys
    1625                1630                1635

Cys Asn  His Ile Arg Glu Val  Lys Ser Leu Leu Glu  Glu Leu Ser
    1640                1645                1650

Phe Gln  Lys Gly Glu Leu Asn  Val Gln Ile Ser Glu  Arg Lys Thr
    1655                1660                1665

Gln Leu  Thr Leu Ile Lys Gln  Glu Ile Glu Lys Glu  Glu Glu Asn
    1670                1675                1680

Leu Gln  Val Val Leu Arg Gln  Met Ser Lys His Lys  Thr Glu Leu
    1685                1690                1695

Lys Asn  Ile Leu Asp Met Leu  Gln Leu Glu Asn His  Glu Leu Gln
    1700                1705                1710

Gly Leu  Lys Leu Gln His Asp  Gln Arg Val Ser Glu  Leu Glu Lys
    1715                1720                1725

Thr Gln  Val Ala Val Leu Glu  Glu Lys Leu Glu Leu  Glu Asn Leu
    1730                1735                1740

Gln Gln  Ile Ser Gln Gln Gln  Lys Gly Glu Ile Glu  Trp Gln Lys
    1745                1750                1755

Gln Leu  Leu Glu Arg Asp Lys  Arg Glu Ile Glu Arg  Met Thr Ala
    1760                1765                1770

Glu Ser  Arg Ala Leu Gln Ser  Cys Val Glu Cys Leu  Ser Lys Glu
    1775                1780                1785

Lys Glu  Asp Leu Gln Glu Lys  Cys Asp Ile Trp Glu  Lys Lys Leu
    1790                1795                1800

Ala Gln  Thr Lys Arg Val Leu  Ala Ala Ala Glu Glu  Asn Ser Lys
    1805                1810                1815

Met Glu  Gln Ser Asn Leu Glu  Lys Leu Glu Leu Asn  Val Arg Lys
    1820                1825                1830

Leu Gln  Gln Glu Leu Asp Gln  Leu Asn Arg Asp Lys  Leu Ser Leu
    1835                1840                1845

His Asn  Asp Ile Ser Ala Met  Gln Gln Gln Leu Gln  Glu Lys Arg
    1850                1855                1860

Glu Ala  Val Asn Ser Leu Gln  Glu Glu Leu Ala Asn  Val Gln Asp
    1865                1870                1875
```

```
His Leu  Asn Leu Ala Lys Gln  Asp Leu Leu His Thr  Thr Lys His
    1880                 1885                 1890

Gln Asp  Val Leu Leu Ser Glu  Gln Thr Arg Leu Gln  Lys Asp Ile
    1895                 1900                 1905

Ser Glu  Trp Ala Asn Arg Phe  Glu Asp Cys Gln Lys  Glu Glu Glu
    1910                 1915                 1920

Thr Lys  Gln Gln Gln Leu Gln  Val Leu Gln Asn Glu  Ile Glu Glu
    1925                 1930                 1935

Asn Lys  Leu Lys Leu Val Gln  Gln Glu Met Met Phe  Gln Arg Leu
    1940                 1945                 1950

Gln Lys  Glu Arg Glu Ser Glu  Glu Ser Lys Leu Glu  Thr Ser Lys
    1955                 1960                 1965

Val Thr  Leu Lys Glu Gln Gln  His Gln Leu Glu Lys  Glu Leu Thr
    1970                 1975                 1980

Asp Gln  Lys Ser Lys Leu Asp  Gln Val Leu Ser Lys  Val Leu Ala
    1985                 1990                 1995

Ala Glu  Glu Arg Val Arg Thr  Leu Gln Glu Glu Glu  Arg Trp Cys
    2000                 2005                 2010

Glu Ser  Leu Glu Lys Thr Leu  Ser Gln Thr Lys Arg  Gln Leu Ser
    2015                 2020                 2025

Glu Arg  Glu Gln Gln Leu Val  Glu Lys Ser Gly Glu  Leu Leu Ala
    2030                 2035                 2040

Leu Gln  Lys Glu Ala Asp Ser  Met Arg Ala Asp Phe  Ser Leu Leu
    2045                 2050                 2055

Arg Asn  Gln Phe Leu Thr Glu  Arg Lys Lys Ala Glu  Lys Gln Val
    2060                 2065                 2070

Ala Ser  Leu Lys Glu Ala Leu  Lys Ile Gln Arg Ser  Gln Leu Glu
    2075                 2080                 2085

Lys Asn  Leu Leu Glu Gln Lys  Gln Glu Asn Ser Cys  Ile Gln Lys
    2090                 2095                 2100

Glu Met  Ala Thr Ile Glu Leu  Val Ala Gln Asp Asn  His Glu Arg
    2105                 2110                 2115

Ala Arg  Arg Leu Met Lys Glu  Leu Asn Gln Met Gln  Tyr Glu Tyr
    2120                 2125                 2130

Thr Glu  Leu Lys Lys Gln Met  Ala Asn Gln Lys Asp  Leu Glu Arg
    2135                 2140                 2145

Arg Gln  Met Glu Ile Ser Asp  Ala Met Arg Thr Leu  Lys Ser Glu
    2150                 2155                 2160

Val Lys  Asp Glu Ile Arg Thr  Ser Leu Lys Asn Leu  Asn Gln Phe
    2165                 2170                 2175

Leu Pro  Glu Leu Pro Ala Asp  Leu Glu Ala Ile Leu  Glu Arg Asn
    2180                 2185                 2190

Glu Asn  Leu Glu Gly Glu Leu  Glu Ser Leu Lys Glu  Asn Leu Pro
    2195                 2200                 2205

Phe Thr  Met Asn Glu Gly Pro  Phe Glu Glu Lys Leu  Asn Phe Ser
    2210                 2215                 2220

Gln Val  His Ile Met Asp Glu  His Trp Arg Gly Glu  Ala Leu Arg
    2225                 2230                 2235

Glu Lys  Leu Arg His Arg Glu  Asp Arg Leu Lys Ala  Gln Leu Arg
    2240                 2245                 2250

His Cys  Met Ser Lys Gln Ala  Glu Val Leu Ile Lys  Gly Lys Arg
    2255                 2260                 2265
```

```
Gln Thr  Glu Gly Thr Leu His  Ser Leu Arg Arg Gln  Val Asp Ala
    2270                2275                2280

Leu Gly  Glu Leu Val Thr Ser  Thr Ser Ala Asp Ser  Ala Ser Ser
    2285                2290                2295

Pro Ser  Leu Ser Gln Leu Glu  Ser Ser Leu Thr Glu  Asp Ser Gln
    2300                2305                2310

Leu Gly  Gln Asn Gln Glu Lys  Asn Ala Ser Ala Arg
    2315                2320                2325


<210> SEQ ID NO 31
<211> LENGTH: 18
<212> TYPE: DNA
<213> ORGANISM: Artificial Sequence
<220> FEATURE:
<223> OTHER INFORMATION: Synthetic primer

<400> SEQUENCE: 31

gcagcaaaag actcagac                                                    18


<210> SEQ ID NO 32
<211> LENGTH: 18
<212> TYPE: DNA
<213> ORGANISM: Artificial Sequence
<220> FEATURE:
<223> OTHER INFORMATION: Synthetic primer

<400> SEQUENCE: 32

aagttgcaac atgtccag                                                    18


<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33

ggatccatga agaaaggttc tcag                                             24


<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34

gtcgactcag ggtcggtgcg cgtc                                             24


<210> SEQ ID NO 35
<211> LENGTH: 23
<212> TYPE: DNA
<213> ORGANISM: Artificial Sequence
<220> FEATURE:
<223> OTHER INFORMATION: Synthetic primer

<400> SEQUENCE: 35

gtcgacctat gcggaggggt ctg                                              23


<210> SEQ ID NO 36
<211> LENGTH: 25
<212> TYPE: DNA
<213> ORGANISM: Artificial Sequence
<220> FEATURE:
<223> OTHER INFORMATION: Synthetic primer
```

<400> SEQUENCE: 36

```
ggatccatga agaaaggttc tcaac                                           25
```

<210> SEQ ID NO 37
<211> LENGTH: 25
<212> TYPE: DNA
<213> ORGANISM: Artificial Sequence
<220> FEATURE:
<223> OTHER INFORMATION: Synthetic primer

<400> SEQUENCE: 37

```
gtcgactcat ctggctgagg cattc                                           25
```

<210> SEQ ID NO 38
<211> LENGTH: 6046
<212> TYPE: DNA
<213> ORGANISM: Canis familiaris
<220> FEATURE:
<221> NAME/KEY: CDS
<222> LOCATION: (1)..(5934)

<400> SEQUENCE: 38

```
atg tcg tcc tgg ctc ggg ggc ctg ggc tcc ggc ctg ggc cag tcg ctg        48
Met Ser Ser Trp Leu Gly Gly Leu Gly Ser Gly Leu Gly Gln Ser Leu
1               5                   10                  15

ggg caa gtc gga ggc agc ctg gcc tcc ctc act ggc cag att tca aac        96
Gly Gln Val Gly Gly Ser Leu Ala Ser Leu Thr Gly Gln Ile Ser Asn
            20                  25                  30

ttt acg aag gac atg ctg atg gag ggc acg gag gag gtg gaa gca gaa       144
Phe Thr Lys Asp Met Leu Met Glu Gly Thr Glu Glu Val Glu Ala Glu
        35                  40                  45

tta cct aat tct agg aga aag gaa gtt gaa gcc att cat gca atc tta       192
Leu Pro Asn Ser Arg Arg Lys Glu Val Glu Ala Ile His Ala Ile Leu
    50                  55                  60

aga tca gag aat gag aga ctc aaa gaa ctt tgt act gat tta gaa gag       240
Arg Ser Glu Asn Glu Arg Leu Lys Glu Leu Cys Thr Asp Leu Glu Glu
65                  70                  75                  80

aag cat gaa gca tca gag ctt caa ata aag caa caa tct aca aat tac       288
Lys His Glu Ala Ser Glu Leu Gln Ile Lys Gln Gln Ser Thr Asn Tyr
                85                  90                  95

cga aat caa cta caa cag aaa gag gta gaa atc agc cat ctt aaa gca       336
Arg Asn Gln Leu Gln Gln Lys Glu Val Glu Ile Ser His Leu Lys Ala
            100                 105                 110

aga cag att gca ctg cag gat cag ttg ctg aag ctg cag tca gct gct       384
Arg Gln Ile Ala Leu Gln Asp Gln Leu Leu Lys Leu Gln Ser Ala Ala
        115                 120                 125

cag tct gca cat tca gga gct agc agc gta cca gca gcc ctg gca tca       432
Gln Ser Ala His Ser Gly Ala Ser Ser Val Pro Ala Ala Leu Ala Ser
    130                 135                 140

tct ccg ttc agc tat tct gtc agt cat cat gct tca gct ttc cat gac       480
Ser Pro Phe Ser Tyr Ser Val Ser His His Ala Ser Ala Phe His Asp
145                 150                 155                 160

gat gac atg gac ttc agt gac ata att tca tca caa caa gaa ata aac       528
Asp Asp Met Asp Phe Ser Asp Ile Ile Ser Ser Gln Gln Glu Ile Asn
                165                 170                 175

aga tta tca aat gaa gtt tca aga ctt gag tct gag gtt ggc cat tgg       576
Arg Leu Ser Asn Glu Val Ser Arg Leu Glu Ser Glu Val Gly His Trp
            180                 185                 190

agg cat att gct cag act tct aaa gca caa gga tca aat agc tct gat       624
Arg His Ile Ala Gln Thr Ser Lys Ala Gln Gly Ser Asn Ser Ser Asp
        195                 200                 205
```

```
caa agt gaa atc tgt aaa cta caa agt atc att aag gaa ctc aaa cag      672
Gln Ser Glu Ile Cys Lys Leu Gln Ser Ile Ile Lys Glu Leu Lys Gln
    210                 215                 220

att cga agt cag gaa atc gat gac cat caa cat gaa atg tca gtg ttg      720
Ile Arg Ser Gln Glu Ile Asp Asp His Gln His Glu Met Ser Val Leu
225                 230                 235                 240

cag aat gca cat caa cag aag ttg aca gat ata agt cgt cgg cat cga      768
Gln Asn Ala His Gln Gln Lys Leu Thr Asp Ile Ser Arg Arg His Arg
                245                 250                 255

gaa gaa tta cgt gac tat gaa gaa cga att gaa gaa ctg gaa aat ctg      816
Glu Glu Leu Arg Asp Tyr Glu Glu Arg Ile Glu Glu Leu Glu Asn Leu
            260                 265                 270

tta gaa caa ggt ggc tca gga att gta ata cct gat cac tca aaa atc      864
Leu Glu Gln Gly Gly Ser Gly Ile Val Ile Pro Asp His Ser Lys Ile
        275                 280                 285

cat gag atg caa aaa act att cag aat cta caa act gaa aaa gta gca      912
His Glu Met Gln Lys Thr Ile Gln Asn Leu Gln Thr Glu Lys Val Ala
    290                 295                 300

tct ata aaa aaa att gaa gaa ctt gag gat aaa ata aaa gac ata gat      960
Ser Ile Lys Lys Ile Glu Glu Leu Glu Asp Lys Ile Lys Asp Ile Asp
305                 310                 315                 320

aaa aaa ttg tct tct gca gaa aat gac aga gat gtt ttg agg aag gag     1008
Lys Lys Leu Ser Ser Ala Glu Asn Asp Arg Asp Val Leu Arg Lys Glu
                325                 330                 335

aaa gaa tgc cta aat gtt gaa aac aga caa ata aca gaa caa tgt gaa     1056
Lys Glu Cys Leu Asn Val Glu Asn Arg Gln Ile Thr Glu Gln Cys Glu
            340                 345                 350

agc ttg aaa ctg gaa tgt aaa ttg cag cat gat gct gag aag caa ggt     1104
Ser Leu Lys Leu Glu Cys Lys Leu Gln His Asp Ala Glu Lys Gln Gly
        355                 360                 365

gat act gtg aca gaa aaa gaa aga atc ctt cca cag agt aca tca gtg     1152
Asp Thr Val Thr Glu Lys Glu Arg Ile Leu Pro Gln Ser Thr Ser Val
    370                 375                 380

gaa gag gaa gtg ctc aaa ctg cag caa gca ctg tct gat gcg gaa aat     1200
Glu Glu Glu Val Leu Lys Leu Gln Gln Ala Leu Ser Asp Ala Glu Asn
385                 390                 395                 400

gaa att atg aga ctg agt aat tta tac cag gat aac agt ctc act gaa     1248
Glu Ile Met Arg Leu Ser Asn Leu Tyr Gln Asp Asn Ser Leu Thr Glu
                405                 410                 415

gat aat ttg aaa ctt aaa atg cat gtc gaa ttt tta gaa aaa cag aag     1296
Asp Asn Leu Lys Leu Lys Met His Val Glu Phe Leu Glu Lys Gln Lys
            420                 425                 430

tcc tta ttg agt caa gaa aag gaa gag ctt caa cta tca ctt tta aag     1344
Ser Leu Leu Ser Gln Glu Lys Glu Glu Leu Gln Leu Ser Leu Leu Lys
        435                 440                 445

ttg aac aat gaa tat gaa gtg att aaa agt aca gct gtg aga gac atg     1392
Leu Asn Asn Glu Tyr Glu Val Ile Lys Ser Thr Ala Val Arg Asp Met
    450                 455                 460

gat atg gat tca aca tta tgt gat tta aga ctg acc ttg gag gca aag     1440
Asp Met Asp Ser Thr Leu Cys Asp Leu Arg Leu Thr Leu Glu Ala Lys
465                 470                 475                 480

gac cag gaa ctc aat cag agt ctc act gag aag gaa ata ttg gtt gct     1488
Asp Gln Glu Leu Asn Gln Ser Leu Thr Glu Lys Glu Ile Leu Val Ala
                485                 490                 495

gag tta gag gaa ttg gac aga caa aac caa gaa gct aca aag cac atg     1536
Glu Leu Glu Glu Leu Asp Arg Gln Asn Gln Glu Ala Thr Lys His Met
            500                 505                 510

att ctg ata aaa gat cag cta tca aaa caa caa agt gag gga gaa act     1584
Ile Leu Ile Lys Asp Gln Leu Ser Lys Gln Gln Ser Glu Gly Glu Thr
```

```
        515                 520                 525

atc att agt aaa ctg aga aaa gat cta aat gat gaa aac aag aga gtc     1632
Ile Ile Ser Lys Leu Arg Lys Asp Leu Asn Asp Glu Asn Lys Arg Val
    530                 535                 540

cat caa ctt gaa gat gat aaa aag aat atg act aaa gaa cta aat gtg     1680
His Gln Leu Glu Asp Asp Lys Lys Asn Met Thr Lys Glu Leu Asn Val
545                 550                 555                 560

cag aaa gag aag tta gtt caa agt gaa ctc gtc cta aat ggc ttg cat     1728
Gln Lys Glu Lys Leu Val Gln Ser Glu Leu Val Leu Asn Gly Leu His
                565                 570                 575

tta gcc aag cag aag ctt gag gag aaa gta gaa gat tta gtg gat cag     1776
Leu Ala Lys Gln Lys Leu Glu Glu Lys Val Glu Asp Leu Val Asp Gln
            580                 585                 590

cta aat aaa tca caa aaa agt aat tta aac atg cag aag gag aac ttt     1824
Leu Asn Lys Ser Gln Lys Ser Asn Leu Asn Met Gln Lys Glu Asn Phe
        595                 600                 605

gga ctt aag gaa cat att aaa caa aat gag gaa gag ctt tct aga gtc     1872
Gly Leu Lys Glu His Ile Lys Gln Asn Glu Glu Glu Leu Ser Arg Val
    610                 615                 620

agg gat gag tta act cag tct cta agt cga gac tct ggc agt gat ttt     1920
Arg Asp Glu Leu Thr Gln Ser Leu Ser Arg Asp Ser Gly Ser Asp Phe
625                 630                 635                 640

aag gat gac tta ctt aaa gaa agg gaa gct gaa gtc aga aac tta aaa     1968
Lys Asp Asp Leu Leu Lys Glu Arg Glu Ala Glu Val Arg Asn Leu Lys
                645                 650                 655

caa aat ctt tca gaa ata gaa cag ctc aat gac agt tta aac aaa gtt     2016
Gln Asn Leu Ser Glu Ile Glu Gln Leu Asn Asp Ser Leu Asn Lys Val
            660                 665                 670

gcc ttt gat ctc aaa atg gaa aat gaa aag ttg gtc tta gcg tgt gaa     2064
Ala Phe Asp Leu Lys Met Glu Asn Glu Lys Leu Val Leu Ala Cys Glu
        675                 680                 685

gat ata aga cat cag ttg gaa gaa tca att gtt ggc agc aat cag atg     2112
Asp Ile Arg His Gln Leu Glu Glu Ser Ile Val Gly Ser Asn Gln Met
    690                 695                 700

tct ctg gaa aga aac act att gtg gag gct cta aaa atg gaa aaa gga     2160
Ser Leu Glu Arg Asn Thr Ile Val Glu Ala Leu Lys Met Glu Lys Gly
705                 710                 715                 720

cag tta gaa gca gaa ttg agt cga gct gac caa agg ctg ttg gaa gaa     2208
Gln Leu Glu Ala Glu Leu Ser Arg Ala Asp Gln Arg Leu Leu Glu Glu
                725                 730                 735

gcc agt aag tat gaa cag acg att caa gag cta tca aag gca cgt gat     2256
Ala Ser Lys Tyr Glu Gln Thr Ile Gln Glu Leu Ser Lys Ala Arg Asp
            740                 745                 750

ttg agg acc tct gct tta cag ctg gag cag cag cat tta atg aaa ctc     2304
Leu Arg Thr Ser Ala Leu Gln Leu Glu Gln Gln His Leu Met Lys Leu
        755                 760                 765

agt caa gag aag gac ttc gaa ata gca gaa ctt aaa aag aac att gaa     2352
Ser Gln Glu Lys Asp Phe Glu Ile Ala Glu Leu Lys Lys Asn Ile Glu
    770                 775                 780

cag atg gat act gat cat aaa gaa act aag gca att ttg tca tct att     2400
Gln Met Asp Thr Asp His Lys Glu Thr Lys Ala Ile Leu Ser Ser Ile
785                 790                 795                 800

tta gaa gag cag aag caa ttg acg caa ctt ata agt gag aag gaa att     2448
Leu Glu Glu Gln Lys Gln Leu Thr Gln Leu Ile Ser Glu Lys Glu Ile
                805                 810                 815

ttt att gag aaa ctt aaa gaa aga agt tca gag ctt cag gag gaa tta     2496
Phe Ile Glu Lys Leu Lys Glu Arg Ser Ser Glu Leu Gln Glu Glu Leu
            820                 825                 830

gag aaa tct act cag gcc tca agg aaa att gaa att tta aag caa acc     2544
```

```
Glu Lys Ser Thr Gln Ala Ser Arg Lys Ile Glu Ile Leu Lys Gln Thr
        835                 840                 845

att gag gag aaa gac aga agt ctt ggg tcc atg aaa gaa gaa aac aat      2592
Ile Glu Glu Lys Asp Arg Ser Leu Gly Ser Met Lys Glu Glu Asn Asn
    850                 855                 860

cat ctg aaa gaa gaa ctg gaa cgg ctc cgt gaa cag cag agt cga gcc      2640
His Leu Lys Glu Glu Leu Glu Arg Leu Arg Glu Gln Gln Ser Arg Ala
865                 870                 875                 880

gtg cct gtg gtg gag cct aaa ccc ctg gat agt gtt aca gag cta gaa      2688
Val Pro Val Val Glu Pro Lys Pro Leu Asp Ser Val Thr Glu Leu Glu
                885                 890                 895

tct gag gtg ttg cag cta aat ata gta aag agg aat ctt gag gag gaa      2736
Ser Glu Val Leu Gln Leu Asn Ile Val Lys Arg Asn Leu Glu Glu Glu
            900                 905                 910

ata aaa cgt cat cag aag att ata gaa gat caa aac cag agt aaa atg      2784
Ile Lys Arg His Gln Lys Ile Ile Glu Asp Gln Asn Gln Ser Lys Met
        915                 920                 925

cag ctg ctt cag tct cta gag gag cag aag aag gaa atg gat gaa ttt      2832
Gln Leu Leu Gln Ser Leu Glu Glu Gln Lys Lys Glu Met Asp Glu Phe
    930                 935                 940

aag tgc cag cat gag caa atg aac gtc aca cac acc caa ctc ttc tta      2880
Lys Cys Gln His Glu Gln Met Asn Val Thr His Thr Gln Leu Phe Leu
945                 950                 955                 960

gag aaa gat gag gag att aag aat ttg caa aaa aca att gaa caa atc      2928
Glu Lys Asp Glu Glu Ile Lys Asn Leu Gln Lys Thr Ile Glu Gln Ile
                965                 970                 975

aaa acc caa tgg cat gaa gaa aga cag gac gtt caa atg gag aat tct      2976
Lys Thr Gln Trp His Glu Glu Arg Gln Asp Val Gln Met Glu Asn Ser
            980                 985                 990

gag ttc ttt caa gaa aca aaa gtg  cag agc ctt aat cta  gaa aat ggc    3024
Glu Phe Phe Gln Glu Thr Lys Val  Gln Ser Leu Asn Leu  Glu Asn Gly
        995                 1000                1005

agt gaa  aag cat gat tta tcg  aaa gcc gaa act gag  agg tta gta      3069
Ser Glu  Lys His Asp Leu Ser  Lys Ala Glu Thr Glu  Arg Leu Val
    1010                1015                1020

aaa gga  ata aaa gaa cga gag  ctg gag att aaa ctt  cta aat gaa      3114
Lys Gly  Ile Lys Glu Arg Glu  Leu Glu Ile Lys Leu  Leu Asn Glu
    1025                1030                1035

aag aat  ata tct tta aca aaa  caa att gat cag ctg  tcc aaa gat      3159
Lys Asn  Ile Ser Leu Thr Lys  Gln Ile Asp Gln Leu  Ser Lys Asp
    1040                1045                1050

gag gtt  ggt aaa ctc act cag  atc atc cag cag aaa  gac tta gag      3204
Glu Val  Gly Lys Leu Thr Gln  Ile Ile Gln Gln Lys  Asp Leu Glu
    1055                1060                1065

ata caa  gct ctt cat gct agg  att tct tca gct tcc  tac acc cag      3249
Ile Gln  Ala Leu His Ala Arg  Ile Ser Ser Ala Ser  Tyr Thr Gln
    1070                1075                1080

gat gtt  gtc tac ctt cag cag  cag ctg cag gcc tat  gct atg gag      3294
Asp Val  Val Tyr Leu Gln Gln  Gln Leu Gln Ala Tyr  Ala Met Glu
    1085                1090                1095

aga gaa  caa gta tta gct gtt  ttg agt gag aag acc  agg gaa aat      3339
Arg Glu  Gln Val Leu Ala Val  Leu Ser Glu Lys Thr  Arg Glu Asn
    1100                1105                1110

agc cat  ctg aaa aca gaa tac  cac aaa atg atg gat  atc gtt gct      3384
Ser His  Leu Lys Thr Glu Tyr  His Lys Met Met Asp  Ile Val Ala
    1115                1120                1125

gct aaa  gaa gca gct ctc att  aag ctg caa gat gaa  aat aaa aaa      3429
Ala Lys  Glu Ala Ala Leu Ile  Lys Leu Gln Asp Glu  Asn Lys Lys
    1130                1135                1140
```

-continued

```
ttg tct  gct aga tcc gaa ggt  ggt ggc cag gat atg  ttt aga gag      3474
Leu Ser  Ala Arg Ser Glu Gly  Gly Gly Gln Asp Met  Phe Arg Glu
    1145                 1150                 1155

act gtc  cag aat tta tca cgt  atc att cga gaa aaa  gac att gag      3519
Thr Val  Gln Asn Leu Ser Arg  Ile Ile Arg Glu Lys  Asp Ile Glu
    1160                 1165                 1170

ata gat  gcg tta agt cag aag  tgc cag acc tta ttg  aca gtt tta      3564
Ile Asp  Ala Leu Ser Gln Lys  Cys Gln Thr Leu Leu  Thr Val Leu
    1175                 1180                 1185

caa aca  tcg agc act ggg aat  gag gtt gga ggc gtt  aat agc aat      3609
Gln Thr  Ser Ser Thr Gly Asn  Glu Val Gly Gly Val  Asn Ser Asn
    1190                 1195                 1200

cag ttt  gag gag ctt cta cag  gaa cgc gac aaa tta  aaa caa caa      3654
Gln Phe  Glu Glu Leu Leu Gln  Glu Arg Asp Lys Leu  Lys Gln Gln
    1205                 1210                 1215

gta aag  aag atg gaa gag tgg  aaa cag cag gtg atg  acc aca gtt      3699
Val Lys  Lys Met Glu Glu Trp  Lys Gln Gln Val Met  Thr Thr Val
    1220                 1225                 1230

cag aat  atg cag cat gag tca  gcc cag ctt caa gaa  gaa ctt cat      3744
Gln Asn  Met Gln His Glu Ser  Ala Gln Leu Gln Glu  Glu Leu His
    1235                 1240                 1245

cag ctt  cag gca caa gtt ttg  gtt gac agt gat aat  aat tct aaa      3789
Gln Leu  Gln Ala Gln Val Leu  Val Asp Ser Asp Asn  Asn Ser Lys
    1250                 1255                 1260

tta caa  gtg gat tat act ggc  ctg atc caa agt tat  gag cag aat      3834
Leu Gln  Val Asp Tyr Thr Gly  Leu Ile Gln Ser Tyr  Glu Gln Asn
    1265                 1270                 1275

gaa act  aaa ctc aaa aat ttt  ggg cag gag cta gca  caa gtt cag      3879
Glu Thr  Lys Leu Lys Asn Phe  Gly Gln Glu Leu Ala  Gln Val Gln
    1280                 1285                 1290

cac agc  ata ggg cag ctg tac  agt acc aaa gac ctt  ctc tta gga      3924
His Ser  Ile Gly Gln Leu Tyr  Ser Thr Lys Asp Leu  Leu Leu Gly
    1295                 1300                 1305

aaa ctt  gat att att tct cct  caa ctc ccc tcc gga  tca tcg cct      3969
Lys Leu  Asp Ile Ile Ser Pro  Gln Leu Pro Ser Gly  Ser Ser Pro
    1310                 1315                 1320

cct tcc  cag tca gca gag tct  ctt gga atg gat aag  cgt gat aca      4014
Pro Ser  Gln Ser Ala Glu Ser  Leu Gly Met Asp Lys  Arg Asp Thr
    1325                 1330                 1335

tca agt  gag tct tca aaa cag  gag cta gaa gag cta  aga aag tca      4059
Ser Ser  Glu Ser Ser Lys Gln  Glu Leu Glu Glu Leu  Arg Lys Ser
    1340                 1345                 1350

ctg cag  gaa aaa gat gca acg  att aaa aca ctc cag  gaa aat aac      4104
Leu Gln  Glu Lys Asp Ala Thr  Ile Lys Thr Leu Gln  Glu Asn Asn
    1355                 1360                 1365

cac aga  ttg tcc gat tca att  gct gcc acc tca gag  cta gaa aga      4149
His Arg  Leu Ser Asp Ser Ile  Ala Ala Thr Ser Glu  Leu Glu Arg
    1370                 1375                 1380

aaa gaa  cac gaa cag act gat  tca gaa att aag cag  cta aag gag      4194
Lys Glu  His Glu Gln Thr Asp  Ser Glu Ile Lys Gln  Leu Lys Glu
    1385                 1390                 1395

aaa caa  gat gtt tta caa aag  tca ctt aag gag aaa  gac ctc tta      4239
Lys Gln  Asp Val Leu Gln Lys  Ser Leu Lys Glu Lys  Asp Leu Leu
    1400                 1405                 1410

atc aaa  gcc aaa agt gat cag  tta ctt tct tta aat  gaa aat ttc      4284
Ile Lys  Ala Lys Ser Asp Gln  Leu Leu Ser Leu Asn  Glu Asn Phe
    1415                 1420                 1425

acc aac  aaa gtg aat gaa aat  gaa ctc ttg agg cag  gca gta acc      4329
Thr Asn  Lys Val Asn Glu Asn  Glu Leu Leu Arg Gln  Ala Val Thr
    1430                 1435                 1440
```

```
aac ctg  aag gag cgg gta tta  att tta gaa atg gac  att ggt aaa      4374
Asn Leu  Lys Glu Arg Val Leu  Ile Leu Glu Met Asp  Ile Gly Lys
    1445                 1450                 1455

cta aaa  gaa gaa aat gaa aaa  ata gtt gaa aga acc  agg gaa aag      4419
Leu Lys  Glu Glu Asn Glu Lys  Ile Val Glu Arg Thr  Arg Glu Lys
    1460                 1465                 1470

gaa acg  gag tat caa gca tta  cag gag act aat atg  aag ttt tcc      4464
Glu Thr  Glu Tyr Gln Ala Leu  Gln Glu Thr Asn Met  Lys Phe Ser
    1475                 1480                 1485

atg atg  ctt cga gaa aaa gag  ttt gag tgc cat tca  atg aag gaa      4509
Met Met  Leu Arg Glu Lys Glu  Phe Glu Cys His Ser  Met Lys Glu
    1490                 1495                 1500

aaa tct  ctt gca ttt gag cag  cta ctg aaa gaa aaa  gag cag ggc      4554
Lys Ser  Leu Ala Phe Glu Gln  Leu Leu Lys Glu Lys  Glu Gln Gly
    1505                 1510                 1515

aag act  ggg gag tta aat caa  ctt tta aat gca gtt  aag tca atg      4599
Lys Thr  Gly Glu Leu Asn Gln  Leu Leu Asn Ala Val  Lys Ser Met
    1520                 1525                 1530

cag gag  aag aca gtt aag ttt  caa caa gag aga gac  cag gtc atg      4644
Gln Glu  Lys Thr Val Lys Phe  Gln Gln Glu Arg Asp  Gln Val Met
    1535                 1540                 1545

ttg gcc  ctg aaa cag aaa caa  atg gaa aac agt gct  tta cag aat      4689
Leu Ala  Leu Lys Gln Lys Gln  Met Glu Asn Ser Ala  Leu Gln Asn
    1550                 1555                 1560

gag gtt  caa cat tta cgc gac  aaa gaa tta cgc tta  aac cag gag      4734
Glu Val  Gln His Leu Arg Asp  Lys Glu Leu Arg Leu  Asn Gln Glu
    1565                 1570                 1575

cta gag  aga ttg cgt aac cat  ctt tta gaa tca gag  gat tct tac      4779
Leu Glu  Arg Leu Arg Asn His  Leu Leu Glu Ser Glu  Asp Ser Tyr
    1580                 1585                 1590

acc cgt  gaa gct ttg gct gca  gaa gag aga gag gcc  aaa ctg aga      4824
Thr Arg  Glu Ala Leu Ala Ala  Glu Glu Arg Glu Ala  Lys Leu Arg
    1595                 1600                 1605

agg aaa  gtc aca gta ttg gag  gaa aag cta gtt tca  tct tct aat      4869
Arg Lys  Val Thr Val Leu Glu  Glu Lys Leu Val Ser  Ser Ser Asn
    1610                 1615                 1620

gca atg  gaa aat gca agc cat  cag gcc agt ttg cag  gta gag tca      4914
Ala Met  Glu Asn Ala Ser His  Gln Ala Ser Leu Gln  Val Glu Ser
    1625                 1630                 1635

ctg cag  gag cag ctg aat gtg  gtc tct aag cag agg  gat gaa acc      4959
Leu Gln  Glu Gln Leu Asn Val  Val Ser Lys Gln Arg  Asp Glu Thr
    1640                 1645                 1650

gcc ctg  cag ctc tct gtg tct  cgg gaa caa gta aag  cag tat gct      5004
Ala Leu  Gln Leu Ser Val Ser  Arg Glu Gln Val Lys  Gln Tyr Ala
    1655                 1660                 1665

ctc tca  ctc tcc aac ctg cag  atg gta cta gag cat  ttc cag caa      5049
Leu Ser  Leu Ser Asn Leu Gln  Met Val Leu Glu His  Phe Gln Gln
    1670                 1675                 1680

gag gaa  aaa gct gtg tat tct  gct gaa cta gaa aag  cac aaa cag      5094
Glu Glu  Lys Ala Val Tyr Ser  Ala Glu Leu Glu Lys  His Lys Gln
    1685                 1690                 1695

ctt gta  gct gaa tgg aag aaa  aag gca gaa aat ctg  gaa gga aaa      5139
Leu Val  Ala Glu Trp Lys Lys  Lys Ala Glu Asn Leu  Glu Gly Lys
    1700                 1705                 1710

ctg atg  tca tta cag gag cgt  ttt gat gaa gca aat  gct gcg ttg      5184
Leu Met  Ser Leu Gln Glu Arg  Phe Asp Glu Ala Asn  Ala Ala Leu
    1715                 1720                 1725

gat tca  gca tca aga ctt aca  gag cag tta gat tta  aag gaa gaa      5229
Asp Ser  Ala Ser Arg Leu Thr  Glu Gln Leu Asp Leu  Lys Glu Glu
```

```
    1730                1735                1740

caa att  gaa gaa ctt aaa aaa  caa aat gaa ctc cga  caa gaa atg      5274
Gln Ile  Glu Glu Leu Lys Lys  Gln Asn Glu Leu Arg  Gln Glu Met
    1745                1750                1755

ctg gat  gat gta caa aag aaa  ttg atg aac tta gta  aac agc aca      5319
Leu Asp  Asp Val Gln Lys Lys  Leu Met Asn Leu Val  Asn Ser Thr
    1760                1765                1770

gaa gga  aaa gtg gac aaa gtc  cta atg aga aac ctc  ttc att gga      5364
Glu Gly  Lys Val Asp Lys Val  Leu Met Arg Asn Leu  Phe Ile Gly
    1775                1780                1785

cat ttc  cac aca cca aag cat  cag cgc cac gag gtg  tta cga tta      5409
His Phe  His Thr Pro Lys His  Gln Arg His Glu Val  Leu Arg Leu
    1790                1795                1800

atg gga  agc atc ctt ggt atc  aag agg gag gaa atg  gaa cag ttg      5454
Met Gly  Ser Ile Leu Gly Ile  Lys Arg Glu Glu Met  Glu Gln Leu
    1805                1810                1815

ctt cat  gaa gat cag ggt ggt  gtt acc agg tgg atg  act gga tgg      5499
Leu His  Glu Asp Gln Gly Gly  Val Thr Arg Trp Met  Thr Gly Trp
    1820                1825                1830

ctt gga  gga gga tca aaa agt  gtc ccc aac aca cct  ctg aga cca      5544
Leu Gly  Gly Gly Ser Lys Ser  Val Pro Asn Thr Pro  Leu Arg Pro
    1835                1840                1845

aat caa  caa tct gtg ctt aat  agc tct ttt tca gaa  ctt ttt gtt      5589
Asn Gln  Gln Ser Val Leu Asn  Ser Ser Phe Ser Glu  Leu Phe Val
    1850                1855                1860

aaa ttt  cta gaa aca gaa tct  cat cca tct gtt cca  cca cca aag      5634
Lys Phe  Leu Glu Thr Glu Ser  His Pro Ser Val Pro  Pro Pro Lys
    1865                1870                1875

ctt tct  gtt cat gat atg aaa  cct ctg gat tca cca  gga agg aga      5679
Leu Ser  Val His Asp Met Lys  Pro Leu Asp Ser Pro  Gly Arg Arg
    1880                1885                1890

aaa gta  gtc ata cat gta tca  gaa agt ttt aaa gaa  acc aca gag      5724
Lys Val  Val Ile His Val Ser  Glu Ser Phe Lys Glu  Thr Thr Glu
    1895                1900                1905

tcc aga  tgt gga agg aga aca  gat gtg aat cca ttc  ttg gct ccc      5769
Ser Arg  Cys Gly Arg Arg Thr  Asp Val Asn Pro Phe  Leu Ala Pro
    1910                1915                1920

cgc tct  gca gct gtg cct ctc  att aac cca gct gga  ctt gga cct      5814
Arg Ser  Ala Ala Val Pro Leu  Ile Asn Pro Ala Gly  Leu Gly Pro
    1925                1930                1935

ggt ggg  cct ggg cat ctt ctt  ttg aag ccc atc tca  gac gtg ttg      5859
Gly Gly  Pro Gly His Leu Leu  Leu Lys Pro Ile Ser  Asp Val Leu
    1940                1945                1950

ccc aca  ttt aca cct ttg ccg  gtg tca cct gac aac  agt gct gga      5904
Pro Thr  Phe Thr Pro Leu Pro  Val Ser Pro Asp Asn  Ser Ala Gly
    1955                1960                1965

gtt gtg  ttg aaa gac ctt tta  aag caa tag atgattctca agccagagac     5954
Val Val  Leu Lys Asp Leu Leu  Lys Gln
    1970                1975

aacatatgta gcactttaaa gaaaccatga acactatgtg tatgtacttt atcacaaagt   6014

ggcctttcag aaaaagtcat gtgtttgttt gc                                 6046


<210> SEQ ID NO 39
<211> LENGTH: 1977
<212> TYPE: PRT
<213> ORGANISM: Canis familiaris

<400> SEQUENCE: 39

Met Ser Ser Trp Leu Gly Gly Leu Gly Ser Gly Leu Gly Gln Ser Leu
```

```
1               5                   10                  15

Gly Gln Val Gly Gly Ser Leu Ala Ser Leu Thr Gly Gln Ile Ser Asn
            20                  25                  30

Phe Thr Lys Asp Met Leu Met Glu Gly Thr Glu Glu Val Glu Ala Glu
        35                  40                  45

Leu Pro Asn Ser Arg Arg Lys Glu Val Glu Ala Ile His Ala Ile Leu
    50                  55                  60

Arg Ser Glu Asn Glu Arg Leu Lys Glu Leu Cys Thr Asp Leu Glu Glu
65                  70                  75                  80

Lys His Glu Ala Ser Glu Leu Gln Ile Lys Gln Gln Ser Thr Asn Tyr
                85                  90                  95

Arg Asn Gln Leu Gln Gln Lys Glu Val Glu Ile Ser His Leu Lys Ala
            100                 105                 110

Arg Gln Ile Ala Leu Gln Asp Gln Leu Leu Lys Leu Gln Ser Ala Ala
        115                 120                 125

Gln Ser Ala His Ser Gly Ala Ser Ser Val Pro Ala Ala Leu Ala Ser
    130                 135                 140

Ser Pro Phe Ser Tyr Ser Val Ser His His Ala Ser Ala Phe His Asp
145                 150                 155                 160

Asp Asp Met Asp Phe Ser Asp Ile Ile Ser Ser Gln Gln Glu Ile Asn
                165                 170                 175

Arg Leu Ser Asn Glu Val Ser Arg Leu Glu Ser Glu Val Gly His Trp
            180                 185                 190

Arg His Ile Ala Gln Thr Ser Lys Ala Gln Gly Ser Asn Ser Ser Asp
        195                 200                 205

Gln Ser Glu Ile Cys Lys Leu Gln Ser Ile Ile Lys Glu Leu Lys Gln
    210                 215                 220

Ile Arg Ser Gln Glu Ile Asp Asp His Gln His Glu Met Ser Val Leu
225                 230                 235                 240

Gln Asn Ala His Gln Gln Lys Leu Thr Asp Ile Ser Arg Arg His Arg
                245                 250                 255

Glu Glu Leu Arg Asp Tyr Glu Glu Arg Ile Glu Glu Leu Glu Asn Leu
            260                 265                 270

Leu Glu Gln Gly Gly Ser Gly Ile Val Ile Pro Asp His Ser Lys Ile
        275                 280                 285

His Glu Met Gln Lys Thr Ile Gln Asn Leu Gln Thr Glu Lys Val Ala
    290                 295                 300

Ser Ile Lys Lys Ile Glu Glu Leu Glu Asp Lys Ile Lys Asp Ile Asp
305                 310                 315                 320

Lys Lys Leu Ser Ser Ala Glu Asn Asp Arg Asp Val Leu Arg Lys Glu
                325                 330                 335

Lys Glu Cys Leu Asn Val Glu Asn Arg Gln Ile Thr Glu Gln Cys Glu
            340                 345                 350

Ser Leu Lys Leu Glu Cys Lys Leu Gln His Asp Ala Glu Lys Gln Gly
        355                 360                 365

Asp Thr Val Thr Glu Lys Glu Arg Ile Leu Pro Gln Ser Thr Ser Val
    370                 375                 380

Glu Glu Glu Val Leu Lys Leu Gln Gln Ala Leu Ser Asp Ala Glu Asn
385                 390                 395                 400

Glu Ile Met Arg Leu Ser Asn Leu Tyr Gln Asp Asn Ser Leu Thr Glu
                405                 410                 415

Asp Asn Leu Lys Leu Lys Met His Val Glu Phe Leu Glu Lys Gln Lys
            420                 425                 430
```

```
Ser Leu Leu Ser Gln Glu Lys Glu Glu Leu Gln Leu Ser Leu Leu Lys
        435                 440                 445

Leu Asn Asn Glu Tyr Glu Val Ile Lys Ser Thr Ala Val Arg Asp Met
    450                 455                 460

Asp Met Asp Ser Thr Leu Cys Asp Leu Arg Leu Thr Leu Glu Ala Lys
465                 470                 475                 480

Asp Gln Glu Leu Asn Gln Ser Leu Thr Glu Lys Glu Ile Leu Val Ala
                485                 490                 495

Glu Leu Glu Glu Leu Asp Arg Gln Asn Gln Glu Ala Thr Lys His Met
            500                 505                 510

Ile Leu Ile Lys Asp Gln Leu Ser Lys Gln Gln Ser Glu Gly Glu Thr
        515                 520                 525

Ile Ile Ser Lys Leu Arg Lys Asp Leu Asn Asp Glu Asn Lys Arg Val
    530                 535                 540

His Gln Leu Glu Asp Asp Lys Lys Asn Met Thr Lys Glu Leu Asn Val
545                 550                 555                 560

Gln Lys Glu Lys Leu Val Gln Ser Glu Leu Val Leu Asn Gly Leu His
                565                 570                 575

Leu Ala Lys Gln Lys Leu Glu Glu Lys Val Glu Asp Leu Val Asp Gln
            580                 585                 590

Leu Asn Lys Ser Gln Lys Ser Asn Leu Asn Met Gln Lys Glu Asn Phe
        595                 600                 605

Gly Leu Lys Glu His Ile Lys Gln Asn Glu Glu Glu Leu Ser Arg Val
    610                 615                 620

Arg Asp Glu Leu Thr Gln Ser Leu Ser Arg Asp Ser Gly Ser Asp Phe
625                 630                 635                 640

Lys Asp Asp Leu Leu Lys Glu Arg Glu Ala Glu Val Arg Asn Leu Lys
                645                 650                 655

Gln Asn Leu Ser Glu Ile Glu Gln Leu Asn Asp Ser Leu Asn Lys Val
            660                 665                 670

Ala Phe Asp Leu Lys Met Glu Asn Glu Lys Leu Val Leu Ala Cys Glu
        675                 680                 685

Asp Ile Arg His Gln Leu Glu Glu Ser Ile Val Gly Ser Asn Gln Met
    690                 695                 700

Ser Leu Glu Arg Asn Thr Ile Val Glu Ala Leu Lys Met Glu Lys Gly
705                 710                 715                 720

Gln Leu Glu Ala Glu Leu Ser Arg Ala Asp Gln Arg Leu Leu Glu Glu
                725                 730                 735

Ala Ser Lys Tyr Glu Gln Thr Ile Gln Glu Leu Ser Lys Ala Arg Asp
            740                 745                 750

Leu Arg Thr Ser Ala Leu Gln Leu Glu Gln Gln His Leu Met Lys Leu
        755                 760                 765

Ser Gln Glu Lys Asp Phe Glu Ile Ala Glu Leu Lys Lys Asn Ile Glu
    770                 775                 780

Gln Met Asp Thr Asp His Lys Glu Thr Lys Ala Ile Leu Ser Ser Ile
785                 790                 795                 800

Leu Glu Glu Gln Lys Gln Leu Thr Gln Leu Ile Ser Glu Lys Glu Ile
                805                 810                 815

Phe Ile Glu Lys Leu Lys Glu Arg Ser Ser Glu Leu Gln Glu Glu Leu
            820                 825                 830

Glu Lys Ser Thr Gln Ala Ser Arg Lys Ile Glu Ile Leu Lys Gln Thr
        835                 840                 845
```

```
Ile Glu Glu Lys Asp Arg Ser Leu Gly Ser Met Lys Glu Glu Asn Asn
    850                 855                 860

His Leu Lys Glu Glu Leu Glu Arg Leu Arg Glu Gln Gln Ser Arg Ala
865                 870                 875                 880

Val Pro Val Val Glu Pro Lys Pro Leu Asp Ser Val Thr Glu Leu Glu
                885                 890                 895

Ser Glu Val Leu Gln Leu Asn Ile Val Lys Arg Asn Leu Glu Glu Glu
            900                 905                 910

Ile Lys Arg His Gln Lys Ile Ile Glu Asp Gln Asn Gln Ser Lys Met
        915                 920                 925

Gln Leu Leu Gln Ser Leu Glu Glu Gln Lys Lys Glu Met Asp Glu Phe
    930                 935                 940

Lys Cys Gln His Glu Gln Met Asn Val Thr His Thr Gln Leu Phe Leu
945                 950                 955                 960

Glu Lys Asp Glu Glu Ile Lys Asn Leu Gln Lys Thr Ile Glu Gln Ile
                965                 970                 975

Lys Thr Gln Trp His Glu Glu Arg Gln Asp Val Gln Met Glu Asn Ser
            980                 985                 990

Glu Phe Phe Gln Glu Thr Lys Val  Gln Ser Leu Asn Leu  Glu Asn Gly
        995                 1000                1005

Ser Glu  Lys His Asp Leu Ser  Lys Ala Glu Thr Glu  Arg Leu Val
    1010                1015                1020

Lys Gly  Ile Lys Glu Arg Glu  Leu Glu Ile Lys Leu  Leu Asn Glu
    1025                1030                1035

Lys Asn  Ile Ser Leu Thr Lys  Gln Ile Asp Gln Leu  Ser Lys Asp
    1040                1045                1050

Glu Val  Gly Lys Leu Thr Gln  Ile Ile Gln Gln Lys  Asp Leu Glu
    1055                1060                1065

Ile Gln  Ala Leu His Ala Arg  Ile Ser Ser Ala Ser  Tyr Thr Gln
    1070                1075                1080

Asp Val  Val Tyr Leu Gln Gln  Gln Leu Gln Ala Tyr  Ala Met Glu
    1085                1090                1095

Arg Glu  Gln Val Leu Ala Val  Leu Ser Glu Lys Thr  Arg Glu Asn
    1100                1105                1110

Ser His  Leu Lys Thr Glu Tyr  His Lys Met Met Asp  Ile Val Ala
    1115                1120                1125

Ala Lys  Glu Ala Ala Leu Ile  Lys Leu Gln Asp Glu  Asn Lys Lys
    1130                1135                1140

Leu Ser  Ala Arg Ser Glu Gly  Gly Gly Gln Asp Met  Phe Arg Glu
    1145                1150                1155

Thr Val  Gln Asn Leu Ser Arg  Ile Ile Arg Glu Lys  Asp Ile Glu
    1160                1165                1170

Ile Asp  Ala Leu Ser Gln Lys  Cys Gln Thr Leu Leu  Thr Val Leu
    1175                1180                1185

Gln Thr  Ser Ser Thr Gly Asn  Glu Val Gly Gly Val  Asn Ser Asn
    1190                1195                1200

Gln Phe  Glu Glu Leu Leu Gln  Glu Arg Asp Lys Leu  Lys Gln Gln
    1205                1210                1215

Val Lys  Lys Met Glu Glu Trp  Lys Gln Gln Val Met  Thr Thr Val
    1220                1225                1230

Gln Asn  Met Gln His Glu Ser  Ala Gln Leu Gln Glu  Glu Leu His
    1235                1240                1245

Gln Leu  Gln Ala Gln Val Leu  Val Asp Ser Asp Asn  Asn Ser Lys
```

```
    1250                1255                1260

Leu Gln  Val Asp Tyr Thr Gly  Leu Ile Gln Ser Tyr  Glu Gln Asn
    1265                1270                1275

Glu Thr  Lys Leu Lys Asn Phe  Gly Gln Glu Leu Ala  Gln Val Gln
    1280                1285                1290

His Ser  Ile Gly Gln Leu Tyr  Ser Thr Lys Asp Leu  Leu Leu Gly
    1295                1300                1305

Lys Leu  Asp Ile Ile Ser Pro  Gln Leu Pro Ser Gly  Ser Ser Pro
    1310                1315                1320

Pro Ser  Gln Ser Ala Glu Ser  Leu Gly Met Asp Lys  Arg Asp Thr
    1325                1330                1335

Ser Ser  Glu Ser Ser Lys Gln  Glu Leu Glu Glu Leu  Arg Lys Ser
    1340                1345                1350

Leu Gln  Glu Lys Asp Ala Thr  Ile Lys Thr Leu Gln  Glu Asn Asn
    1355                1360                1365

His Arg  Leu Ser Asp Ser Ile  Ala Ala Thr Ser Glu  Leu Glu Arg
    1370                1375                1380

Lys Glu  His Glu Gln Thr Asp  Ser Glu Ile Lys Gln  Leu Lys Glu
    1385                1390                1395

Lys Gln  Asp Val Leu Gln Lys  Ser Leu Lys Glu Lys  Asp Leu Leu
    1400                1405                1410

Ile Lys  Ala Lys Ser Asp Gln  Leu Leu Ser Leu Asn  Glu Asn Phe
    1415                1420                1425

Thr Asn  Lys Val Asn Glu Asn  Glu Leu Leu Arg Gln  Ala Val Thr
    1430                1435                1440

Asn Leu  Lys Glu Arg Val Leu  Ile Leu Glu Met Asp  Ile Gly Lys
    1445                1450                1455

Leu Lys  Glu Glu Asn Glu Lys  Ile Val Glu Arg Thr  Arg Glu Lys
    1460                1465                1470

Glu Thr  Glu Tyr Gln Ala Leu  Gln Glu Thr Asn Met  Lys Phe Ser
    1475                1480                1485

Met Met  Leu Arg Glu Lys Glu  Phe Glu Cys His Ser  Met Lys Glu
    1490                1495                1500

Lys Ser  Leu Ala Phe Glu Gln  Leu Leu Lys Glu Lys  Glu Gln Gly
    1505                1510                1515

Lys Thr  Gly Glu Leu Asn Gln  Leu Leu Asn Ala Val  Lys Ser Met
    1520                1525                1530

Gln Glu  Lys Thr Val Lys Phe  Gln Gln Glu Arg Asp  Gln Val Met
    1535                1540                1545

Leu Ala  Leu Lys Gln Lys Gln  Met Glu Asn Ser Ala  Leu Gln Asn
    1550                1555                1560

Glu Val  Gln His Leu Arg Asp  Lys Glu Leu Arg Leu  Asn Gln Glu
    1565                1570                1575

Leu Glu  Arg Leu Arg Asn His  Leu Leu Glu Ser Glu  Asp Ser Tyr
    1580                1585                1590

Thr Arg  Glu Ala Leu Ala Ala  Glu Glu Arg Glu Ala  Lys Leu Arg
    1595                1600                1605

Arg Lys  Val Thr Val Leu Glu  Glu Lys Leu Val Ser  Ser Ser Asn
    1610                1615                1620

Ala Met  Glu Asn Ala Ser His  Gln Ala Ser Leu Gln  Val Glu Ser
    1625                1630                1635

Leu Gln  Glu Gln Leu Asn Val  Val Ser Lys Gln Arg  Asp Glu Thr
    1640                1645                1650
```

```
Ala Leu  Gln Leu Ser Val Ser  Arg Glu Gln Val Lys  Gln Tyr Ala
    1655                 1660                 1665

Leu Ser  Leu Ser Asn Leu Gln  Met Val Leu Glu His  Phe Gln Gln
    1670                 1675                 1680

Glu Glu  Lys Ala Val Tyr Ser  Ala Glu Leu Glu Lys  His Lys Gln
    1685                 1690                 1695

Leu Val  Ala Glu Trp Lys Lys  Lys Ala Glu Asn Leu  Glu Gly Lys
    1700                 1705                 1710

Leu Met  Ser Leu Gln Glu Arg  Phe Asp Glu Ala Asn  Ala Ala Leu
    1715                 1720                 1725

Asp Ser  Ala Ser Arg Leu Thr  Glu Gln Leu Asp Leu  Lys Glu Glu
    1730                 1735                 1740

Gln Ile  Glu Glu Leu Lys Lys  Gln Asn Glu Leu Arg  Gln Glu Met
    1745                 1750                 1755

Leu Asp  Asp Val Gln Lys Lys  Leu Met Asn Leu Val  Asn Ser Thr
    1760                 1765                 1770

Glu Gly  Lys Val Asp Lys Val  Leu Met Arg Asn Leu  Phe Ile Gly
    1775                 1780                 1785

His Phe  His Thr Pro Lys His  Gln Arg His Glu Val  Leu Arg Leu
    1790                 1795                 1800

Met Gly  Ser Ile Leu Gly Ile  Lys Arg Glu Glu Met  Glu Gln Leu
    1805                 1810                 1815

Leu His  Glu Asp Gln Gly Gly  Val Thr Arg Trp Met  Thr Gly Trp
    1820                 1825                 1830

Leu Gly  Gly Gly Ser Lys Ser  Val Pro Asn Thr Pro  Leu Arg Pro
    1835                 1840                 1845

Asn Gln  Gln Ser Val Leu Asn  Ser Ser Phe Ser Glu  Leu Phe Val
    1850                 1855                 1860

Lys Phe  Leu Glu Thr Glu Ser  His Pro Ser Val Pro  Pro Pro Lys
    1865                 1870                 1875

Leu Ser  Val His Asp Met Lys  Pro Leu Asp Ser Pro  Gly Arg Arg
    1880                 1885                 1890

Lys Val  Val Ile His Val Ser  Glu Ser Phe Lys Glu  Thr Thr Glu
    1895                 1900                 1905

Ser Arg  Cys Gly Arg Arg Thr  Asp Val Asn Pro Phe  Leu Ala Pro
    1910                 1915                 1920

Arg Ser  Ala Ala Val Pro Leu  Ile Asn Pro Ala Gly  Leu Gly Pro
    1925                 1930                 1935

Gly Gly  Pro Gly His Leu Leu  Leu Lys Pro Ile Ser  Asp Val Leu
    1940                 1945                 1950

Pro Thr  Phe Thr Pro Leu Pro  Val Ser Pro Asp Asn  Ser Ala Gly
    1955                 1960                 1965

Val Val  Leu Lys Asp Leu Leu  Lys Gln
    1970                 1975
```

<210> SEQ ID NO 40
<211> LENGTH: 6452
<212> TYPE: DNA
<213> ORGANISM: Homo sapiens
<220> FEATURE:
<221> NAME/KEY: CDS
<222> LOCATION: (357)..(6296)

<400> SEQUENCE: 40

```
cgagcgagtg tcatggcggc cggcgtcgag ttggcaggag taacccacgg aactgaggaa     60
```

```
agtcattaga gctgagaaag aagtggccca atctggacgg tgggaattcg tgggaatgag    120

cagaaggccc tccgtagtga ctgtgtcact agaggcgggc ccctggtaaa attccaggcc    180

aggcctctgc gtttctaggc agaacctgga gtcggccttg cctgagaacc cagctttgtg    240

ttatcgtatc ctgtctcgcg aaggcaggcg ttcaaggata tttggtcgga tcgcccggcg    300

gcgctaaacg ttttcttttt tccgagcgga ccgggtcgtt ctctaaactc gccgcg atg    359
                                                              Met
                                                              1

tcg tcc tgg ctt ggg ggc ctc ggc tcc gga ttg ggc cag tct ctg ggt      407
Ser Ser Trp Leu Gly Gly Leu Gly Ser Gly Leu Gly Gln Ser Leu Gly
            5                   10                  15

caa gtc ggg ggc agc ctg gct tcc ctc act ggc cag ata tca aac ttt      455
Gln Val Gly Gly Ser Leu Ala Ser Leu Thr Gly Gln Ile Ser Asn Phe
        20                  25                  30

aca aag gat atg ctg atg gag ggc acg gag gaa gtg gaa gca gaa tta      503
Thr Lys Asp Met Leu Met Glu Gly Thr Glu Glu Val Glu Ala Glu Leu
    35                  40                  45

cct gat tct agg aca aag gaa att gaa gcc att cat gca atc ttg aga      551
Pro Asp Ser Arg Thr Lys Glu Ile Glu Ala Ile His Ala Ile Leu Arg
50                  55                  60                  65

tca gag aat gaa agg ctt aag aaa ctt tgt act gat cta gaa gag aaa      599
Ser Glu Asn Glu Arg Leu Lys Lys Leu Cys Thr Asp Leu Glu Glu Lys
                70                  75                  80

cat gaa gca tca gag att caa ata aag cag caa tct aca agt tac cga      647
His Glu Ala Ser Glu Ile Gln Ile Lys Gln Gln Ser Thr Ser Tyr Arg
            85                  90                  95

aat caa ctt caa caa aaa gag gta gaa atc agc cat ctt aaa gcc aga      695
Asn Gln Leu Gln Gln Lys Glu Val Glu Ile Ser His Leu Lys Ala Arg
        100                 105                 110

cag att gca ctc cag gat cag ttg ctg aaa ctg cag tca gct gct cag      743
Gln Ile Ala Leu Gln Asp Gln Leu Leu Lys Leu Gln Ser Ala Ala Gln
    115                 120                 125

tca gta cct tca gga gct ggt gta cca gca acc act gca tca tct tca      791
Ser Val Pro Ser Gly Ala Gly Val Pro Ala Thr Thr Ala Ser Ser Ser
130                 135                 140                 145

ttc gct tat ggg att agt cat cat cct tca gct ttc cat gac gat gac      839
Phe Ala Tyr Gly Ile Ser His His Pro Ser Ala Phe His Asp Asp Asp
                150                 155                 160

atg gac ttt ggt gat ata att tca tcc caa caa gaa ata aac cga ctc      887
Met Asp Phe Gly Asp Ile Ile Ser Ser Gln Gln Glu Ile Asn Arg Leu
            165                 170                 175

tca aat gaa gtt tca aga ctt gag tct gaa gtt ggc cat tgg agg cat      935
Ser Asn Glu Val Ser Arg Leu Glu Ser Glu Val Gly His Trp Arg His
        180                 185                 190

att gct cag act tcc aaa gca caa gga aca gat aac tct gat caa agt      983
Ile Ala Gln Thr Ser Lys Ala Gln Gly Thr Asp Asn Ser Asp Gln Ser
    195                 200                 205

gaa ata tgt aaa cta caa aat atc att aag gaa cta aaa cag aac cga     1031
Glu Ile Cys Lys Leu Gln Asn Ile Ile Lys Glu Leu Lys Gln Asn Arg
210                 215                 220                 225

agt cag gaa att gat gac cat caa cat gaa atg tca gta ctg cag aat     1079
Ser Gln Glu Ile Asp Asp His Gln His Glu Met Ser Val Leu Gln Asn
                230                 235                 240

gca cac caa cag aaa ttg aca gaa ata agt cga cga cat cga gaa gaa     1127
Ala His Gln Gln Lys Leu Thr Glu Ile Ser Arg Arg His Arg Glu Glu
            245                 250                 255

tta agt gac tat gaa gaa cga att gaa gaa ctt gaa aat ctg tta caa     1175
Leu Ser Asp Tyr Glu Glu Arg Ile Glu Glu Leu Glu Asn Leu Leu Gln
```

```
        260                 265                 270

caa ggt ggc tct gga gtt ata gaa act gat ctc tct aaa atc tat gag     1223
Gln Gly Gly Ser Gly Val Ile Glu Thr Asp Leu Ser Lys Ile Tyr Glu
    275                 280                 285

atg caa aaa act att caa gtt cta caa ata gaa aaa gtg gag tct acc     1271
Met Gln Lys Thr Ile Gln Val Leu Gln Ile Glu Lys Val Glu Ser Thr
290                 295                 300                 305

aaa aaa atg gaa caa ctt gag gat aaa ata aaa gat ata aat aaa aaa     1319
Lys Lys Met Glu Gln Leu Glu Asp Lys Ile Lys Asp Ile Asn Lys Lys
                310                 315                 320

tta tct tct gca gaa aat gac aga gat att ttg agg agg gaa caa gaa     1367
Leu Ser Ser Ala Glu Asn Asp Arg Asp Ile Leu Arg Arg Glu Gln Glu
            325                 330                 335

cag cta aat gtg gaa aag aga caa ata atg gaa gaa tgt gaa aac ttg     1415
Gln Leu Asn Val Glu Lys Arg Gln Ile Met Glu Glu Cys Glu Asn Leu
        340                 345                 350

aaa ttg gaa tgt agt aaa ttg cag cct tct gct gtg aag caa agt gat     1463
Lys Leu Glu Cys Ser Lys Leu Gln Pro Ser Ala Val Lys Gln Ser Asp
    355                 360                 365

act atg aca gaa aag gaa aga att ctt gcc cag agt gca tca gtg gaa     1511
Thr Met Thr Glu Lys Glu Arg Ile Leu Ala Gln Ser Ala Ser Val Glu
370                 375                 380                 385

gaa gtg ttc aga cta caa caa gca ctg tct gat gcc gaa aat gaa ata     1559
Glu Val Phe Arg Leu Gln Gln Ala Leu Ser Asp Ala Glu Asn Glu Ile
                390                 395                 400

atg aga ttg agt agt tta aac cag gat aac agt ctt gct gaa gac aat     1607
Met Arg Leu Ser Ser Leu Asn Gln Asp Asn Ser Leu Ala Glu Asp Asn
            405                 410                 415

ctg aaa ctt aaa atg cgt atc gaa gtt tta gaa aaa gag aag tca tta     1655
Leu Lys Leu Lys Met Arg Ile Glu Val Leu Glu Lys Glu Lys Ser Leu
        420                 425                 430

ctg agt caa gaa aag gaa gaa ctt cag atg tca ctt tta aaa ttg aac     1703
Leu Ser Gln Glu Lys Glu Glu Leu Gln Met Ser Leu Leu Lys Leu Asn
    435                 440                 445

aat gaa tat gaa gta att aaa agt aca gct aca aga gac ata agt ttg     1751
Asn Glu Tyr Glu Val Ile Lys Ser Thr Ala Thr Arg Asp Ile Ser Leu
450                 455                 460                 465

gat tca gaa tta cat gac tta aga ctt aat ttg gag gca aag gaa caa     1799
Asp Ser Glu Leu His Asp Leu Arg Leu Asn Leu Glu Ala Lys Glu Gln
                470                 475                 480

gaa ctc aat cag agt att agt gaa aag gaa aca ctg ata gct gag ata     1847
Glu Leu Asn Gln Ser Ile Ser Glu Lys Glu Thr Leu Ile Ala Glu Ile
            485                 490                 495

gaa gaa ttg gac aga cag aat caa gaa gct aca aag cac atg att ttg     1895
Glu Glu Leu Asp Arg Gln Asn Gln Glu Ala Thr Lys His Met Ile Leu
        500                 505                 510

ata aaa gat cag cta tca aaa caa caa aat gaa gga gat agc atc atc     1943
Ile Lys Asp Gln Leu Ser Lys Gln Gln Asn Glu Gly Asp Ser Ile Ile
    515                 520                 525

agt aaa ctg aaa caa gat cta aat gat gaa aaa aag aga gtt cat caa     1991
Ser Lys Leu Lys Gln Asp Leu Asn Asp Glu Lys Lys Arg Val His Gln
530                 535                 540                 545

ctt gaa gat gat aaa atg gac att act aaa gag tta gat gta cag aaa     2039
Leu Glu Asp Asp Lys Met Asp Ile Thr Lys Glu Leu Asp Val Gln Lys
                550                 555                 560

gaa aag cta att caa agt gaa gtg gcc cta aat gat tta cat tta acc     2087
Glu Lys Leu Ile Gln Ser Glu Val Ala Leu Asn Asp Leu His Leu Thr
            565                 570                 575

aag cag aaa ctt gag gac aaa gta gaa aat tta gta gat cag cta aat     2135
```

```
Lys Gln Lys Leu Glu Asp Lys Val Glu Asn Leu Val Asp Gln Leu Asn
        580                 585                 590

aaa tca caa gaa agt aat gta agc atc cag aag gag aat tta gaa ctt      2183
Lys Ser Gln Glu Ser Asn Val Ser Ile Gln Lys Glu Asn Leu Glu Leu
    595                 600                 605

aag gag cat att aga caa aat gag gag gag ctt tct aga ata agg aat      2231
Lys Glu His Ile Arg Gln Asn Glu Glu Glu Leu Ser Arg Ile Arg Asn
610                 615                 620                 625

gag tta atg cag tct cta aat caa gac tct aat agt aat ttt aag gat      2279
Glu Leu Met Gln Ser Leu Asn Gln Asp Ser Asn Ser Asn Phe Lys Asp
                630                 635                 640

acc tta ctt aaa gaa aga gaa gct gaa gtt aga aac tta aag caa aat      2327
Thr Leu Leu Lys Glu Arg Glu Ala Glu Val Arg Asn Leu Lys Gln Asn
            645                 650                 655

ctt tca gaa tta gaa cag ctc aat gaa aat tta aag aaa gtt gct ttt      2375
Leu Ser Glu Leu Glu Gln Leu Asn Glu Asn Leu Lys Lys Val Ala Phe
        660                 665                 670

gat gtc aaa atg gaa aat gaa aag tta gtt tta gca tgt gaa gat gtg      2423
Asp Val Lys Met Glu Asn Glu Lys Leu Val Leu Ala Cys Glu Asp Val
    675                 680                 685

agg cat cag tta gaa gaa tgt ctt gct ggt aac aat cag ctt tct ctg      2471
Arg His Gln Leu Glu Glu Cys Leu Ala Gly Asn Asn Gln Leu Ser Leu
690                 695                 700                 705

gaa aaa aac act att gtg gag act cta aaa atg gaa aaa gga gag ata      2519
Glu Lys Asn Thr Ile Val Glu Thr Leu Lys Met Glu Lys Gly Glu Ile
                710                 715                 720

gag gca gaa ttg tgt tgg gct aaa aag agg ctg ttg gaa gaa gca aac      2567
Glu Ala Glu Leu Cys Trp Ala Lys Lys Arg Leu Leu Glu Glu Ala Asn
            725                 730                 735

aag tat gag aaa acc att gaa gaa ctg tca aat gca cgt aat ttg aat      2615
Lys Tyr Glu Lys Thr Ile Glu Glu Leu Ser Asn Ala Arg Asn Leu Asn
        740                 745                 750

acc tct gcc tta cag ctg gaa cat gag cat tta att aaa ctc aat caa      2663
Thr Ser Ala Leu Gln Leu Glu His Glu His Leu Ile Lys Leu Asn Gln
    755                 760                 765

aag aaa gac atg gaa ata gca gaa ctc aaa aag aat att gaa caa atg      2711
Lys Lys Asp Met Glu Ile Ala Glu Leu Lys Lys Asn Ile Glu Gln Met
770                 775                 780                 785

gat act gac cat aaa gaa act aag gac gtt ttg tca tct agt tta gaa      2759
Asp Thr Asp His Lys Glu Thr Lys Asp Val Leu Ser Ser Ser Leu Glu
                790                 795                 800

gag cag aag cag ttg aca caa ctt ata aac aag aaa gaa att ttt att      2807
Glu Gln Lys Gln Leu Thr Gln Leu Ile Asn Lys Lys Glu Ile Phe Ile
            805                 810                 815

gaa aag ctt aaa gaa aga agt tca aag ctg cag gag gaa ttg gat aaa      2855
Glu Lys Leu Lys Glu Arg Ser Ser Lys Leu Gln Glu Glu Leu Asp Lys
        820                 825                 830

tat tct cag gcc tta aga aaa aat gaa att tta aga cag acc ata gag      2903
Tyr Ser Gln Ala Leu Arg Lys Asn Glu Ile Leu Arg Gln Thr Ile Glu
    835                 840                 845

gaa aaa gac cga agt ctt gga tcc atg aaa gag gaa aat aat cat ctg      2951
Glu Lys Asp Arg Ser Leu Gly Ser Met Lys Glu Glu Asn Asn His Leu
850                 855                 860                 865

caa gaa gaa ttg gaa cga ctc agg gaa gag cag agt cga acc gca cct      2999
Gln Glu Glu Leu Glu Arg Leu Arg Glu Glu Gln Ser Arg Thr Ala Pro
                870                 875                 880

gtg gct gac cct aaa acc ctt gat agt gtt act gaa cta gca tct gag      3047
Val Ala Asp Pro Lys Thr Leu Asp Ser Val Thr Glu Leu Ala Ser Glu
            885                 890                 895
```

```
gta tct caa ctg aac acg atc aag gaa cat ctt gaa gag gaa att aaa     3095
Val Ser Gln Leu Asn Thr Ile Lys Glu His Leu Glu Glu Glu Ile Lys
        900                 905                 910

cat cat caa aag ata att gaa gat caa aac cag agt aag atg caa cta     3143
His His Gln Lys Ile Ile Glu Asp Gln Asn Gln Ser Lys Met Gln Leu
    915                 920                 925

ctt cag tct tta caa gag caa aag aag gaa atg gat gag ttt aga tac     3191
Leu Gln Ser Leu Gln Glu Gln Lys Lys Glu Met Asp Glu Phe Arg Tyr
930                 935                 940                 945

cag cat gag caa atg aac gcc aca cac acc cag ctc ttt tta gag aag     3239
Gln His Glu Gln Met Asn Ala Thr His Thr Gln Leu Phe Leu Glu Lys
                950                 955                 960

gat gag gaa att aag agt ttg caa aaa aca att gaa caa atc aaa acc     3287
Asp Glu Glu Ile Lys Ser Leu Gln Lys Thr Ile Glu Gln Ile Lys Thr
            965                 970                 975

cag ttg cat gaa gaa aga cag gac att caa aca gat aac tct gat att     3335
Gln Leu His Glu Glu Arg Gln Asp Ile Gln Thr Asp Asn Ser Asp Ile
        980                 985                 990

ttt caa gaa aca aaa gtt cag  agc ctt aat ata gaa  aat gga agt gaa   3383
Phe Gln Glu Thr Lys Val Gln  Ser Leu Asn Ile Glu  Asn Gly Ser Glu
    995                 1000                1005

aag  cat gat tta tct aaa  gct gaa acg gaa aga  tta gtg aaa gga     3428
Lys  His Asp Leu Ser Lys  Ala Glu Thr Glu Arg  Leu Val Lys Gly
1010                 1015                 1020

ata  aaa gag cga gaa ctg  gag att aaa ctt cta  aat gaa aag aat     3473
Ile  Lys Glu Arg Glu Leu  Glu Ile Lys Leu Leu  Asn Glu Lys Asn
1025                 1030                 1035

ata  tct tta act aaa cag  att gat cag ttg tcc  aaa gat gaa gtt     3518
Ile  Ser Leu Thr Lys Gln  Ile Asp Gln Leu Ser  Lys Asp Glu Val
1040                 1045                 1050

ggt  aaa cta act cag att  att cag cag aaa gat  ttg gag ata caa     3563
Gly  Lys Leu Thr Gln Ile  Ile Gln Gln Lys Asp  Leu Glu Ile Gln
1055                 1060                 1065

gct  ctt cat gct aga att  tct tca act tcc cat  act caa gat gtt     3608
Ala  Leu His Ala Arg Ile  Ser Ser Thr Ser His  Thr Gln Asp Val
1070                 1075                 1080

gtt  tac ctt caa cag caa  ctg cag gct tat gct  atg gaa aga gaa     3653
Val  Tyr Leu Gln Gln Gln  Leu Gln Ala Tyr Ala  Met Glu Arg Glu
1085                 1090                 1095

aag  gta ttt gct gtt ttg  aat gag aag act agg  gaa aat agc cat     3698
Lys  Val Phe Ala Val Leu  Asn Glu Lys Thr Arg  Glu Asn Ser His
1100                 1105                 1110

cta  aaa aca gaa tat cac  aaa atg atg gat att  gtt gct gcc aag     3743
Leu  Lys Thr Glu Tyr His  Lys Met Met Asp Ile  Val Ala Ala Lys
1115                 1120                 1125

gaa  gca gct ctt atc aaa  ctg caa gat gaa aat  aaa aaa ttg tcc     3788
Glu  Ala Ala Leu Ile Lys  Leu Gln Asp Glu Asn  Lys Lys Leu Ser
1130                 1135                 1140

act  aga ttt gaa agt agt  ggc caa gat atg ttt  aga gaa act att     3833
Thr  Arg Phe Glu Ser Ser  Gly Gln Asp Met Phe  Arg Glu Thr Ile
1145                 1150                 1155

cag  aat tta tca cgt atc  att cga gaa aaa gac  atc gaa ata gat     3878
Gln  Asn Leu Ser Arg Ile  Ile Arg Glu Lys Asp  Ile Glu Ile Asp
1160                 1165                 1170

gca  cta agt cag aaa tgt  cag act tta ttg gca  gtt tta caa aca     3923
Ala  Leu Ser Gln Lys Cys  Gln Thr Leu Leu Ala  Val Leu Gln Thr
1175                 1180                 1185

tcc  agc act ggt aat gag  gct gga ggt gtt aat  agt cat caa ttt     3968
Ser  Ser Thr Gly Asn Glu  Ala Gly Gly Val Asn  Ser His Gln Phe
1190                 1195                 1200
```

```
gag  gag ctt cta cag gaa  cgt gac aag tta aaa  cag caa gta aag      4013
Glu  Glu Leu Leu Gln Glu  Arg Asp Lys Leu Lys  Gln Gln Val Lys
1205                 1210                 1215

aaa  atg gaa gag tgg aag  cag cag gtg atg acc  aca gta caa aat      4058
Lys  Met Glu Glu Trp Lys  Gln Gln Val Met Thr  Thr Val Gln Asn
1220                 1225                 1230

atg  caa cac gag tca gcc  cag ctt cag gaa gag  ctt cac caa ctt      4103
Met  Gln His Glu Ser Ala  Gln Leu Gln Glu Glu  Leu His Gln Leu
1235                 1240                 1245

caa  gca cag gtt ttg gtt  gac agt gat aat aat  tct aaa tta caa      4148
Gln  Ala Gln Val Leu Val  Asp Ser Asp Asn Asn  Ser Lys Leu Gln
1250                 1255                 1260

gtg  gac tat act ggc ctg  atc caa agt tat gag  cag aat gaa acc      4193
Val  Asp Tyr Thr Gly Leu  Ile Gln Ser Tyr Glu  Gln Asn Glu Thr
1265                 1270                 1275

aaa  ctc aaa aat ttt ggg  cag gaa tta gca caa  gtt cag cac agc      4238
Lys  Leu Lys Asn Phe Gly  Gln Glu Leu Ala Gln  Val Gln His Ser
1280                 1285                 1290

att  ggg cag ctt tgc aat  acc aag gat ctt ctt  tta gga aaa ctt      4283
Ile  Gly Gln Leu Cys Asn  Thr Lys Asp Leu Leu  Leu Gly Lys Leu
1295                 1300                 1305

gat  att att tca ccc cag  ctg tct tct gca tca  ttg ctt act ccc      4328
Asp  Ile Ile Ser Pro Gln  Leu Ser Ser Ala Ser  Leu Leu Thr Pro
1310                 1315                 1320

cag  tct gca gag tgt ctt  aga gca agt aag tct  gaa gta ttg agt      4373
Gln  Ser Ala Glu Cys Leu  Arg Ala Ser Lys Ser  Glu Val Leu Ser
1325                 1330                 1335

gaa  tct tct gaa ttg ctt  cag caa gag tta gaa  gag cta aga aaa      4418
Glu  Ser Ser Glu Leu Leu  Gln Gln Glu Leu Glu  Glu Leu Arg Lys
1340                 1345                 1350

tca  cta cag gaa aaa gat  gca aca att aga act  ctc cag gaa aat      4463
Ser  Leu Gln Glu Lys Asp  Ala Thr Ile Arg Thr  Leu Gln Glu Asn
1355                 1360                 1365

aac  cac aga ttg tct gat  tcg att gct gcc acc  tca gag cta gaa      4508
Asn  His Arg Leu Ser Asp  Ser Ile Ala Ala Thr  Ser Glu Leu Glu
1370                 1375                 1380

aga  aaa gaa cac gaa caa  acc gat tca gaa atc  aag cag cta aag      4553
Arg  Lys Glu His Glu Gln  Thr Asp Ser Glu Ile  Lys Gln Leu Lys
1385                 1390                 1395

gag  aaa caa gat gtt ttg  caa aag tta ctt aag  gaa aaa gac ctc      4598
Glu  Lys Gln Asp Val Leu  Gln Lys Leu Leu Lys  Glu Lys Asp Leu
1400                 1405                 1410

tta  atc aaa gcc aaa agt  gat caa cta ctt tct  tcc aat gaa aat      4643
Leu  Ile Lys Ala Lys Ser  Asp Gln Leu Leu Ser  Ser Asn Glu Asn
1415                 1420                 1425

ttc  act aac aaa gta aat  gaa aac gaa ctt ttg  agg cag gca gta      4688
Phe  Thr Asn Lys Val Asn  Glu Asn Glu Leu Leu  Arg Gln Ala Val
1430                 1435                 1440

aca  aac ctg aag gag aga  ata tta att cta gag  atg gac att ggc      4733
Thr  Asn Leu Lys Glu Arg  Ile Leu Ile Leu Glu  Met Asp Ile Gly
1445                 1450                 1455

aaa  cta aaa gga gaa aat  gaa aaa ata gtg gaa  aca tac agg gga      4778
Lys  Leu Lys Gly Glu Asn  Glu Lys Ile Val Glu  Thr Tyr Arg Gly
1460                 1465                 1470

aag  gaa aca gaa tat caa  gcg tta caa gag act  aac atg aag ttt      4823
Lys  Glu Thr Glu Tyr Gln  Ala Leu Gln Glu Thr  Asn Met Lys Phe
1475                 1480                 1485

tct  atg atg ctg cga gaa  aaa gag ttt gag tgc  cac tca atg aag      4868
Ser  Met Met Leu Arg Glu  Lys Glu Phe Glu Cys  His Ser Met Lys
```

-continued

```
1490                1495                1500

gag  aag gct ctt gct ttt  gaa cag cta ttg aaa  gag aaa gaa cag      4913
Glu  Lys Ala Leu Ala Phe  Glu Gln Leu Leu Lys  Glu Lys Glu Gln
1505                1510                1515

ggc  aag act gga gag tta  aat cag ctt tta aat  gca gtt aaa tca      4958
Gly  Lys Thr Gly Glu Leu  Asn Gln Leu Leu Asn  Ala Val Lys Ser
1520                1525                1530

atg  cag gag aag aca gtt  gtg ttt caa cag gag  aga gac caa gtc      5003
Met  Gln Glu Lys Thr Val  Val Phe Gln Gln Glu  Arg Asp Gln Val
1535                1540                1545

atg  ttg gcc ctg aaa caa  aaa caa atg gaa aat  act gcc cta cag      5048
Met  Leu Ala Leu Lys Gln  Lys Gln Met Glu Asn  Thr Ala Leu Gln
1550                1555                1560

aat  gag gtt caa cgt tta  cgt gac aaa gaa ttt  cgt tca aac caa      5093
Asn  Glu Val Gln Arg Leu  Arg Asp Lys Glu Phe  Arg Ser Asn Gln
1565                1570                1575

gag  cta gag aga ttg cgt  aat cat ctt tta gaa  tca gaa gat tct      5138
Glu  Leu Glu Arg Leu Arg  Asn His Leu Leu Glu  Ser Glu Asp Ser
1580                1585                1590

tat  acc cgt gaa gct ttg  gct gca gaa gat aga  gag gct aaa cta      5183
Tyr  Thr Arg Glu Ala Leu  Ala Ala Glu Asp Arg  Glu Ala Lys Leu
1595                1600                1605

aga  aag aaa gtc aca gta  ttg gag gaa aag cta  gtt tca tcc tct      5228
Arg  Lys Lys Val Thr Val  Leu Glu Glu Lys Leu  Val Ser Ser Ser
1610                1615                1620

aat  gca atg gaa aat gca  agc cat caa gcc agt  gtg cag gta gag      5273
Asn  Ala Met Glu Asn Ala  Ser His Gln Ala Ser  Val Gln Val Glu
1625                1630                1635

tca  ttg caa gaa cag ttg  aat gta gtt tcc aag  caa agg gat gaa      5318
Ser  Leu Gln Glu Gln Leu  Asn Val Val Ser Lys  Gln Arg Asp Glu
1640                1645                1650

act  gcg ctg cag ctt tct  gtc tct cag gaa caa  gta aag cag tat      5363
Thr  Ala Leu Gln Leu Ser  Val Ser Gln Glu Gln  Val Lys Gln Tyr
1655                1660                1665

gct  ctg tca ctg gcc aac  ctg cag atg gta cta  gag cat ttc caa      5408
Ala  Leu Ser Leu Ala Asn  Leu Gln Met Val Leu  Glu His Phe Gln
1670                1675                1680

caa  gag gaa aaa gct atg  tat tct gct gaa ctc  gaa aag caa aaa      5453
Gln  Glu Glu Lys Ala Met  Tyr Ser Ala Glu Leu  Glu Lys Gln Lys
1685                1690                1695

cag  ctt ata gct gaa tgg  aag aaa aac gca gaa  aat ctg gaa gga      5498
Gln  Leu Ile Ala Glu Trp  Lys Lys Asn Ala Glu  Asn Leu Glu Gly
1700                1705                1710

aaa  gtg ata tca tta cag  gaa tgt ttg gat gaa  gca aat gct gca      5543
Lys  Val Ile Ser Leu Gln  Glu Cys Leu Asp Glu  Ala Asn Ala Ala
1715                1720                1725

ttg  gat tca gca tca aga  ctt aca gaa cag tta  gat gta aaa gaa      5588
Leu  Asp Ser Ala Ser Arg  Leu Thr Glu Gln Leu  Asp Val Lys Glu
1730                1735                1740

gaa  caa att gaa gaa ctt  aaa aga caa aat gag  ctc cga caa gaa      5633
Glu  Gln Ile Glu Glu Leu  Lys Arg Gln Asn Glu  Leu Arg Gln Glu
1745                1750                1755

atg  ctg gat gat gta caa  aag aaa ttg atg agc  tta gca aac agc      5678
Met  Leu Asp Asp Val Gln  Lys Lys Leu Met Ser  Leu Ala Asn Ser
1760                1765                1770

tca  gaa gga aaa gta gac  aaa gtc cta atg aga  aac ctc ttc att      5723
Ser  Glu Gly Lys Val Asp  Lys Val Leu Met Arg  Asn Leu Phe Ile
1775                1780                1785

ggt  cat ttc cac aca ccg  aaa aat cag cgt cat  gaa gtg tta cgg      5768
```

-continued

```
Gly  His Phe His Thr Pro  Lys Asn Gln Arg His  Glu Val Leu Arg
1790                1795                1800

tta  atg ggg agc atc ctg  ggc gtc aga agg gag  gag atg gag cag      5813
Leu  Met Gly Ser Ile Leu  Gly Val Arg Arg Glu  Glu Met Glu Gln
1805                1810                1815

ttg  ttt cat gac gat cag  ggc agt gtt acc agg  tgg atg act ggg      5858
Leu  Phe His Asp Asp Gln  Gly Ser Val Thr Arg  Trp Met Thr Gly
1820                1825                1830

tgg  ctt gga gga gga tca  aaa agt gtt ccc aac  aca cct ttg aga      5903
Trp  Leu Gly Gly Gly Ser  Lys Ser Val Pro Asn  Thr Pro Leu Arg
1835                1840                1845

cca  aat cag caa tct gtg  gtt aat agt tct ttt  tca gaa ctt ttt      5948
Pro  Asn Gln Gln Ser Val  Val Asn Ser Ser Phe  Ser Glu Leu Phe
1850                1855                1860

gtt  aaa ttt cta gaa aca  gaa tct cat cca tcc  att cca cca cca      5993
Val  Lys Phe Leu Glu Thr  Glu Ser His Pro Ser  Ile Pro Pro Pro
1865                1870                1875

aag  ctt tct gtt cat gat  atg aaa cct ctg gat  tca cca gga aga      6038
Lys  Leu Ser Val His Asp  Met Lys Pro Leu Asp  Ser Pro Gly Arg
1880                1885                1890

aga  aaa aga gat aca aat  gca cca gaa agt ttt  aaa gat aca gca      6083
Arg  Lys Arg Asp Thr Asn  Ala Pro Glu Ser Phe  Lys Asp Thr Ala
1895                1900                1905

gaa  tcc agg tct ggt aga  aga aca gat gta aat  ccg ttt ttg gct      6128
Glu  Ser Arg Ser Gly Arg  Arg Thr Asp Val Asn  Pro Phe Leu Ala
1910                1915                1920

cct  cgc tcg gca gct gta  cct ctt att aac cca  gct gga ctt gga      6173
Pro  Arg Ser Ala Ala Val  Pro Leu Ile Asn Pro  Ala Gly Leu Gly
1925                1930                1935

cct  ggt ggg ccc ggg cat  ctt ctt ctg aaa ccc  atc tca gat gtt      6218
Pro  Gly Gly Pro Gly His  Leu Leu Leu Lys Pro  Ile Ser Asp Val
1940                1945                1950

ttg  ccc aca ttt aca cct  ttg cca gcg tta cct  gac aac agt gct      6263
Leu  Pro Thr Phe Thr Pro  Leu Pro Ala Leu Pro  Asp Asn Ser Ala
1955                1960                1965

ggg  gtt gtg ctg aaa gac  ctt tta aag caa tag atgattctca            6306
Gly  Val Val Leu Lys Asp  Leu Leu Lys Gln
1970                1975

agccagagac aatctagcac tttaaagaaa ccatgaacac tatatgtatg tactttatca   6366

caaagtggcc tttggggaga aagtcatgta tttgttcgca attatgcttt ctctgaattt   6426

aataaaaata ttcctaatgc ttttag                                        6452


<210> SEQ ID NO 41
<211> LENGTH: 1979
<212> TYPE: PRT
<213> ORGANISM: Homo sapiens

<400> SEQUENCE: 41

Met Ser Ser Trp Leu Gly Gly Leu Gly Ser Gly Leu Gly Gln Ser Leu
1               5                   10                  15

Gly Gln Val Gly Gly Ser Leu Ala Ser Leu Thr Gly Gln Ile Ser Asn
            20                  25                  30

Phe Thr Lys Asp Met Leu Met Glu Gly Thr Glu Glu Val Glu Ala Glu
        35                  40                  45

Leu Pro Asp Ser Arg Thr Lys Glu Ile Glu Ala Ile His Ala Ile Leu
    50                  55                  60

Arg Ser Glu Asn Glu Arg Leu Lys Lys Leu Cys Thr Asp Leu Glu Glu
65                  70                  75                  80
```

```
Lys His Glu Ala Ser Glu Ile Gln Ile Lys Gln Gln Ser Thr Ser Tyr
                85                  90                  95

Arg Asn Gln Leu Gln Gln Lys Glu Val Glu Ile Ser His Leu Lys Ala
            100                 105                 110

Arg Gln Ile Ala Leu Gln Asp Gln Leu Leu Lys Leu Gln Ser Ala Ala
        115                 120                 125

Gln Ser Val Pro Ser Gly Ala Gly Val Pro Ala Thr Thr Ala Ser Ser
    130                 135                 140

Ser Phe Ala Tyr Gly Ile Ser His His Pro Ser Ala Phe His Asp Asp
145                 150                 155                 160

Asp Met Asp Phe Gly Asp Ile Ile Ser Ser Gln Gln Glu Ile Asn Arg
                165                 170                 175

Leu Ser Asn Glu Val Ser Arg Leu Glu Ser Glu Val Gly His Trp Arg
            180                 185                 190

His Ile Ala Gln Thr Ser Lys Ala Gln Gly Thr Asp Asn Ser Asp Gln
        195                 200                 205

Ser Glu Ile Cys Lys Leu Gln Asn Ile Ile Lys Glu Leu Lys Gln Asn
    210                 215                 220

Arg Ser Gln Glu Ile Asp Asp His Gln His Glu Met Ser Val Leu Gln
225                 230                 235                 240

Asn Ala His Gln Gln Lys Leu Thr Glu Ile Ser Arg Arg His Arg Glu
                245                 250                 255

Glu Leu Ser Asp Tyr Glu Glu Arg Ile Glu Glu Leu Glu Asn Leu Leu
            260                 265                 270

Gln Gln Gly Gly Ser Gly Val Ile Glu Thr Asp Leu Ser Lys Ile Tyr
        275                 280                 285

Glu Met Gln Lys Thr Ile Gln Val Leu Gln Ile Glu Lys Val Glu Ser
    290                 295                 300

Thr Lys Lys Met Glu Gln Leu Glu Asp Lys Ile Lys Asp Ile Asn Lys
305                 310                 315                 320

Lys Leu Ser Ser Ala Glu Asn Asp Arg Asp Ile Leu Arg Arg Glu Gln
                325                 330                 335

Glu Gln Leu Asn Val Glu Lys Arg Gln Ile Met Glu Glu Cys Glu Asn
            340                 345                 350

Leu Lys Leu Glu Cys Ser Lys Leu Gln Pro Ser Ala Val Lys Gln Ser
        355                 360                 365

Asp Thr Met Thr Glu Lys Glu Arg Ile Leu Ala Gln Ser Ala Ser Val
    370                 375                 380

Glu Glu Val Phe Arg Leu Gln Gln Ala Leu Ser Asp Ala Glu Asn Glu
385                 390                 395                 400

Ile Met Arg Leu Ser Ser Leu Asn Gln Asp Asn Ser Leu Ala Glu Asp
                405                 410                 415

Asn Leu Lys Leu Lys Met Arg Ile Glu Val Leu Glu Lys Glu Lys Ser
            420                 425                 430

Leu Leu Ser Gln Glu Lys Glu Glu Leu Gln Met Ser Leu Leu Lys Leu
        435                 440                 445

Asn Asn Glu Tyr Glu Val Ile Lys Ser Thr Ala Thr Arg Asp Ile Ser
    450                 455                 460

Leu Asp Ser Glu Leu His Asp Leu Arg Leu Asn Leu Glu Ala Lys Glu
465                 470                 475                 480

Gln Glu Leu Asn Gln Ser Ile Ser Glu Lys Glu Thr Leu Ile Ala Glu
                485                 490                 495
```

-continued

```
Ile Glu Glu Leu Asp Arg Gln Asn Gln Glu Ala Thr Lys His Met Ile
            500                 505                 510

Leu Ile Lys Asp Gln Leu Ser Lys Gln Gln Asn Glu Gly Asp Ser Ile
        515                 520                 525

Ile Ser Lys Leu Lys Gln Asp Leu Asn Asp Glu Lys Lys Arg Val His
    530                 535                 540

Gln Leu Glu Asp Asp Lys Met Asp Ile Thr Lys Glu Leu Asp Val Gln
545                 550                 555                 560

Lys Glu Lys Leu Ile Gln Ser Glu Val Ala Leu Asn Asp Leu His Leu
                565                 570                 575

Thr Lys Gln Lys Leu Glu Asp Lys Val Glu Asn Leu Val Asp Gln Leu
            580                 585                 590

Asn Lys Ser Gln Glu Ser Asn Val Ser Ile Gln Lys Glu Asn Leu Glu
        595                 600                 605

Leu Lys Glu His Ile Arg Gln Asn Glu Glu Glu Leu Ser Arg Ile Arg
    610                 615                 620

Asn Glu Leu Met Gln Ser Leu Asn Gln Asp Ser Asn Ser Asn Phe Lys
625                 630                 635                 640

Asp Thr Leu Leu Lys Glu Arg Glu Ala Glu Val Arg Asn Leu Lys Gln
                645                 650                 655

Asn Leu Ser Glu Leu Glu Gln Leu Asn Glu Asn Leu Lys Lys Val Ala
            660                 665                 670

Phe Asp Val Lys Met Glu Asn Glu Lys Leu Val Leu Ala Cys Glu Asp
        675                 680                 685

Val Arg His Gln Leu Glu Glu Cys Leu Ala Gly Asn Asn Gln Leu Ser
    690                 695                 700

Leu Glu Lys Asn Thr Ile Val Glu Thr Leu Lys Met Glu Lys Gly Glu
705                 710                 715                 720

Ile Glu Ala Glu Leu Cys Trp Ala Lys Lys Arg Leu Leu Glu Glu Ala
                725                 730                 735

Asn Lys Tyr Glu Lys Thr Ile Glu Glu Leu Ser Asn Ala Arg Asn Leu
            740                 745                 750

Asn Thr Ser Ala Leu Gln Leu Glu His Glu His Leu Ile Lys Leu Asn
        755                 760                 765

Gln Lys Lys Asp Met Glu Ile Ala Glu Leu Lys Lys Asn Ile Glu Gln
    770                 775                 780

Met Asp Thr Asp His Lys Glu Thr Lys Asp Val Leu Ser Ser Ser Leu
785                 790                 795                 800

Glu Glu Gln Lys Gln Leu Thr Gln Leu Ile Asn Lys Lys Glu Ile Phe
                805                 810                 815

Ile Glu Lys Leu Lys Glu Arg Ser Ser Lys Leu Gln Glu Glu Leu Asp
            820                 825                 830

Lys Tyr Ser Gln Ala Leu Arg Lys Asn Glu Ile Leu Arg Gln Thr Ile
        835                 840                 845

Glu Glu Lys Asp Arg Ser Leu Gly Ser Met Lys Glu Glu Asn Asn His
    850                 855                 860

Leu Gln Glu Glu Leu Glu Arg Leu Arg Glu Glu Gln Ser Arg Thr Ala
865                 870                 875                 880

Pro Val Ala Asp Pro Lys Thr Leu Asp Ser Val Thr Glu Leu Ala Ser
                885                 890                 895

Glu Val Ser Gln Leu Asn Thr Ile Lys Glu His Leu Glu Glu Glu Ile
            900                 905                 910

Lys His His Gln Lys Ile Ile Glu Asp Gln Asn Gln Ser Lys Met Gln
```

-continued

```
        915                 920                 925

Leu Leu Gln Ser Leu Gln Glu Gln Lys Lys Glu Met Asp Glu Phe Arg
    930                 935                 940

Tyr Gln His Glu Gln Met Asn Ala Thr His Thr Gln Leu Phe Leu Glu
945                 950                 955                 960

Lys Asp Glu Glu Ile Lys Ser Leu Gln Lys Thr Ile Glu Gln Ile Lys
                965                 970                 975

Thr Gln Leu His Glu Glu Arg Gln Asp Ile Gln Thr Asp Asn Ser Asp
            980                 985                 990

Ile Phe Gln Glu Thr Lys Val Gln  Ser Leu Asn Ile Glu  Asn Gly Ser
        995                 1000                 1005

Glu Lys  His Asp Leu Ser Lys  Ala Glu Thr Glu Arg  Leu Val Lys
    1010                 1015                 1020

Gly Ile  Lys Glu Arg Glu Leu  Glu Ile Lys Leu Leu  Asn Glu Lys
    1025                 1030                 1035

Asn Ile  Ser Leu Thr Lys Gln  Ile Asp Gln Leu Ser  Lys Asp Glu
    1040                 1045                 1050

Val Gly  Lys Leu Thr Gln Ile  Ile Gln Gln Lys Asp  Leu Glu Ile
    1055                 1060                 1065

Gln Ala  Leu His Ala Arg Ile  Ser Ser Thr Ser His  Thr Gln Asp
    1070                 1075                 1080

Val Val  Tyr Leu Gln Gln Gln  Leu Gln Ala Tyr Ala  Met Glu Arg
    1085                 1090                 1095

Glu Lys  Val Phe Ala Val Leu  Asn Glu Lys Thr Arg  Glu Asn Ser
    1100                 1105                 1110

His Leu  Lys Thr Glu Tyr His  Lys Met Met Asp Ile  Val Ala Ala
    1115                 1120                 1125

Lys Glu  Ala Ala Leu Ile Lys  Leu Gln Asp Glu Asn  Lys Lys Leu
    1130                 1135                 1140

Ser Thr  Arg Phe Glu Ser Ser  Gly Gln Asp Met Phe  Arg Glu Thr
    1145                 1150                 1155

Ile Gln  Asn Leu Ser Arg Ile  Ile Arg Glu Lys Asp  Ile Glu Ile
    1160                 1165                 1170

Asp Ala  Leu Ser Gln Lys Cys  Gln Thr Leu Leu Ala  Val Leu Gln
    1175                 1180                 1185

Thr Ser  Ser Thr Gly Asn Glu  Ala Gly Gly Val Asn  Ser His Gln
    1190                 1195                 1200

Phe Glu  Glu Leu Leu Gln Glu  Arg Asp Lys Leu Lys  Gln Gln Val
    1205                 1210                 1215

Lys Lys  Met Glu Glu Trp Lys  Gln Gln Val Met Thr  Thr Val Gln
    1220                 1225                 1230

Asn Met  Gln His Glu Ser Ala  Gln Leu Gln Glu Glu  Leu His Gln
    1235                 1240                 1245

Leu Gln  Ala Gln Val Leu Val  Asp Ser Asp Asn Asn  Ser Lys Leu
    1250                 1255                 1260

Gln Val  Asp Tyr Thr Gly Leu  Ile Gln Ser Tyr Glu  Gln Asn Glu
    1265                 1270                 1275

Thr Lys  Leu Lys Asn Phe Gly  Gln Glu Leu Ala Gln  Val Gln His
    1280                 1285                 1290

Ser Ile  Gly Gln Leu Cys Asn  Thr Lys Asp Leu Leu  Leu Gly Lys
    1295                 1300                 1305

Leu Asp  Ile Ile Ser Pro Gln  Leu Ser Ser Ala Ser  Leu Leu Thr
    1310                 1315                 1320
```

```
Pro Gln Ser Ala Glu Cys Leu Arg Ala Ser Lys Ser Glu Val Leu
    1325                1330                1335

Ser Glu Ser Ser Glu Leu Leu Gln Gln Glu Leu Glu Glu Leu Arg
    1340                1345                1350

Lys Ser Leu Gln Glu Lys Asp Ala Thr Ile Arg Thr Leu Gln Glu
    1355                1360                1365

Asn Asn His Arg Leu Ser Asp Ser Ile Ala Ala Thr Ser Glu Leu
    1370                1375                1380

Glu Arg Lys Glu His Glu Gln Thr Asp Ser Glu Ile Lys Gln Leu
    1385                1390                1395

Lys Glu Lys Gln Asp Val Leu Gln Lys Leu Leu Lys Glu Lys Asp
    1400                1405                1410

Leu Leu Ile Lys Ala Lys Ser Asp Gln Leu Leu Ser Ser Asn Glu
    1415                1420                1425

Asn Phe Thr Asn Lys Val Asn Glu Asn Glu Leu Leu Arg Gln Ala
    1430                1435                1440

Val Thr Asn Leu Lys Glu Arg Ile Leu Ile Leu Glu Met Asp Ile
    1445                1450                1455

Gly Lys Leu Lys Gly Glu Asn Glu Lys Ile Val Glu Thr Tyr Arg
    1460                1465                1470

Gly Lys Glu Thr Glu Tyr Gln Ala Leu Gln Glu Thr Asn Met Lys
    1475                1480                1485

Phe Ser Met Met Leu Arg Glu Lys Glu Phe Glu Cys His Ser Met
    1490                1495                1500

Lys Glu Lys Ala Leu Ala Phe Glu Gln Leu Leu Lys Glu Lys Glu
    1505                1510                1515

Gln Gly Lys Thr Gly Glu Leu Asn Gln Leu Leu Asn Ala Val Lys
    1520                1525                1530

Ser Met Gln Glu Lys Thr Val Val Phe Gln Gln Glu Arg Asp Gln
    1535                1540                1545

Val Met Leu Ala Leu Lys Gln Lys Gln Met Glu Asn Thr Ala Leu
    1550                1555                1560

Gln Asn Glu Val Gln Arg Leu Arg Asp Lys Glu Phe Arg Ser Asn
    1565                1570                1575

Gln Glu Leu Glu Arg Leu Arg Asn His Leu Leu Glu Ser Glu Asp
    1580                1585                1590

Ser Tyr Thr Arg Glu Ala Leu Ala Ala Glu Asp Arg Glu Ala Lys
    1595                1600                1605

Leu Arg Lys Lys Val Thr Val Leu Glu Glu Lys Leu Val Ser Ser
    1610                1615                1620

Ser Asn Ala Met Glu Asn Ala Ser His Gln Ala Ser Val Gln Val
    1625                1630                1635

Glu Ser Leu Gln Glu Gln Leu Asn Val Val Ser Lys Gln Arg Asp
    1640                1645                1650

Glu Thr Ala Leu Gln Leu Ser Val Ser Gln Glu Gln Val Lys Gln
    1655                1660                1665

Tyr Ala Leu Ser Leu Ala Asn Leu Gln Met Val Leu Glu His Phe
    1670                1675                1680

Gln Gln Glu Glu Lys Ala Met Tyr Ser Ala Glu Leu Glu Lys Gln
    1685                1690                1695

Lys Gln Leu Ile Ala Glu Trp Lys Lys Asn Ala Glu Asn Leu Glu
    1700                1705                1710
```

```
Gly Lys  Val Ile Ser Leu Gln  Glu Cys Leu Asp Glu  Ala Asn Ala
    1715                 1720                 1725

Ala Leu  Asp Ser Ala Ser Arg  Leu Thr Glu Gln Leu  Asp Val Lys
    1730                 1735                 1740

Glu Glu  Gln Ile Glu Glu Leu  Lys Arg Gln Asn Glu  Leu Arg Gln
    1745                 1750                 1755

Glu Met  Leu Asp Asp Val Gln  Lys Lys Leu Met Ser  Leu Ala Asn
    1760                 1765                 1770

Ser Ser  Glu Gly Lys Val Asp  Lys Val Leu Met Arg  Asn Leu Phe
    1775                 1780                 1785

Ile Gly  His Phe His Thr Pro  Lys Asn Gln Arg His  Glu Val Leu
    1790                 1795                 1800

Arg Leu  Met Gly Ser Ile Leu  Gly Val Arg Arg Glu  Glu Met Glu
    1805                 1810                 1815

Gln Leu  Phe His Asp Asp Gln  Gly Ser Val Thr Arg  Trp Met Thr
    1820                 1825                 1830

Gly Trp  Leu Gly Gly Gly Ser  Lys Ser Val Pro Asn  Thr Pro Leu
    1835                 1840                 1845

Arg Pro  Asn Gln Gln Ser Val  Val Asn Ser Ser Phe  Ser Glu Leu
    1850                 1855                 1860

Phe Val  Lys Phe Leu Glu Thr  Glu Ser His Pro Ser  Ile Pro Pro
    1865                 1870                 1875

Pro Lys  Leu Ser Val His Asp  Met Lys Pro Leu Asp  Ser Pro Gly
    1880                 1885                 1890

Arg Arg  Lys Arg Asp Thr Asn  Ala Pro Glu Ser Phe  Lys Asp Thr
    1895                 1900                 1905

Ala Glu  Ser Arg Ser Gly Arg  Arg Thr Asp Val Asn  Pro Phe Leu
    1910                 1915                 1920

Ala Pro  Arg Ser Ala Ala Val  Pro Leu Ile Asn Pro  Ala Gly Leu
    1925                 1930                 1935

Gly Pro  Gly Gly Pro Gly His  Leu Leu Leu Lys Pro  Ile Ser Asp
    1940                 1945                 1950

Val Leu  Pro Thr Phe Thr Pro  Leu Pro Ala Leu Pro  Asp Asn Ser
    1955                 1960                 1965

Ala Gly  Val Val Leu Lys Asp  Leu Leu Lys Gln
    1970                 1975
```

<210> SEQ ID NO 42
<211> LENGTH: 18
<212> TYPE: DNA
<213> ORGANISM: Artificial Sequence
<220> FEATURE:
<223> OTHER INFORMATION: Synthetic primer

<400> SEQUENCE: 42
gaagctacaa agcacatg 18

<210> SEQ ID NO 43
<211> LENGTH: 18
<212> TYPE: DNA
<213> ORGANISM: Artificial Sequence
<220> FEATURE:
<223> OTHER INFORMATION: Synthetic primer

<400> SEQUENCE: 43
tcctgtcttt cttcatgc 18

```
<210> SEQ ID NO 44
<211> LENGTH: 24
<212> TYPE: DNA
<213> ORGANISM: Artificial Sequence
<220> FEATURE:
<223> OTHER INFORMATION: Synthetic primer

<400> SEQUENCE: 44

gtcgacatgt cgtcctggct cggg                                          24


<210> SEQ ID NO 45
<211> LENGTH: 24
<212> TYPE: DNA
<213> ORGANISM: Artificial Sequence
<220> FEATURE:
<223> OTHER INFORMATION: Synthetic primer

<400> SEQUENCE: 45

ctcgagctat tgctttaaaa ggtc                                          24


<210> SEQ ID NO 46
<211> LENGTH: 24
<212> TYPE: DNA
<213> ORGANISM: Artificial Sequence
<220> FEATURE:
<223> OTHER INFORMATION: Synthetic primer

<400> SEQUENCE: 46

catatgtcgt cctggcttgg gggc                                          24


<210> SEQ ID NO 47
<211> LENGTH: 25
<212> TYPE: DNA
<213> ORGANISM: Artificial Sequence
<220> FEATURE:
<223> OTHER INFORMATION: Synthetic primer

<400> SEQUENCE: 47

ggtaccttgc tttaaaaggt ctttc                                         25
```